(12) United States Patent
Glick et al.

(10) Patent No.: US 11,339,136 B2
(45) Date of Patent: May 24, 2022

(54) COMPOUNDS AND COMPOSITIONS FOR TREATING CONDITIONS ASSOCIATED WITH NLRP ACTIVITY

(71) Applicant: Novartis AG, Basel (CH)

(72) Inventors: Gary Glick, Ann Arbor, MI (US); Shomir Ghosh, Brookline, MA (US); William R. Roush, Jupiter, FL (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/094,499

(22) PCT Filed: Apr. 18, 2017

(86) PCT No.: PCT/US2017/028167
§ 371 (c)(1),
(2) Date: Oct. 18, 2018

(87) PCT Pub. No.: WO2017/184624
PCT Pub. Date: Oct. 26, 2017

(65) Prior Publication Data
US 2019/0119224 A1    Apr. 25, 2019

Related U.S. Application Data

(60) Provisional application No. 62/324,081, filed on Apr. 18, 2016, provisional application No. 62/324,071, filed on Apr. 18, 2016.

(51) Int. Cl.
| | |
|---|---|
| *C07D 263/46* | (2006.01) |
| *C07D 333/34* | (2006.01) |
| *C07D 405/12* | (2006.01) |
| *C07D 417/12* | (2006.01) |
| *C07D 295/096* | (2006.01) |
| *C07D 213/34* | (2006.01) |
| *C07D 307/64* | (2006.01) |
| *C07D 311/54* | (2006.01) |

(Continued)

(52) U.S. Cl.
CPC .......... *C07D 263/46* (2013.01); *C07C 317/22* (2013.01); *C07D 213/34* (2013.01); *C07D 213/71* (2013.01); *C07D 277/36* (2013.01); *C07D 295/096* (2013.01); *C07D 307/64* (2013.01); *C07D 311/54* (2013.01); *C07D 333/34* (2013.01); *C07D 405/12* (2013.01); *C07D 417/12* (2013.01); *C07C 2603/10* (2017.05)

(58) Field of Classification Search
CPC ...... A61P 9/10; A61P 9/00; A61P 7/06; A61P 5/40; A61P 5/14; A61P 43/00; A61P 37/06; A61P 37/02; A61P 35/04; A61P 35/02; A61P 35/00; A61P 31/18; A61P 31/12; A61P 3/04; A61P 3/00; A61P 29/00; A61P 27/06; A61P 27/02; A61P 9/14; A61P 25/28; A61P 25/16; A61P 25/00; A61P 21/02; A61P 21/00; A61P 19/10; A61P 19/08; A61P 19/06; A61P 19/02; A61P 19/00; A61P 17/06; A61P 17/00; A61P 13/12; A61P 11/06; A61P 11/00; A61P 1/18; A61P 1/16; A61P 1/04; A61P 1/00; C07D 263/46; C07D 317/22; C07D 213/34; C07D 295/096; C07D 307/64; C07D 333/34; C07D 405/12; C07D 417/12; C07D 2603/10
USPC ........................................................ 549/475
See application file for complete search history.

(56) References Cited

U.S. PATENT DOCUMENTS

| | | | |
|---|---|---|---|
| 5,169,860 A | 12/1992 | Mohamadi et al. | |
| 5,302,724 A * | 4/1994 | Howbert .............. | C07D 207/36 548/452 |

(Continued)

FOREIGN PATENT DOCUMENTS

| | | |
|---|---|---|
| DK | 200600313 A | 3/2006 |
| EP | 1236468 A1 | 9/2002 |

(Continued)

OTHER PUBLICATIONS

Abou Ouf et al., "Thiophene Sulfonylureas Structurally Related to Antidiabetic Drugs," J Drug Res Egypt. 6(2):123-9 (1974).

(Continued)

*Primary Examiner* — Taylor V Oh
(74) *Attorney, Agent, or Firm* — Asha K. Nadipuram

(57) ABSTRACT

In one aspect, compounds of Formulae (I) and (II), or pharmaceutically acceptable salts thereof, are featured; Formula (I), Formula (II) or a pharmaceutically acceptable salt thereof, wherein the variables shown in Formulae (I) and (II) can be as defined anywhere herein.

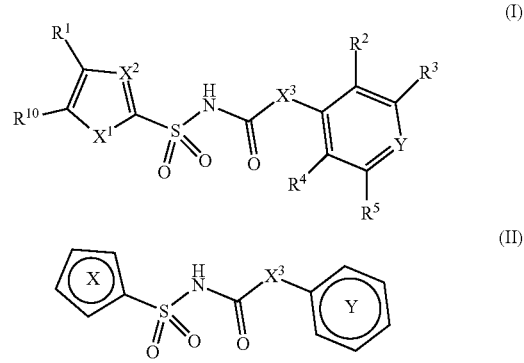

12 Claims, No Drawings

(51) Int. Cl.
  *C07D 213/71* (2006.01)
  *C07D 277/36* (2006.01)
  *C07C 317/22* (2006.01)

(56) References Cited

U.S. PATENT DOCUMENTS

| | | | |
|---|---|---|---|
| 5,565,494 | A | 10/1996 | Grindey et al. |
| 6,433,009 | B1 | 8/2002 | Dombroski et al. |
| 6,461,822 | B2 | 10/2002 | Gabel et al. |
| 2002/0034764 | A1 | 3/2002 | Gabel et al. |
| 2003/0143230 | A1* | 7/2003 | Gabel .................... A61P 29/00 424/145.1 |
| 2019/0119203 | A1 | 4/2019 | Glick et al. |

FOREIGN PATENT DOCUMENTS

| | | |
|---|---|---|
| JP | H0649052 A | 2/1994 |
| JP | H06211777 A | 8/1994 |
| JP | 2004339232 A | 12/2004 |
| WO | 98/32733 A1 | 7/1998 |
| WO | 01/19390 A1 | 3/2001 |
| WO | 2014/190015 A1 | 11/2014 |
| WO | 2016/131098 A1 | 8/2016 |

OTHER PUBLICATIONS

Salla et al., "Identification, Synthesis, and Biological Evaluation of the Major Human Metabolite of NLRP3 Inflammasome Inhibitor MCC950," ACS Med Chem Lett. 7(12):1034-8 (2016).
Saczewski et al., "Synthesis of novel aryl(heteroaryl)sulfonyl ureas of possible biological interest," Molecules. 15 (3):1113-26 (2010).
Youssef et al., "Synthesis of Certain Diarylsulfonylureas as Antitumor Agents," Med Chem Res. 10(6):404-18 (2001).
Jia et al., "Synthesis of N'-substituted phenyl-2-benzothiazolesulfonylureas derivatives," Chinese Journal of Medicinal Chemistry. 23(6):467-72 (2013). (English abstract provided).
ACS on STN Registry, 2-Thiophenesulfonamide, N-[[(3,4-dichlorophenyl)animo]carbonyl]-5-ethyl, dated Oct. 12, 2004 (1 page).
International Search Report and Written Opinion dated Jun. 14, 2017 for International Application No. PCT/US2017/028167 (15 pages).
International Search Report and Written Opinion dated Jun. 20, 2017 for PCT/US2017/028166 (22 pages).

* cited by examiner

COMPOUNDS AND COMPOSITIONS FOR TREATING CONDITIONS ASSOCIATED WITH NLRP ACTIVITY

This application is a National Stage application under 35 U.S.C. § 371 of International Patent Application No. PCT/US2017/028167, filed Apr. 18, 2017, which claims priority to U.S. Provisional Patent Application Ser. Nos. 62/324,081, filed Apr. 18, 2016 and 62/324,071, filed Apr. 18, 2016; the entire contents of which are herein incorporated by reference.

TECHNICAL FIELD

This disclosure features chemical entities (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination of the compound) that are useful, e.g., for treating a condition, disease or disorder in which a decrease or increase in NLRP1/3 activity (e.g., an increase, e.g., a condition, disease or disorder associated with NLRP1/3 signaling) contributes to the pathology and/or symptoms and/or progression of the condition, disease or disorder in a subject (e.g., a human). This disclosure also features compositions as well as other methods of using and making the same.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

The NLRP1 inflammasome is a component of the inflammatory process and its aberrant activation is pathogenic in inherited disorders such as generalized vitiligo associated with autoimmune disease (autoimmune thyroid disease, latent autoimmune diabetes in adults, rheumatoid arthritis, psoriasis, pernicious anemia, systemic lupus erythematosus, and Addison's disease).

NLRP1 and NLRP3 can form a complex and they have been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune diseases such as rheumatoid arthritis, systemic Lupus erythematosus, autoimmune thyroiditis; Addison's disease, and pernicious anemia, cancer, and aging.

In light of the above, it would be desirable to provide compounds that modulate (e.g., antagonize) NLRP1/3, wherein the compounds inhibit NLRP3 or NLRP1 or both NLRP3 and NLRP1.

SUMMARY

This disclosure features chemical entities (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination of the compound) that are useful, e.g., for treating a condition, disease or disorder in which a decrease or increase in NLRP1 or NLRP3 or both NLRP1 and NLRP3 activity, also referred to herein "NLRP1/3" activity (e.g., an increase, e.g., a condition, disease or disorder associated with NLRP1/3 signaling).

This disclosure also features compositions as well as other methods of using and making the same.

An "antagonist" of NLRP1/3 includes compounds that inhibit the ability of NLRP1/3 to induce the production of IL-1β and/or IL-18 by directly binding to NLRP1/3, or by inactivating, destabilizing, altering distribution, of NLRP1/3 or otherwise.

In one aspect, compounds of Formula I, or a pharmaceutically acceptable salt thereof, are featured:

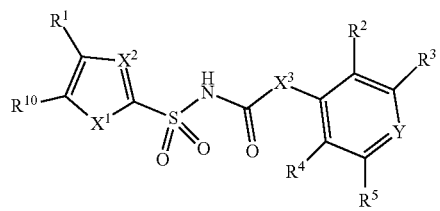

Formula I or a pharmaceutically acceptable salt thereof, wherein the variables shown in Formula I can be as defined anywhere herein.

In one aspect, compounds of Formula II, or a pharmaceutically acceptable salt thereof, are featured:

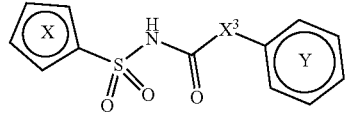

Formula II wherein the variables shown in Formula I can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP1 or NLRP3 or both NLRP1 and NLRP3 activity are featured that include contacting NLRP1 or NLRP3 or both NLRP1 and NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP1 or NLRP3 or both NLRP1 and NLRP3 (also referred to herein as "NLRP1/3"), as well as in vivo methods.

In a further aspect, methods of treatment of a disease in which NLRP1/3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP1/3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune diseases such as rheumatoid arthritis, systemic Lupus erythematosus, autoimmune thyroiditis; Addison's disease, and pernicious anemia, cancer, and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification, each of the applications from which this application claims priority, and any attached appendices, are incorporated herein by reference in their entireties. In case of conflict between the present specification and any subject matter incorporated by reference herein, the present specification, including definitions, will control As used herein, the term "NLRP1/3" is meant to include, without limitation, nucleic acids, polynucleotides, oligonucleotides, sense and antisense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP1/3 or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy, 21st ed.;* Lippincott Williams & Wilkins: Philadelphia, Pa., 2005; *Handbook of Pharmaceutical Excipients, 6th ed.;* Rowe et al., Eds.; The Pharmaceutical Press and the American Pharmaceutical Association: 2009; *Handbook of Pharmaceutical Additives, 3rd ed.;* Ash and Ash Eds.; Gower Publishing Company: 2007; *Pharmaceutical Preformulation and Formulation, 2nd ed.;* Gibson Ed.; CRC Press LLC: Boca Raton, Fla., 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described here inform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclic rings include five-membered, six-membered, and seven-membered heterocyclic rings.

The term "cycloalkyl" as used herein includes an aromatic or nonaromatic cyclic hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to an aromatic or nonaromatic 5-8 membered monocyclic, 8-12 membered bicyclic, or 11-14 membered tricyclic ring system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "hydroxy" refers to an OH group.

The term "amino" refers to an NH$_2$ group.

The term "oxo" refers to O. By way of example, substitution of a CH$_2$ a group with oxo gives a C=O group.

As used herein, a curved line connecting two atoms indicates a chain of length as specified by the recited number or number range. For example, a chain connecting an atom "Atom 1" to an atomo "Atom 2" may be depicted as

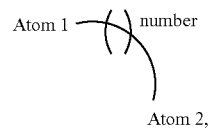

where the number outside the parenthetical indicates the number or range of numbers in the chain.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The details of one or more embodiments of the invention are set forth in the accompanying drawings and the description below. Other features and advantages of the invention will be apparent from the description and drawings, and from the claims.

DETAILED DESCRIPTION

In some embodiments, provided herein is a compound of Formula I

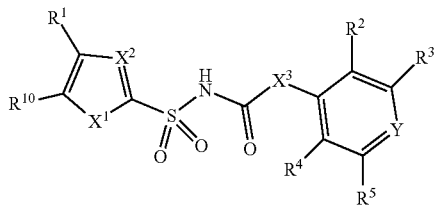

Formula I or a pharmaceutically acceptable salt thereof, wherein:
$X^1$ is O, S, or NH;
$X^2$ is N or $CR^9$;
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

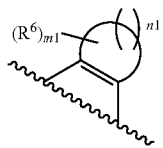

Ring A and ring B is

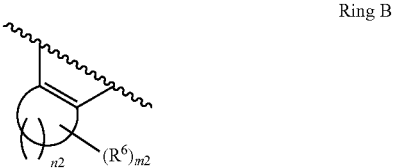

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl, $C_3$-$C_6$ cycloalkyl and $C_3$-$C_6$ heterocycloalkyl;
wherein $R^1$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{10}$ is selected from H, $C_1$-$C_6$ alkyl, $C_3$-$C_6$ cycloalkyl and $C_3$-$C_6$ heterocycloalkyl;
wherein $R^{10}$ is optionally substituted with one or more substituents each independently selected from hydroxy, oxo, $C_1$-$C_6$ alkoxy, $NR^{11}R^{12}$, $=NR^1$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;
provided that if the compound of formula I comprises ring A and ring B; $X^3$ is NH; $X^2$ is CH; and $R^{10}$ is H, then (i) if $X^1$ is O and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$, then Y is not N, CF, CCl or CH, (ii) if $X^1$ is O and $R^1$ is $C_1$-$C_6$ alkyl substituted with oxo, then Y is not CH, and (iii) if $X^1$ is S, then Y is not CH;
and provided that if $R^2$ and $R^4$ are each isopropyl; $X^3$ is NH; $X^2$ is CH; $R^{10}$ is H; and $R^1$ is $C_1$-$C_6$ alkyl optionally substituted with hydroxy, $C_1$-$C_6$ alkoxy, $NR^{11}R^{12}$, =$NR^{13}$, $COOC_1$-$C_6$ alkyl, or $CONR^{11}R^{12}$,
then Y is not CH or CCl.

In some embodiments, provided herein is a compound of Formula I

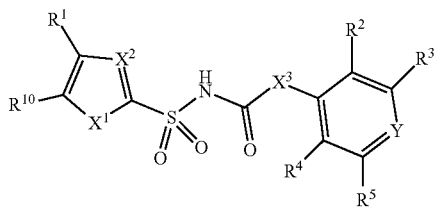

Formula I or a pharmaceutically acceptable salt thereof, wherein:
$X^1$ is O, S, or NH;
$X^2$ is N or $CR^9$;
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

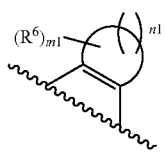

Ring A and ring B is

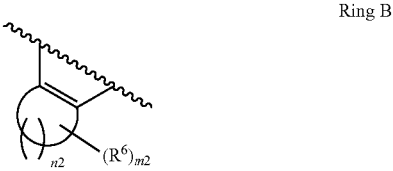

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and =$NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl, $C_3$-$C_6$ cycloalkyl, and $C_3$-$C_6$ heterocycloalkyl;
wherein $R^1$ is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;
$R^{10}$ is selected from H, $C_1$-$C_6$ alkyl, $C_3$-$C_6$ cycloalkyl, and $C_3$-$C_6$ heterocycloalkyl;
wherein $R^{10}$ is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl; each $R^{16}$ is the same or different and is selected from H, $C_1$-$C_6$ alkyl, $C_1$-$C_6$ alkoxy, $NR^{11}R^{12}$, oxo, and =$NR^{13}$;
provided that if the compound of formula I comprises ring A and ring B; $X^3$ is NH; $X^2$ is CH; and $R^{10}$ is H, then (i) if $X^1$ is O and $R^1$ is $C_1$-$C_6$ alkyl substituted with hydroxy, oxo, $C_1$-$C_6$ alkoxy, $NR^{11}R^{12}$, =$NR^{13}$, $COOC_1$-$C_6$ alkyl, and $CONR^{11}R^{12}$, then Y is not N, CF, CCl or CH, and (ii) if $X^1$ is S, then Y is not CH;
and provided that if $R^2$ and $R^4$ are each isopropyl; $X^3$ is NH; $X^2$ is CH; $R^{10}$ is H; and $R^1$ is $C_1$-$C_6$ alkyl optionally substituted with hydroxy, $C_1$-$C_6$ alkoxy, $NR^{11}R^{12}$, =$NR^{13}$, $COOC_1$-$C_6$ alkyl, or $CONR^{11}R^{12}$, then Y is not CH or CCl.

In some embodiments, provided herein is a compound of Formula II
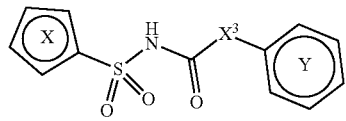
Formula II
or a pharmaceutically acceptable salt thereof, wherein Formula II is selected from
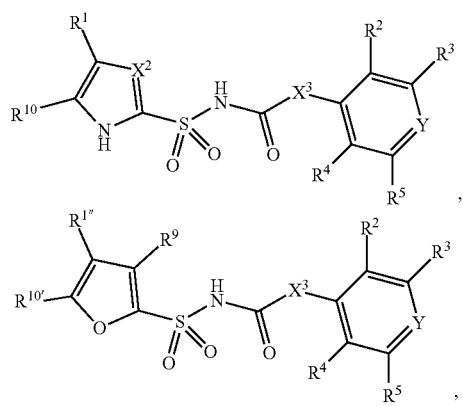
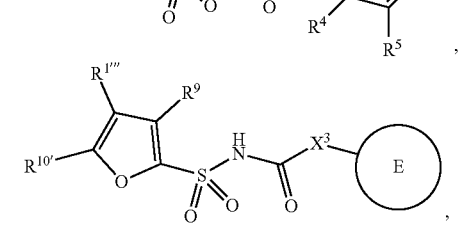
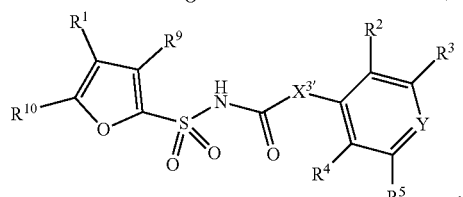
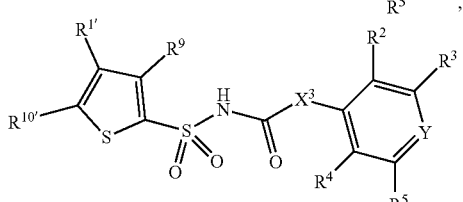
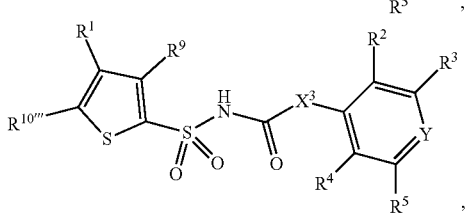
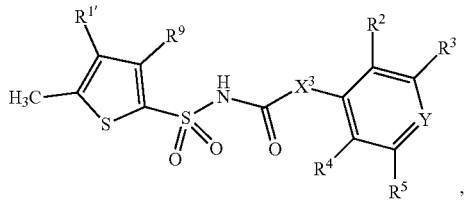
-continued
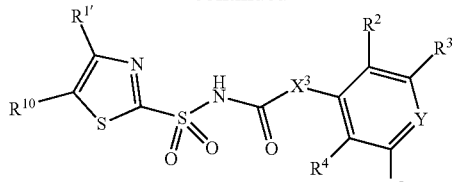
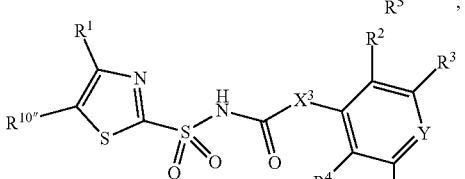
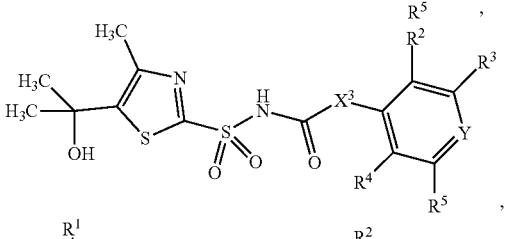
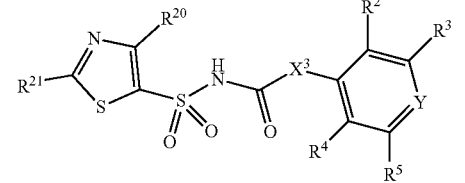
or
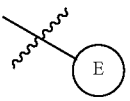
is selected from
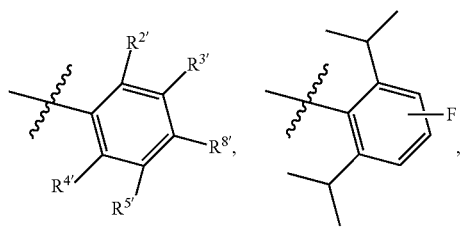
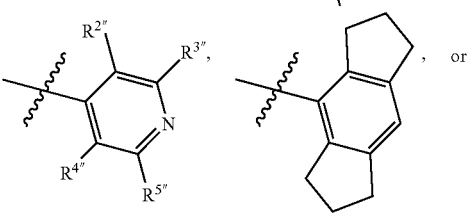

-continued

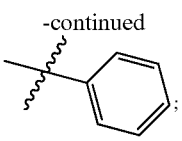

$X^2$ is N or $CR^9$;
$X^3$ is NH or O;
$X^{3'}$ is O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$; Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^{8'}$ is selected from CN, $CO_2C_1$-$C_6$ alkyl, $CO_2C_3$-$C_8$ cycloalkyl, $CONR^{11}R^{12}$, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^{2'}$ is hydrogen, halo, or $C_1$-$C_6$ alkyl optionally substituted with hydroxy;
$R^{2''}$ is hydrogen or $C_1$-$C_6$ alkyl;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^{3'}$ is hydrogen, halo, or $C_1$-$C_6$ alkyl optionally substituted with hydroxy;
$R^{3''}$ is hydrogen, CN, or $C_1$-$C_6$ alkyl;
$R^4$ is hydrogen, $C_1$-$C_6$ alkoxy, halo, $C_1$-$C_6$ haloalkyl, or $C_1$-$C_6$ alkyl optionally substituted with hydroxy;
$R^{4'}$ is hydrogen, halo, or $C_1$-$C_6$ alkyl optionally substituted with hydroxy;
$R^{4''}$ is hydrogen or $C_1$-$C_6$ alkyl;
$R^5$ is hydrogen, $C_1$-$C_6$ alkoxy, halo, $C_1$-$C_6$ haloalkyl, or $C_1$-$C_6$ alkyl optionally substituted with hydroxy;
$R^{5'}$ is hydrogen, halo, or $C_1$-$C_6$ alkyl optionally substituted with hydroxy;
$R^{5''}$ is hydrogen, CN, or $C_1$-$C_6$ alkyl;
or $R^2$ and $R^3$ taken together with the carbons connecting them form a four-membered to seven-membered ring A,
or $R^{2'}$ and $R^{3'}$ taken together with the carbons connecting them form a four-membered to seven-membered ring A,
or $R^4$ and $R^5$ taken together with the carbons connecting them form a four-membered to seven-membered ring B,
or $R^{4'}$ and $R^{5'}$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
or $R^{2'}$ and $R^{3'}$ taken together with the carbons connecting them form a four-membered to seven-membered ring A and $R^{4'}$ and $R^{5'}$ taken together with the carbons connecting them form a four-membered to seven-membered ring B, wherein ring A is

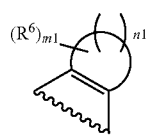

Ring A and ring B is

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{1''}$ is selected from unsubstituted $C_1$-$C_6$ alkyl, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{1'''}$ is selected from $C(R^{19})_2OH$;
$R^{10}$ is selected from H, Cl, $C_1$-$C_6$ alkyl, $C_3$-$C_6$ cycloalkyl and $C_3$-$C_6$ heterocycloalkyl;
wherein $R^{10}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10'}$ is selected from H, Cl, $C_3$-$C_6$ cycloalkyl and $C_3$-$C_6$ heterocycloalkyl;
wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{10''}$ is selected from Cl, $C_1$-$C_6$ alkyl, $C_3$-$C_6$ cycloalkyl, and $C_3$-$C_6$ heterocycloalkyl;

wherein $R^{10'''}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10'''}$ is selected from Cl, $C_1$-$C_6$ alkyl substituted with hydroxy, $C_3$-$C_6$ cycloalkyl, and $C_3$-$C_6$ heterocycloalkyl;

wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is selected from $C_1$-$C_6$ alkyl;

$R^{20}$ is selected from H, halo, or $C_1$-$C_6$ alkyl optionally substituted with hydroxy;

$R^{21}$ is selected from H, halo, or $C_1$-$C_6$ alkyl substituted with hydroxy;

provided that if (1) Formula II is

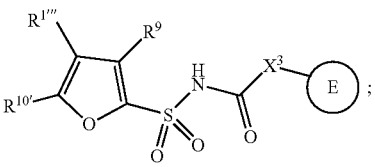

and if (2) $R^{10'}$ is H or $C_3$-$C_6$ heterocycloalkyl; then

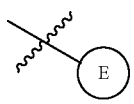

is not

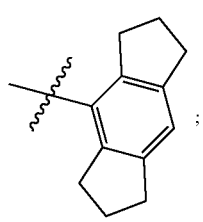 [SMILES: *c1c2c(cc3c1CCC3)CCC2]

and provided that if: (1) Formula II is

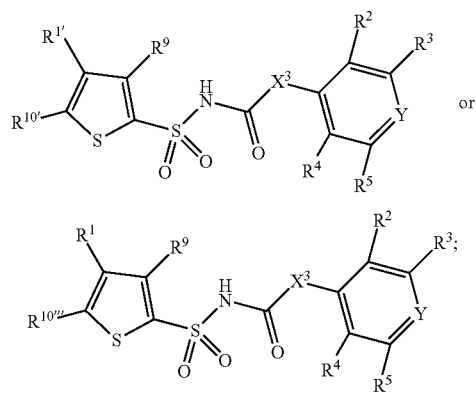

and (2) either of $R^1$ or $R^{1'}$, when present, is $C(R^{19})_2OH$; and (3) either of $R^{10'}$, or $R^{10'''}$, when present, is not Cl; then

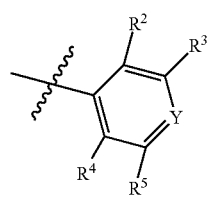

is not

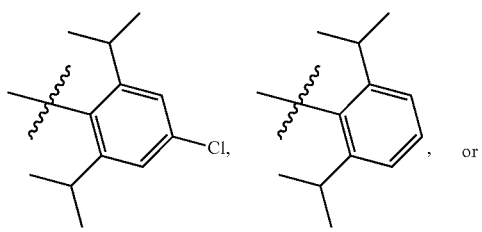

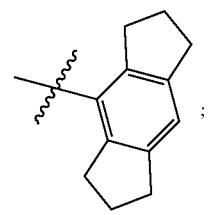

and provided that if: (1) Formula II is

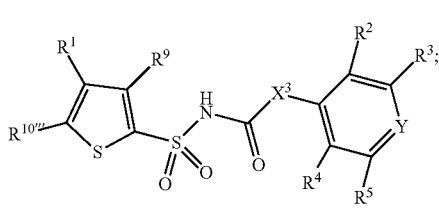

and (2) $R^{10''''}$ is $C_1$-$C_6$ alkyl substituted with hydroxy; then
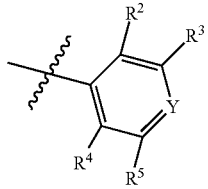
is not
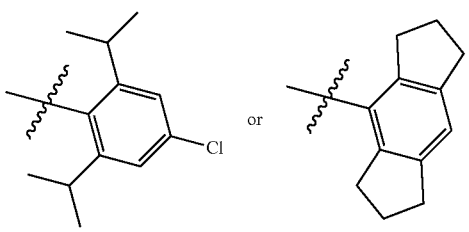
In some embodiments, provided herein is a compound of Formula II
Formula II
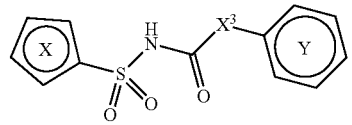
or a pharmaceutically acceptable salt thereof, wherein Formula II is selected from
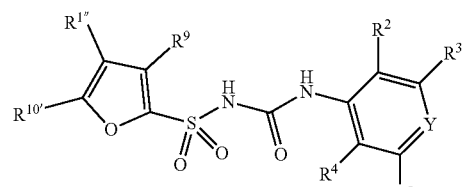
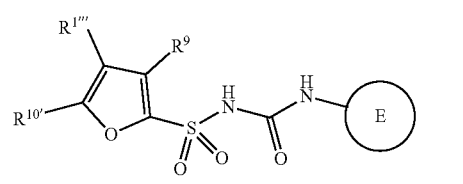
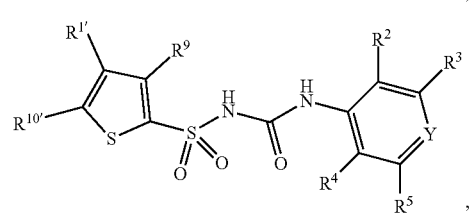
-continued
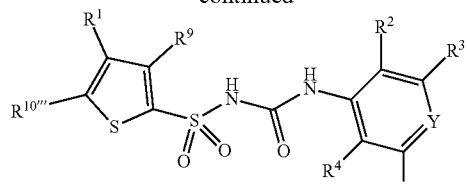
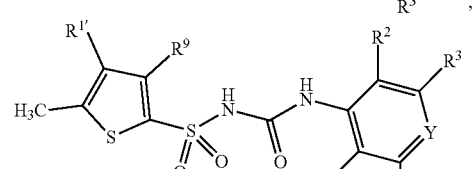
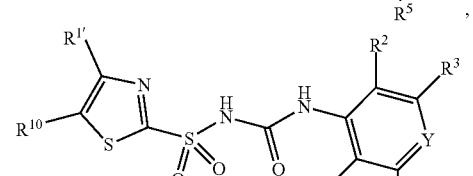
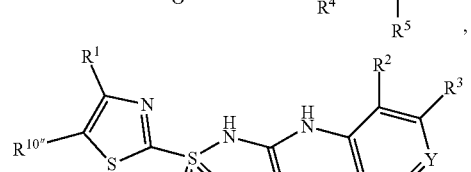
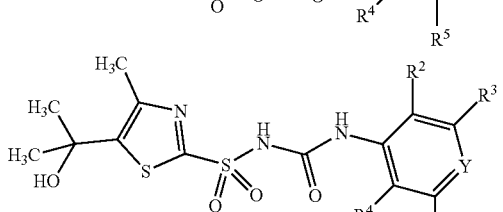
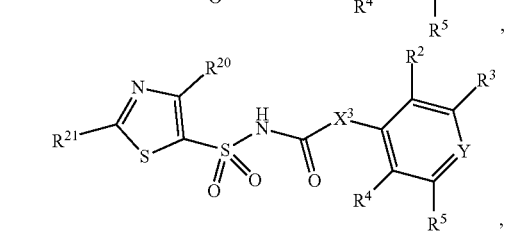
,  or
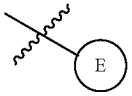
is selected from
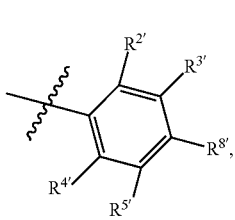
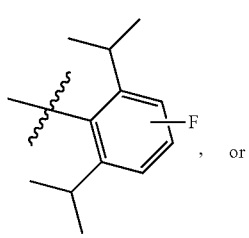
, or

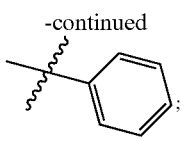

Y is N or $CR^8$;
$R^8$ is selected from H, CN, Cl, and F;
$R^{8'}$ is selected from CN and $CONR^{11}R^{12}$;
$R^9$ is selected from H;
$R^2$ is hydrogen or $C_1$-$C_6$ alkyl;
$R^{2'}$ is $C_1$-$C_6$ alkyl;
$R^3$ is hydrogen, CN, $C_1$-$C_6$ alkoxy, or halo;
$R^{3'}$ is hydrogen or halo;
$R^4$ is hydrogen or $C_1$-$C_6$ alkyl;
$R^{4'}$ is $C_1$-$C_6$ alkyl;
$R^5$ is hydrogen;
$R^{5'}$ is hydrogen;
or $R^2$ and $R^3$ taken together with the carbons connecting them form a four-membered to seven-membered ring A,
or $R^{2'}$ and $R^{3'}$ taken together with the carbons connecting them form a four-membered to seven-membered ring A,
or $R^4$ and $R^5$ taken together with the carbons connecting them form a four-membered to seven-membered ring B,
or $R^{4'}$ and $R^{5'}$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
or $R^{2'}$ and $R^{3'}$ taken together with the carbons connecting them form a four-membered to seven-membered ring A and $R^{4'}$ and $R^{5'}$ taken together with the carbons connecting them form a four-membered to seven-membered ring B,
wherein ring A is

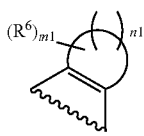

Ring A and ring B is

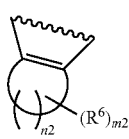

Ring B wherein
ring A is a saturated carbocyclic ring;
n1 is 3;
m1 is 0;
wherein ring B is a saturated carbocyclic ring;
n2 is 3;
m2 is 0;
$R^1$ is selected from H;
$R^{1'}$ is selected from $C(R^{19})_2OH$ and $C_3$-$C_6$ cycloalkyl;
wherein the $C_3$-$C_6$ cycloalkyl above is optionally substituted with one or more hydroxy;
$R^{1''}$ is selected from $C_3$-$C_6$ cycloalkyl;
wherein the $C_3$-$C_6$ cycloalkyl above is optionally substituted with one or more hydroxy;
$R^{1'''}$ is selected from $C(R^{19})_2OH$;
$R^{10}$ is selected from H, Cl, $C_1$-$C_6$ alkyl, and $C_3$-$C_6$ cycloalkyl;
wherein $R^{10}$ is optionally substituted with one or more substituents each independently selected from hydroxy;
$R^{10'}$ is selected from H or Cl;
$R^{10''}$ is selected from $C_1$-$C_6$ alkyl, and $C_3$-$C_6$ cycloalkyl;
wherein $R^{10''}$ is optionally substituted with one or more hydroxy;
$R^{10'''}$ is selected from $C_1$-$C_6$ alkyl and $C_3$-$C_6$ cycloalkyl;
wherein $R^{10'''}$ is optionally substituted with one or more hydroxy;
each of $R^{11}$ and $R^{12}$ at each occurrence is independently selected from hydrogen;
each $R^{19}$ is the same and is selected from $C_1$-$C_6$ alkyl;
$R^{20}$ is selected from H or $C_1$-$C_6$ alkyl optionally substituted with hydroxy;
$R^{21}$ is selected from H or $C_1$-$C_6$ alkyl substituted with hydroxy;
provided that if: (1) Formula II is

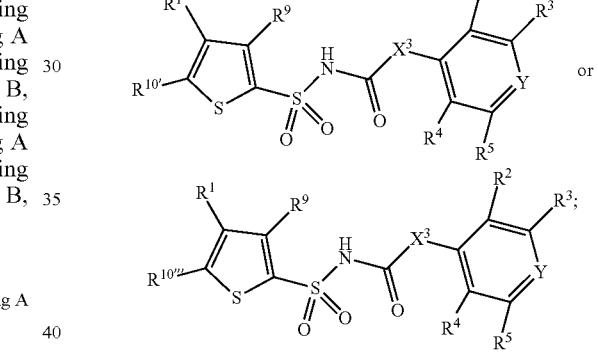

and (2) either of $R^1$ or $R^{1'}$, when present, is $C(R^{19})_2OH$; and (3) either of $R^{10'}$ or $R^{10'''}$, when present, is not Cl; then

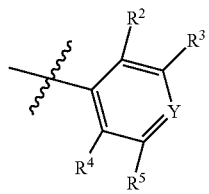

is not

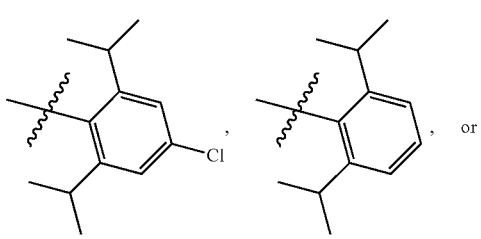

-continued

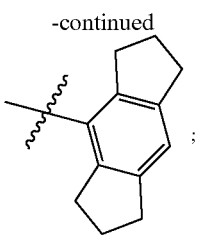

and provided that if: (1) Formula II is

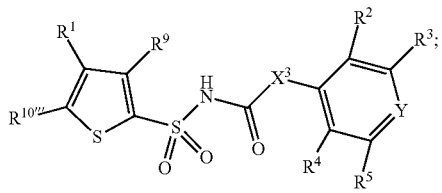

and if (2) $R^{10'''}$ is $C_1$-$C_6$ alkyl substituted with hydroxy; then

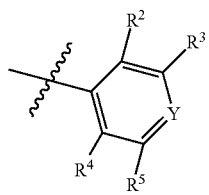

is not

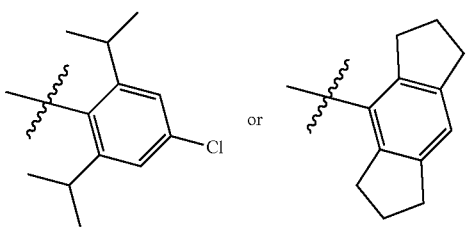

In some embodiments the variables shown in the formulae herein are as follows:

The Groups $X^1$ and $X^2$

In some embodiments of one or more formulae herein, $X^1$ is O.

In some embodiments of one or more formulae herein, $X^1$ is S.

In some embodiments of one or more formulae herein, $X^1$ is NH.

In some embodiments of one or more formulae herein, $X^2$ is $CR^9$.

In some embodiments of one or more formulae herein, $X^2$ is CH.

In some embodiments of one or more formulae herein, $X^2$ is N.

In some embodiments of one or more formulae herein, $X^1$ is O and $X^2$ is $CR^9$.

In some embodiments of one or more formulae herein, $X^1$ is S and $X^2$ is $CR^9$.

In some embodiments of one or more formulae herein, $X^1$ is O and $X^2$ is CH.

In some embodiments of one or more formulae herein, $X^1$ is S and $X^2$ is CH.

In some embodiments of one or more formulae herein, $X^1$ is O and $X^2$ is N.

In some embodiments of one or more formulae herein, $X^1$ is S and $X^2$ is N.

In some embodiments of one or more formulae herein, $X^1$ is NH and $X^2$ is N.

The Groups $X^3$ and $X^{3'}$

In some embodiments of one or more formulae herein, $X^3$ is NH.

In some embodiments of one or more formulae herein, $X^3$ is O.

In some embodiments, $X^3$ and $R^2$ taken together with the atoms connecting them form a four-to-seven-membered heterocyclic ring optionally substituted with one or more $R^{16}$.

In some embodiments, $X^3$ and $R^4$ taken together with the atoms connecting them form a four-to-seven-membered heterocyclic ring optionally substituted with one or more $R^{16}$.

In some embodiments, $X^3$ and $R^2$ taken together with the atoms connecting them form a four-to-seven-membered ring C of the formula

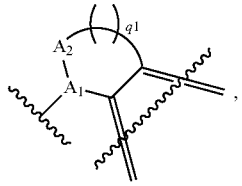

Ring C wherein q1 is 0, 1, 2 or 3; A1 is N; A2 is O, NH, or $CH_2$, provided that A1 and A2 are not both heteroatoms; and ring C is optionally substituted with 1 to 8 $R^{16}$.

In some embodiments of ring C, A1 is N and A2 is $CH_2$.

In some embodiments of ring C, $R^{16}$ is H.

In some embodiments, ring C is a heterocyclic ring containing one heteroatom selected from O, N and S.

In some embodiments, ring C is a heterocyclic ring containing two heteroatoms each independently selected from O, N and S.

In some embodiments of one or more formulae herein, $X^{3'}$ is O.

The Group Y

In some embodiments of one or more formulae herein, Y is $CR^8$.

In some embodiments of one or more formulae herein, Y is N.

The Groups $R^2$, $R^4$, $R^3$ and $R^5$

In some embodiments of one or more formulae herein, $R^2$ is hydrogen.

In some embodiments of one or more formulae herein, $R^2$ is $C_1$-$C_6$ alkoxy.

In some embodiments of one or more formulae herein, $R^2$ is methoxy.

In some embodiments of one or more formulae herein, $R^2$ is halo.

In some embodiments of one or more formulae herein, $R^2$ is $C_1$-$C_6$ haloalkyl.

In some embodiments of one or more formulae herein, $R^2$ is $CF_3$.

In some embodiments of one or more formulae herein, $R^2$ is $C_1$-$C_6$ alkyl optionally substituted with hydroxy.

In some embodiments of one or more formulae herein, $R^2$ is isopropyl.

In some embodiments of one or more formulae herein, $R^2$ is methyl.

In some embodiments of one or more formulae herein, $R^3$ is hydrogen.

In some embodiments of one or more formulae herein, $R^3$ is $C_1$-$C_6$ alkoxy.

In some embodiments of one or more formulae herein, $R^3$ is methoxy.

In some embodiments of one or more formulae herein, $R^3$ is halo.

In some embodiments of one or more formulae herein, $R^3$ is $C_1$-$C_6$ haloalkyl.

In some embodiments of one or more formulae herein, $R^3$ is $CF_3$.

In some embodiments of one or more formulae herein, $R^3$ is $C_1$-$C_6$ alkyl optionally substituted with hydroxy.

In some embodiments of one or more formulae herein, $R^3$ is isopropyl.

In some embodiments of one or more formulae herein, $R^3$ is methyl.

In some embodiments of one or more formulae herein, $R^3$ is CN.

In some embodiments of one or more formulae herein, $R^4$ is hydrogen.

In some embodiments of one or more formulae herein, $R^4$ is $C_1$-$C_6$ alkoxy.

In some embodiments of one or more formulae herein, $R^4$ is methoxy.

In some embodiments of one or more formulae herein, $R^4$ is halo.

In some embodiments of one or more formulae herein, $R^4$ is $C_1$-$C_6$ haloalkyl.

In some embodiments of one or more formulae herein, $R^4$ is $CF_3$.

In some embodiments of one or more formulae herein, $R^4$ is $C_1$-$C_6$ alkyl optionally substituted with hydroxy.

In some embodiments of one or more formulae herein, $R^4$ is isopropyl.

In some embodiments of one or more formulae herein, $R^4$ is methyl.

In some embodiments of one or more formulae herein, $R^5$ is hydrogen.

In some embodiments of one or more formulae herein, $R^5$ is $C_1$-$C_6$ alkoxy.

In some embodiments of one or more formulae herein, $R^5$ is methoxy.

In some embodiments of one or more formulae herein, $R^5$ is halo.

In some embodiments of one or more formulae herein, $R^5$ is $C_1$-$C_6$ haloalkyl.

In some embodiments of one or more formulae herein, $R^5$ is $CF_3$.

In some embodiments of one or more formulae herein, $R^5$ is $C_1$-$C_6$ alkyl optionally substituted with hydroxy.

In some embodiments of one or more formulae herein, each of $R^2$ and $R^4$ is hydrogen.

In some embodiments of one or more formulae herein, each of $R^2$ and $R^4$ is $C_1$-$C_6$ alkyl optionally substituted with hydroxy.

In some embodiments of one or more formulae herein, $R^5$ is isopropyl.

In some embodiments of one or more formulae herein, $R^5$ is methyl.

In some embodiments of one or more formulae herein, each of $R^2$ and $R^4$ is isopropyl.

In some embodiments of one or more formulae herein, each of $R^2$ and $R^4$ is t-butyl.

In some embodiments of one or more formulae herein, each of $R^2$ and $R^4$ is methyl.

In some embodiments of one or more formulae herein, each of $R^2$ and $R^4$ is hydroxymethyl.

In some embodiments of one or more formulae herein, each of $R^3$ and $R^5$ is hydrogen.

In some embodiments of one or more formulae herein, each of $R^3$ and $R^5$ is $C_1$-$C_6$ alkyl optionally substituted with hydroxy.

In some embodiments of one or more formulae herein, each of $R^3$ and $R^5$ is isopropyl.

In some embodiments of one or more formulae herein, each of $R^3$ and $R^5$ is t-butyl.

In some embodiments of one or more formulae herein, each of $R^3$ and $R^5$ is methyl.

In some embodiments of one or more formulae herein, each of $R^3$ and $R^5$ is hydroxymethyl.

In some embodiments of one or more formulae herein, each of $R^3$ and $R^5$ is hydrogen and each of $R^2$ and $R^4$ is $C_1$-$C_6$ alkyl optionally substituted with hydroxy.

In some embodiments of one or more formulae herein, each of $R^3$ and $R^5$ is hydrogen and each of $R^2$ and $R^4$ is isopropyl.

In some embodiments of one or more formulae herein, each of $R^3$ and $R^5$ is hydrogen and each of $R^2$ and $R^4$ is t-butyl.

In some embodiments of one or more formulae herein, each of $R^3$ and $R^5$ is hydrogen and each of $R^2$ and $R^4$ is methyl.

In some embodiments of one or more formulae herein, each of $R^3$ and $R^5$ is hydrogen and each of $R^2$ and $R^4$ is hydroxymethyl.

In some embodiments of one or more formulae herein, $R^3$ is halo and $R^5$ is H.

In some embodiments of one or more formulae herein, $R^3$ is CN and $R^5$ is H.

In some embodiments of one or more formulae herein, each of $R^2$ and $R^4$ is hydrogen and each of $R^3$ and $R^5$ is $C_1$-$C_6$ alkyl optionally substituted with hydroxy.

In some embodiments of one or more formulae herein, each of $R^2$ and $R^4$ is hydrogen and each of $R^3$ and $R^5$ is isopropyl.

In some embodiments of one or more formulae herein, each of $R^2$ and $R^4$ is hydrogen and each of $R^3$ and $R^5$ is t-butyl.

In some embodiments of one or more formulae herein, each of $R^2$ and $R^4$ is hydrogen and each of $R^3$ and $R^5$ is methyl.

In some embodiments of one or more formulae herein, each of $R^2$ and $R^4$ is hydrogen and each of $R^3$ and $R^5$ is hydroxymethyl.

In some embodiments of one or more formulae herein, $R^2$ and $R^3$ taken together with the carbons connecting them form ring A.

In some embodiments of one or more formulae herein, $R^4$ and $R^5$ taken together with the carbons connecting them form ring B.

In some embodiments of one or more formulae herein, $R^2$ and $R^3$ taken together with the carbons connecting them form ring A and $R^4$ and $R^5$ taken together with the carbons connecting them form ring B.

In some embodiments of one or more formulae herein, $R^2$ and $R^3$ taken together with the carbons connecting them form a five membered carbocyclic ring and $R^4$ and $R^5$ taken together with the carbons connecting them form a five membered carbocyclic ring.

The Groups $R^{2'}$, $R^{4'}$, $R^{3'}$ and $R^{5'}$

In some embodiments of one or more formulae herein, $R^{2'}$ is hydrogen.

In some embodiments of one or more formulae herein, $R^{2'}$ is halo.

In some embodiments of one or more formulae herein, $R^{2'}$ is $C_1$-$C_6$ alkyl optionally substituted with hydroxy.

In some embodiments of one or more formulae herein, $R^{2'}$ is isopropyl.

In some embodiments of one or more formulae herein, $R^{2'}$ is methyl.

In some embodiments of one or more formulae herein, is hydrogen.

In some embodiments of one or more formulae herein, $R^{3'}$ is halo.

In some embodiments of one or more formulae herein, $R^{3'}$ is $C_1$-$C_6$ alkyl optionally substituted with hydroxy.

In some embodiments of one or more formulae herein, $R^{3'}$ is isopropyl.

In some embodiments of one or more formulae herein, $R^{3'}$ is methyl.

In some embodiments of one or more formulae herein, $R^{4'}$ is hydrogen.

In some embodiments of one or more formulae herein, $R^{4'}$ is halo.

In some embodiments of one or more formulae herein, $R^{4'}$ is $C_1$-$C_6$ alkyl optionally substituted with hydroxy.

In some embodiments of one or more formulae herein, $R^{4'}$ is isopropyl.

In some embodiments of one or more formulae herein, $R^{4'}$ is methyl.

In some embodiments of one or more formulae herein, $R^{5'}$ is hydrogen.

In some embodiments of one or more formulae herein, $R^{5'}$ is halo.

In some embodiments of one or more formulae herein, $R^{5'}$ is $C_1$-$C_6$ alkyl optionally substituted with hydroxy.

In some embodiments of one or more formulae herein, each of $R^{2'}$ and $R^{4'}$ is hydrogen.

In some embodiments of one or more formulae herein, each of $R^{2'}$ and $R^{4'}$ is $C_1$-$C_6$ alkyl optionally substituted with hydroxy.

In some embodiments of one or more formulae herein, $R^{5'}$ is isopropyl.

In some embodiments of one or more formulae herein, $R^{5'}$ is methyl.

In some embodiments of one or more formulae herein, each of $R^{2'}$ and $R^{4'}$ is isopropyl.

In some embodiments of one or more formulae herein, each of $R^{2'}$ and $R^{4'}$ is t-butyl.

In some embodiments of one or more formulae herein, each of $R^{2'}$ and $R^{4'}$ is methyl.

In some embodiments of one or more formulae herein, each of $R^{2'}$ and $R^{4'}$ is hydroxymethyl.

In some embodiments of one or more formulae herein, each of $R^{3'}$ and $R^{5'}$ is hydrogen.

In some embodiments of one or more formulae herein, each of $R^{3'}$ and $R^{5'}$ is $C_1$-$C_6$ alkyl optionally substituted with hydroxy.

In some embodiments of one or more formulae herein, each of $R^{3'}$ and $R^{5'}$ is isopropyl.

In some embodiments of one or more formulae herein, each of $R^{3'}$ and $R^{5'}$ is t-butyl.

In some embodiments of one or more formulae herein, each of $R^{3'}$ and $R^{5'}$ is methyl.

In some embodiments of one or more formulae herein, each of $R^{3'}$ and $R^{5'}$ is hydroxymethyl.

In some embodiments of one or more formulae herein, each of $R^{3'}$ and $R^{5'}$ is hydrogen and each of $R^{2'}$ and $R^{4'}$ is $C_1$-$C_6$ alkyl optionally substituted with hydroxy.

In some embodiments of one or more formulae herein, each of $R^{3'}$ and $R^{5'}$ is hydrogen and each of $R^{2'}$ and $R^{4'}$ is isopropyl.

In some embodiments of one or more formulae herein, each of $R^{3'}$ and $R^{5'}$ is hydrogen and each of $R^{2'}$ and $R^{4'}$ is t-butyl.

In some embodiments of one or more formulae herein, each of $R^{3'}$ and $R^{5'}$ is hydrogen and each of $R^{2'}$ and $R^{4'}$ is methyl.

In some embodiments of one or more formulae herein, each of $R^{3'}$ and $R^{5'}$ is hydrogen and each of $R^{2'}$ and $R^{4'}$ is hydroxymethyl.

In some embodiments of one or more formulae herein, each of $R^{2'}$ and $R^{4'}$ is hydrogen and each of $R^{3'}$ and $R^{5'}$ is $C_1$-$C_6$ alkyl optionally substituted with hydroxy.

In some embodiments of one or more formulae herein, each of $R^{2'}$ and $R^{4'}$ is hydrogen and each of $R^{3'}$ and $R^{5'}$ is isopropyl.

In some embodiments of one or more formulae herein, each of $R^{2'}$ and $R^{4'}$ is hydrogen and each of $R^{3'}$ and $R^{5'}$ is t-butyl.

In some embodiments of one or more formulae herein, each of $R^{2'}$ and $R^{4'}$ is hydrogen and each of $R^{3'}$ and $R^{5'}$ is methyl.

In some embodiments of one or more formulae herein, each of $R^{2'}$ and $R^{4'}$ is hydrogen and each of $R^{3'}$ and $R^{5'}$ is hydroxymethyl.

In some embodiments of one or more formulae herein, $R^{2'}$ and $R^{3'}$ taken together with the carbons connecting them form ring A.

In some embodiments of one or more formulae herein, $R^{4'}$ and $R^{5'}$ taken together with the carbons connecting them form ring B.

In some embodiments of one or more formulae herein, $R^{2'}$ and $R^{3'}$ taken together with the carbons connecting them form ring A and $R^{4'}$ and $R^{5'}$ taken together with the carbons connecting them form ring B.

The Groups $R^{2''}$, $R^{4''}$, $R^{3''}$ and $R^{5''}$

In some embodiments of one or more formulae herein, $R^{2''}$ is hydrogen.

In some embodiments of one or more formulae herein, $R^{2''}$ is $C_1$-$C_6$ alkyl.

In some embodiments of one or more formulae herein, $R^{2''}$ is isopropyl.

In some embodiments of one or more formulae herein, $R^{2''}$ is methyl.

In some embodiments of one or more formulae herein, $R^{3''}$ is hydrogen.

In some embodiments of one or more formulae herein, $R^{3''}$ is CN.

In some embodiments of one or more formulae herein, $R^{3''}$ is $C_1$-$C_6$ alkyl.

In some embodiments of one or more formulae herein, $R^{3''}$ is isopropyl.

In some embodiments of one or more formulae herein, $R^{3''}$ is methyl.

In some embodiments of one or more formulae herein, $R^{4''}$ is hydrogen.

In some embodiments of one or more formulae herein, $R^{4''}$ is $C_1$-$C_6$ alkyl.

In some embodiments of one or more formulae herein, $R^{4''}$ is isopropyl.

In some embodiments of one or more formulae herein, $R^{4''}$ is methyl.

In some embodiments of one or more formulae herein, $R^{5''}$ is hydrogen.

In some embodiments of one or more formulae herein, $R^{5''}$ is CN.

In some embodiments of one or more formulae herein, $R^{5''}$ is $C_1$-$C_6$ alkyl.

In some embodiments of one or more formulae herein, each of $R^{2''}$ and $R^{4''}$ is hydrogen.

In some embodiments of one or more formulae herein, each of $R^{2''}$ and $R^{4''}$ is $C_1$-$C_6$ alkyl.

In some embodiments of one or more formulae herein, $R^{5''}$ is isopropyl.

In some embodiments of one or more formulae herein, $R^{5''}$ is methyl.

In some embodiments of one or more formulae herein, each of $R^{2''}$ and $R^{4''}$ is isopropyl.

In some embodiments of one or more formulae herein, each of $R^{2''}$ and $R^{4''}$ is t-butyl.

In some embodiments of one or more formulae herein, each of $R^{2''}$ and $R^{4''}$ is methyl.

In some embodiments of one or more formulae herein, each of $R^{3''}$ and $R^{5''}$ is hydrogen.

In some embodiments of one or more formulae herein, each of $R^{3''}$ and $R^{5''}$ is $C_1$-$C_6$ alkyl.

In some embodiments of one or more formulae herein, each of $R^{3''}$ and $R^{5''}$ is isopropyl.

In some embodiments of one or more formulae herein, each of $R^{3''}$ and $R^{5''}$ is t-butyl.

In some embodiments of one or more formulae herein, each of $R^{3''}$ and $R^{5''}$ is methyl.

In some embodiments of one or more formulae herein, each of $R^{3''}$ and $R^{5''}$ is hydrogen and each of $R^{2''}$ and $R^{4''}$ is $C_1$-$C_6$ alkyl.

In some embodiments of one or more formulae herein, each of $R^{3''}$ and $R^{5''}$ is hydrogen and each of $R^{2''}$ and $R^{4''}$ is isopropyl.

In some embodiments of one or more formulae herein, each of $R^{3''}$ and $R^{5''}$ is hydrogen and each of $R^{2''}$ and $R^{4''}$ is t-butyl.

In some embodiments of one or more formulae herein, each of $R^{3''}$ and $R^{5''}$ is hydrogen and each of $R^{2''}$ and $R^{4''}$ is methyl.

In some embodiments of one or more formulae herein, each of $R^{2''}$ and $R^{4''}$ is hydrogen and each of $R^{3''}$ and $R^{5''}$ is $C_1$-$C_6$ alkyl.

In some embodiments of one or more formulae herein, each of $R^{2''}$ and $R^{4''}$ is hydrogen and each of $R^{3''}$ and $R^{5''}$ is isopropyl.

In some embodiments of one or more formulae herein, each of $R^{2''}$ and $R^{4''}$ is hydrogen and each of $R^{3''}$ and $R^{5''}$ is t-butyl.

In some embodiments of one or more formulae herein, each of $R^{2''}$ and $R^{4''}$ is hydrogen and each of $R^{3''}$ and $R^{5''}$ is methyl.

Rings A and B

In some embodiments of one or more formulae herein, ring A is a carbocyclic ring.

In some embodiments of one or more formulae herein, ring A is a heterocyclic ring containing 1 or 2 heteroatoms independently selected from O, N, and S.

In some embodiments of one or more formulae herein, ring B is a carbocyclic ring.

In some embodiments of one or more formulae herein, ring B is a heterocyclic ring containing 1 or 2 heteroatoms independently selected from O, N, and S.

In some embodiments, ring A is a carbocyclic ring and n1 is 3.

In some embodiments, ring A is a carbocyclic ring and n1 is 4.

In some embodiments, ring A is a saturated carbocyclic ring.

In some embodiments, ring B is a saturated carbocyclic ring.

In some embodiments, ring A is a heterocyclic ring containing 1 or 2 heteroatoms independently selected from O, N, and S and n1 is 3.

In some embodiments, ring A is a heterocyclic ring containing 1 or 2 heteroatoms independently selected from O, N, and S and n1 is 4.

In some embodiments, ring B is a carbocyclic ring and n2 is 3.

In some embodiments, ring B is a carbocyclic ring and n2 is 4.

In some embodiments, ring B is a heterocyclic ring containing 1 or 2 heteroatoms independently selected from O, N, and S and n2 is 3.

In some embodiments, ring B is a heterocyclic ring containing 1 or 2 heteroatoms independently selected from O, N, and S and n2 is 4.

In some embodiments, ring A is the same as ring B.

In some embodiments, ring A is

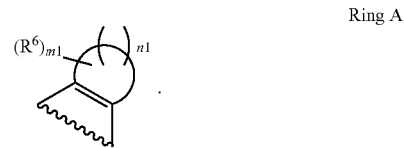

Ring A

.

In some embodiments, ring B is

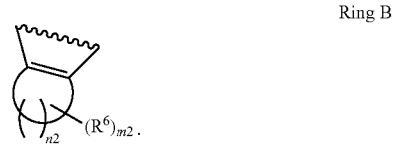

Ring B

.

In some embodiments, ring B is

Ring B and is the same as ring A.

In some embodiments, ring A is

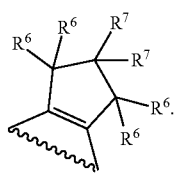

Ring A

In some embodiments, ring B is

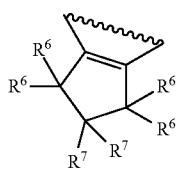

Ring B and is the same as ring A.

In some embodiments, ring A is a heterocyclic ring of the formula

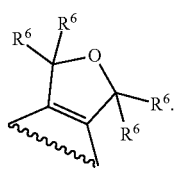

Ring A

In some embodiments, ring A is a heterocyclic ring of the formula

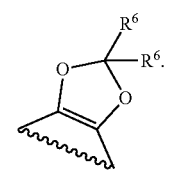

Ring A

The Groups $R^6$ and $R^7$ and the Variables n1, n2, m1 and m2 in Ring A and Ring B In some embodiments of one or more formulae herein, $R^6$ is H.

In some embodiments of one or more formulae herein, $R^6$ is $C_1$-$C_6$ alkyl.

In some embodiments of one or more formulae herein, $R^6$ is $C_1$-$C_6$ alkoxy.

In some embodiments of one or more formulae herein, $R^6$ is methoxy.

In some embodiments of one or more formulae herein, $R^6$ is $NR^{11}R^{12}$.

In some embodiments of one or more formulae herein, $R^6$ is oxo.

In some embodiments of one or more formulae herein, $R^6$ is $=NR^{13}$.

In some embodiments of one or more formulae herein, n1 is 2.

In some embodiments of one or more formulae herein, n1 is 3.

In some embodiments of one or more formulae herein, n1 is 4.

In some embodiments of one or more formulae herein, n1 is 5.

In some embodiments of one or more formulae herein, n2 is 2.

In some embodiments of one or more formulae herein, n2 is 3.

In some embodiments of one or more formulae herein, n2 is 4.

In some embodiments of one or more formulae herein, n2 is 5.

In some embodiments of one or more formulae herein, m1 is 1.

In some embodiments of one or more formulae herein, m1 is 2.

In some embodiments of one or more formulae herein, m1 is 3.

In some embodiments of one or more formulae herein, m1 is 4.

In some embodiments of one or more formulae herein, m2 is 1.

In some embodiments of one or more formulae herein, m2 is 2.

In some embodiments of one or more formulae herein, m2 is 3.

In some embodiments of one or more formulae herein, m2 is 4.

In some embodiments of one or more formulae herein, two $R^6$ taken together with the atom or atoms connecting them form a 3-to-8-membered carbocyclic or saturated heterocyclic ring containing 1 or 2 heteroatoms independently selected from O, N, and S.

In some embodiments of one or more formulae herein, each $R^6$ in each ring is H.

In some embodiments of one or more formulae herein, each $R^6$ in each ring is $C_1$-$C_6$ alkyl.

In some embodiments of one or more formulae herein, each $R^7$ in each ring is H.

In some embodiments of one or more formulae herein, each $R^7$ in each ring is $C_1$-$C_6$ alkyl.

In some embodiments of one or more formulae herein, each $R^6$ in each ring is H and each $R^7$ in each ring is H.

In some embodiments of one or more formulae herein, each $R^6$ in each ring is H and each $R^7$ in each ring is $C_1$-$C_6$ alkyl.

In some embodiments of one or more formulae herein, each $R^6$ in each ring is $C_1$-$C_6$ alkyl and each $R^7$ in each ring is H.

In some embodiments of one or more formulae herein, each $R^6$ in each ring is $C_1$-$C_6$ alkyl and each $R^7$ in each ring is $C_1$-$C_6$ alkyl.

The Ring E

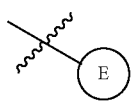

In some embodiments of one or more formulae herein, is selected from

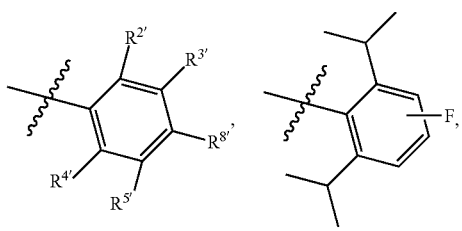

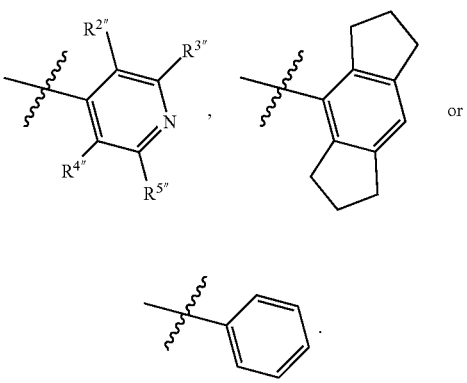

In some embodiments of one or more formulae herein,

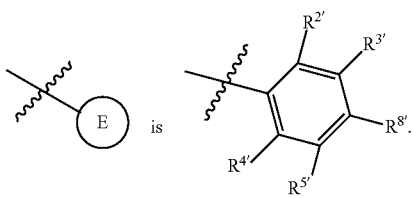

In some embodiments of one or more formulae herein.

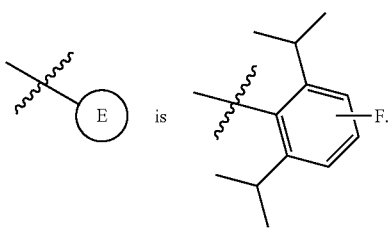

In some embodiments of one or more formulae herein,

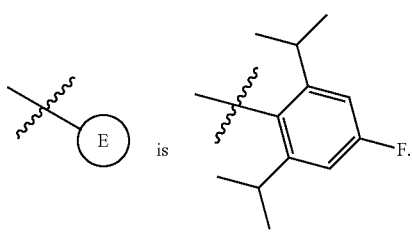

In some embodiments of one or more formulae herein,

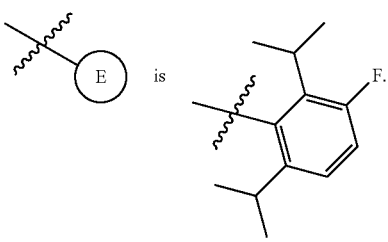

In some embodiments of one or more formulae herein,

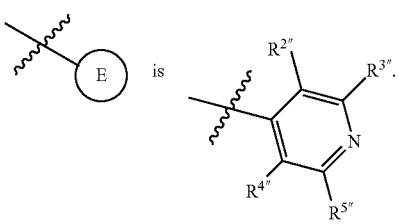

In some embodiments of one or more formulae herein,

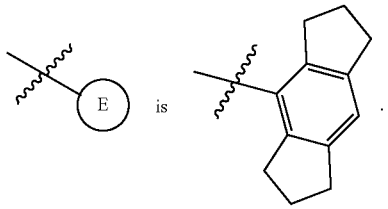

In some embodiments of one or more formulae herein,

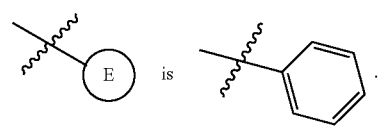

The Group $R^8$ and $R^{8'}$

In some embodiments of one or more formulae herein, $R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl.

In some embodiments of one or more formulae herein, $R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl.

In some embodiments of one or more formulae herein, $R^8$ is selected from H, CN, Cl, F, $CO_2C_1$-$C_6$ alkyl and $CONH_2$.

In some embodiments of one or more formulae herein, $R^8$ is H.

In some embodiments of one or more formulae herein, $R^8$ is CN.

In some embodiments of one or more formulae herein, $R^8$ is Cl.

In some embodiments of one or more formulae herein, $R^8$ is F.

In some embodiments of one or more formulae herein, $R^8$ is $CO_2C_1$-$C_6$ alkyl.

In some embodiments of one or more formulae herein, $R^8$ is $CO_2C_3$-$C_8$ cycloalkyl.

In some embodiments of one or more formulae herein, $R^8$ is $CONH_2$.

In some embodiments of one or more formulae herein, $R^8$ is $CONR^{11}R^{12}$.

In some embodiments of one or more formulae herein, $R^8$ is $C_1$-$C_6$ alkyl.

In some embodiments of one or more formulae herein, $R^8$ is $C_1$-$C_6$ haloalkoxy.

In some embodiments of one or more formulae herein, $R^8$ is $C_1$-$C_6$ haloalkyl.

In some embodiments of one or more formulae herein, $R^8$ is $CF_3$.

In some embodiments of one or more formulae herein, $R^{8'}$ is selected from CN, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl.

In some embodiments of one or more formulae herein, $R^{8'}$ is selected from CN, $CO_2C_1$-$C_6$ alkyl and $CONH_2$.

In some embodiments of one or more formulae herein, $R^{8'}$ is CN.

In some embodiments of one or more formulae herein, $R^{8'}$ is $CO_2C_1$-$C_6$ alkyl.

In some embodiments of one or more formulae herein, $R^{8'}$ is $CO_2C_3$-$C_8$ cycloalkyl.

In some embodiments of one or more formulae herein, $R^{8'}$ is $CONH_2$.

In some embodiments of one or more formulae herein, $R^{8'}$ is $CONR^{11}R^{12}$.

In some embodiments of one or more formulae herein, $R^{8'}$ is $C_1$-$C_6$ alkyl.

In some embodiments of one or more formulae herein, $R^{8'}$ is $C_1$-$C_6$ haloalkyl.

In some embodiments of one or more formulae herein, $R^{8'}$ is $CF_3$.

The Group $R^9$

In some embodiments of one or more formulae herein, $R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl.

In some embodiments of one or more formulae herein, $R^9$ is H.

In some embodiments of one or more formulae herein, $R^9$ is CN.

In some embodiments of one or more formulae herein, $R^9$ is Cl.

In some embodiments of one or more formulae herein, $R^9$ is F.

In some embodiments of one or more formulae herein, $R^9$ is $CO_2C_1$-$C_6$ alkyl.

In some embodiments of one or more formulae herein, $R^9$ is $CO_2C_3$-$C_8$ cycloalkyl.

In some embodiments of one or more formulae herein, $R^9$ is $CONH_2$.

In some embodiments of one or more formulae herein, $R^9$ is $CONR^{11}R^{12}$.

In some embodiments of one or more formulae herein, $R^9$ is $C_1$-$C_6$ alkyl.

In some embodiments of one or more formulae herein, $R^9$ is $C_1$-$C_6$ haloalkyl.

In some embodiments of one or more formulae herein, $R^9$ is $CF_3$.

The Groups $R^1$, $R^{1'}$, $R^{1''}$, and $R^{1'''}$

In some embodiments of one or more formulae herein, $R^1$ is selected from H, $C_1$-$C_6$ alkyl, $C_3$-$C_6$ cycloalkyl and $C_3$-$C_6$ heterocycloalkyl, wherein $R^1$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is H.

In some embodiments of one or more formulae herein, $R^1$ $C_1$-$C_6$ alkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ $C_3$-$C_6$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is $C_1$-$C_6$ alkyl optionally substituted with one or more substituents each independently selected from hydroxy, amino and oxo.

In some embodiments of one or more formulae herein, $R^1$ is $C_1$-$C_6$ alkyl substituted with hydroxy.

In some embodiments of one or more formulae herein, $R^1$ is 2-hydroxy-2-propyl.

In some embodiments of one or more formulae herein, leis $C_3$-$C_6$ cycloalkyl optionally substituted with one or more substituents each independently selected from hydroxy, amino and oxo.

In some embodiments of one or more formulae herein, $R^1$ is $C_3$-$C_6$ cycloalkyl.

In some embodiments of one or more formulae herein, $R^1$ is $C_3$-$C_6$ cycloalkyl substituted with hydroxy.

In some embodiments of one or more formulae herein, $R^1$ is 1-hydroxy-1-cyclopropyl.

In some embodiments of one or more formulae herein, $R^1$ is 1-hydroxy-1-cyclobutyl.

In some embodiments of one or more formulae herein, $R^1$ is 1-hydroxy-1-cyclopentyl.

In some embodiments of one or more formulae herein, $R^1$ is $C_3$-$C_6$ heterocycloalkyl optionally substituted with one or more substituents each independently selected from hydroxy, amino and oxo.

In some embodiments of one or more formulae herein, $R^1$ is $C_3$-$C_6$ heterocycloalkyl.

In some embodiments of one or more formulae herein, $R^1$ is $C_3$-$C_6$ heterocycloalkyl substituted with hydroxy.

$R^{1'}$ is selected from H, unsubstituted $C_1$-$C_6$ alkyl, $C(R^{19})_2OH$, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$ In some embodiments of one or more formulae herein, $R^1$ is $C(R^{19})_2OH$ or $C(O)C_2$-$C_6$ alkyl.

In some embodiments of one or more formulae herein, $R^1$ is $C(R^{19})_2OH$.

In some embodiments of one or more formulae herein, $R^1$ is $C(O)C_2$-$C_6$ alkyl.

In some embodiments of one or more formulae herein, $R^1$ is propanoyl.

In some embodiments of one or more formulae herein, $R^1$ is butanoyl.

In some embodiments of one or more formulae herein, $R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl, wherein each $C(O)$ $C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{1'}$ is unsubstituted $C_1$-$C_6$ alkyl.

In some embodiments of one or more formulae herein, $R^{1'}$ is $C(R^{19})_2OH$.

In some embodiments of one or more formulae herein, $R^{1'}$ is $C_3$-$C_6$ cycloalkyl optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{1'}$ is 2-hydroxy-2-propyl.

In some embodiments of one or more formulae herein, $R^{1'}$ is $C_3$-$C_6$ cycloalkyl optionally substituted with one or more substituents each independently selected from hydroxy or amino.

In some embodiments of one or more formulae herein, $R^{1'}$ is $C_3$-$C_6$ cycloalkyl.

In some embodiments of one or more formulae herein, $R^{1'}$ is $C_3$-$C_6$ cycloalkyl substituted with hydroxy.

In some embodiments of one or more formulae herein, $R^{1'}$ is 1-hydroxy-1-cyclopropyl.

In some embodiments of one or more formulae herein, $R^{1'}$ is 1-hydroxy-1-cyclobutyl.

In some embodiments of one or more formulae herein, $R^{1'}$ is 1-hydroxy-1-cyclopentyl.

In some embodiments of one or more formulae herein, $R^{1'}$ is $C(R^{19})_2OH$ or $C(O)C_2$-$C_6$ alkyl.

In some embodiments of one or more formulae herein, $R^{1'}$ is $C(R^{19})_2OH$.

In some embodiments of one or more formulae herein, $R^{1'}$ is $C(O)C_2$-$C_6$ alkyl.

In some embodiments of one or more formulae herein, $R^{1'}$ is propanoyl.

In some embodiments of one or more formulae herein, $R^{1'}$ is 2-hydroxypropanoyl.

In some embodiments of one or more formulae herein, $R^{1'}$ is butanoyl.

In some embodiments of one or more formulae herein, $R^{1''}$ is selected from unsubstituted $C_1$-$C_6$ alkyl, $C(O)C_2$-$C_6$ alkyl, and $C_3$-$C_6$ cycloalkyl, wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{1''}$ is unsubstituted $C_1$-$C_6$ alkyl.

In some embodiments of one or more formulae herein, $R^{1''}$ is $C_3$-$C_6$ cycloalkyl optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{1''}$ is $C_3$-$C_6$ cycloalkyl optionally substituted with one or more substituents each independently selected from hydroxy or amino.

In some embodiments of one or more formulae herein, $R^{1''}$ is $C_3$-$C_6$ cycloalkyl.

In some embodiments of one or more formulae herein, $R^{1''}$ is $C_3$-$C_6$ cycloalkyl substituted with hydroxy.

In some embodiments of one or more formulae herein, $R^{1''}$ is 1-hydroxy-1-cyclopropyl.

In some embodiments of one or more formulae herein, $R^{1''}$ is 1-hydroxy-1-cyclobutyl.

In some embodiments of one or more formulae herein, $R^{1''}$ is 1-hydroxy-1-cyclopentyl.

In some embodiments of one or more formulae herein, $R^{1''}$ is $C(O)C_2$-$C_6$ alkyl.

In some embodiments of one or more formulae herein, $R^{1''}$ is propanoyl.

In some embodiments of one or more formulae herein, $R^{1'''}$ is 2-hydroxypropanoyl.

In some embodiments of one or more formulae herein, $R^{1'''}$ is butanoyl.

In some embodiments of one or more formulae herein, $R^{1'''}$ is $C(R^{19})_2OH$.

In some embodiments of one or more formulae herein, $R^{1''''}$ is 2-hydroxy-2-propyl.

The Groups $R^{10}$, $R^{10'}$, $R^{10''}$, and $R^{10'''}$

In some embodiments of one or more formulae herein, $R^{10}$ is selected from H, $C_1$-$C_6$ alkyl, $C_3$-$C_6$ cycloalkyl and $C_3$-$C_6$ heterocycloalkyl, wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is selected from H, Cl, $C_1$-$C_6$ alkyl, $C_3$-$C_6$ cycloalkyl and $C_3$-$C_6$ heterocycloalkyl, wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is selected from H, Cl, $C_1$-$C_6$ alkyl, $C_3$-$C_6$ cycloalkyl and $C_3$-$C_6$ heterocycloalkyl, wherein $R^{10}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is H.

In some embodiments of one or more formulae herein, $R^{10}$ is Cl.

In some embodiments of one or more formulae herein, $R^{10}$ is $C_1$-$C_6$ alkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is $C_1$-$C_6$ alkyl optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ $C_3$-$C_6$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10}$ is $C_1$-$C_6$ alkyl optionally substituted with one or more substituents each independently selected from hydroxy, amino and oxo.

In some embodiments of one or more formulae herein, $R^{10}$ is $C_1$-$C_6$ alkyl substituted with hydroxy.

In some embodiments of one or more formulae herein, $R^{10}$ is 2-hydroxy-2-propyl.

In some embodiments of one or more formulae herein, $R^{10}$ is $C_3$-$C_6$ cycloalkyl optionally substituted with one or more substituents each independently selected from hydroxy, amino and oxo.

In some embodiments of one or more formulae herein, $R^{10}$ is $C_3$-$C_6$ cycloalkyl.

In some embodiments of one or more formulae herein, $R^{10}$ is $C_3$-$C_6$ cycloalkyl substituted with hydroxy.

In some embodiments of one or more formulae herein, $R^{10}$ is 1-hydroxy-1-cyclopropyl.

In some embodiments of one or more formulae herein, $R^{10}$ is 1-hydroxy-1-cyclobutyl.

In some embodiments of one or more formulae herein, $R^{10}$ is 1-hydroxy-1-cyclopentyl.

In some embodiments of one or more formulae herein, $R^{10}$ is $C_3$-$C_6$ heterocycloalkyl optionally substituted with one or more substituents each independently selected from hydroxy, amino and oxo.

In some embodiments of one or more formulae herein, $R^{10}$ is $C_3$-$C_6$ heterocycloalkyl.

In some embodiments of one or more formulae herein, $R^{10}$ is $C_3$-$C_6$ heterocycloalkyl substituted with hydroxy.

In some embodiments of one or more formulae herein, $R^{10}$ is selected from H, Cl, $C_3$-$C_6$ cycloalkyl and $C_3$-$C_6$ heterocycloalkyl, wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10'}$ is H.

In some embodiments of one or more formulae herein, $R^{10'}$ $C_3$-$C_6$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10'}$ is $C_3$-$C_6$ cycloalkyl optionally substituted with one or more substituents each independently selected from hydroxy, amino and oxo.

In some embodiments of one or more formulae herein, $R^{10'}$ is $C_3$-$C_6$ cycloalkyl.

In some embodiments of one or more formulae herein, $R^{10'}$ is $C_3$-$C_6$ cycloalkyl substituted with hydroxy.

In some embodiments of one or more formulae herein, $R^{10'}$ is 1-hydroxy-1-cyclopropyl.

In some embodiments of one or more formulae herein, $R^{10'}$ is 1-hydroxy-1-cyclobutyl.

In some embodiments of one or more formulae herein, $R^{10'}$ is 1-hydroxy-1-cyclopentyl.

In some embodiments of one or more formulae herein, $R^{10'}$ is $C_3$-$C_6$ heterocycloalkyl optionally substituted with one or more substituents each independently selected from hydroxy, amino and oxo.

In some embodiments of one or more formulae herein, $R^{10'}$ is $C_3$-$C_6$ heterocycloalkyl.

In some embodiments of one or more formulae herein, $R^{10'}$ is $C_3$-$C_6$ heterocycloalkyl substituted with hydroxy.

In some embodiments of one or more formulae herein, $R^{10''}$ is selected from Cl, $C_1$-$C_6$ alkyl, $C_3$-$C_6$ cycloalkyl and $C_3$-$C_6$ heterocycloalkyl, wherein $R^{10''}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10''}$ is Cl.

In some embodiments of one or more formulae herein, $R^{10''}$ $C_1$-$C_6$ alkyl optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10''}$ $C_3$-$C_6$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10''}$ is $C_1$-$C_6$ alkyl optionally substituted with one or more substituents each independently selected from hydroxyl and amino.

In some embodiments of one or more formulae herein, $R^{10''}$ is $C_1$-$C_6$ alkyl substituted with hydroxy.

In some embodiments of one or more formulae herein, $R^{10''}$ is 2-hydroxy-2-propyl.

In some embodiments of one or more formulae herein, $R^{10''}$ is $C_3$-$C_6$ cycloalkyl optionally substituted with one or more substituents each independently selected from hydroxy and amino.

In some embodiments of one or more formulae herein, $R^{10''}$ is $C_3$-$C_6$ cycloalkyl.

In some embodiments of one or more formulae herein, $R^{10''}$ is $C_3$-$C_6$ cycloalkyl substituted with hydroxy.

In some embodiments of one or more formulae herein, $R^{10''}$ is 1-hydroxy-1-cyclopropyl.

In some embodiments of one or more formulae herein, $R^{10''}$ is 1-hydroxy-1-cyclobutyl.

In some embodiments of one or more formulae herein, $R^{10''}$ is 1-hydroxy-1-cyclopentyl.

In some embodiments of one or more formulae herein, $R^{10''}$ is $C_3$-$C_6$ heterocycloalkyl optionally substituted with one or more substituents each independently selected from hydroxy, amino and oxo.

In some embodiments of one or more formulae herein, $R^{10''}$ is $C_3$-$C_6$ heterocycloalkyl.

In some embodiments of one or more formulae herein, $R^{10''}$ is $C_3$-$C_6$ heterocycloalkyl substituted with hydroxy.

$R^{10'''}$ is selected from Cl, $C_1$-$C_6$ alkyl substituted with hydroxy, $C_3$-$C_6$ cycloalkyl, and $C_3$-$C_6$ heterocycloalkyl; wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$ In some embodiments of one or more formulae herein, $R^{10'''}$ is Cl.

In some embodiments of one or more formulae herein, $R^{10'''}$ is $C_1$-$C_6$ alkyl optionally substituted with hydroxy.

In some embodiments of one or more formulae herein, $R^{10'''}$ $C_3$-$C_6$ cycloalkyl optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{10'''}$ is $C_1$-$C_6$ alkyl substituted with hydroxy.

In some embodiments of one or more formulae herein, $R^{10'''}$ is 2-hydroxy-2-propyl.

In some embodiments of one or more formulae herein, $R^{10'''}$ is $C_3$-$C_6$ cycloalkyl optionally substituted with one or more substituents each independently selected from hydroxy, amino and oxo.

In some embodiments of one or more formulae herein, $R^{10'''}$ is $C_3$-$C_6$ cycloalkyl.

In some embodiments of one or more formulae herein, $R^{10'''}$ is $C_3$-$C_6$ cycloalkyl substituted with hydroxy.

In some embodiments of one or more formulae herein, $R^{10'''}$ is 1-hydroxy-1-cyclopropyl.

In some embodiments of one or more formulae herein, $R^{10'''}$ is 1-hydroxy-1-cyclobutyl.

In some embodiments of one or more formulae herein, $R^{10'''}$ is 1-hydroxy-1-cyclopentyl.

In some embodiments of one or more formulae herein, $R^{10'''}$ is $C_3$-$C_6$ heterocycloalkyl optionally substituted with one or more substituents each independently selected from hydroxy, amino and oxo.

In some embodiments of one or more formulae herein, $R^{10'''}$ is $C_3$-$C_6$ heterocycloalkyl.

In some embodiments of one or more formulae herein, $R^{10'''}$ is $C_3$-$C_6$ heterocycloalkyl substituted with hydroxy.

The Groups $R^1$ and $R^{10}$

In some embodiments of one or more formulae herein, one of $R^1$ and $R^{10}$ is $C_1$-$C_6$ alkyl optionally substituted with one or more substituents each independently selected from hydroxy, amino and oxo, and the other of $R^1$ and $R^{10}$ is $C_3$-$C_6$ cycloalkyl optionally substituted with one or more substituents each independently selected from hydroxy, amino and oxo.

In some embodiments of one or more formulae herein, one of $R^1$ and $R^{10}$ is 2-hydroxy-2-propyl and the other of $R^1$ and $R^{10}$ is 1-hydroxy-1-cyclobutyl.

In some embodiments of one or more formulae herein, one of $R^1$ and $R^{10}$ is 2-hydroxy-2-propyl and the other of $R^1$ and $R^{10}$ is 1-hydroxy-1-cyclopentyl.

In some embodiments of one or more formulae herein, $R^1$ is H and $R^{10}$ is $C_1$-$C_6$ alkyl substituted with hydroxy.

In some embodiments of one or more formulae herein, $R^1$ is $C(R^{19})_2OH$ and $R^{10}$ is H.

In some embodiments of one or more formulae herein, $R^1$ is 2-hydroxy-2-propyl and $R^{10}$ is Cl.

In some embodiments of one or more formulae herein, $R^1$ is optionally substituted with one or more substituents each independently selected from hydroxy, amino and oxo, and the hydroxy, amino or oxo substituent is at the carbon of $R^1$ directly bonded to the five-membered heteroaryl ring of the formulae herein.

In some embodiments of one or more formulae herein, $R^{10}$ is optionally substituted with one or more substituents each independently selected from hydroxy, amino and oxo, and the hydroxy, amino or oxo substituent is at the carbon of $R^{10}$ directly bonded to the five-membered heteroaryl ring of the formulae herein.

In some embodiments of one or more formulae herein, $R^1$ and $R^{10}$ taken together with the atoms connecting them form a three-membered carbocyclic ring.

In some embodiments of one or more formulae herein, $R^1$ and $R^{10}$ taken together with the atoms connecting them form a four-membered carbocyclic ring.

In some embodiments of one or more formulae herein, $R^1$ and $R^{10}$ taken together with the atoms connecting them form a five-membered carbocyclic ring.

In some embodiments of one or more formulae herein, $R^1$ nd $R^{10}$ taken together with the atoms connecting them form a six-membered carbocyclic ring.

In some embodiments of one or more formulae herein, $R^1$ and $R^{10}$ taken together with the atoms connecting them form a seven-membered carbocyclic ring.

In some embodiments of one or more formulae herein, $R^1$ and $R^{10}$ taken together with the atoms connecting them form an eight-membered carbocyclic ring.

In some embodiments of one or more formulae herein, $R^1$ and $R^{10}$ taken together with the atoms connecting them form a three-membered heterocyclic ring containing 1 or 2 heteroatoms independently selected from O, N, and S.

In some embodiments of one or more formulae herein, $R^1$ and $R^{10}$ taken together with the atoms connecting them form a four-membered heterocyclic ring containing 1 or 2 heteroatoms independently selected from O, N, and S.

In some embodiments of one or more formulae herein, $R^1$ and $R^{10}$ taken together with the atoms connecting them form a five-membered heterocyclic ring containing 1 or 2 heteroatoms independently selected from O, N, and S.

In some embodiments of one or more formulae herein, $R^1$ and $R^{10}$ taken together with the atoms connecting them form a six-membered heterocyclic ring containing 1 or 2 heteroatoms independently selected from O, N, and S.

In some embodiments of one or more formulae herein, $R^1$ and $R^{10}$ taken together with the atoms connecting them form a seven-membered heterocyclic ring containing 1 or 2 heteroatoms independently selected from O, N, and S.

In some embodiments of one or more formulae herein, $R^1$ and $R^{10}$ taken together with the atoms connecting them form an eight-membered heterocyclic ring containing 1 or 2 heteroatoms independently selected from O, N, and S.

In some embodiments of one or more formulae herein, $R^1$ and $R^{10}$ taken together with the atoms connecting them form a carbocyclic ring substituted with hydroxy.

In some embodiments of one or more formulae herein, $R^1$ and $R^{10}$ taken together with the atoms connecting them form a carbocyclic ring substituted with oxo.

In some embodiments of one or more formulae herein, $R^1$ and $R^{10}$ taken together with the atoms connecting them form a carbocyclic ring substituted with $C_1$-$C_6$ alkoxy.

In some embodiments of one or more formulae herein, $R^1$ and $R^{10}$ taken together with the atoms connecting them form a carbocyclic ring substituted with $NR^{11}R^{12}$.

In some embodiments of one or more formulae herein, $R^1$ and $R^{10}$ taken together with the atoms connecting them form a carbocyclic ring substituted with $=NR^{13}$.

In some embodiments of one or more formulae herein, $R^1$ and $R^{10}$ taken together with the atoms connecting them form a carbocyclic ring substituted with $COOC_1$-$C_6$ alkyl.

In some embodiments of one or more formulae herein, $R^1$ and $R^{10}$ taken together with the atoms connecting them form a carbocyclic ring substituted with $CONR^{11}R^{12}$.

The Groups $R^{1''}$ and $R^{10'}$

In some embodiments of one or more formulae herein, $R^{10'}$ is selected from H, Cl, $C_3$-$C_6$ cycloalkyl and $C_3$-$C_6$ heterocycloalkyl; wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$ and $R^{1''}$ is selected from unsubstituted $C_1$-$C_6$ alkyl, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

In some embodiments of one or more formulae herein, $R^{10'}$ is selected from H and $R^{1''}$ is selected from unsubstituted $C_1$-$C_6$ alkyl, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

In some embodiments of one or more formulae herein, $R^{10'}$ is selected from H, Cl, $C_3$-$C_6$ cycloalkyl and $C_3$-$C_6$ heterocycloalkyl; wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$ and $R^{1''}$ is selected from $C_3$-$C_6$ cycloalkyl; wherein each $C_3$-$C_6$ cycloalkyl above is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

In some embodiments of one or more formulae herein, $R^{10'}$ is unsubstituted $C_1$-$C_6$ alkyl $R^{1''}$ is $C_3$-$C_6$ cycloalkyl optionally substituted with one or more substituents each independently selected from hydroxy, amino and oxo.

In some embodiments of one or more formulae herein, $R^{1'''}$ is a $C_3$-$C_6$ cycloalkyl substituted with hydroxy directly bonded to the five-membered heteroaryl ring of the formulae herein and $R^{10'}$ is H.

In some embodiments of one or more formulae herein, $R^{1'''}$ is 1-hydroxycyclopentyl and $R^{10'}$ is H.

In some embodiments of one or more formulae herein, $R^{1'''}$ is 1-hydroxycyclobutyl and $R^{10'}$ is H.

In some embodiments of one or more formulae herein, $R^{1'''}$ is 1-hydroxycyclopropyl and $R^{10'}$ is H.

In some embodiments of one or more formulae herein, $R^{1'''}$ is $C(O)C_2$-$C_6$ alkyl and $R^{10'}$ is H.

In some embodiments of one or more formulae herein, $R^{1'''}$ is propanoyl and $R^{10'}$ is H.

The Groups $R^{1'''}$ and $R^{10'}$

In some embodiments of one or more formulae herein, $R^{1'''}$ is $C(R^{19})_2OH$ and $R^{10'}$ is selected from H, Cl, $C_3$-$C_6$ cycloalkyl and $C_3$-$C_6$ heterocycloalkyl; wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^{1'''}$ is $C(R^{19})_2OH$ and $R^{10'}$ is H.

In some embodiments of one or more formulae herein, $R^{1'''}$ is $C(R^{19})_2OH$ and $R^{10'}$ is Cl.

In some embodiments of one or more formulae herein, $R^{1'''}$ is 2-hydroxy-2-propyl and $R^{10'}$ is H.

In some embodiments of one or more formulae herein, $R^{1'''}$ is 2-hydroxy-2-propyl and $R^{10'}$ is Cl.

The Groups $R^{1'}$ and $R^{10'}$

In some embodiments of one or more formulae herein, $R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$ and $R^{10'}$ is selected from H, Cl, $C_3$-$C_6$ cycloalkyl and $C_3$-$C_6$ heterocycloalkyl; wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

In some embodiments of one or more formulae herein, $R^{1'}$ is $C(R^{19})_2OH$ and $R^{10'}$ is selected from H, Cl, $C_3$-$C_6$ cycloalkyl and $C_3$-$C_6$ heterocycloalkyl; wherein $R^{1'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

In some embodiments of one or more formulae herein, $R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$ and $R^{10'}$ is H;

In some embodiments of one or more formulae herein, $R^{1'}$ is $C(R^{19})_2OH$ and $R^{10'}$ is H.

In some embodiments of one or more formulae herein, $R^{1'}$ is 2-hydroxy-2-propyl and $R^{10'}$ is H.

In some embodiments of one or more formulae herein, $R^{1'}$ is $C_3$-$C_6$ cycloalkyl optionally substituted with hydroxyl and $R^{10'}$ is H.

In some embodiments of one or more formulae herein, $R^{1'}$ is a $C_3$-$C_6$ cycloalkyl substituted with hydroxy directly bonded to the five-membered heteroaryl ring of the formulae herein and $R^{10'}$ is H.

In some embodiments of one or more formulae herein, $R^{1'}$ is 1-hydroxycyclopentyl and $R^{10'}$ is H.

In some embodiments of one or more formulae herein, $R^{1'}$ is 1-hydroxycyclobutyl and $R^{10'}$ is H.

In some embodiments of one or more formulae herein, $R^{1'}$ is 1-hydroxycyclopropyl and $R^{10'}$ is H.

The Groups $R^1$ and $R^{10'''}$

In some embodiments of one or more formulae herein, $R^1$ is selected from H, unsubstituted $C_1$-$C_6$ alkyl, $C(R^{19})_2OH$, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$ and $R^{10'''}$ is selected from Cl, $C_1$-$C_6$ alkyl substituted with hydroxy, $C_3$-$C_6$ cycloalkyl, and $C_3$-$C_6$ heterocycloalkyl; wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is selected from H, unsubstituted $C_1$-$C_6$ alkyl, $C(R^{19})_2OH$, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$ and $R^{10'''}$ is selected from Cl, $C_1$-$C_6$ alkyl substituted with hydroxy, $C_3$-$C_6$ cycloalkyl, and $C_3$-$C_6$ heterocycloalkyl; wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is selected from H, unsubstituted $C_1$-$C_6$ alkyl, $C(R^{19})_2OH$, $C(O)C_2$-$C_6$ alkyl, and $C_3$-$C_6$ cycloalkyl; wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$ and $R^{10'''}$ is selected from Cl, $C_1$-$C_6$ alkyl substituted with hydroxy, $C_3$-$C_6$ cycloalkyl, and $C_3$-$C_6$ heterocycloalkyl; wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$.

In some embodiments of one or more formulae herein, $R^1$ is H and $R^{10'''}$ is a $C_3$-$C_6$ cycloalkyl substituted with hydroxy directly bonded to the five-membered heteroaryl ring of the formulae herein.

In some embodiments of one or more formulae herein, $R^1$ is H and $R^{10'''}$ is 1-hydroxycyclopentyl.

In some embodiments of one or more formulae herein, $R^1$ is H and $R^{10'''}$ is 1-hydroxycyclobutyl.

In some embodiments of one or more formulae herein, $R^1$ is H and $R^{10'''}$ is 1-hydroxycyclopropyl.

In some embodiments of one or more formulae herein, $R^1$ is $C(R^{19})_2OH$ and $R^{10'''}$ is Cl.

In some embodiments of one or more formulae herein, $R^1$ is 2-hydroxy-2-propyl and $R^{10'''}$ is Cl.

In some embodiments of one or more formulae herein, $R^1$ is H and $R^{10'''}$ is $C_1$-$C_6$ alkyl substituted with hydroxy.

In some embodiments of one or more formulae herein, $R^1$ is H and $R^{10'''}$ is 2-hydroxy-2-propyl.

The Groups $R^{1'}$ and $R^{10}$

In some embodiments of one or more formulae herein, $R^{1'}$ is selected from unsubstituted $C_1$-$C_6$ alkyl, $C(R^{19})_2OH$, C(O)C$_2$-C$_6$ alkyl, and C$_3$-C$_6$ cycloalkyl; wherein each C(O) C$_2$-C$_6$ alkyl and C$_3$-C$_6$ cycloalkyl above is optionally substituted with one or more substituents each independently selected from hydroxy, C$_1$-C$_6$ alkoxy, NR$^{11}$R$^{12}$, =NR$^{13}$, COOC$_1$-C$_6$ alkyl, and CONR$^{11}$R$^{12}$, and R$^{10}$ is selected from H, Cl, C$_1$-C$_6$ alkyl, C$_3$-C$_6$ cycloalkyl and C$_3$-C$_6$ heterocycloalkyl; wherein R$^{10}$ is optionally substituted with one or more substituents each independently selected from hydroxy, C$_1$-C$_6$ alkoxy, NR$^{11}$R$^{12}$, =NR$^{13}$, COOC$_1$-C$_6$ alkyl, and CONR$^{11}$R$^{12}$.

In some embodiments of one or more formulae herein, R$^{1'}$ is unsubstituted C$_1$-C$_6$ alkyl and R$^{10}$ is C$_1$-C$_6$ alkyl optionally substituted with hydroxy.

In some embodiments of one or more formulae herein, R$^{1'}$ is methyl and R$^{10}$ is 2-hydroxy-2-propyl.

In some embodiments of one or more formulae herein, R$^{1'}$ is C(R$^{19}$)$_2$OH and R$^{10}$ is H.

The Groups R$^1$ and R$^{10''}$

In some embodiments of one or more formulae herein, R$^1$ is selected from H, unsubstituted C$_1$-C$_6$ alkyl, C(R$^{19}$)$_2$OH, C(O)C$_2$-C$_6$ alkyl, and C$_3$-C$_6$ cycloalkyl; wherein each C(O) C$_2$-C$_6$ alkyl and C$_3$-C$_6$ cycloalkyl above is optionally substituted with one or more substituents each independently selected from hydroxy, C$_1$-C$_6$ alkoxy, NR$^{11}$R$^{12}$, =NR$^{13}$, COOC$_1$-C$_6$ alkyl, and CONR$^{11}$R$^{12}$; and R$^{10''}$ is selected from Cl, C$_1$-C$_6$ alkyl, C$_3$-C$_6$ cycloalkyl, and C$_3$-C$_6$ heterocycloalkyl; wherein R$^{10''}$ is optionally substituted with one or more substituents each independently selected from hydroxy, C$_1$-C$_6$ alkoxy, NR$^{11}$R$^{12}$, =NR$^{13}$, COOC$_1$-C$_6$ alkyl, and CONR$^{11}$R$^{11}$.

In some embodiments of one or more formulae herein, R$^1$ is C(R$^{19}$)$_2$OH and R$^{10''}$ is C$_1$-C$_6$ alkyl optionally substituted with hydroxy.

In some embodiments of one or more formulae herein, R$^1$ is H and R$^{10''}$ is C$_3$-C$_6$ cycloalkyl substituted with hydroxy.

The Groups R$^{11}$ and R$^{12}$

In some embodiments of one or more formulae herein, R$^{11}$ is hydrogen.

In some embodiments of one or more formulae herein, R$^{11}$ is C$_1$-C$_6$ alkyl.

In some embodiments of one or more formulae herein, R$^{11}$ is CO$_2$R$^{15}$.

In some embodiments of one or more formulae herein, R$^{11}$ is CONR$^{17}$NR$^{18}$.

In some embodiments of one or more formulae herein, R$^{12}$ is hydrogen.

In some embodiments of one or more formulae herein, R$^{12}$ is C$_1$-C$_6$ alkyl.

In some embodiments of one or more formulae herein, R$^{12}$ is CO$_2$R$^{15}$.

In some embodiments of one or more formulae herein, R$^{12}$ is CONR$^{17}$NR$^{18}$.

The Groups R$^{13}$, R$^{15}$, R$^{17}$ and R$^{18}$

In some embodiments of one or more formulae herein, R$^{13}$ is C$_1$-C$_6$ alkyl.

In some embodiments of one or more formulae herein, R$^{15}$ is C$_1$-C$_6$ alkyl.

In some embodiments of one or more formulae herein, R$^{17}$ is hydrogen.

In some embodiments of one or more formulae herein, R$^{17}$ is C$_1$-C$_6$ alkyl.

In some embodiments of one or more formulae herein, R$^{18}$ is hydrogen.

In some embodiments of one or more formulae herein, R$^{18}$ is C$_1$-C$_6$ alkyl.

The Group R$^{16}$

In some embodiments of one or more formulae herein, R$^{16}$ is hydrogen.

In some embodiments of one or more formulae herein, R$^{16}$ is C$_1$-C$_6$ alkyl.

In some embodiments of one or more formulae herein, R$^{16}$ is C$_1$-C$_6$ alkoxy.

In some embodiments of one or more formulae herein, R$^{16}$ is NR$^{11}$R$^{12}$.

In some embodiments of one or more formulae herein, R$^{16}$ is oxo.

In some embodiments of one or more formulae herein, R$^{16}$ is C$_1$=NR$^{13}$.

The Group R$^{19}$

In some embodiments of one or more formulae herein, each R$^{19}$ is the same and is selected from C$_1$-C$_6$ alkyl.

In some embodiments of one or more formulae herein, each R$^{19}$ is methyl.

In some embodiments of one or more formulae herein, each R$^{19}$ is ethyl.

In some embodiments of one or more formulae herein, each R$^{19}$ is 1-propyl.

In some embodiments of one or more formulae herein, each R$^{19}$ is 2-propyl.

The groups R$^{20}$ and R$^{21}$

In some embodiments of one or more formulae herein, each R$^{20}$ is selected from H, halo, or C$_1$-C$_6$ alkyl optionally substituted with hydroxyl.

In some embodiments of one or more formulae herein, each R$^{20}$ is H.

In some embodiments of one or more formulae herein, each R$^{20}$ is halo.

In some embodiments of one or more formulae herein, each R$^{20}$ is C$_1$-C$_6$ alkyl optionally substituted with hydroxyl.

In some embodiments of one or more formulae herein, each R$^{20}$ is 2-hydroxy-2-propyl.

In some embodiments of one or more formulae herein, each R$^{21}$ is selected from H, halo, or C$_1$-C$_6$ alkyl substituted with hydroxyl.

In some embodiments of one or more formulae herein, each R$^{21}$ is H.

In some embodiments of one or more formulae herein, each R$^{21}$ is halo.

In some embodiments of one or more formulae herein, each R$^{21}$ is C$_1$-C$_6$ alkyl substituted with hydroxyl.

In some embodiments of one or more formulae herein, each R$^{21}$ is 2-hydroxy-2-propyl.

ADDITIONAL EMBODIMENTS

In some embodiments of one or more formulae herein:
if the compound of formula I comprises ring A and ring B; X$^3$ is NH; X$^2$ is CH; and R$^{10}$ is H, then (i) if X$^1$ is O and R$^1$ is C$_1$-C$_6$ alkyl substituted with hydroxy, C$_1$-C$_6$ alkoxy, NR$^{11}$R$^{12}$, =NR$^{13}$, COOC$_1$-C$_6$ alkyl, and CONR$^{11}$R$^{12}$, then Y is not N, CF, CCl or CH, (ii) if X$^1$ is O and R$^1$ is C$_1$-C$_6$ alkyl substituted with oxo, then Y is not CH, and (iii) if X$^1$ is S, then Y is not CH; and if R$^2$ and R$^4$ are each isopropyl; X$^3$ is NH; X$^2$ is CH; R$^{10}$ is H; and R$^1$ is optionally substituted C$_1$-C$_6$ alkyl, then Y is not CH or CCl.

In some embodiments of one or more formulae herein:
if the compound of formula I comprises ring A and ring B; X$^3$ is NH; X$^2$ is CH; and R$^{10}$ is H, then (i) if X$^1$ is O and R$^1$ is C$_1$-C$_6$ alkyl substituted with hydroxy, oxo, C$_1$-C$_6$ alkoxy, NR$^{11}$R$^{12}$, =NR$^{13}$, COOC$_1$-C$_6$ alkyl, and CONR$^{11}$R$^{12}$, then Y is not N, CF, CCl or CH, and (ii) if X$^1$ is S, then Y is not CH; and if R$^2$ and R$^4$ are each isopropyl; $X^3$ is NH; $X^2$ is CH; $R^{10}$ is H; and $R^1$ is optionally substituted $C_1$-$C_6$ alkyl, then Y is not CH or CCl.

In some embodiments of one or more formulae herein:
if (1) Formula II is

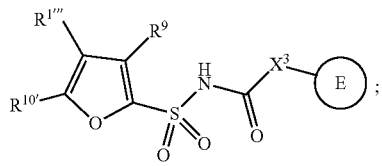

and if (2) $R^{10'}$ is H or $C_3$-$C_6$ heterocycloalkyl; then

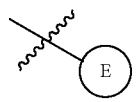

is not

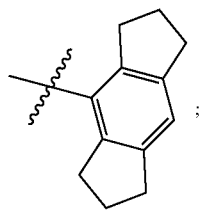 [SMILES: *c1c2c(cc3c1CCC3)CCC2]

and if: (1) Formula II is

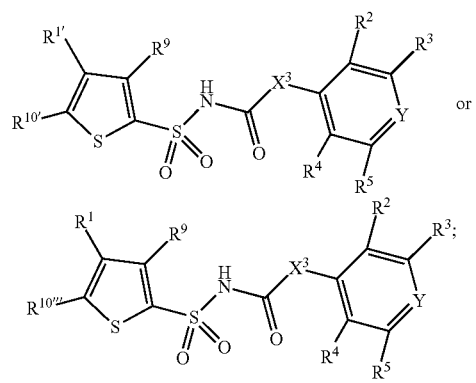

and (2) either of $R^1$ or $R^{1'}$, when present, is $C(R^{19})_2OH$; and (3) either of $R^{10'}$ or $R^{10'''}$, when present, is not Cl; then

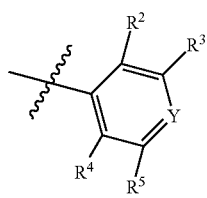

is not

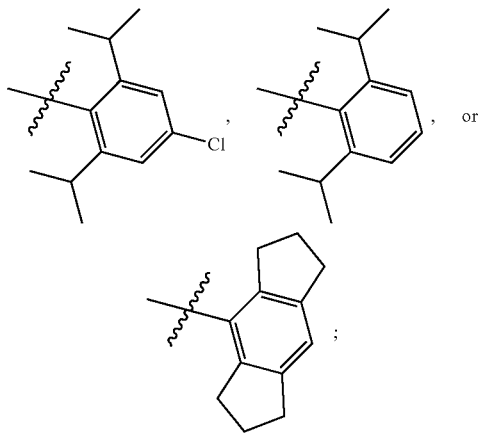

and if: (1) Formula II is

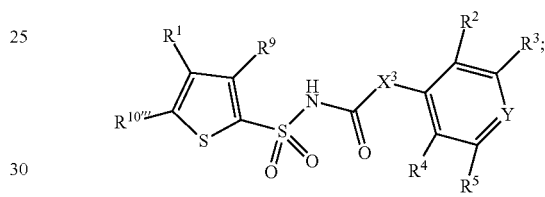

and (2) $R^{10'''}$ is $C_1$-$C_6$ alkyl substituted with hydroxy; then

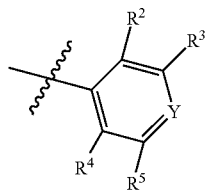

is not

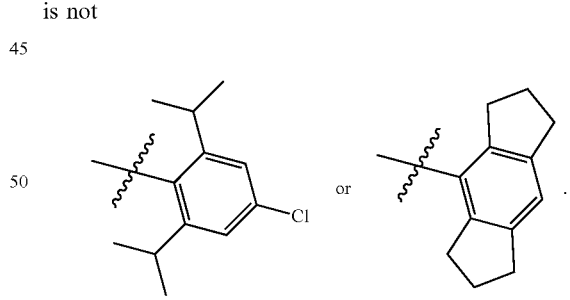

In some embodiments the compound of any of the formulae herein is not a compound disclosed in any of Examples 1-150 of patent publication WO2001/019,390, which are incorporated by reference herein.

In some embodiments the compound of any of the formulae herein is not a compound disclosed in any of Examples 1-130 of patent publication WO 98/32733, which are incorporated by reference herein.

In some embodiments the compound of any of the formulae herein is not a compound disclosed in any of the Examples at [00123] of patent publication WO2016/131, 098, which are incorporated by reference herein.

In some embodiments, provided herein is a compound of Formula I:

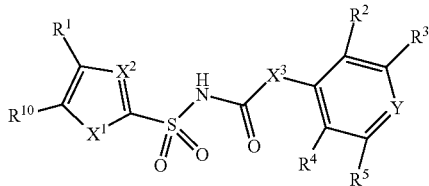

Formula I or a pharmaceutically acceptable salt thereof, wherein:
$X^1$ is O, S, or NH;
$X^2$ is N or $CR^9$;
$X^3$ is NH or O;
Y is N or $CR^8$;
$R^8$ is selected from H, CN, Cl, F, $CO_2C_1$-$C_6$ alkyl and $CONH_2$;
$R^9$ is selected from H and $C_1$-$C_6$ alkyl;
$R^2$ is hydrogen or $C_1$-$C_6$ alkyl optionally substituted with hydroxy;
$R^3$ is hydrogen or $C_1$-$C_6$ alkyl optionally substituted with hydroxy;
$R^4$ is hydrogen or $C_1$-$C_6$ alkyl optionally substituted with hydroxy and is the same as $R^2$; $R^5$ is hydrogen or $C_1$-$C_6$ alkyl optionally substituted with hydroxy and is the same as $R^3$;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a five-membered ring A and
$R^4$ and $R^5$ taken together with the carbons connecting them form a five-membered ring B, wherein ring A is

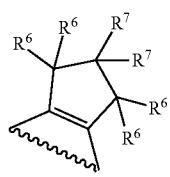

Ring A and ring B is

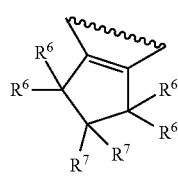

Ring B wherein each $R^6$ in each ring is the same and is H or $C_1$-$C_6$ alkyl, and each $R^7$ in each ring is the same and is H or $C_1$-$C_6$ alkyl;
$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo;
$R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo;

or $R^1$ and $R^{10}$ taken together with the atoms connecting them form a five-membered, a six-membered, or a seven-membered carbocyclic or heterocyclic ring; provided that if the compound of formula I comprises ring A and ring B; $X^3$ is NH; $X^2$ is CH; and $R^{10}$ is H, then (i) if $X^1$ is O and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$, then Y is not N, CF, CCl or CH, (ii) if $X^1$ is O and $R^1$ is $C_1$-$C_6$ alkyl substituted with oxo, then Y is not CH, and (iii) if $X^1$ is S, then Y is not CH;

and provided that if $R^2$ and $R^4$ are each isopropyl; $X^3$ is NH; $X^2$ is CH; $R^{10}$ is H; and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$, then Y is not CH or CCl.

In some embodiments, provided herein is a compound of Formula I:

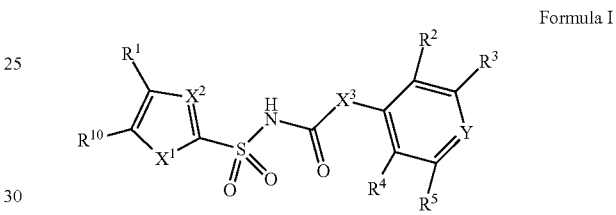

Formula I or a pharmaceutically acceptable salt thereof, wherein:
$X^1$ is O, S, or NH;
$X^2$ is N or $CR^9$;
$X^3$ is NH or O;
Y is N or $CR^8$;
$R^8$ is selected from H, CN, Cl, F, $CO_2C_1$-$C_6$ alkyl and $CONH_2$;
$R^9$ is selected from H and $C_1$-$C_6$ alkyl;
$R^2$ is hydrogen or $C_1$-$C_6$ alkyl optionally substituted with hydroxy;
$R^3$ is hydrogen or $C_1$-$C_6$ alkyl optionally substituted with hydroxy;
$R^4$ is hydrogen or $C_1$-$C_6$ alkyl optionally substituted with hydroxy and is the same as $R^2$;
$R^5$ is hydrogen or $C_1$-$C_6$ alkyl optionally substituted with hydroxy and is the same as $R^3$; or $R^2$ and $R^3$ taken together with the carbons connecting them form a five-membered ring A and
$R^4$ and $R^5$ taken together with the carbons connecting them form a five-membered ring B, wherein ring A is

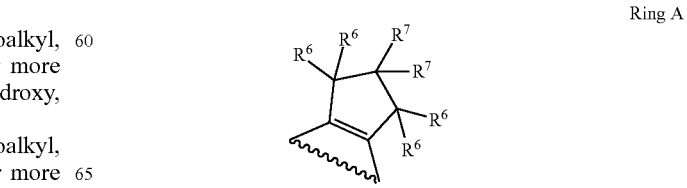

Ring A and ring B is

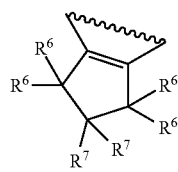

Ring B wherein each $R^6$ in each ring is the same and is H or $C_1$-$C_6$ alkyl, and each $R^7$ in each ring is the same and is H or $C_1$-$C_6$ alkyl;

$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo;

$R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo; or $R^1$ and $R^{10}$ taken together with the atoms connecting them form a five-membered, a six-membered, or a seven-membered carbocyclic or heterocyclic ring;

provided that if the compound of formula I comprises ring A and ring B; $X^3$ is NH; $X^2$ is CH; and $R^{10}$ is H, then (i) if $X^1$ is O and $R^1$ is $C_1$-$C_6$ alkyl optionally substituted with hydroxy, oxo, $C_1$-$C_6$ alkoxy, $NR^{11}R^{12}$, $=NR^{13}$, $COOC_1$-$C_6$ alkyl, or $CONR^{11}R^{12}$, then Y is not N, CF, CCl or CH, and (ii) if $X^1$ is S, then Y is not CH;

and provided that if $R^2$ and $R^4$ are each isopropyl; $X^3$ is NH; $X^2$ is CH; $R^{10}$ is H; and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$, then Y is not CH or CCl.

In some embodiments, the compound of Formula I is a compound of Formula Ia

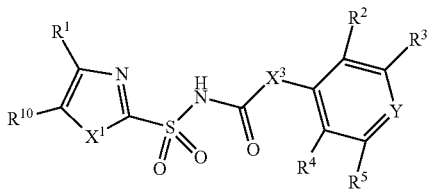

Formula Ia or a pharmaceutically acceptable salt thereof, wherein:
$X^1$ is O, S, or NH;
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$; Y is N or $CR^8$;
$R^8$ is selected from H, CN, Cl, F, $CO_2C_1$-$C_6$ alkyl and $CONH_2$;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

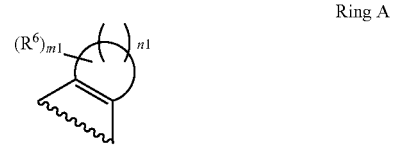

Ring A and ring B is

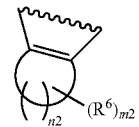

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$.

In some embodiments, the compound of Formula I is a compound of Formula Ia

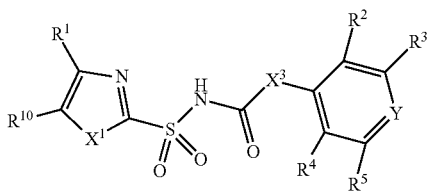

Formula Ia or a pharmaceutically acceptable salt thereof, wherein $X^1$ is O, S, or NH;

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl and $CONH_2$;

$R^2$ is hydrogen or $C_1$-$C_6$ alkyl optionally substituted with hydroxy;

$R^3$ is hydrogen or $C_1$-$C_6$ alkyl optionally substituted with hydroxy;

$R^4$ is hydrogen or $C_1$-$C_6$ alkyl optionally substituted with hydroxy and is the same as $R^2$;

$R^5$ is hydrogen or $C_1$-$C_6$ alkyl optionally substituted with hydroxy and is the same as $R^3$;

provided that at least one of $R^2$, $R^3$, $R^4$ and $R^5$ is not hydrogen, and that $R^2$ and $R^4$ are not both hydroxymethyl;

or $R^2$ and $R^3$ taken together with the carbons connecting them form a five-membered ring A and $R^4$ and $R^5$ taken together with the carbons connecting them form a five-membered ring B, wherein ring A is

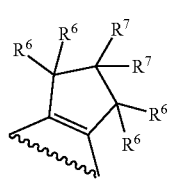

Ring A and ring B is

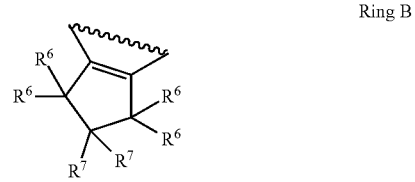

Ring B wherein each $R^6$ in each ring is the same and is H or $C_1$-$C_6$ alkyl, and each $R^7$ in each ring is the same and is H or $C_1$-$C_6$ alkyl;

$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo;

$R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo; or $R^1$ and $R^{10}$ taken together with the atoms connecting them form a five-membered, a six-membered, or a seven-membered carbocyclic or heterocyclic ring.

In some embodiments, the compound of Formula Ia is a compound of Formula Ia-i:

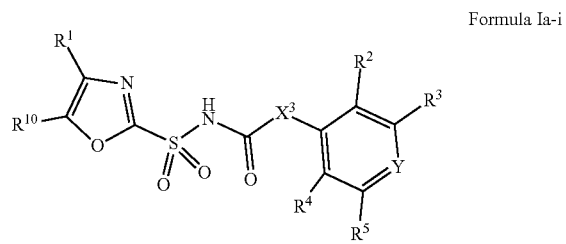

Formula Ia-i or a pharmaceutically acceptable salt thereof, wherein:

$X^3$ is NH or O;

Y is N or $CR^8$;

$R^8$ is selected from H, CN, Cl, F, $CO_2C_1$-$C_6$ alkyl and $CONH_2$;

$R^2$ is $C_1$-$C_6$ alkoxy, halo, $C_1$-$C_6$ haloalkyl, or $C_1$-$C_6$ alkyl optionally substituted with hydroxy;

$R^3$ is hydrogen;

$R^4$ is $C_1$-$C_6$ alkoxy, halo, $C_1$-$C_6$ haloalkyl, or $C_1$-$C_6$ alkyl optionally substituted with hydroxy;

$R^5$ is hydrogen;

$R^1$ is selected from H, $C_1$-$C_6$ alkyl and $C_3$-$C_6$ cycloalkyl, wherein $R^1$ is optionally substituted with hydroxy, amino or oxo;

$R^{10}$ is selected from H, $C_1$-$C_6$ alkyl and $C_3$-$C_6$ cycloalkyl, wherein $R^{10}$ is optionally substituted with hydroxy, amino or oxo;

or $R^1$ and $R^{10}$ taken together with the atoms connecting them form a five-membered, a six-membered, or a seven-membered carbocyclic or heterocyclic ring.

In some embodiments, the compound of Formula Ia is a compound of Formula Ia-i:

Formula Ia-i

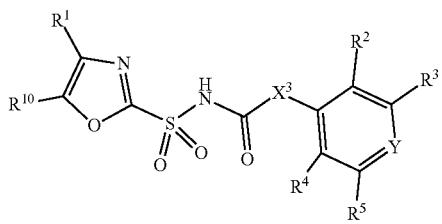

or a pharmaceutically acceptable salt thereof,
wherein:
$X^3$ is NH or O;
Y is N or $CR^8$;
$R^8$ is selected from H, CN, Cl, F, $CO_2C_1$-$C_6$ alkyl and $CONH_2$;
$R^3$ is $C_1$-$C_6$ alkoxy, halo, $C_1$-$C_6$ haloalkyl, or $C_1$-$C_6$ alkyl optionally substituted with hydroxy;
$R^2$ is hydrogen;
$R^5$ is $C_1$-$C_6$ alkoxy, halo, $C_1$-$C_6$ haloalkyl, or $C_1$-$C_6$ alkyl optionally substituted with hydroxy;
$R^4$ is hydrogen;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

In some embodiments, the compound of Formula Ia is a compound of Formula Ia-i:

Formula Ia-i

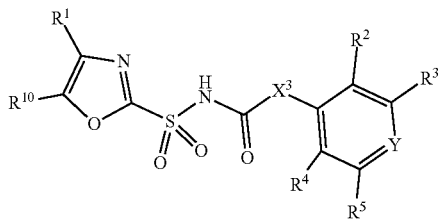

or a pharmaceutically acceptable salt thereof,
wherein:
$X^3$ is NH or O;
Y is N or $CR^8$;
$R^8$ is selected from H, CN, Cl, F, $CO_2C_1$-$C_6$ alkyl and $CONH_2$;
$R^2$ and $R^3$ taken together with the carbons connecting them form a four-membered to seven-membered ring A and $R^4$ and $R^5$ taken together with the carbons connecting them form a four-membered to seven-membered ring B,
wherein ring A is Ring A

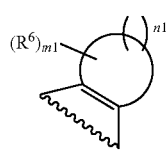

and ring B is

Ring B

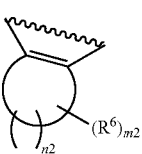

wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

In some embodiments, the compound of Formula Ia-i is a compound of Formula Ia-i(A)

Formula Ia-i(A)

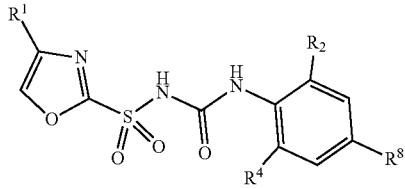

or a pharmaceutically acceptable salt thereof, wherein $R^8$ is H, CN, F, $CO_2C_1$-$C_6$ alkyl, or $CONH_2$. In some embodiments of the compound of Formula Ia-i(A), $R^8$ is H. In some embodiments of the compound of Formula Ia-i(A), $R^8$ is CN. In some embodiments of the compound of Formula Ia-i(A), $R^8$ is F. In some embodiments of the compound of Formula Ia-i(A), $R^8$ is $CO_2C_1$-$C_6$ alkyl. In some embodiments of the compound of Formula Ia-i(A), $R^8$ is $CONH_2$. In some embodiments of the compound of Formula Ia-i(A), $R^2$ and $R^4$ are each isopropyl.

In some embodiments, the compound of Formula Ia-i is a compound of Formula Ia-i(B)

Formula Ia-i(B)

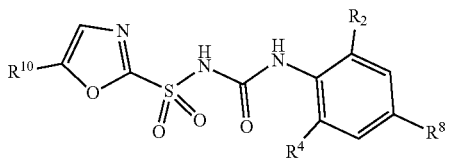

or a pharmaceutically acceptable salt thereof, wherein $R^8$ is H, CN, F, $CO_2C_1$-$C_6$ alkyl, or $CONH_2$. In some embodiments of the compound of Formula Ia-i(B), $R^8$ is H. In some embodiments of the compound of Formula Ia-i(B), $R^8$ is CN. In some embodiments of the compound of Formula Ia-i(B), $R^8$ is F. In some embodiments of the compound of Formula Ia-i(B), $R^8$ is $CO_2C_1$-$C_6$ alkyl. In some embodiments of the compound of Formula Ia-i(B), $R^8$ is $CONH_2$. In some embodiments of the compound of Formula Ia-i(B), $R^2$ and $R^4$ are each isopropyl.

In some embodiments, the compound of Formula Ia-i is a compound of Formula Ia-i(C):

Formula Ia-i(C)

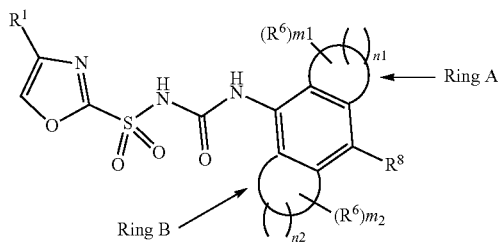

or a pharmaceutically acceptable salt thereof, wherein $R^8$ is H, CN, Cl or F. In some embodiments of the compound of Formula Ia-i(C), $R^8$ is H. In some embodiments of the compound of Formula Ia-i(C), $R^8$ is CN. In some embodiments of the compound of Formula Ia-i(C), $R^8$ is Cl. In some embodiments of the compound of Formula Ia-i(C), $R^8$ is F. In some embodiments of the compound of Formula Ia-i(C), $R^2$ and $R^4$ are each isopropyl.

In some embodiments, the compound of Formula Ia-i is a compound of Formula Ia-i(D)

Formula Ia-i(D)

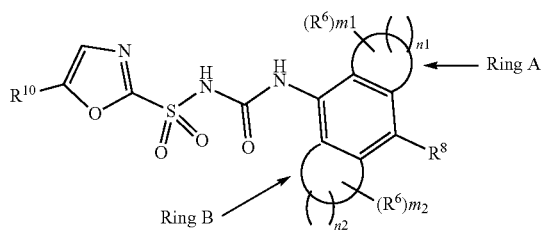

or a pharmaceutically acceptable salt thereof, wherein $R^8$ is H, CN, Cl or F. In some embodiments of the compound of Formula Ia-i(D), $R^8$ is H. In some embodiments of the compound of Formula Ia-i(D), $R^8$ is CN. In some embodiments of the compound of Formula Ia-i(D), $R^8$ is Cl. In some embodiments of the compound of Formula Ia-i(D), $R^8$ is F. In some embodiments of the compound of Formula Ia-i(D), $R^2$ and $R^4$ are each isopropyl.

In some embodiments, the compound of Formula Ia-i(C) is a compound of Formula Ia-i(C1)

Formula Ia-i(C1)

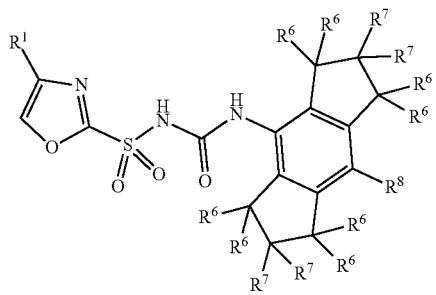

or a pharmaceutically acceptable salt thereof, wherein $R^8$ is H, CN, Cl or F. In some embodiments of the compound of Formula Ia-i(C1), $R^8$ is H. In some embodiments of the compound of Formula Ia-i(C1), $R^8$ is CN. In some embodiments of the compound of Formula Ia-i(C1), $R^8$ is Cl. In some embodiments of the compound of Formula Ia-i(C1), $R^8$ is F. In some embodiments of the compound of Formula Ia-i(C1), $R^2$ and $R^4$ are each isopropyl.

In some embodiments, the compound of Formula Ia-i is a compound of Formula Ia-i(D1)

Formula Ia-i(D1)

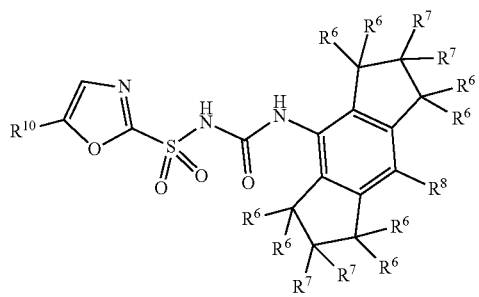

or a pharmaceutically acceptable salt thereof, wherein $R^8$ is H, CN, Cl or F. In some embodiments of the compound of Formula Ia-i(D1), $R^8$ is H. In some embodiments of the compound of Formula Ia-i(D1), $R^8$ is CN. In some embodiments of the compound of Formula Ia-i(D1), $R^8$ is Cl. In some embodiments of the compound of Formula Ia-i(D1), $R^8$ is F. In some embodiments of the compound of Formula Ia-i(D1), $R^2$ and $R^4$ are each isopropyl.

In some embodiments, the compound of Formula Ia-i is a compound of Formula Ia-i(E)

Formula Ia-i(E)

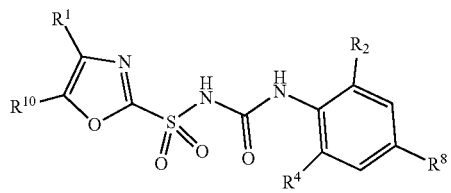

or a pharmaceutically acceptable salt thereof, wherein $R^8$ is H, CN, F, $CO_2C_1$-$C_6$ alkyl, or $CONH_2$. In some embodiments of the compound of Formula Ia-i(E), $R^8$ is H. In some embodiments of the compound of Formula Ia-i(E), $R^8$ is CN. In some embodiments of the compound of Formula Ia-i(E), $R^8$ is F. In some embodiments of the compound of Formula Ia-i(E), $R^8$ is $CO_2C_1$-$C_6$ alkyl. In some embodiments of the compound of Formula Ia-i(E), $R^8$ is $CONH_2$. In some embodiments of the compound of Formula Ia-i(B), $R^2$ and $R^4$ are each isopropyl.

In some embodiments, the compound of Formula Ia-i is a compound of Formula Ia-i(F)

Formula Ia-i(F)

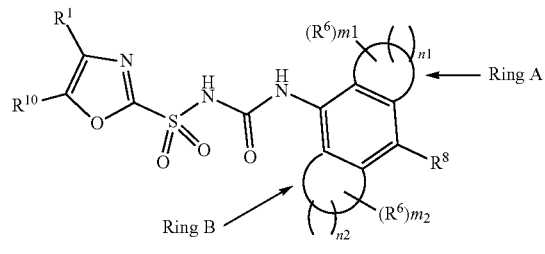

or a pharmaceutically acceptable salt thereof, wherein $R^8$ is H, CN, Cl or F. In some embodiments of the compound of Formula Ia-i(F), $R^8$ is H. In some embodiments of the compound of Formula Ia-i(F), $R^8$ is CN. In some embodiments of the compound of Formula Ia-i(F), $R^8$ is Cl. In some embodiments of the compound of Formula Ia-i(F), $R^8$ is F. In some embodiments of the compound of Formula Ia-i(F), $R^2$ and $R^4$ are each isopropyl.

In some embodiments, the compound of Formula Ia-i is a compound of Formula Ia-i(G)

Formula Ia-i(G)

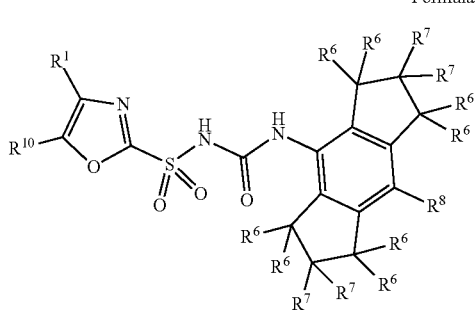

or a pharmaceutically acceptable salt thereof, wherein $R^8$ is H, CN, Cl or F. In some embodiments of the compound of Formula Ia-i(G), $R^8$ is H. In some embodiments of the compound of Formula Ia-i(G), $R^8$ is CN. In some embodiments of the compound of Formula Ia-i(G), $R^8$ is Cl. In some embodiments of the compound of Formula Ia-i(G), $R^8$ is F. In some embodiments of the compound of Formula Ia-i(G), $R^2$ and $R^4$ are each isopropyl.

In some embodiments, the compound of Formula I is a compound of Formula Ia-ii

Formula Ia-ii

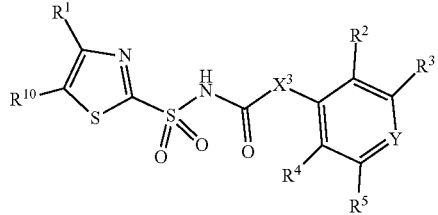

or a pharmaceutically acceptable salt thereof.

In some embodiments, the compound of Formula I is a compound of Formula Ia-iii

Formula Ia-iii

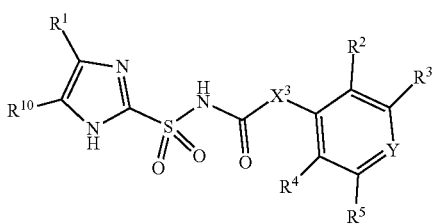

or a pharmaceutically acceptable salt thereof.

In some embodiments of the compound of Formulae Ia, Ia-i, Ia-i(A), Ia-i(C), Ia-i(C1), Ia-i(E), Ia-i(F), Ia-i(G), Ia-iii, and Ib, $R^1$ is $C_1$-$C_6$ alkyl or $C_3$-$C_6$ cycloalkyl, wherein $R^1$ is optionally substituted with one or more substituents each independently selected from hydroxy, amino and oxo. In some embodiments of the compound of Formulae Ia, Ia-i, Ia-i(A), Ia-i(C), Ia-i(C1), Ia-i(E), Ia-i(F), Ia-i(G), Ia-iii, and Ib, $R^1$ is $C_1$-$C_6$ alkyl optionally substituted with one or more hydroxy. In some embodiments of the compound of Formulae Ia, Ia-i, Ia-i(A), Ia-i(C), Ia-i(C1), Ia-i(E), Ia-i(F), Ia-i(G), Ia-iii, and Ib, $R^1$ is $C_1$-$C_6$ alkyl substituted with hydroxy. In some embodiments, the hydroxy is at the carbon of $R^1$ directly bonded to the five-membered heteroaryl ring in Formulae Ia, Ia-i, Ia-i(A), Ia-i(C), Ia-i(C1), Ia-i(E), Ia-i(F), Ia-i(G), Ia-ii, Ia-iii, and Ib, In some embodiments of the compound of Formulae Ia, Ia-i, Ia-i(A), Ia-i(C), Ia-i(C1), Ia-i(E), Ia-i(F), Ia-i(G), Ia-iii, and Ib, $R^1$ is 2-hydroxy-2-propyl.

In some embodiments of the compound of Formulae Ia, Ia-i, Ia-i(B), Ia-i(D), Ia-i(D1), Ia-i(E), Ia-i(F), Ia-i(G), Ia-iii, and Ic, $R^{10}$ is $C_1$-$C_6$ alkyl or $C_3$-$C_6$ cycloalkyl, wherein $R^{10}$ is optionally substituted with one or more substituents each independently selected from hydroxy, amino and oxo. In some embodiments of the compound of Formulae Ia, Ia-i, Ia-i(B), Ia-i(D), Ia-i(D1), Ia-i(E), Ia-i(F), Ia-i(G), Ia-iii, and Ic, $R^{10}$ is $C_1$-$C_6$ alkyl optionally substituted with one or more hydroxy. In some embodiments of the compound of Formulae Ia, Ia-i, Ia-i(B), Ia-i(D), Ia-i(D1), Ia-i(E), Ia-i(F), Ia-i(G), Ia-iii, and Ic, $R^{10}$ is $C_1$-$C_6$ alkyl substituted with hydroxy. In some embodiments, the hydroxy is at the carbon of $R^{10}$ directly bonded to the five-membered heteroaryl ring in Formulae Ia, Ia-i, Ia-i(B), Ia-i(D), Ia-i(D1), Ia-i(E), Ia-i(F), Ia-i(G), Ia-iii, and Ic, In some embodiments of the compound of Formulae Ia, Ia-i, Ia-i(B), Ia-i(D), Ia-i(D1), Ia-i(E), Ia-i(F), Ia-i(G), Ia-iii, and Ic, $R^{10}$ is 2-hydroxy-2-propyl.

In some embodiments of the compound of Formulae Ia, Ia-i, Ia-i(E), Ia-i(F), Ia-i(G), and Ia-iii, $R^1$ and $R^{10}$ taken together with the atoms connecting them form a 3-to-8- membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, =$NR^{13}$, $COOC_1$-$C_6$ alkyl, and $CONR^{11}R^{12}$;

In some embodiments of the compound of Formulae Ia, Ia-i, Ia-i(E), Ia-i(F), Ia-i(G), and Ia-iii, $R^1$ and $R^{10}$ taken together with the atoms connecting them form a five-membered carbocyclic ring. In some embodiments of the compound of Formulae Ia, Ia-i, Ia-i(E), Ia-i(F), Ia-i(G), Ia-ii, and Ia-iii, $R^1$ and $R^{10}$ taken together with the atoms connecting them form a six-membered carbocyclic ring. In some embodiments of the compound of Formulae Ia, Ia-i, Ia-i(E), Ia-i(F), Ia-i(G), Ia-ii, and Ia-iii, $R^1$ and $R^{10}$ taken together with the atoms connecting them form a five-membered heterocyclic ring containing 1 or 2 heteroatoms independently selected from O, N, and S. In some embodiments of the compound of Formulae Ia, Ia-i, Ia-i(E), Ia-i(F), Ia-i(G), Ia-ii, and Ia-iii, $R^1$ and $R^{10}$ taken together with the atoms connecting them form a five-membered heterocyclic ring containing 1 or 2 heteroatoms independently selected from O, N, and S.

In some embodiments of the compound of Formula Ia (including Ia-i, Ia-i(F), Ia-ii and Ia-iii), ring A is a carbocyclic ring and n1 is 3.

In some embodiments of the compound of Formula Ia (including Ia-i, Ia-i(F), Ia-ii and Ia-iii), ring A is a carbocyclic ring and n1 is 4.

In some embodiments of the compound of Formula Ia (including Ia-i, Ia-i(F), Ia-ii and Ia-iii), ring A is a heterocyclic ring containing 1 or 2 heteroatoms independently selected from O, N, and S and n1 is 3.

In some embodiments of the compound of Formula Ia (including Ia-i, Ia-i(F), Ia-ii and Ia-iii), ring A is a heterocyclic ring containing 1 or 2 heteroatoms independently selected from O, N, and S and n1 is 4.

In some embodiments of the compound of Formula Ia (including Ia-i, Ia-i(F), Ia-ii and Ia-iii), ring B is a carbocyclic ring and n2 is 3.

In some embodiments of the compound of Formula Ia (including Ia-i, Ia-i(F), Ia-ii and Ia-iii), ring B is a carbocyclic ring and n2 is 4.

In some embodiments of the compound of Formula Ia (including Ia-i, Ia-i(F), Ia-ii and Ia-iii), ring B is a heterocyclic ring containing 1 or 2 heteroatoms independently selected from O, N, and S and n2 is 3.

In some embodiments of the compound of Formula Ia (including Ia-i, Ia-i(F), Ia-ii and Ia-iii), ring B is a heterocyclic ring containing 1 or 2 heteroatoms independently selected from O, N, and S and n2 is 4.

In some embodiments, the compound of Formula I is a compound of Formula Ib

Formula Ib

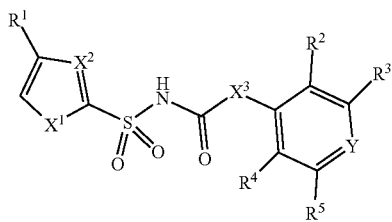

or a pharmaceutically acceptable salt thereof.

In some embodiments, the compound of Formula I is a compound of Formula Ic

Formula Ic

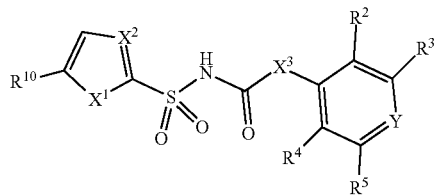

or a pharmaceutically acceptable salt thereof.

In some embodiments, the compound of Formula II is a compound of Formula IIa

Formula IIa

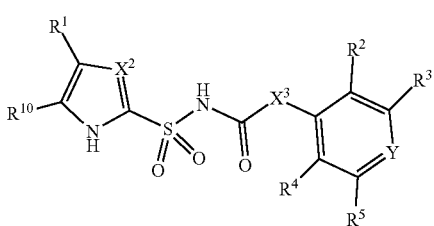

or a pharmaceutically acceptable salt thereof, and wherein:

$X^2$ is N or $CR^9$;

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;

$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

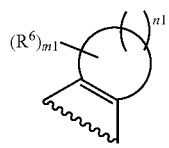

Ring A and ring B is

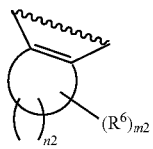

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10}$ is selected from H, Cl, $C_1$-$C_6$ alkyl, $C_3$-$C_6$ cycloalkyl and $C_3$-$C_6$ heterocycloalkyl; wherein $R^{10}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl; each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl.

In some embodiments, the compound of Formula II is a compound of Formula IIb

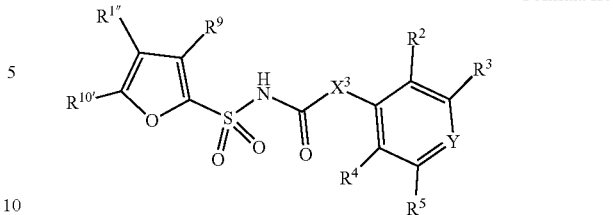

Formula IIb or a pharmaceutically acceptable salt thereof, and wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

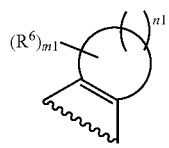

Ring A and ring B is

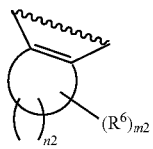

Ring B wherein
ring A is a saturated carbocyclic ring;
n1 is from 2 to 5;

m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{1'}$ is selected from unsubstituted $C_1$-$C_6$ alkyl, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{10'}$ is selected from H, Cl, $C_3$-$C_6$ cycloalkyl and $C_3$-$C_6$ heterocycloalkyl;
wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$.
In some embodiments, the compound of Formula II is a compound of Formula IIc

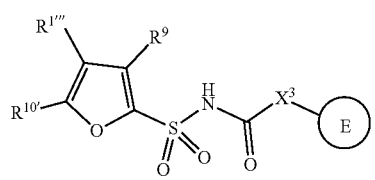

Formula IIc or a pharmaceutically acceptable salt thereof, and wherein:

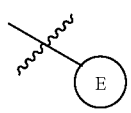

is selected from

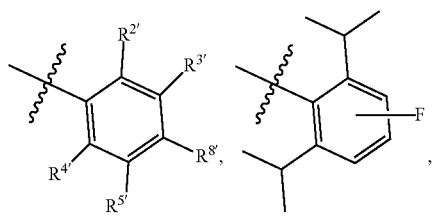

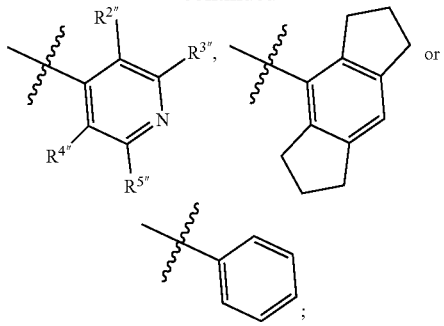

$X^3$ is NH or O;
$R^{8'}$ is selected from CN, $CO_2C_1$-$C_6$ alkyl, $CO_2C_3$-$C_8$ cycloalkyl, $CONR^{11}R^{12}$, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^{2'}$ is hydrogen, halo, or $C_1$-$C_6$ alkyl optionally substituted with hydroxy;
$R^{2''}$ is hydrogen or $C_1$-$C_6$ alkyl;
$R^{3'}$ is hydrogen, halo, or $C_1$-$C_6$ alkyl optionally substituted with hydroxy;
$R^{3''}$ is hydrogen, CN, or $C_1$-$C_6$ alkyl;
$R^{4'}$ is hydrogen, halo, or $C_1$-$C_6$ alkyl optionally substituted with hydroxy;
$R^{4''}$ is hydrogen or $C_1$-$C_6$ alkyl;
$R^{5'}$ is hydrogen, halo, or $C_1$-$C_6$ alkyl optionally substituted with hydroxy;
$R^{5''}$ is hydrogen, CN, or $C_1$-$C_6$ alkyl;
or $R^{2'}$ and $R^{3'}$ taken together with the carbons connecting them form a four-membered to seven-membered ring A,
or $R^{4'}$ and $R^{5'}$ taken together with the carbons connecting them form a four-membered to seven-membered ring B,
or $R^{2'}$ and $R^{3'}$ taken together with the carbons connecting them form a four-membered to seven-membered ring A and $R^{4'}$ and $R^{5'}$ taken together with the carbons connecting them form a four-membered to seven-membered ring B,
wherein ring A is

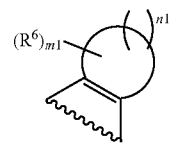

Ring A and ring B is

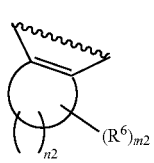

Ring B wherein
ring A is a saturated carbocyclic ring;
n1 is from 2 to 5;
m1 is from 1 to 10;

wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{1'''}$ is selected from $C(R^{19})_2OH$;
$R^{10'}$ is selected from H, Cl, $C_3$-$C_6$ cycloalkyl and $C_3$-$C_6$ heterocycloalkyl;
wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$; $R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl; each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl;
provided that if $R^{10'}$ is H or $C_3$-$C_6$ heterocycloalkyl; then

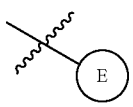

is not

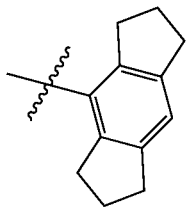

In some embodiments, the compound of Formula II is a compound of Formula IId

Formula IId

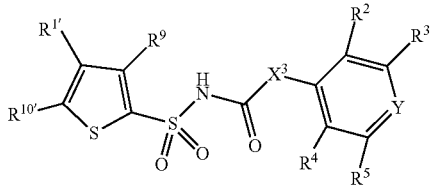

or a pharmaceutically acceptable salt thereof, and wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is Ring A

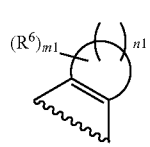

and ring B is

Ring B

wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10'}$ is selected from H, Cl, $C_3$-$C_6$ cycloalkyl and $C_3$-$C_6$ heterocycloalkyl; wherein $R^{10'}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is selected from $C_1$-$C_6$ alkyl;

provided that if (1) $R^{1'}$ is $C(R^{19})_2OH$; and (2) $R^{10'}$ is not Cl; then

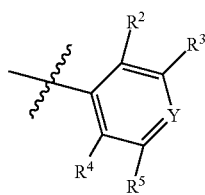

is not

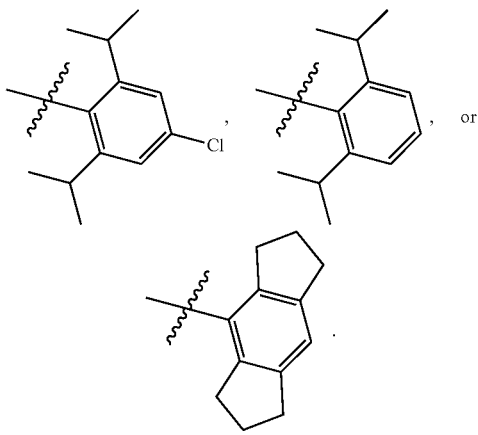

, or

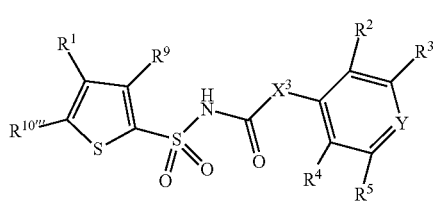

In some embodiments, the compound of Formula II is a compound of Formula IIe

Formula IIe

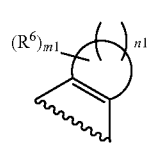

or a pharmaceutically acceptable salt thereof, and wherein:

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;

$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is Ring A

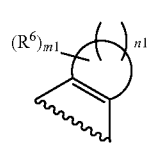

and ring B is

Ring B

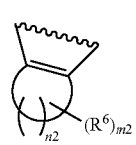

wherein ring A is a saturated carbocyclic ring;

n1 is from 2 to 5;

m1 is from 1 to 10;

wherein ring B is a saturated carbocyclic ring;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;

wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{4'''}$ is selected from Cl, $C_1$-$C_6$ alkyl substituted with hydroxy, $C_3$-$C_6$ cycloalkyl, and $C_3$-$C_6$ heterocycloalkyl;

wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is selected from $C_1$-$C_6$ alkyl;

provided that if (1) $R^1$ is $C(R^{19})_2OH$; and (2) $R^{10'''}$ is not Cl; then

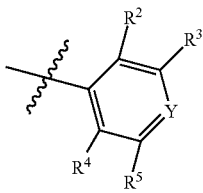

is not

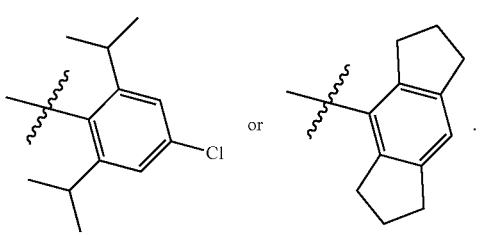 [SMILES: *c1c(C(C)C)cc(Cl)cc1C(C)C ; *c1c2c(cc3c1CCC3)CCC2]

In some embodiments, the compound of Formula II is a compound of Formula IIf

Formula IIf

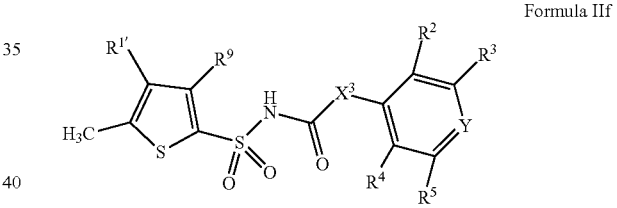

or a pharmaceutically acceptable salt thereof, and wherein:

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;

$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A,

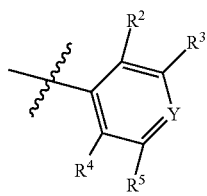

is not

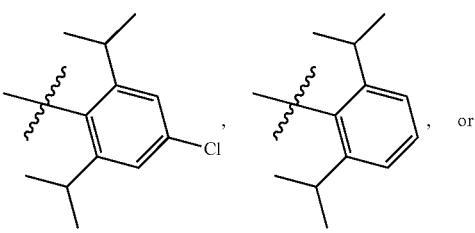

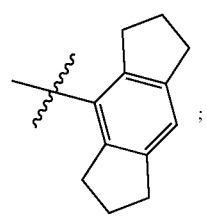

;

and provided that if $R^{10'''}$ is $C_1$-$C_6$ alkyl substituted with hydroxy; then or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

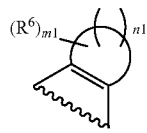

Ring A and ring B is

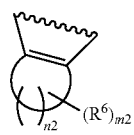

Ring B wherein ring A is a saturated carbocyclic ring;

n1 is from 2 to 5;

m1 is from 1 to 10;

wherein ring B is a saturated carbocyclic ring;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl;

herein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is selected from $C_1$-$C_6$ alkyl.

In some embodiments, the compound of Formula II is a compound of Formula IIg

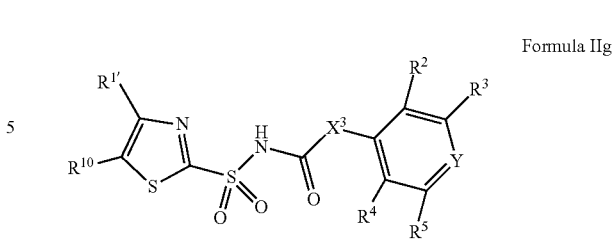

Formula IIg or a pharmaceutically acceptable salt thereof, and wherein:

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;

$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

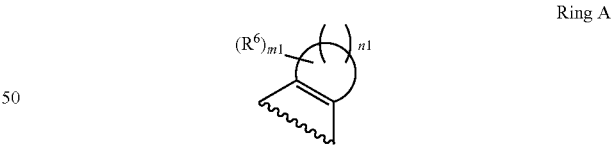

Ring A and ring B is

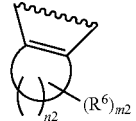

Ring B wherein ring A is a saturated carbocyclic ring;

n1 is from 2 to 5;

m1 is from 1 to 10;

wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10}$ is selected from H, Cl, $C_1$-$C_6$ alkyl, $C_3$-$C_6$ cycloalkyl and $C_3$-$C_6$ heterocycloalkyl; wherein $R^{10}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$; $R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl.

In some embodiments, the compound of Formula II is a compound of Formula IIh

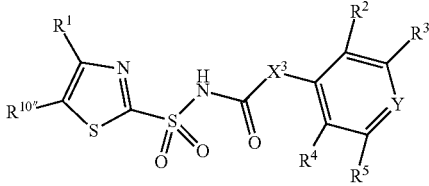

Formula IIh or a pharmaceutically acceptable salt thereof, and wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

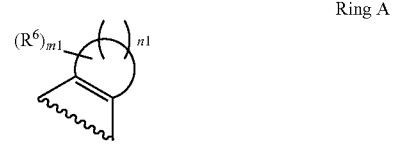

Ring A and ring B is

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10''}$ is selected from Cl, $C_1$-$C_6$ alkyl, $C_3$-$C_6$ cycloalkyl, and $C_3$-$C_6$ heterocycloalkyl; wherein $R^{10''}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl.

In some embodiments, the compound of Formula II is a compound of Formula IIi

Formula IIi

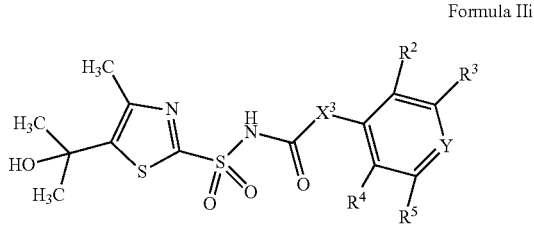

or a pharmaceutically acceptable salt thereof, and wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is Ring A

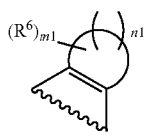

and ring B is

Ring B

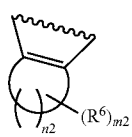

wherein
ring A is a saturated carbocyclic ring;
n1 is from 2 to 5;
m1 is from 1 to 10;

wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl; each $R^{16}$ is the same or different and is selected from H, $C_1$-$C_6$ alkyl, $C_1$-$C_6$ alkoxy, $NR^{11}R^{12}$, oxo, and $=NR^{13}$.

In some embodiments, the compound of Formula II is a compound of Formula IIj

Formula IIj

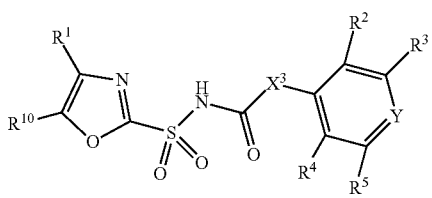

or a pharmaceutically acceptable salt thereof, and wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is Ring A and ring B is Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10}$ is selected from H, Cl, $C_1$-$C_6$ alkyl, $C_3$-$C_6$ cycloalkyl and $C_3$-$C_6$ heterocycloalkyl; wherein $R^{10}$ is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl.

In some embodiments, the compound of Formula II is a compound of Formula IIk

Formula IIk or a pharmaceutically acceptable salt thereof, and wherein $X^{3'}$ is O and all other variables are as defined herein.

In some embodiments, the compound of Formula II is a compound of Formula II-1

Formula II-1 or a pharmaceutically acceptable salt thereof, and wherein all other variables are as defined herein.

Exemplary embodiments provided herein include the following embodiments 1)-98):
1) A compound of Formula I, Formula I or a pharmaceutically acceptable salt thereof, wherein:
$X^1$ is O, S, or NH;
$X^2$ is N or $CR^9$;
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;

provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

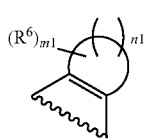

Ring A and ring B is

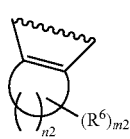

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl, $C_3$-$C_6$ cycloalkyl and $C_3$-$C_6$ heterocycloalkyl; wherein $R^1$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$; $R^{10}$ is selected from H, $C_1$-$C_6$ alkyl, $C_3$-$C_6$ cycloalkyl and $C_3$-$C_6$ heterocycloalkyl; wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$; or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl; each $R^{16}$ is the same or different and is selected from H, $C_1$-$C_6$ alkyl, $C_1$-$C_6$ alkoxy, $NR^{11}R^{12}$, oxo, and $=NR^{13}$;
provided that if the compound of formula I comprises ring A and ring B; $X^3$ is NH; $X^2$ is CH; and $R^{10}$ is H,
then (i) if $X^1$ is O and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$, then Y is not N, CF, CCl or CH, (ii) if $X^1$ is O and $R^1$ is $C_1$-$C_6$ alkyl substituted with oxo, then Y is not CH, and (iii) if $X^1$ is S, then Y is not CH;
and provided that if $R^2$ and $R^4$ are each isopropyl; $X^3$ is NH; $X^2$ is CH; $R^{10}$ is H; and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$,
then Y is not CH or CCl.

2) A compound of Formula I,

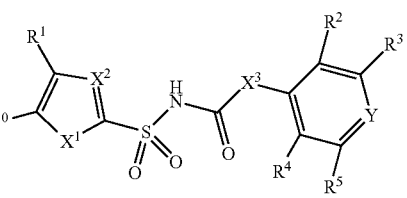

Formula I or a pharmaceutically acceptable salt thereof, wherein:
$X^1$ is O, S, or NH;
$X^2$ is N or $CR^9$;
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^9$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

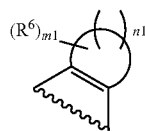

Ring A and ring B is

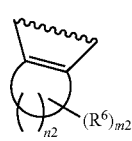

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl, $C_3$-$C_6$ cycloalkyl and $C_3$-$C_6$ heterocycloalkyl; wherein $R^1$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{10}$ is selected from H, $C_1$-$C_6$ alkyl, $C_3$-$C_6$ cycloalkyl and $C_3$-$C_6$ heterocycloalkyl; wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;

provided that if the compound of formula I comprises ring A and ring B; $X^3$ is NH; $X^2$ is CH; and $R^{10}$ is H,
then (i) if $X^1$ is O and $R^1$ is $C_1$-$C_6$ alkyl substituted with hydroxy, oxo, $C_1$-$C_6$ alkoxy, $NR^{11}R^{12}$, $=NR^{13}$, $COOC_1$-$C_6$ alkyl, and $CONR^{11}R^{12}$, then Y is not N, CF, CCl or CH, and (ii) if $X^1$ is S, then Y is not CH;
and provided that if $R^2$ and $R^4$ are each isopropyl; $X^3$ is NH; $X^2$ is CH; $R^{10}$ is H; and $R^1$ is $C_1$-$C_6$ alkyl optionally substituted with hydroxy, $C_1$-$C_6$ alkoxy, $NR^{11}R^{12}$, $=NR^{13}$, $COOC_1$-$C_6$ alkyl, or $CONR^{11}R^{12}$,
then Y is not CH or CCl.

3) The compound of exemplary embodiment 1 or 2, wherein $X^1$ is O.

4) The compound of exemplary embodiment 1 or 2 wherein $X^1$ is S.

5) The compound of exemplary embodiment 1 or 2, wherein $X^1$ is NH.

6) The compound of any one of exemplary embodiments 1 to 5, wherein $X^2$ is $CR^9$.

7) The compound of any one of exemplary embodiments 1 to 5, wherein $X^2$ is CH.

8) The compound of any one of exemplary embodiments 1 to 5, wherein $X^2$ is N.

9) The compound of any one of exemplary embodiments 1 to 8, wherein $X^3$ is NH.

10) The compound of any one of exemplary embodiments 1 to 8, wherein $X^3$ is O.

11) The compound of any one of exemplary embodiments 1 to 8, wherein $X^2$ is $C(C_1$-$C_6$ alkyl).

12) The compound of exemplary embodiment 1, wherein $X^3$ and $R^2$ taken together with the atoms connecting them form a four-to-seven-membered heterocyclic ring optionally substituted with one or more $R^{16}$.

13) The compound of exemplary embodiment 1, wherein $X^3$ and $R^4$ taken together with the atoms connecting them form a four-to-seven-membered heterocyclic ring optionally substituted with one or more $R^{16}$.

14) The compound of exemplary embodiment 1, wherein $X^3$ and $R^2$ taken together with the atoms connecting them form a four-to-seven-membered heterocyclic ring optionally substituted with one or more H.

15) The compound of exemplary embodiment 1, wherein $X^3$ and $R^4$ taken together with the atoms connecting them form a four-to-seven-membered heterocyclic ring optionally substituted with one or more $C_1$-$C_6$ alkyl.

16) The compound of any one of exemplary embodiments 1 to 15, wherein Y is $CR^8$.

17) The compound of any one of exemplary embodiments 1 to 15, wherein Y is N.

18) The compound of exemplary embodiment 16 or 17, wherein $R^2$ is hydrogen.

19) The compound of exemplary embodiment 16 or 17, wherein $R^2$ is $C_1$-$C_6$ alkyl optionally substituted with hydroxy.

20) The compound of exemplary embodiment 16 or 17, wherein $R^2$ is isopropyl.

21) The compound of exemplary embodiment 16 or 17, wherein $R^2$ is methyl.

22) The compound of any one of exemplary embodiments 16 to 21, wherein $R^3$ is hydrogen.

23) The compound of any one of exemplary embodiments 16 to 21, wherein $R^3$ is $C_1$-$C_6$ alkyl optionally substituted with hydroxy.

24) The compound of any one of exemplary embodiments 16 to 21, wherein $R^3$ is isopropyl.

25) The compound of any one of exemplary embodiments 16 to 21, wherein $R^3$ is methyl.

26) The compound of any one of exemplary embodiments 16 to 25, wherein $R^4$ is hydrogen.

27) The compound of any one of exemplary embodiments 16 to 25, wherein $R^4$ is $C_1$-$C_6$ alkyl optionally substituted with hydroxy.

28) The compound of any one of exemplary embodiments 16 to 25, wherein $R^4$ is isopropyl.

29) The compound of any one of exemplary embodiments 16 to 25, wherein $R^4$ is methyl.

30) The compound of any one of exemplary embodiments 16 to 29, wherein $R^5$ is hydrogen.

31) The compound of any one of exemplary embodiments 16 to 29, wherein $R^5$ is $C_1$-$C_6$ alkyl optionally substituted with hydroxy.

32) The compound of any one of exemplary embodiments 16 to 29, wherein $R^5$ is isopropyl.

33) The compound of any one of exemplary embodiments 16 to 29, wherein $R^5$ is methyl.

34) The compound of any one of exemplary embodiments 14 to 17 or 26 to 33, wherein $R^2$ and $R^3$ taken together with the carbons connecting them form ring A.

35) The compound of any one of exemplary embodiments 14 to 17 or 26 to 34, wherein $R^2$ and $R^3$ taken together with the carbons connecting them form ring B.

36) The compound of exemplary embodiments 34 or 35, wherein ring A is the same as ring B.

37) The compound of exemplary embodiments 34, 35 or 36, wherein ring A is

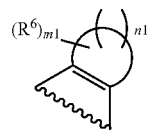

Ring A

38) The compound of any one of exemplary embodiments 34 to 37, wherein ring B is

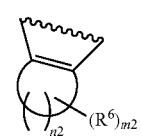

Ring B

39) The compound of exemplary embodiment 37 or 38, wherein n1 is 3.

40) The compound of exemplary embodiment 37 or 38, wherein n1 is 4.

41) The compound of any one of exemplary embodiments 37 to 40, wherein n2 is 3.

42) The compound of any one of exemplary embodiments 37 to 40, wherein n2 is 4.

43) The compound of any one of exemplary embodiments 37 to 42, wherein $R^6$ is H.

44) The compound of any one of exemplary embodiments 1 to 16 or 17 to 41, wherein $R^8$ is H.

45) The compound of any one of exemplary embodiments 1 to 16 or 17 to 41, wherein $R^8$ is CN.

46) The compound of any one of exemplary embodiments 1 to 16 or 17 to 41, wherein $R^8$ is Cl.

47) The compound of any one of exemplary embodiments 1 to 16 or 17 to 41, wherein $R^8$ is F.

48) The compound of any one of exemplary embodiments 1 to 16 or 17 to 41, wherein $R^8$ is $C_1$-$C_6$ alkyl.

49) The compound of any one of exemplary embodiments 1 to 16 or 17 to 41, wherein $R^8$ is $C_1$-$C_6$ haloalkyl.

50) The compound of any one of exemplary embodiments 1 to 16 or 17 to 41, wherein $R^8$ is $CF_3$.

51) The compound of any one of exemplary embodiments 1 to 50, wherein $R^9$ is H.

52) The compound of any one of exemplary embodiments 1 to 50, wherein $R^9$ is CN.

53) The compound of any one of exemplary embodiments 1 to 50, wherein $R^9$ is Cl.

54) The compound of any one of exemplary embodiments 1 to 50, wherein $R^9$ is F.

55) The compound of any one of exemplary embodiments 1 to 54, wherein $R^1$ is H.

56) The compound of any one of exemplary embodiments 1 to 54, wherein $R^1$ is $C_1$-$C_6$ alkyl optionally substituted with one or more substituents each independently selected from hydroxy, amino and oxo.

57) The compound of any one of exemplary embodiments 1 to 54, wherein $R^1$ is $C_1$-$C_6$ alkyl substituted with hydroxy.

58) The compound of any one of exemplary embodiments 1 to 54, wherein $R^1$ is 2-hydroxy-2-propyl.

59) The compound of any one of exemplary embodiments 1 to 54, wherein $R^1$ is $C_3$-$C_6$ cycloalkyl optionally substituted with one or more substituents each independently selected from hydroxy, amino and oxo.

60) The compound of any one of exemplary embodiments 1 to 54, wherein $R^1$ s $C_3$-$C_6$ cycloalkyl substituted with hydroxy.

61) The compound of any one of exemplary embodiments 1 to 54, wherein $R^1$ is 1-hydroxy-1-cyclopropyl.

62) The compound of any one of exemplary embodiments 1 to 54, wherein $R^1$ is 1-hydroxy-1-cyclobutyl.

63) The compound of any one of exemplary embodiments 1 to 54, wherein $R^1$ is 1-hydroxy-1-cyclopentyl.

64) The compound of any one of exemplary embodiments 1 to 63, wherein $R^{10}$ is H.

65) The compound of any one of exemplary embodiments 1 to 63, wherein $R^{10}$ is $C_1$-$C_6$ alkyl optionally substituted with one or more substituents each independently selected from hydroxy, amino and oxo.

66) The compound of any one of exemplary embodiments 1 to 63, wherein $R^{10}$ is $C_1$-$C_6$ alkyl substituted with hydroxy.

67) The compound of any one of exemplary embodiments 1 to 63, wherein $R^{10}$ is 2-hydroxy-2-propyl.

68) The compound of any one of exemplary embodiments 1 to 63, wherein $R^{10}$ is $C_3$-$C_6$ cycloalkyl optionally substituted with one or more substituents each independently selected from hydroxy, amino and oxo.

69) The compound of any one of exemplary embodiments 1 to 63, wherein $R^{10}$ is $C_3$-$C_6$ cycloalkyl substituted with hydroxy.

70) The compound of any one of exemplary embodiments 1 to 63, wherein $R^{10}$ is 1-hydroxy-1-cyclopropyl.

71) The compound of any one of exemplary embodiments 1 to 63, wherein $R^{10}$ is 1-hydroxy-1-cyclobutyl.

72) The compound of any one of exemplary embodiments 1 to 63, wherein $R^{10}$ is 1-hydroxy-1-cyclopentyl.

73) The compound of any one of exemplary embodiments 1 to 63, wherein $R^1$ and $R^{10}$ taken together with the atoms connecting them form a five-membered carbocyclic ring.

74) The compound of any one of exemplary embodiments 1 to 63, wherein $R^1$ and $R^{10}$ taken together with the atoms connecting them form a six-membered carbocyclic ring.

75) The compound of any one of exemplary embodiments 1 to 63, wherein $R^1$ and $R^{10}$ taken together with the atoms connecting them form a five-membered heterocyclic ring containing 1 or 2 heteroatoms independently selected from O, N, and S.

76) The compound of any one of exemplary embodiments 1 to 63, wherein $R^1$ and $R^{10}$ taken together with the atoms connecting them form a six-membered heterocyclic ring containing 1 or 2 heteroatoms independently selected from O, N, and S.

77) The compound of any one of exemplary embodiments 82 to 85, wherein ring formed by $R^1$ and $R^{10}$ is substituted with hydroxy.

78) The compound of any one of exemplary embodiments 82 to 85, wherein ring formed by $R^1$ and $R^{10}$ is substituted with oxo.

79) The compound of any one of exemplary embodiments 82 to 85, wherein ring formed by $R^1$ and $R^{10}$ is substituted with $C_1$-$C_6$ alkoxy.

80) The compound of exemplary embodiment 1, wherein each $R^{11}$ is hydrogen.

81) The compound of exemplary embodiment 1, wherein each $R^{11}$ is $C_1$-$C_6$ alkyl.

82) The compound of exemplary embodiment 1 or 81 to 82, wherein each $R^{12}$ is hydrogen.

83) The compound of exemplary embodiment 1 or 81 to 82, wherein each $R^{12}$ is $C_1$-$C_6$ alkyl.

84) The compound of any one of exemplary embodiments 1 to 2 or 12 to 15, wherein each $R^{16}$ is hydrogen.

85) The compound of any one of exemplary embodiments 1 to 84, wherein if the compound of formula I comprises ring A and ring B; $X^3$ is NH; $X^2$ is CH; and $R^{10}$ is H, then (i) if $X^1$ is O and $R^1$ is $C_1$-$C_6$ alkyl substituted with hydroxy, $C_1$-$C_6$ alkoxy, $NR^{11}R^{12}$, $=NR^{13}$, $COOC_1$-$C_6$ alkyl, and $CONR^{11}R^{12}$, then Y is not N, CF, CCl or CH, (ii) if $X^1$ is O and $R^1$ is $C_1$-$C_6$ alkyl substituted with oxo, then Y is not CH, and (iii) if $X^1$ is S, then Y is not CH; and if $R^2$ and $R^4$ are each isopropyl; $X^3$ is NH; $X^2$ is CH; $R^{10}$ is H; and $R^1$ is optionally substituted $C_1$-$C_6$ alkyl, then Y is not CH or CCl.

86) The compound of any one of exemplary embodiments 1 to 84, wherein if the compound of formula I comprises ring A and ring B; $X^3$ is NH; $X^2$ is CH; and $R^{10}$ is H, then (i) if $X^1$ is O and $R^1$ is $C_1$-$C_6$ alkyl substituted with hydroxy, oxo, $C_1$-$C_6$ alkoxy, $NR^{11}R^{12}$, $=NR^{13}$, $COOC_1$-$C_6$ alkyl, and $CONR^{11}R^{12}$, then Y is not N, CF, CCl or CH, and (ii) if $X^1$ is S,
then Y is not CH;
and if $R^2$ and $R^4$ are each isopropyl; $X^3$ is NH; $X^2$ is CH; $R^{10}$ is H; and $R^1$ is optionally substituted $C_1$-$C_6$ alkyl, then Y is not CH or CCl.

87) A compound of any one of exemplary embodiments 1 to 2, wherein the compound of Formula I is a compound of Formula Ia

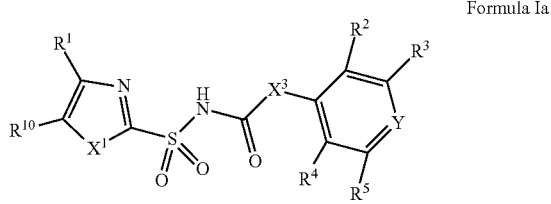

Formula Ia or a pharmaceutically acceptable salt thereof, wherein:
$X^1$ is O, S, or NH;
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl and $CONH_2$;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
provided that at least one of $R^2$, $R^3$, $R^4$ and $R^5$ is not hydrogen, and that $R^2$ and $R^4$ are not both hydroxymethyl;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

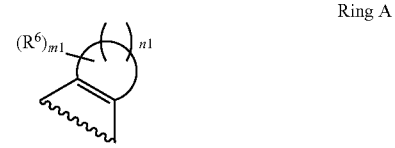

Ring A and ring B is

Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;

$R^1$ is selected from H, $C_1$-$C_6$ alkyl and $C_3$-$C_6$ cycloalkyl, wherein $R^1$ is optionally substituted with hydroxy, amino or oxo; $R^{10}$ is selected from H, $C_1$-$C_6$ alkyl and $C_3$-$C_6$ cycloalkyl, wherein $R^{10}$ is optionally substituted with hydroxy, amino or oxo;

wherein $R^{10}$ is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$.

88) A compound of any one of exemplary embodiments 1 to 2, wherein the compound of Formula I is a compound of Formula Ia

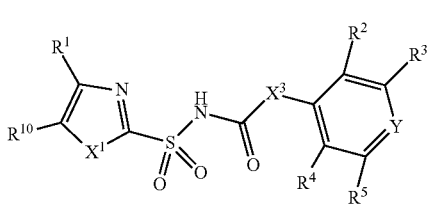

Formula Ia or a pharmaceutically acceptable salt thereof, wherein $X^1$ is O, S, or NH;

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl and $CONH_2$;

$R^2$ is hydrogen or $C_1$-$C_6$ alkyl optionally substituted with hydroxy;

$R^3$ is hydrogen or $C_1$-$C_6$ alkyl optionally substituted with hydroxy;

$R^4$ is hydrogen or $C_1$-$C_6$ alkyl optionally substituted with hydroxy and is the same as $R^2$;

$R^5$ is hydrogen or $C_1$-$C_6$ alkyl optionally substituted with hydroxy and is the same as $R^3$;

provided that at least one of $R^2$, $R^3$, $R^4$ and $R^5$ is not hydrogen, and that $R^2$ and $R^4$ are not both hydroxymethyl;

or $R^2$ and $R^3$ taken together with the carbons connecting them form a five-membered ring A and $R^4$ and $R^5$ taken together with the carbons connecting them form a five-membered ring B, wherein ring A is

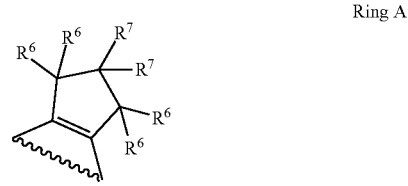

Ring A and ring B is

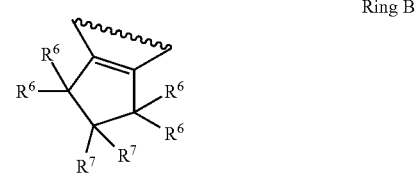

Ring B wherein each $R^6$ in each ring is the same and is H or $C_1$-$C_6$ alkyl, and each $R^7$ in each ring is the same and is H or $C_1$-$C_6$ alkyl;

$R^1$ is selected from H, $C_1$-$C_6$ alkyl and $C_3$-$C_6$ cycloalkyl, wherein $R^1$ is optionally substituted with one or more substituents each independently selected from hydroxy, amino and oxo; $R^{10}$ is selected from H, $C_1$-$C_6$ alkyl and $C_3$-$C_6$ cycloalkyl, wherein $R^{10}$ is optionally substituted with one or more substituents each independently selected from hydroxy, amino and oxo; or $R^1$ and $R^{10}$ taken together with the atoms connecting them form a five-membered, a six-membered, or a seven-membered carbocyclic or heterocyclic ring.

89) The compound of exemplary embodiment 1 or 87, wherein the compound is a compound of Formula Ia-i:

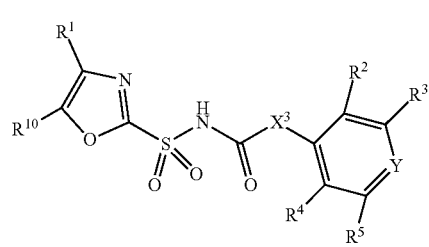

Formula Ia-i or a pharmaceutically acceptable salt thereof, wherein:

$X^3$ is NH or O;

Y is N or $CR^8$;

$R^8$ is selected from H, CN, Cl, F, $CO_2C_1$-$C_6$ alkyl and $CONH_2$;

89

$R^2$ is $C_1$-$C_6$ alkoxy, halo, $C_1$-$C_6$ haloalkyl, or $C_1$-$C_6$ alkyl optionally substituted with hydroxy;
$R^3$ is hydrogen;
$R^4$ is $C_1$-$C_6$ alkoxy, halo, $C_1$-$C_6$ haloalkyl, or $C_1$-$C_6$ alkyl optionally substituted with hydroxy;
$R^5$ is hydrogen;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

90) The compound of exemplary embodiment 1 or 87, wherein the compound is a compound of Formula Ia-i:

Formula Ia-i or a pharmaceutically acceptable salt thereof,
wherein:
$X^3$ is NH or O;
Y is N or $CR^8$;
$R^8$ is selected from H, CN, Cl, F, $CO_2C_1$-$C_6$ alkyl and $CONH_2$;
$R^3$ is $C_1$-$C_6$ alkoxy, halo, $C_1$-$C_6$ haloalkyl, or $C_1$-$C_6$ alkyl optionally substituted with hydroxy;
$R^2$ is hydrogen;
$R^5$ is $C_1$-$C_6$ alkoxy, halo, $C_1$-$C_6$ haloalkyl, or $C_1$-$C_6$ alkyl optionally substituted with hydroxy;
$R^4$ is hydrogen;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

91) The compound of exemplary embodiment 1 or 87, wherein the compound is a compound of Formula Ia-i:

Formula Ia-i or a pharmaceutically acceptable salt thereof,

90 wherein:
$X^3$ is NH or O;
Y is N or $CR^8$;
$R^8$ is selected from H, CN, Cl, F, $CO_2C_1$-$C_6$ alkyl and $CONH_2$;
$R^2$ and $R^3$ taken together with the carbons connecting them form a four-membered to seven-membered ring A and $R^4$ and $R^5$ taken together with the carbons connecting them form a four-membered to seven-membered ring B,
wherein ring A is Ring A and ring B is Ring B wherein
ring A is a carbocyclic ring or a heterocyclic ring containing 1 or 2 heteroatoms independently selected from O, N, and S;
n1 is from 2 to 5;
m1 is from 1 to 10;
wherein ring B is a carbocyclic ring or a heterocyclic ring containing 1 or 2 heteroatoms independently selected from O, N, and S;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, $C_1$-$C_6$ alkyl and $C_3$-$C_6$ cycloalkyl, wherein $R^1$ is optionally substituted with hydroxy, amino or oxo;
$R^{10}$ is selected from H, $C_1$-$C_6$ alkyl and $C_3$-$C_6$ cycloalkyl, wherein $R^{10}$ is optionally substituted with hydroxy, amino or oxo;
or $R^1$ and $R^{10}$ taken together with the atoms connecting them form a five-membered, a six-membered, or a seven-membered carbocyclic or heterocyclic ring.

92) The compound of exemplary embodiment 1 or 87, wherein the compound is a compound of Formula Ia-i(A):

Formula Ia-i(A)

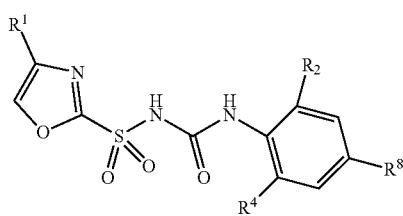

or a pharmaceutically acceptable salt thereof, wherein $R^8$ is H, CN, F, $CO_2C_1$-$C_6$ alkyl, or $CONH_2$.

93) The compound of exemplary embodiment 1 or 87, wherein the compound is a compound of Formula Ia-i(B):

Formula Ia-i(B)

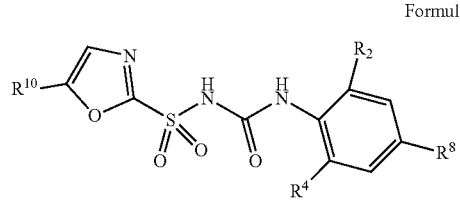

or a pharmaceutically acceptable salt thereof, wherein $R^8$ is H, CN, F, $CO_2C_1$-$C_6$ alkyl, or $CONH_2$.

94) The compound of exemplary embodiment 1 or 87, wherein the compound of Formula Ia is a compound of Formula Ia-i(C):

Formula Ia-i(C)

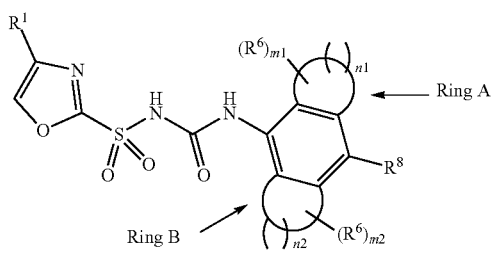

or a pharmaceutically acceptable salt thereof, wherein $R^8$ is H, CN, Cl or F.

95) The compound of exemplary embodiment 1 or 87, wherein the compound of Formula Ia is a compound of Formula Ia-i(D):

Formula Ia-i(D)

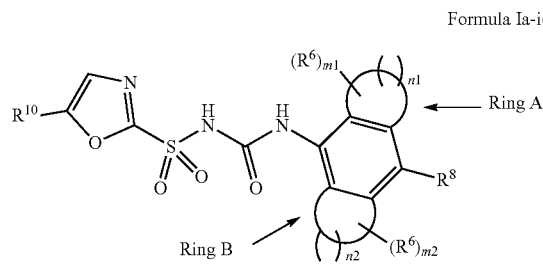

or a pharmaceutically acceptable salt thereof, wherein $R^8$ is H, CN, Cl or F.

96) The compound of exemplary embodiment 1 or 87, wherein the compound of Formula Ia is a compound of Formula Ia-i(E):

Formula Ia-i(E)

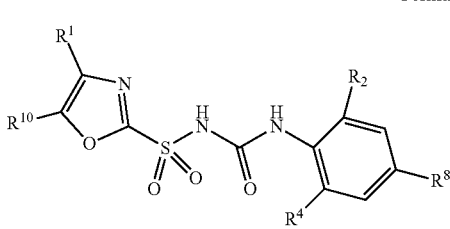

or a pharmaceutically acceptable salt thereof, wherein $R^8$ is H, CN, F, $CO_2C_1$-$C_6$ alkyl, or $CONH_2$.

97) The compound of exemplary embodiment 1 or 87, wherein the compound of Formula Ia is a compound of Formula Ia-i(F):

Formula Ia-i(F)

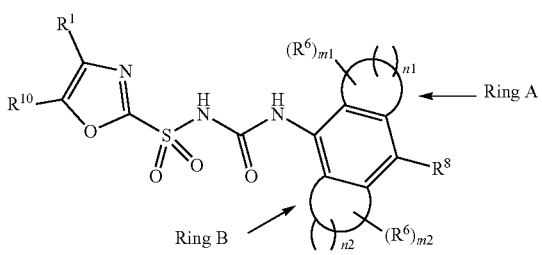

or a pharmaceutically acceptable salt thereof, wherein $R^8$ is H, CN, Cl or F.

98) The compound of exemplary embodiment 1 or 87, wherein the compound of Formula Ia is a compound of Formula Ia-i(G):

Formula Ia-i(G)

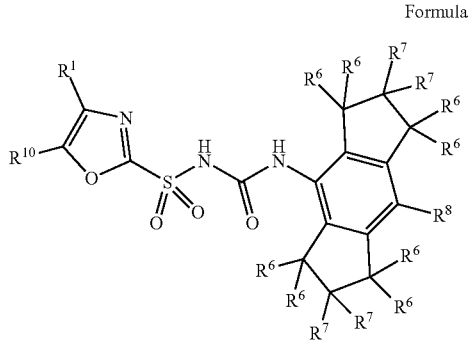

or a pharmaceutically acceptable salt thereof, wherein $R^8$ is H, CN, Cl or F.

In some embodiments, the compound of Formula I is a compound selected from the group consisting of compounds in Table 1 below, and NLRP1 antagonist activity is shown where available. <1 μM="++++"; ≥1 and <5 μM="+++"; ≥5 and <15 μM="++"; ≥15 and <35 μM="+".

TABLE 1

| Compound | Structure | hNLRP3 (THP-1, IL-1β) Average IC$_{50}$ (μM) |
|---|---|---|
| 101 | (structure) | |
| 102 | (structure) | |
| 103 | (structure) | |
| 104 | (structure) | ++++ |
| 105 | (structure) | ++++ |
| 106 | (structure) | |
| 108 | (structure) | |

TABLE 1-continued

| Compound | Structure | hNLRP3 (THP-1, IL-1β) Average IC$_{50}$ (μM) |
|---|---|---|
| 109 | 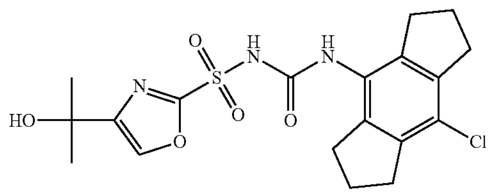 [SMILES: CC(C)(O)c1coc(S(=O)(=O)NC(=O)Nc2c3c(c(Cl)c4c2CCC4)CCC3)n1] | |
| 110 | 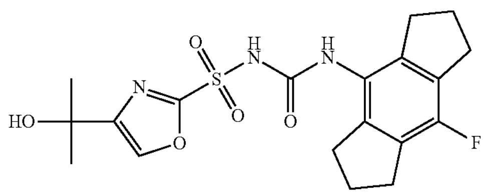 [SMILES: CC(C)(O)c1coc(S(=O)(=O)NC(=O)Nc2c3c(c(F)c4c2CCC4)CCC3)n1] | |
| 111 | 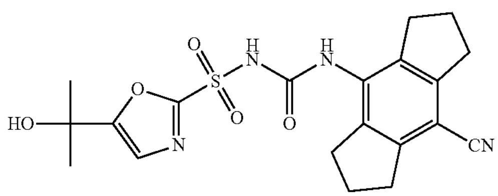 [SMILES: CC(C)(O)c1cnc(S(=O)(=O)NC(=O)Nc2c3c(c(C#N)c4c2CCC4)CCC3)o1] | |
| 112 | 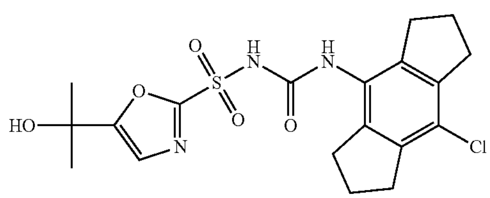 [SMILES: CC(C)(O)c1cnc(S(=O)(=O)NC(=O)Nc2c3c(c(Cl)c4c2CCC4)CCC3)o1] | |
| 113 | 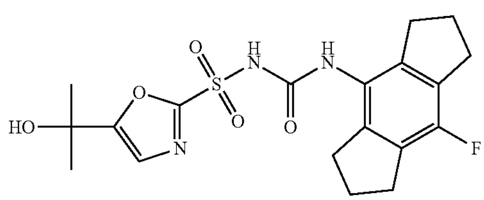 [SMILES: CC(C)(O)c1cnc(S(=O)(=O)NC(=O)Nc2c3c(c(F)c4c2CCC4)CCC3)o1] | |
| 114 | 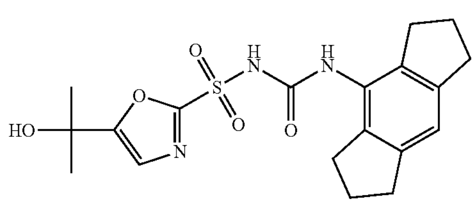 [SMILES: CC(C)(O)c1cnc(S(=O)(=O)NC(=O)Nc2c3c(cc4c2CCC4)CCC3)o1] | |
| 115 | 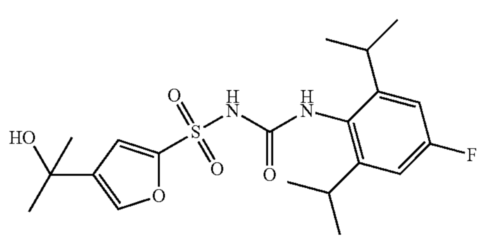 [SMILES: CC(C)c1cc(F)cc(C(C)C)c1NC(=O)NS(=O)(=O)c1cc(C(C)(C)O)co1] | ++++ |

TABLE 1-continued

| Compound | Structure | hNLRP3 (THP-1, IL-1β) Average IC$_{50}$ (μM) |
|---|---|---|
| 116 | 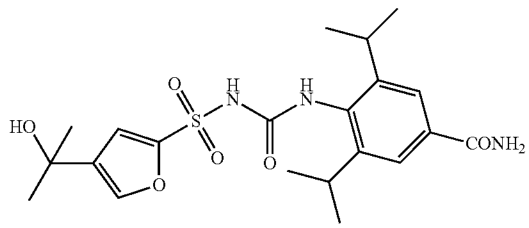 [SMILES: CC(C)c1cc(C(N)=O)cc(C(C)C)c1NC(=O)NS(=O)(=O)c1cc(C(C)(C)O)co1] | + |
| 117 | 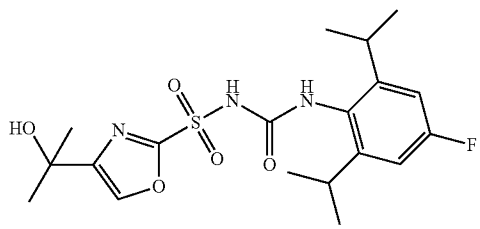 [SMILES: CC(C)c1cc(F)cc(C(C)C)c1NC(=O)NS(=O)(=O)c1nc(C(C)(C)O)co1] | |
| 118 | 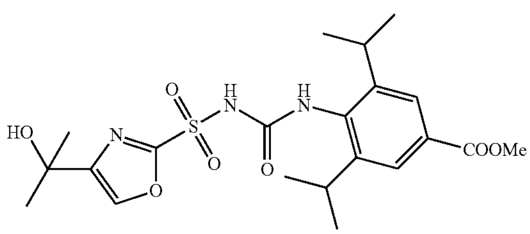 [SMILES: COC(=O)c1cc(C(C)C)c(NC(=O)NS(=O)(=O)c2nc(C(C)(C)O)co2)c(C(C)C)c1] | |
| 119 | 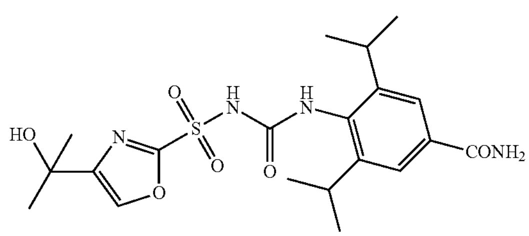 [SMILES: CC(C)c1cc(C(N)=O)cc(C(C)C)c1NC(=O)NS(=O)(=O)c1nc(C(C)(C)O)co1] | |
| 120 | 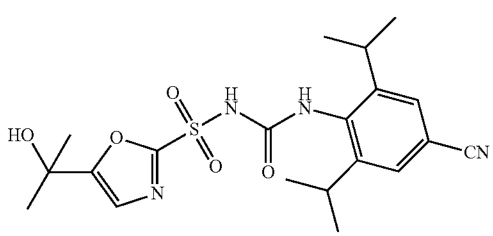 [SMILES: CC(C)c1cc(C#N)cc(C(C)C)c1NC(=O)NS(=O)(=O)c1ncc(C(C)(C)O)o1] | |
| 121 | 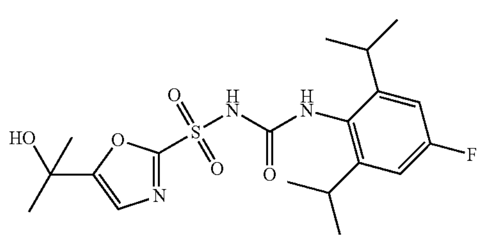 [SMILES: CC(C)c1cc(F)cc(C(C)C)c1NC(=O)NS(=O)(=O)c1ncc(C(C)(C)O)o1] | |

TABLE 1-continued

| Compound | Structure | hNLRP3 (THP-1, IL-1β) Average IC$_{50}$ (μM) |
|---|---|---|
| 122 | 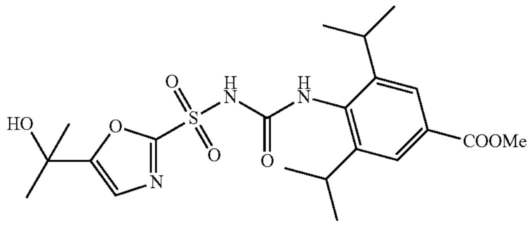 [SMILES: COC(=O)c1cc(C(C)C)c(NC(=O)NS(=O)(=O)c2ncc(C(C)(C)O)o2)c(C(C)C)c1] | |
| 123 | 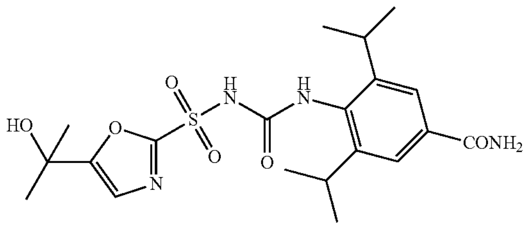 [SMILES: CC(C)c1cc(C(N)=O)cc(C(C)C)c1NC(=O)NS(=O)(=O)c1ncc(C(C)(C)O)o1] | |
| 124 | 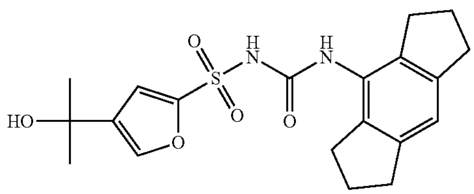 [SMILES: CC(C)(O)c1coc(S(=O)(=O)NC(=O)Nc2c3c(cc4c2CCC4)CCC3)c1] | |
| 126 | 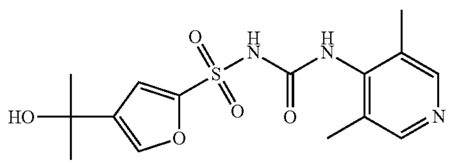 [SMILES: Cc1cncc(C)c1NC(=O)NS(=O)(=O)c1cc(C(C)(C)O)co1] | |
| 127 | 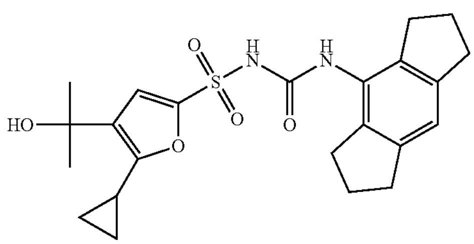 [SMILES: CC(C)(O)c1cc(S(=O)(=O)NC(=O)Nc2c3c(cc4c2CCC4)CCC3)oc1C1CC1] | |
| 128 | 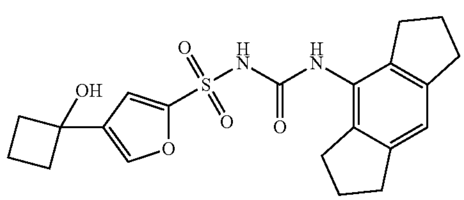 [SMILES: O=C(Nc1c2c(cc3c1CCC3)CCC2)NS(=O)(=O)c1cc(C2(O)CCC2)co1] | |
| 129 | 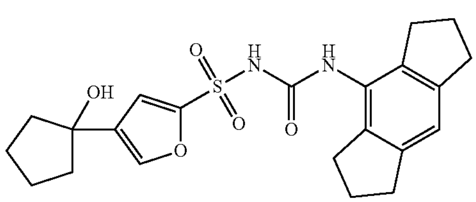 [SMILES: O=C(Nc1c2c(cc3c1CCC3)CCC2)NS(=O)(=O)c1cc(C2(O)CCCC2)co1] | |

TABLE 1-continued

| Compound | Structure | hNLRP3 (THP-1, IL-1β) Average IC$_{50}$ (μM) |
|---|---|---|
| 130 | 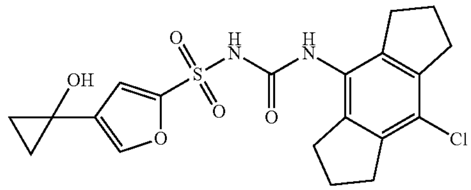 [SMILES: O=C(Nc1c2c(c(Cl)c3c1CCC3)CCC2)NS(=O)(=O)c1cc(C2(O)CC2)co1] | ++++ |
| 132 | 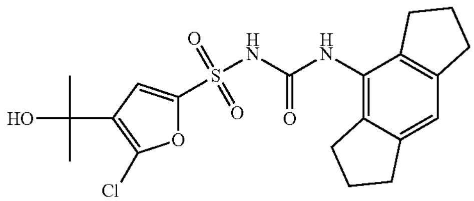 [SMILES: CC(C)(O)c1cc(S(=O)(=O)NC(=O)Nc2c3c(cc4c2CCC4)CCC3)oc1Cl] | |
| 135 | 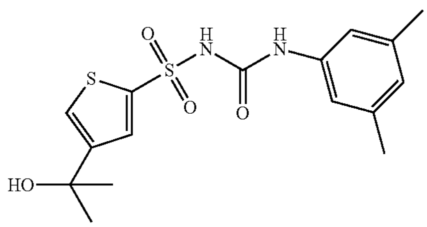 [SMILES: Cc1cc(C)cc(NC(=O)NS(=O)(=O)c2cc(C(C)(C)O)cs2)c1] | |
| 136 | 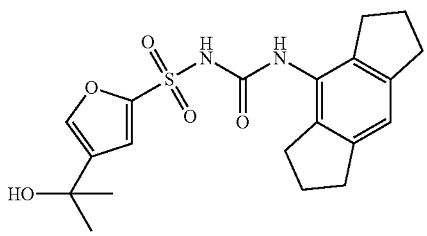 [SMILES: CC(C)(O)c1coc(S(=O)(=O)NC(=O)Nc2c3c(cc4c2CCC4)CCC3)c1] | |
| 137 | 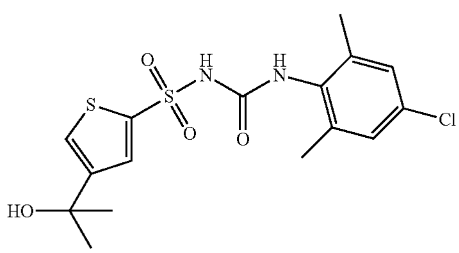 [SMILES: Cc1cc(Cl)cc(C)c1NC(=O)NS(=O)(=O)c1cc(C(C)(C)O)cs1] | |
| 138a | | | and pharmaceutically acceptable salts thereof.

In some embodiments, the compound of Formula I is a compound selected from the group consisting of compounds in Table 2 below, and NLRP1 antagonist activity is shown where available. <1 μM="++++"; ≥1 and <5 μM="+++"; ≥5 and <15 μM="++"; ≥15 and <35 μM="+".

TABLE 2

| Compound | Structure | hNLRP3 (THP-1, IL-1β) Average IC$_{50}$ (μM) |
|---|---|---|
| 138 | 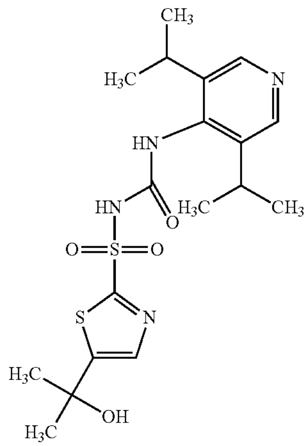 [SMILES: CC(C)c1cncc(C(C)C)c1NC(=O)NS(=O)(=O)c1ncc(C(C)(C)O)s1] | +++ |
| 139 | 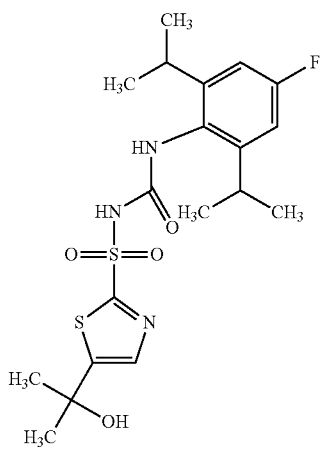 | ++++ |
| 142 | 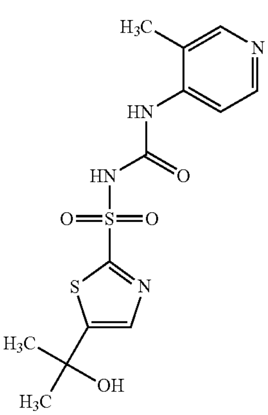 [SMILES: Cc1cnccc1NC(=O)NS(=O)(=O)c1ncc(C(C)(C)O)s1] | |

TABLE 2-continued

| Compound | Structure | hNLRP3 (THP-1, IL-1β) Average IC$_{50}$ (μM) |
|---|---|---|
| 143 | 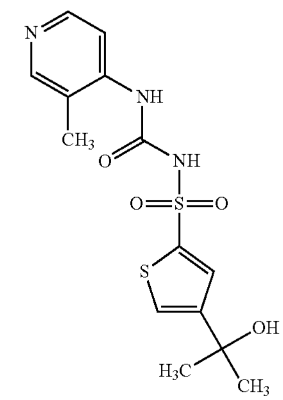 [SMILES: Cc1cnccc1NC(=O)NS(=O)(=O)c1cc(C(C)(C)O)cs1] | |
| 144 | 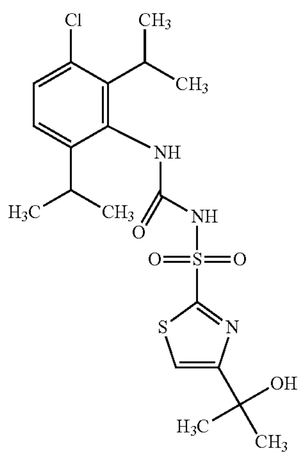 | +++ |
| 145 | 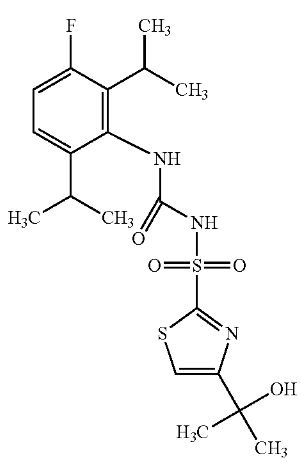 [SMILES: CC(C)c1ccc(F)c(C(C)C)c1NC(=O)NS(=O)(=O)c1nc(C(C)(C)O)cs1] | +++ |

TABLE 2-continued

| Compound | Structure | hNLRP3 (THP-1, IL-1β) Average IC$_{50}$ (μM) |
|---|---|---|
| 146 | (structure) | +++ |
| 147 | (structure) | +++ |
| 148 | (structure) | +++ |

TABLE 2-continued
| Compound | Structure | hNLRP3 (THP-1, IL-1β) Average IC$_{50}$ (μM) |
|---|---|---|
| 149 | 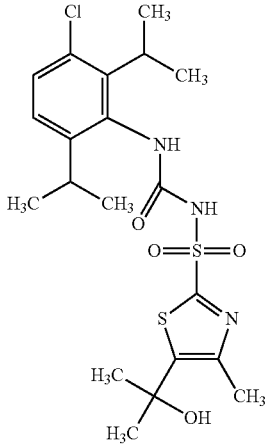 [SMILES: Cc1nc(S(=O)(=O)NC(=O)Nc2c(C(C)C)ccc(Cl)c2C(C)C)sc1C(C)(C)O] | + |
| 150 | 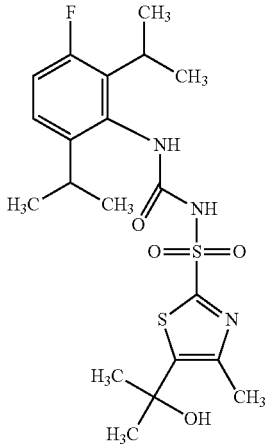 [SMILES: Cc1nc(S(=O)(=O)NC(=O)Nc2c(C(C)C)ccc(F)c2C(C)C)sc1C(C)(C)O] | ++++ |
| 151 | 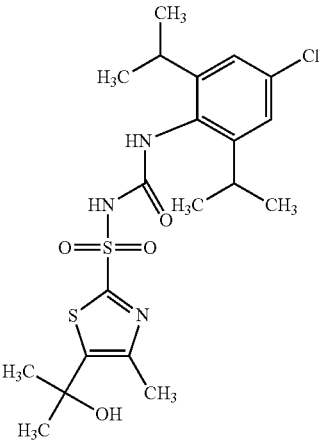 [SMILES: Cc1nc(S(=O)(=O)NC(=O)Nc2c(C(C)C)cc(Cl)cc2C(C)C)sc1C(C)(C)O] | +++ |

TABLE 2-continued

| Compound | Structure | hNLRP3 (THP-1, IL-1β) Average IC$_{50}$ (μM) |
|---|---|---|
| 152 | 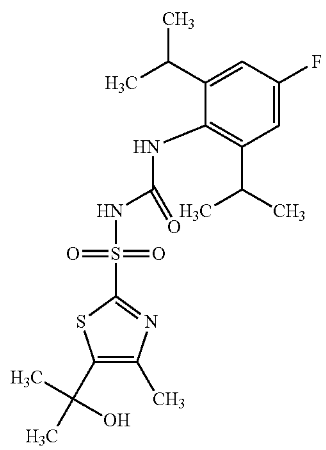 [SMILES: Cc1nc(S(=O)(=O)NC(=O)Nc2c(C(C)C)cc(F)cc2C(C)C)sc1C(C)(C)O] | ++ |
| 153 | 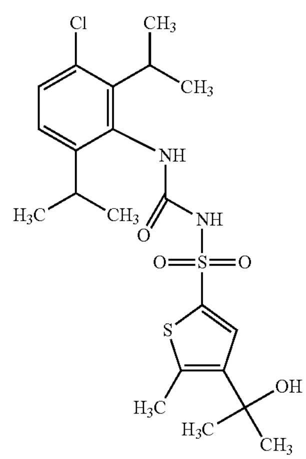 [SMILES: Cc1sc(S(=O)(=O)NC(=O)Nc2c(C(C)C)ccc(Cl)c2C(C)C)cc1C(C)(C)O] | ++ |
| 154 | 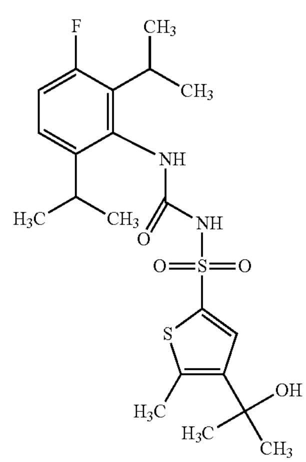 [SMILES: Cc1sc(S(=O)(=O)NC(=O)Nc2c(C(C)C)ccc(F)c2C(C)C)cc1C(C)(C)O] | +++ |

TABLE 2-continued

| Compound | Structure | hNLRP3 (THP-1, IL-1β) Average IC$_{50}$ (μM) |
|---|---|---|
| 155 | 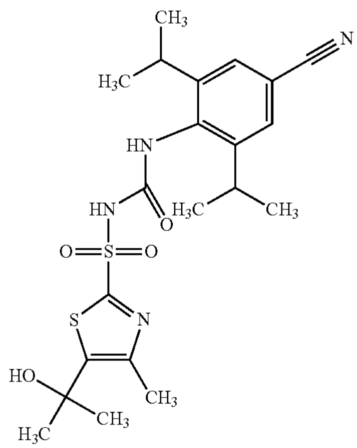 [SMILES: Cc1nc(S(=O)(=O)NC(=O)Nc2c(C(C)C)cc(C#N)cc2C(C)C)sc1C(C)(C)O] | ++ |
| 156 | 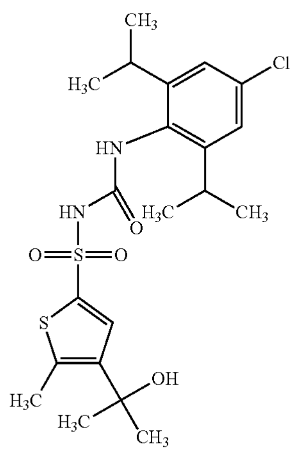 [SMILES: Cc1sc(S(=O)(=O)NC(=O)Nc2c(C(C)C)cc(Cl)cc2C(C)C)cc1C(C)(C)O] | ++++ |
| 157 | 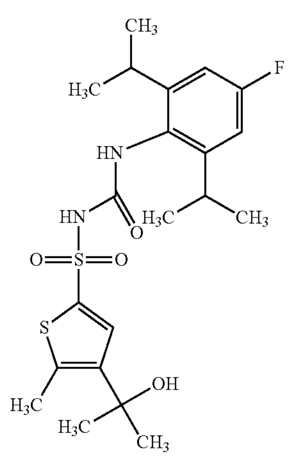 [SMILES: Cc1sc(S(=O)(=O)NC(=O)Nc2c(C(C)C)cc(F)cc2C(C)C)cc1C(C)(C)O] | ++++ |

TABLE 2-continued

| Compound | Structure | hNLRP3 (THP-1, IL-1β) Average IC$_{50}$ (μM) |
|---|---|---|
| 158 | 4-cyano-2,6-diethylphenyl urea linked to sulfonyl-thiazole with 2-hydroxypropan-2-yl substituent | +++ |
| 159 | 4-cyano-2,6-diethylphenyl urea linked to sulfonyl-thiophene with 2-hydroxypropan-2-yl substituent | +++ |
| 160 | 4-fluoro-2,6-diethylphenyl urea linked to sulfonyl-thiazole with 2-hydroxypropan-2-yl substituent | |

TABLE 2-continued

| Compound | Structure | hNLRP3 (THP-1, IL-1β) Average IC$_{50}$ (μM) |
|---|---|---|
| 161 | 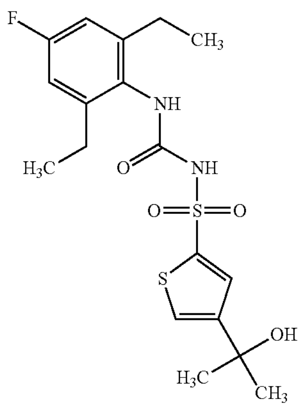 [SMILES: CCc1cc(F)cc(CC)c1NC(=O)NS(=O)(=O)c1cc(C(C)(C)O)cs1] | +++ |
| 162 | 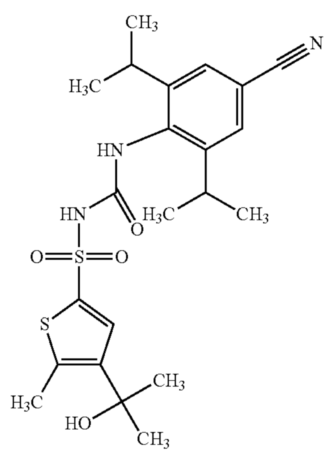 [SMILES: Cc1sc(S(=O)(=O)NC(=O)Nc2c(C(C)C)cc(C#N)cc2C(C)C)cc1C(C)(C)O] | ++++ |
| 163 | 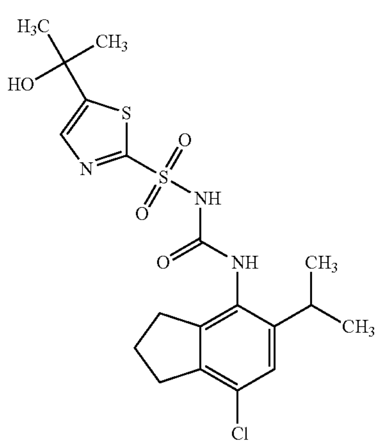 [SMILES: CC(C)c1cc(Cl)c2c(c1NC(=O)NS(=O)(=O)c1ncc(C(C)(C)O)s1)CCC2] | |

TABLE 2-continued

| Compound | Structure | hNLRP3 (THP-1, IL-1β) Average IC$_{50}$ (μM) |
|---|---|---|
| 164 | ![structure] | |
| 165 | ![structure] | +++ |
| 166 | ![structure] | +++ |

TABLE 2-continued

| Compound | Structure | hNLRP3 (THP-1, IL-1β) Average IC$_{50}$ (μM) |
|---|---|---|
| 167 | 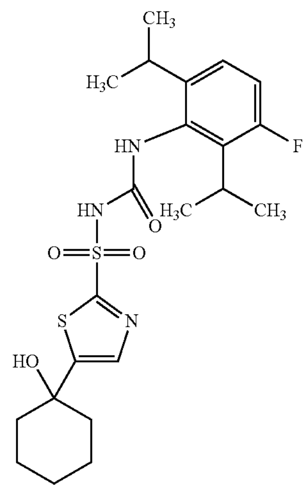 [SMILES: CC(C)c1ccc(F)c(C(C)C)c1NC(=O)NS(=O)(=O)c1ncc(C2(O)CCCCC2)s1] | ++ |
| 168 | 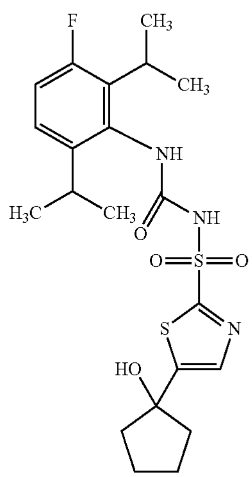 [SMILES: CC(C)c1ccc(F)c(C(C)C)c1NC(=O)NS(=O)(=O)c1ncc(C2(O)CCCC2)s1] | ++ |
| 169 | 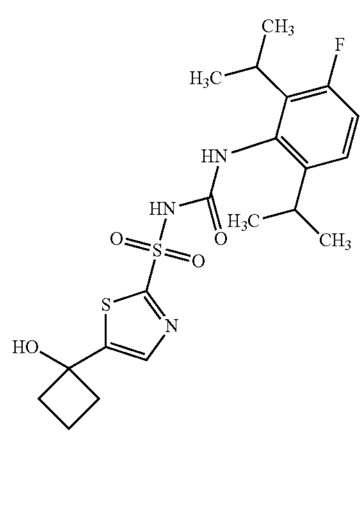 [SMILES: CC(C)c1ccc(F)c(C(C)C)c1NC(=O)NS(=O)(=O)c1ncc(C2(O)CCC2)s1] | ++ |

TABLE 2-continued

| Compound | Structure | hNLRP3 (THP-1, IL-1β) Average IC$_{50}$ (μM) |
| --- | --- | --- |
| 170 | 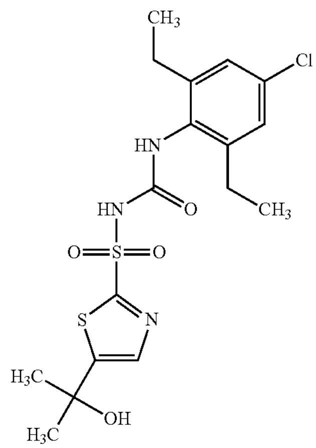 [SMILES: CCc1cc(Cl)cc(CC)c1NC(=O)NS(=O)(=O)c1ncc(C(C)(C)O)s1] | ++ |
| 171 | 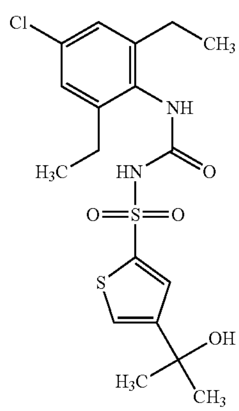 [SMILES: CCc1cc(Cl)cc(CC)c1NC(=O)NS(=O)(=O)c1cc(C(C)(C)O)cs1] | +++ |
| 172 | 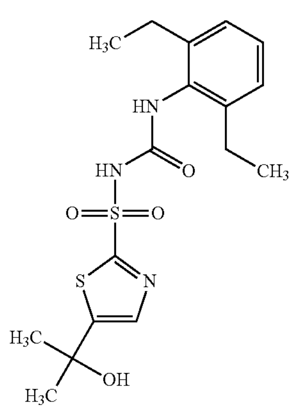 [SMILES: CCc1cccc(CC)c1NC(=O)NS(=O)(=O)c1ncc(C(C)(C)O)s1] | +++ |

TABLE 2-continued

| Compound | Structure | hNLRP3 (THP-1, IL-1β) Average IC$_{50}$ (μM) |
|---|---|---|
| 173 | (2,6-diethylphenyl)-NH-C(O)-NH-SO$_2$-thiophene-C(CH$_3$)$_2$OH | + |
| 175 | HO-C(CH$_3$)$_2$-thiophene-SO$_2$-NH-C(O)-NH-(6-isopropyl-2,3-dihydro-1H-inden-5-yl) | + |
| 176 | HO-C(CH$_3$)$_2$-thiophene-SO$_2$-NH-C(O)-NH-(8-fluoro-1,2,3,5,6,7-hexahydro-s-indacen-4-yl) | ++++ |
| 178 | HO-C(cyclopropyl)-thiophene-SO$_2$-NH-C(O)-NH-(8-cyano-1,2,3,5,6,7-hexahydro-s-indacen-4-yl) | +++ |

TABLE 2-continued

| Compound | Structure | hNLRP3 (THP-1, IL-1β) Average IC$_{50}$ (μM) |
|---|---|---|
| 179 | *structure: 3-chloro-2,6-diisopropylphenyl urea linked to sulfonyl-thiazole bearing 2-hydroxypropan-2-yl group* | +++ |
| 180 | *structure: 3-chloro-2,6-diisopropylphenyl urea linked to sulfonyl-thiophene bearing 2-hydroxypropan-2-yl group* | ++++ |
| 181 | *structure: 4-(1-hydroxycyclopropyl)furan-2-sulfonyl urea linked to 3-chloro-2,6-diisopropylphenyl* | ++++ |
| 182 | *structure: 5-(2-hydroxypropan-2-yl)thiazole-2-sulfonyl urea linked to 6-methoxy-2,3-dihydro-1H-inden-4-yl* | +++ |

TABLE 2-continued

| Compound | Structure | hNLRP3 (THP-1, IL-1β) Average IC$_{50}$ (μM) |
|---|---|---|
| 183 | 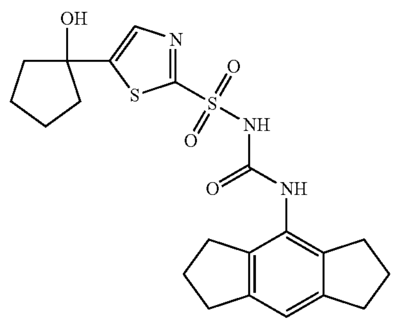 [SMILES: O=C(Nc1c2c(cc3c1CCC3)CCC2)NS(=O)(=O)c1ncc(C2(O)CCCC2)s1] | ++++ |
| 184 | 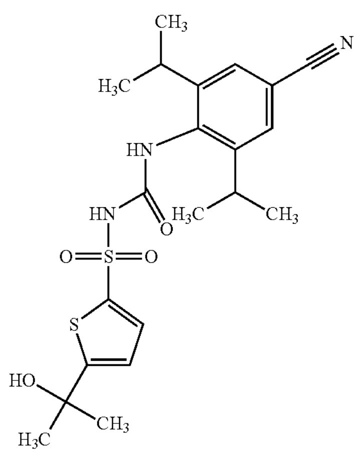 [SMILES: CC(C)c1cc(C#N)cc(C(C)C)c1NC(=O)NS(=O)(=O)c1ccc(C(C)(C)O)s1] | ++++ |
| 185 | 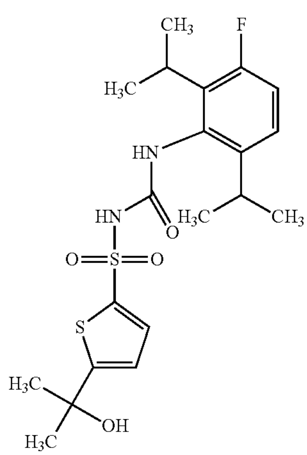 [SMILES: CC(C)c1ccc(F)c(C(C)C)c1NC(=O)NS(=O)(=O)c1ccc(C(C)(C)O)s1] | +++ |

TABLE 2-continued

| Compound | Structure | hNLRP3 (THP-1, IL-1β) Average IC$_{50}$ (μM) |
|---|---|---|
| 187 | 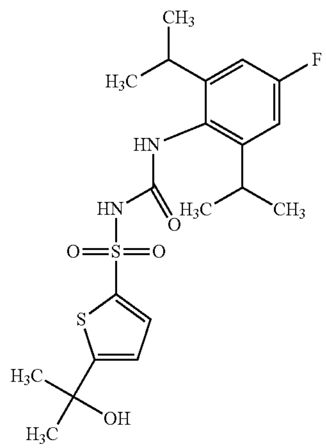 [SMILES: CC(C)c1cc(F)cc(C(C)C)c1NC(=O)NS(=O)(=O)c1ccc(C(C)(C)O)s1] | ++++ |
| 188 | 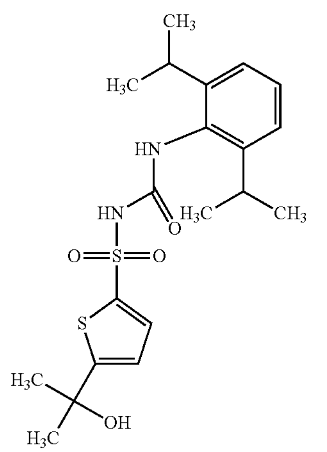 [SMILES: CC(C)c1cccc(C(C)C)c1NC(=O)NS(=O)(=O)c1ccc(C(C)(C)O)s1] | +++ |
| 189 | 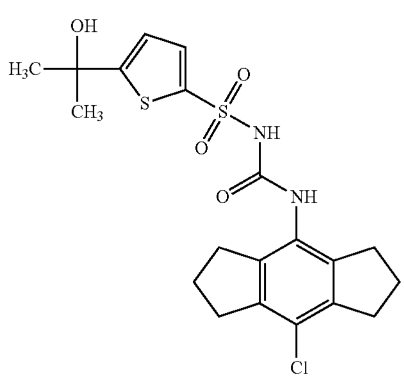 [SMILES: CC(C)(O)c1ccc(S(=O)(=O)NC(=O)Nc2c3c(c(Cl)c4c2CCC4)CCC3)s1] | ++++ |

TABLE 2-continued
| Compound | Structure | hNLRP3 (THP-1, IL-1β) Average IC$_{50}$ (μM) |
|---|---|---|
| 190 | 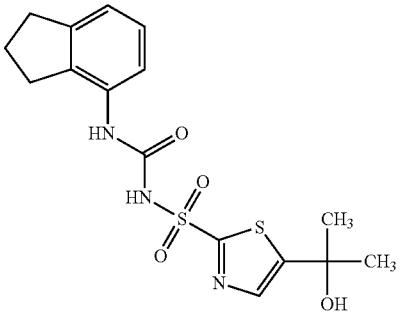 [SMILES: CC(C)(O)c1cnc(S(=O)(=O)NC(=O)Nc2cccc3c2CCC3)s1] | +++ |
| 191 | 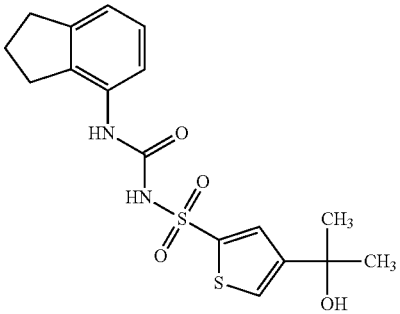 [SMILES: CC(C)(O)c1csc(S(=O)(=O)NC(=O)Nc2cccc3c2CCC3)c1] | +++ |
| 192 | 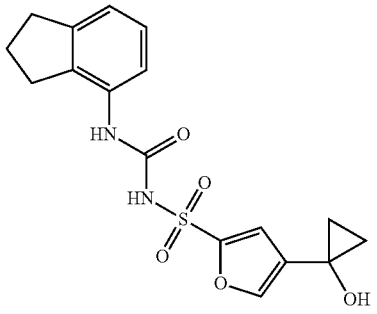 [SMILES: O=C(Nc1cccc2c1CCC2)NS(=O)(=O)c1cc(C2(O)CC2)co1] | +++ |
| 193 | 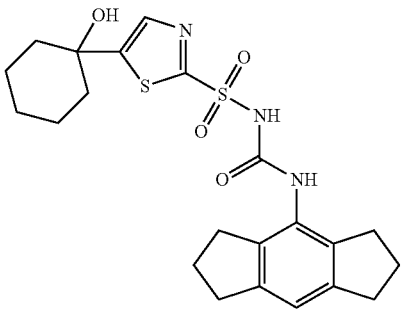 [SMILES: O=C(Nc1c2c(cc3c1CCC3)CCC2)NS(=O)(=O)c1ncc(C2(O)CCCCC2)s1] | +++ |

TABLE 2-continued

| Compound | Structure | hNLRP3 (THP-1, IL-1β) Average IC$_{50}$ (μM) |
|---|---|---|
| 194 | 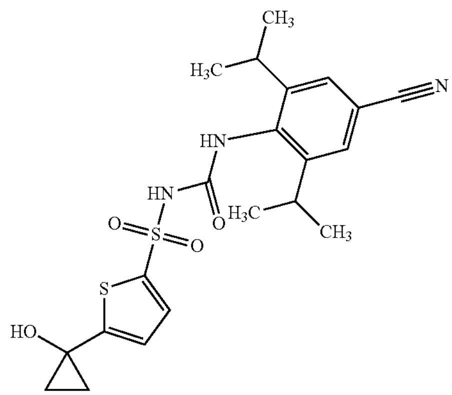 [SMILES: CC(C)c1cc(C#N)cc(C(C)C)c1NC(=O)NS(=O)(=O)c1ccc(C2(O)CC2)s1] | +++ |
| 195 | 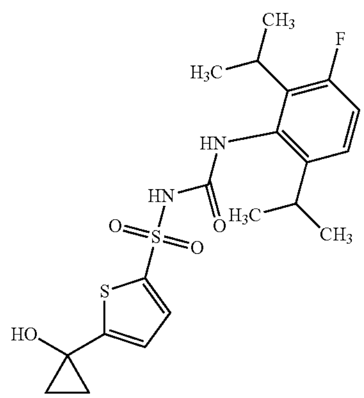 [SMILES: CC(C)c1ccc(F)c(C(C)C)c1NC(=O)NS(=O)(=O)c1ccc(C2(O)CC2)s1] | +++ |
| 196 | 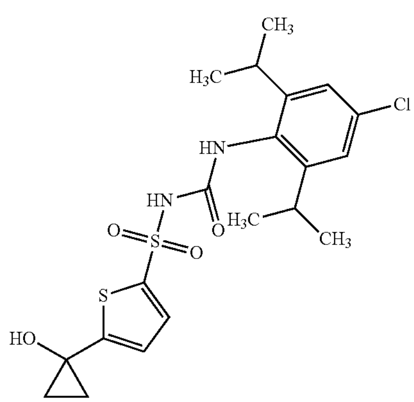 [SMILES: CC(C)c1cc(Cl)cc(C(C)C)c1NC(=O)NS(=O)(=O)c1ccc(C2(O)CC2)s1] | ++++ |
| 197 | 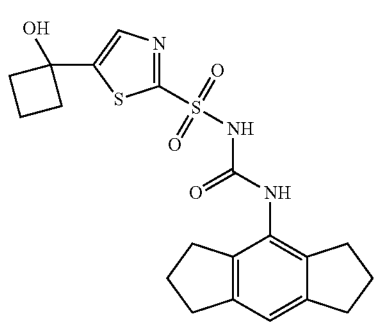 [SMILES: O=C(Nc1c2c(cc3c1CCC3)CCC2)NS(=O)(=O)c1ncc(C2(O)CCC2)s1] | ++++ |

TABLE 2-continued

| Compound | Structure | hNLRP3 (THP-1, IL-1β) Average IC$_{50}$ (µM) |
|---|---|---|
| 198 | 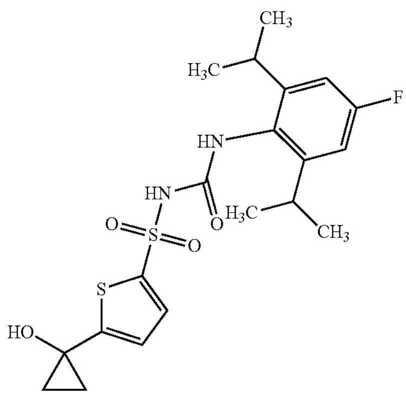 [SMILES: CC(C)c1cc(F)cc(C(C)C)c1NC(=O)NS(=O)(=O)c1ccc(C2(O)CC2)s1] | ++++ |
| 199 | 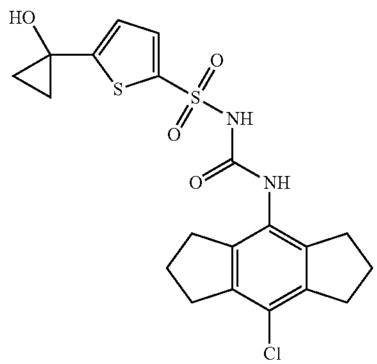 [SMILES: O=C(Nc1c2c(c(Cl)c3c1CCC3)CCC2)NS(=O)(=O)c1ccc(C2(O)CC2)s1] | +++ |
| 200 | 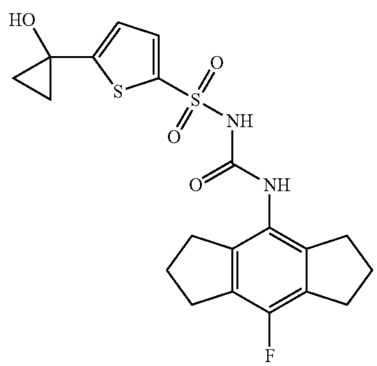 | ++++ |
| 201 | 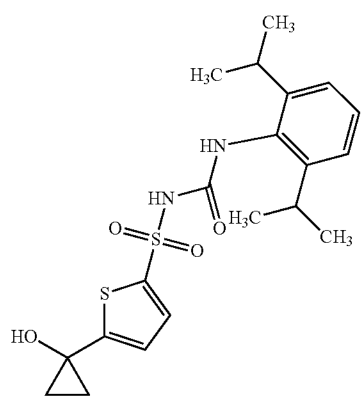 [SMILES: CC(C)c1cccc(C(C)C)c1NC(=O)NS(=O)(=O)c1ccc(C2(O)CC2)s1] | +++ |

TABLE 2-continued

| Compound | Structure | hNLRP3 (THP-1, IL-1β) Average IC$_{50}$ (μM) |
|---|---|---|
| 202 | 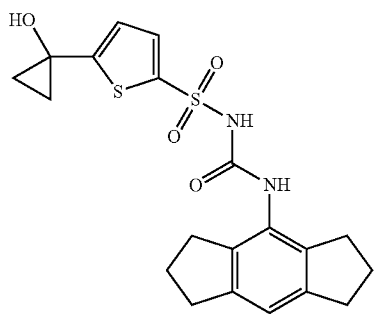 [SMILES: O=C(Nc1c2c(cc3c1CCC3)CCC2)NS(=O)(=O)c1ccc(C2(O)CC2)s1] | ++++ |
| 204 | 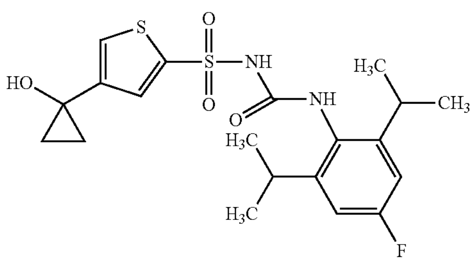 [SMILES: CC(C)c1cc(F)cc(C(C)C)c1NC(=O)NS(=O)(=O)c1cc(C2(O)CC2)cs1] | ++++ |
| 205 | 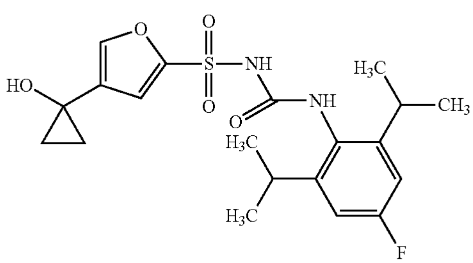 [SMILES: CC(C)c1cc(F)cc(C(C)C)c1NC(=O)NS(=O)(=O)c1cc(C2(O)CC2)co1] | ++++ |
| 206 | 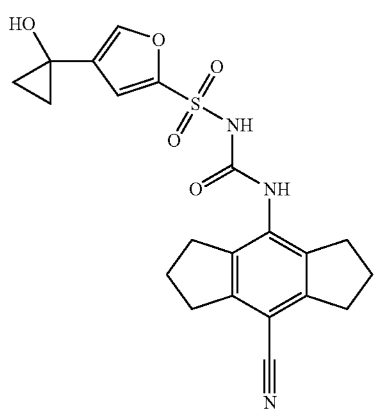 [SMILES: N#Cc1c2c(c(NC(=O)NS(=O)(=O)c3cc(C4(O)CC4)co3)c3c1CCC3)CCC2] | ++++ |

TABLE 2-continued

| Compound | Structure | hNLRP3 (THP-1, IL-1β) Average IC$_{50}$ (μM) |
|---|---|---|
| 207 | 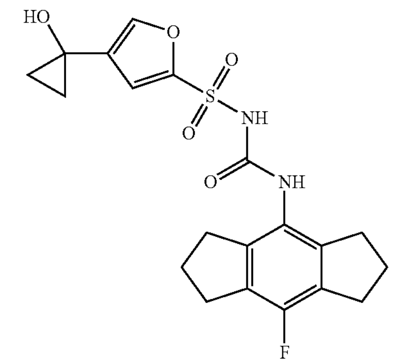 [SMILES: O=C(Nc1c2c(c(F)c3c1CCC3)CCC2)NS(=O)(=O)c1cc(C2(O)CC2)co1] | ++++ |
| 209 | 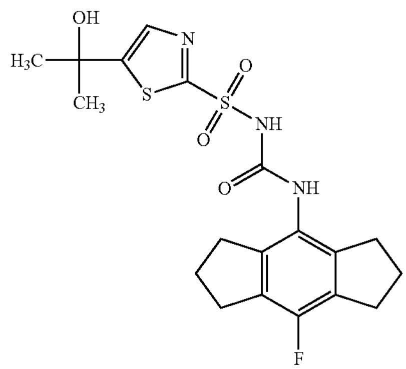 | ++++ |
| 210 | 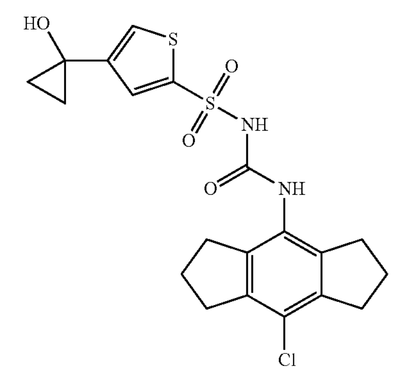 [SMILES: O=C(Nc1c2c(c(Cl)c3c1CCC3)CCC2)NS(=O)(=O)c1cc(C2(O)CC2)cs1] | ++++ |
| 211 | 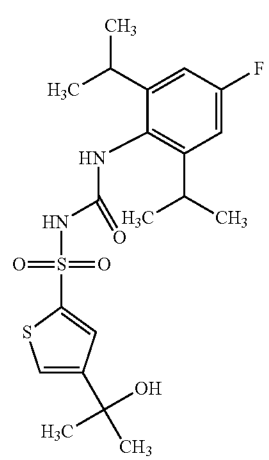 [SMILES: CC(C)c1cc(F)cc(C(C)C)c1NC(=O)NS(=O)(=O)c1cc(C(C)(C)O)cs1] | ++++ |

TABLE 2-continued

| Compound | Structure | hNLRP3 (THP-1, IL-1β) Average IC$_{50}$ (μM) |
|---|---|---|
| 212 | 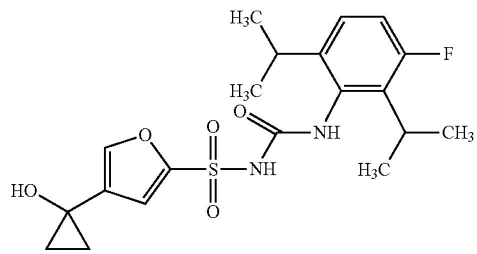 [SMILES: CC(C)c1ccc(F)c(C(C)C)c1NC(=O)NS(=O)(=O)c1cc(C2(O)CC2)co1] | ++++ |
| 213 | 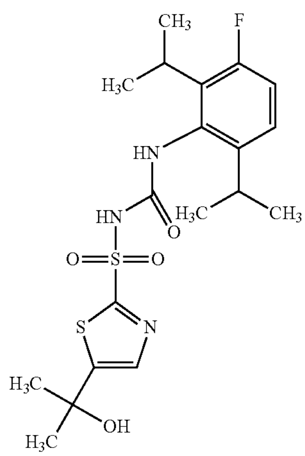 [SMILES: CC(C)c1ccc(F)c(C(C)C)c1NC(=O)NS(=O)(=O)c1ncc(C(C)(C)O)s1] | ++++ |
| 214 | 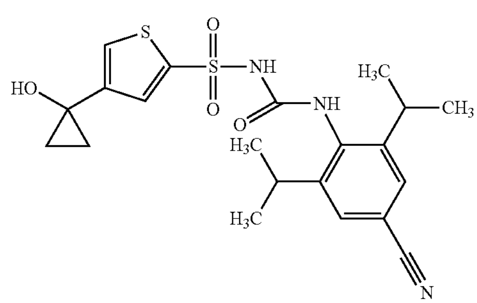 [SMILES: CC(C)c1cc(C#N)cc(C(C)C)c1NC(=O)NS(=O)(=O)c1cc(C2(O)CC2)cs1] | |
| 215 | 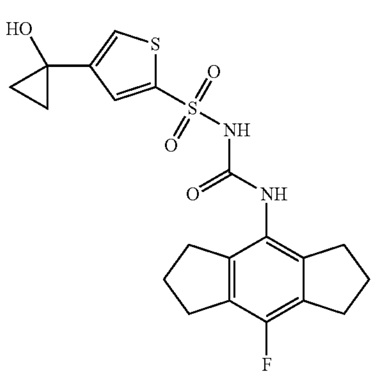 [SMILES: O=C(Nc1c2c(c(F)c3c1CCC3)CCC2)NS(=O)(=O)c1cc(C2(O)CC2)cs1] | |

TABLE 2-continued
| Compound | Structure | hNLRP3 (THP-1, IL-1β) Average IC$_{50}$ (μM) |
|---|---|---|
| 216 | 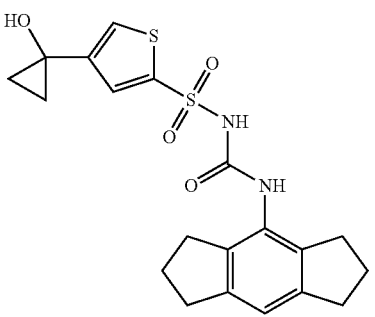 | ++++ |
| 217 | 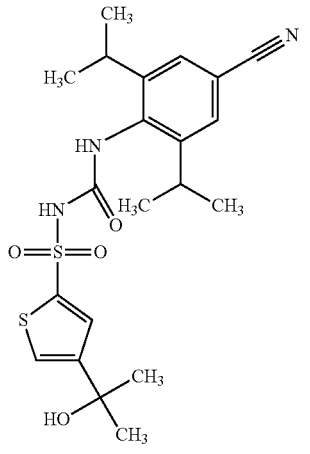 [SMILES: CC(C)c1cc(C#N)cc(C(C)C)c1NC(=O)NS(=O)(=O)c1cc(C(C)(C)O)cs1] | ++++ |
| 218 | 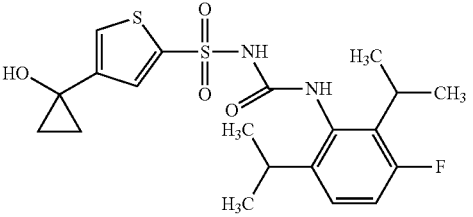 [SMILES: CC(C)c1ccc(F)c(C(C)C)c1NC(=O)NS(=O)(=O)c1cc(C2(O)CC2)cs1] | ++++ |
| 219 | 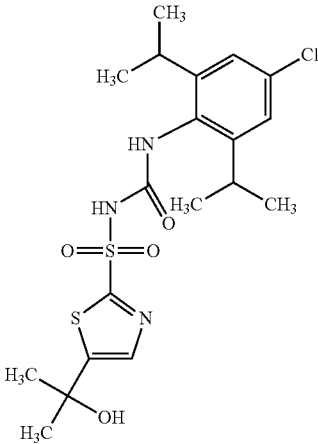 [SMILES: CC(C)c1cc(Cl)cc(C(C)C)c1NC(=O)NS(=O)(=O)c1ncc(C(C)(C)O)s1] | ++++ |

TABLE 2-continued

| Compound | Structure | hNLRP3 (THP-1, IL-1β) Average IC$_{50}$ (μM) |
|---|---|---|
| 220 | 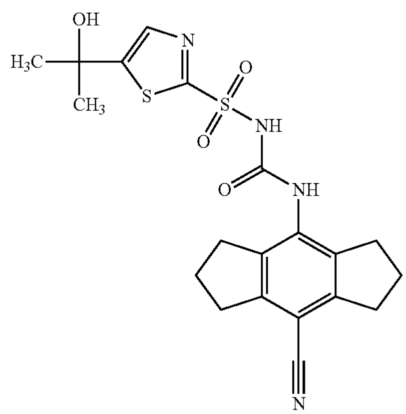 [SMILES: CC(C)(O)c1cnc(S(=O)(=O)NC(=O)Nc2c3c(c(C#N)c4c2CCC4)CCC3)s1] | +++ |
| 221 | 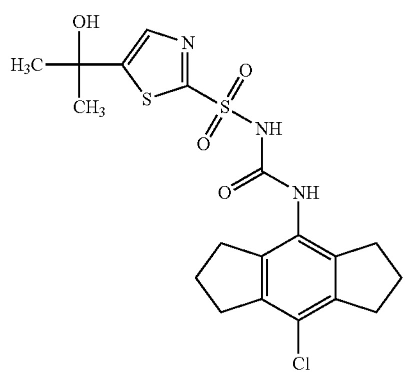 [SMILES: CC(C)(O)c1cnc(S(=O)(=O)NC(=O)Nc2c3c(c(Cl)c4c2CCC4)CCC3)s1] | ++++ |
| 222 | 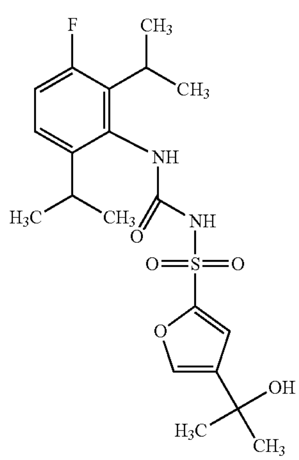 | |

TABLE 2-continued

| Compound | Structure | hNLRP3 (THP-1, IL-1β) Average IC$_{50}$ (μM) |
|---|---|---|
| 223 | 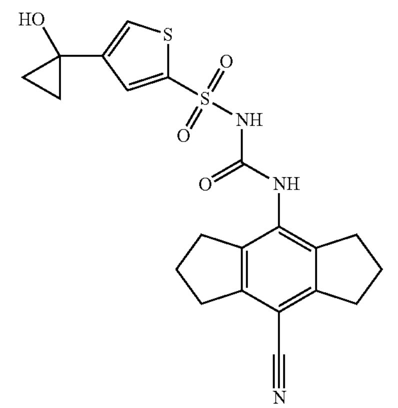 [SMILES: N#Cc1c2c(c(NC(=O)NS(=O)(=O)c3cc(C4(O)CC4)cs3)c3c1CCC3)CCC2] | ++++ |
| 224 | 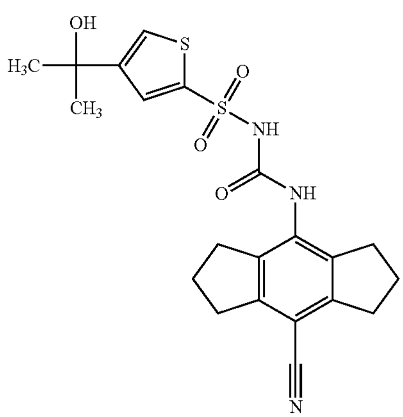 [SMILES: CC(C)(O)c1csc(S(=O)(=O)NC(=O)Nc2c3c(c(C#N)c4c2CCC4)CCC3)c1] | ++++ |
| 225 | 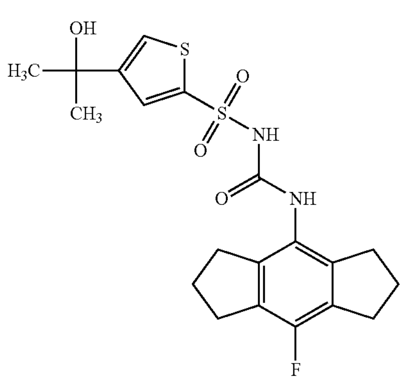 [SMILES: CC(C)(O)c1csc(S(=O)(=O)NC(=O)Nc2c3c(c(F)c4c2CCC4)CCC3)c1] | |

TABLE 2-continued
| Compound | Structure | hNLRP3 (THP-1, IL-1β) Average IC$_{50}$ (μM) |
|---|---|---|
| 226 | 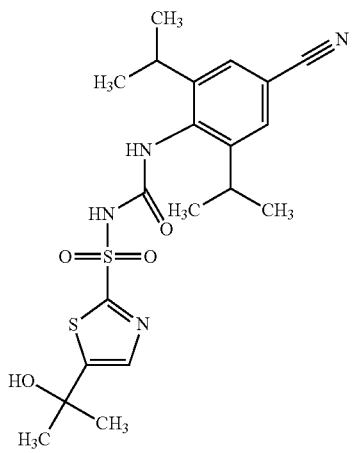 [SMILES: CC(C)c1cc(C#N)cc(C(C)C)c1NC(=O)NS(=O)(=O)c1ncc(C(C)(C)O)s1] | ++++ |
| 227 | 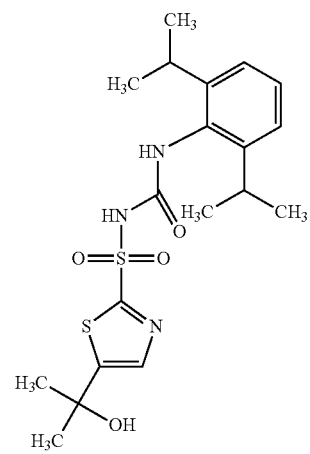 [SMILES: CC(C)c1cccc(C(C)C)c1NC(=O)NS(=O)(=O)c1ncc(C(C)(C)O)s1] | ++++ |
| 228 | 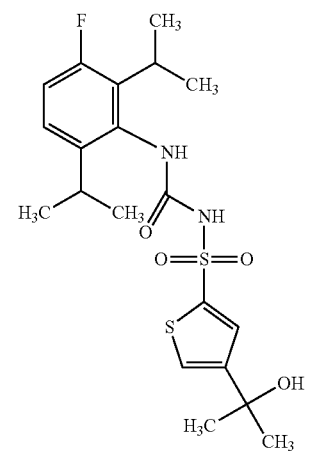 [SMILES: CC(C)c1ccc(F)c(C(C)C)c1NC(=O)NS(=O)(=O)c1cc(C(C)(C)O)cs1] | ++++ |

TABLE 2-continued

| Compound | Structure | hNLRP3 (THP-1, IL-1β) Average IC$_{50}$ (μM) |
|---|---|---|
| 229 | 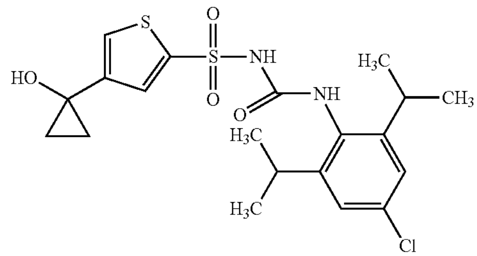 | ++++ |
| 230 | 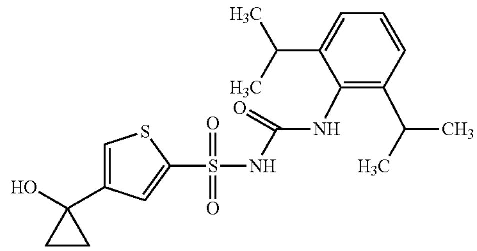 [SMILES: CC(C)c1cccc(C(C)C)c1NC(=O)NS(=O)(=O)c1cc(C2(O)CC2)cs1] | ++++ |
| 232 | 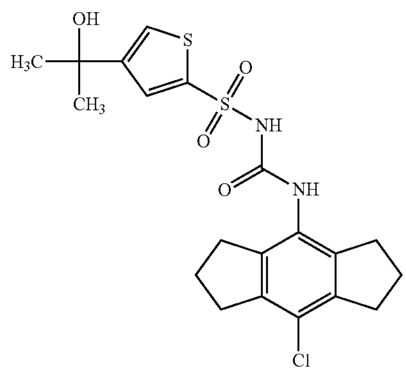 [SMILES: CC(C)(O)c1csc(S(=O)(=O)NC(=O)Nc2c3c(c(Cl)c4c2CCC4)CCC3)c1] | ++++ |
| 233 | 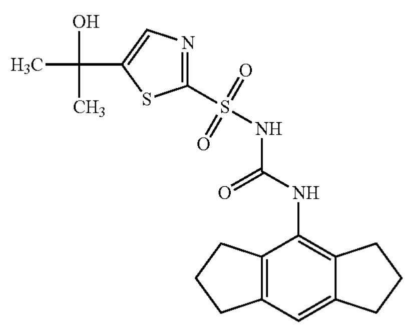 [SMILES: CC(C)(O)c1cnc(S(=O)(=O)NC(=O)Nc2c3c(cc4c2CCC4)CCC3)s1] | ++++ |
| 235 | 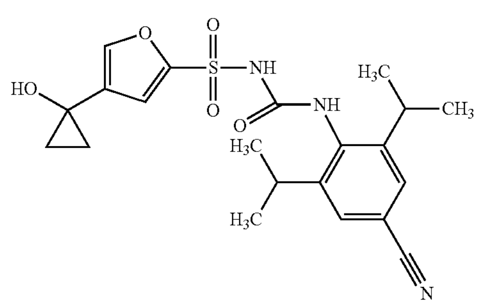 [SMILES: CC(C)c1cc(C#N)cc(C(C)C)c1NC(=O)NS(=O)(=O)c1cc(C2(O)CC2)co1] | ++++ |

TABLE 2-continued
| Compound | Structure | hNLRP3 (THP-1, IL-1β) Average IC$_{50}$ (μM) |
|---|---|---|
| 236 | 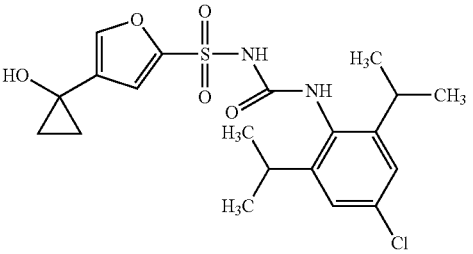 [SMILES: CC(C)c1cc(Cl)cc(C(C)C)c1NC(=O)NS(=O)(=O)c1cc(C2(O)CC2)co1] | ++++ |
| 239 | 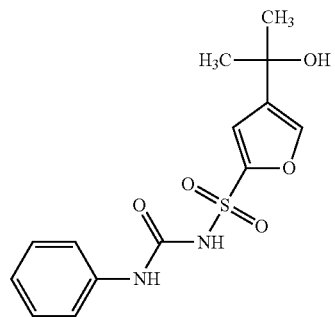 [SMILES: CC(C)(O)c1coc(S(=O)(=O)NC(=O)Nc2ccccc2)c1] | |
| 240 | 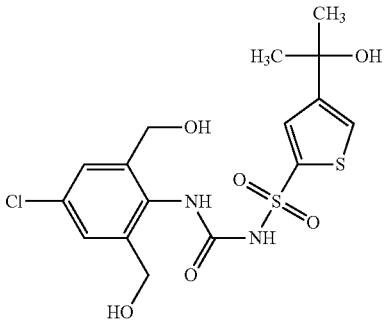 [SMILES: CC(C)(O)c1csc(S(=O)(=O)NC(=O)Nc2c(CO)cc(Cl)cc2CO)c1] | |
| 241 | 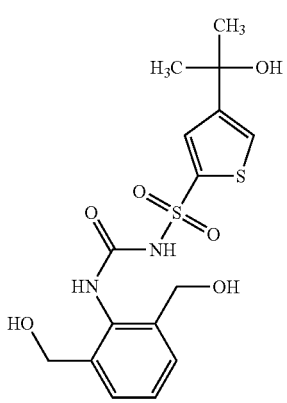 [SMILES: CC(C)(O)c1csc(S(=O)(=O)NC(=O)Nc2c(CO)cccc2CO)c1] | |

TABLE 2-continued

| Compound | Structure | hNLRP3 (THP-1, IL-1β) Average IC$_{50}$ (μM) |
|---|---|---|
| 242 | 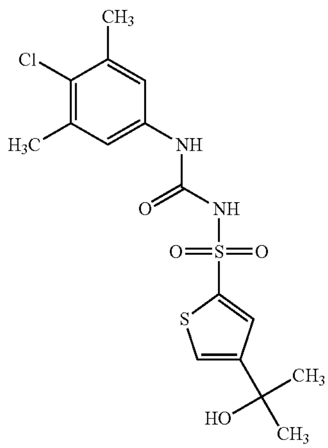 [SMILES: Cc1cc(NC(=O)NS(=O)(=O)c2cc(C(C)(C)O)cs2)cc(C)c1Cl] | |
| 243 | 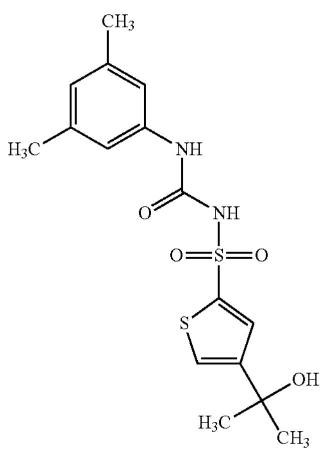 [SMILES: Cc1cc(C)cc(NC(=O)NS(=O)(=O)c2cc(C(C)(C)O)cs2)c1] | |
| 244 | 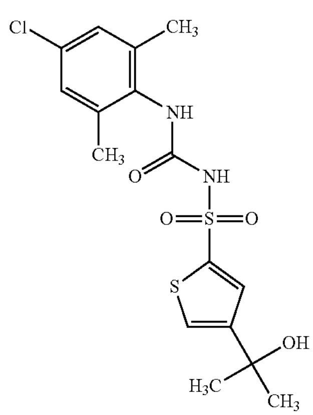 [SMILES: Cc1cc(Cl)cc(C)c1NC(=O)NS(=O)(=O)c1cc(C(C)(C)O)cs1] | |

TABLE 2-continued

| Compound | Structure | hNLRP3 (THP-1, IL-1β) Average IC$_{50}$ (μM) |
|---|---|---|
| 247 | 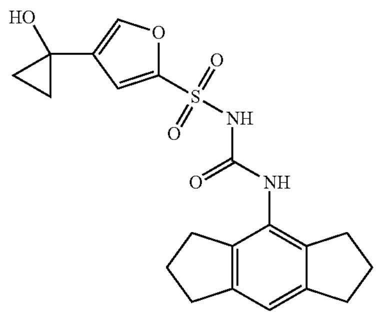 | ++++ |
| 250 | 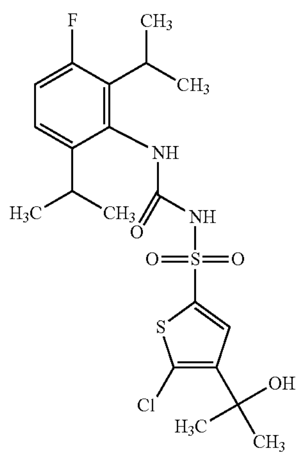 [SMILES: CC(C)c1ccc(F)c(C(C)C)c1NC(=O)NS(=O)(=O)c1cc(C(C)(C)O)c(Cl)s1] | +++ |
| 251 | 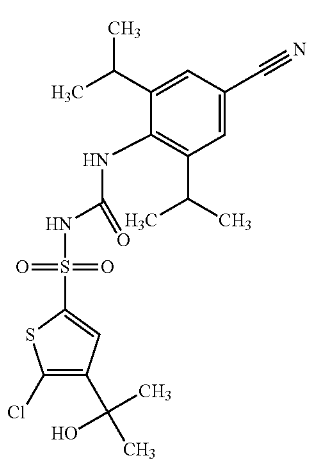 [SMILES: CC(C)c1cc(C#N)cc(C(C)C)c1NC(=O)NS(=O)(=O)c1cc(C(C)(C)O)c(Cl)s1] | ++++ |

TABLE 2-continued

| Compound | Structure | hNLRP3 (THP-1, IL-1β) Average IC$_{50}$ (μM) |
|---|---|---|
| 252 | 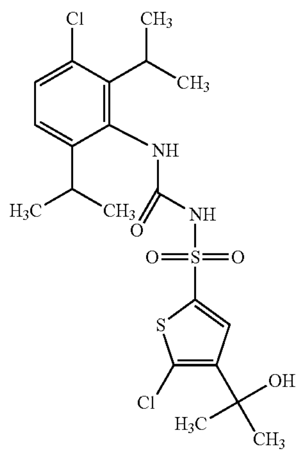 [SMILES: CC(C)c1ccc(Cl)c(C(C)C)c1NC(=O)NS(=O)(=O)c1cc(C(C)(C)O)c(Cl)s1] | ++ |
| 253 | 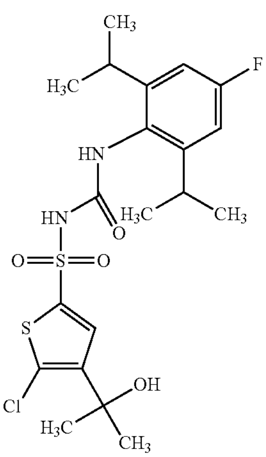 [SMILES: CC(C)c1cc(F)cc(C(C)C)c1NC(=O)NS(=O)(=O)c1cc(C(C)(C)O)c(Cl)s1] | ++++ |
| 254 | 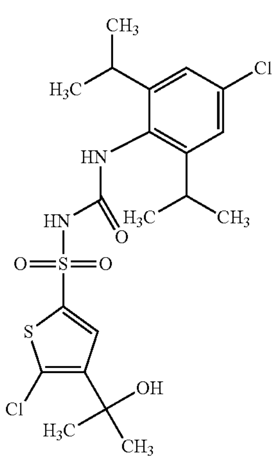 [SMILES: CC(C)c1cc(Cl)cc(C(C)C)c1NC(=O)NS(=O)(=O)c1cc(C(C)(C)O)c(Cl)s1] | ++++ |

TABLE 2-continued

| Compound | Structure | hNLRP3 (THP-1, IL-1β) Average IC$_{50}$ (μM) |
|---|---|---|
| 255 | 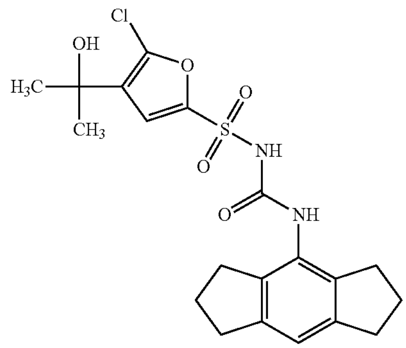 [SMILES: CC(C)(O)c1cc(S(=O)(=O)NC(=O)Nc2c3c(cc4c2CCC4)CCC3)oc1Cl] | ++++ |
| 257 | 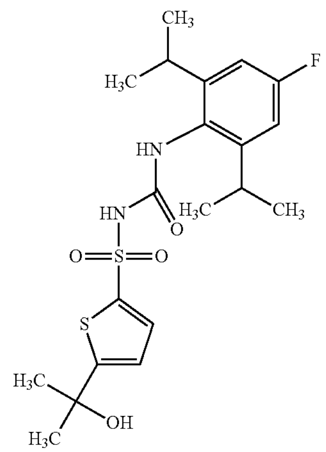 | ++++ |
| 258 | 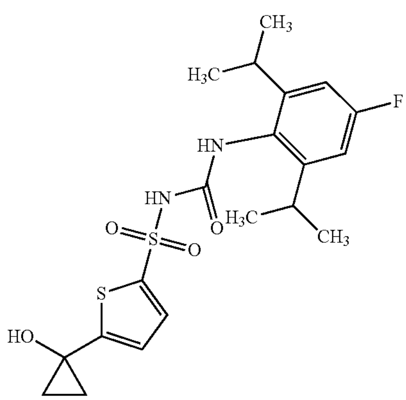 [SMILES: CC(C)c1cc(F)cc(C(C)C)c1NC(=O)NS(=O)(=O)c1ccc(C2(O)CC2)s1] | ++++ |
| 259 | 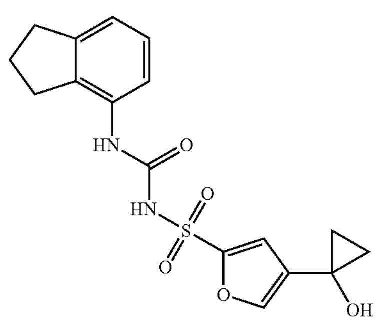 [SMILES: O=C(Nc1cccc2c1CCC2)NS(=O)(=O)c1cc(C2(O)CC2)co1] | +++ |

TABLE 2-continued

| Compound | Structure | hNLRP3 (THP-1, IL-1β) Average IC$_{50}$ (μM) |
|---|---|---|
| 260 | 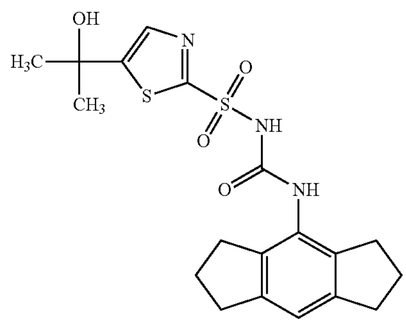 [SMILES: CC(C)(O)c1cnc(S(=O)(=O)NC(=O)Nc2c3c(cc4c2CCC4)CCC3)s1] | |
| 261 | 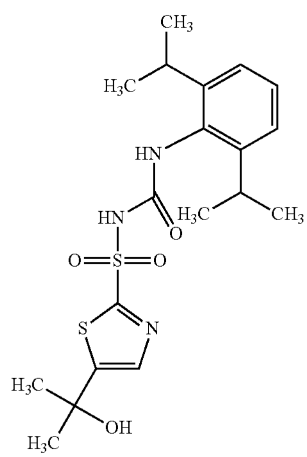 [SMILES: CC(C)c1cccc(C(C)C)c1NC(=O)NS(=O)(=O)c1ncc(C(C)(C)O)s1] | +++ |
| 262 | 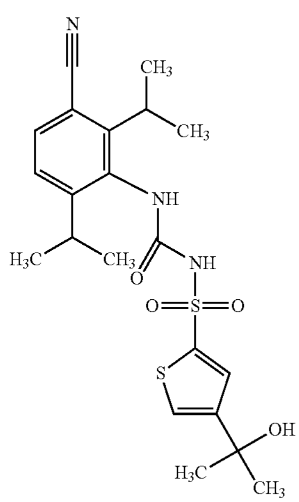 [SMILES: CC(C)c1ccc(C#N)c(C(C)C)c1NC(=O)NS(=O)(=O)c1cc(C(C)(C)O)cs1] | +++ |

TABLE 2-continued

| Compound | Structure | hNLRP3 (THP-1, IL-1β) Average IC$_{50}$ (μM) |
|---|---|---|
| 263 | 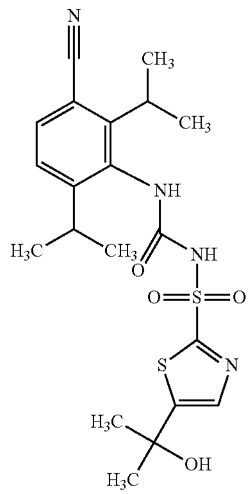 [SMILES: CC(C)c1ccc(C#N)c(C(C)C)c1NC(=O)NS(=O)(=O)c1ncc(C(C)(C)O)s1] | +++ |
| 264 | 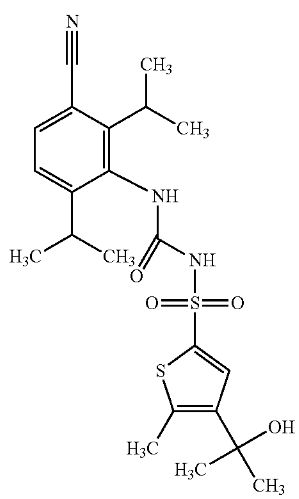 [SMILES: Cc1sc(S(=O)(=O)NC(=O)Nc2c(C(C)C)ccc(C#N)c2C(C)C)cc1C(C)(C)O] | ++ |
| 265 | 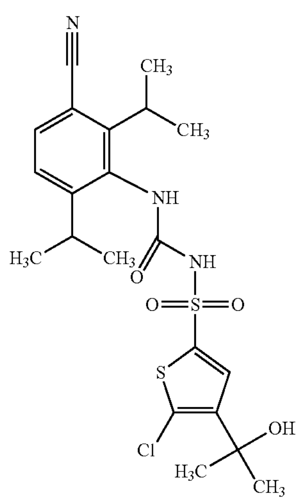 [SMILES: CC(C)c1ccc(C#N)c(C(C)C)c1NC(=O)NS(=O)(=O)c1cc(C(C)(C)O)c(Cl)s1] | ++ |

TABLE 2-continued

| Compound | Structure | hNLRP3 (THP-1, IL-1β) Average IC$_{50}$ (μM) |
|---|---|---|
| 266 | 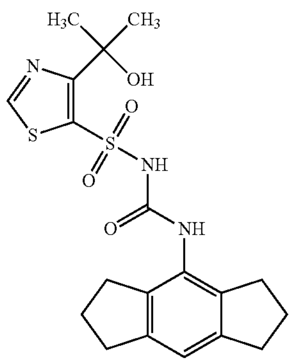 [SMILES: CC(C)(O)c1ncsc1S(=O)(=O)NC(=O)Nc1c2c(cc3c1CCC3)CCC2] | +++ |
| 267 | 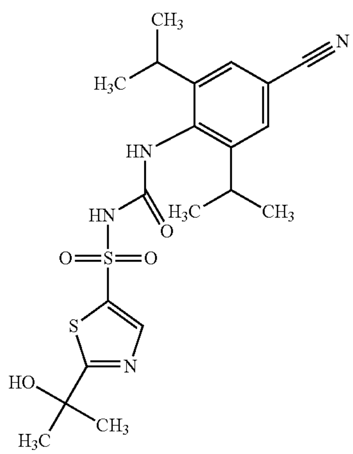 [SMILES: CC(C)c1cc(C#N)cc(C(C)C)c1NC(=O)NS(=O)(=O)c1cnc(C(C)(C)O)s1] | +++ |
| 268 | 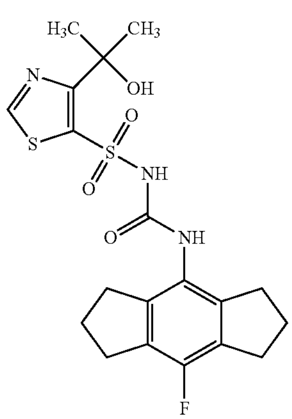 [SMILES: CC(C)(O)c1ncsc1S(=O)(=O)NC(=O)Nc1c2c(c(F)c3c1CCC3)CCC2] | +++ |

TABLE 2-continued
| Compound | Structure | hNLRP3 (THP-1, IL-1β) Average IC$_{50}$ (μM) |
|---|---|---|
| 269 | 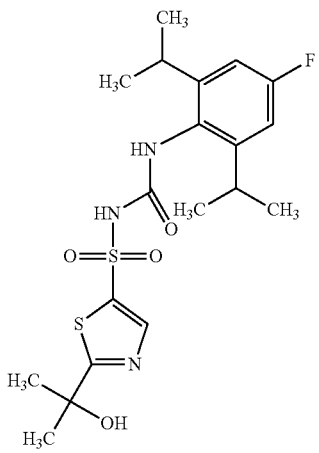 [SMILES: CC(C)c1cc(F)cc(C(C)C)c1NC(=O)NS(=O)(=O)c1cnc(C(C)(C)O)s1] | +++ |
| 270 | 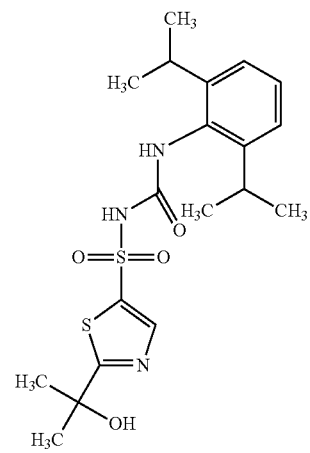 [SMILES: CC(C)c1cccc(C(C)C)c1NC(=O)NS(=O)(=O)c1cnc(C(C)(C)O)s1] | +++ |
| 271 | 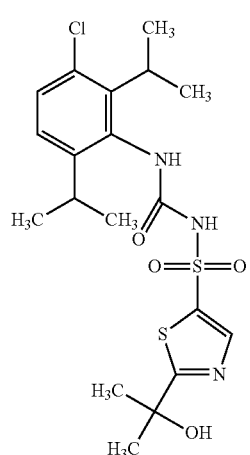 | +++ |

TABLE 2-continued

| Compound | Structure | hNLRP3 (THP-1, IL-1β) Average IC$_{50}$ (μM) |
|---|---|---|
| 272 | 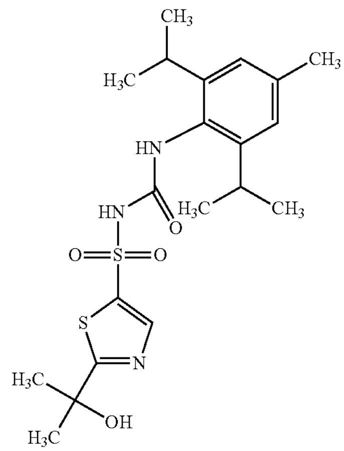 [SMILES: Cc1cc(C(C)C)c(NC(=O)NS(=O)(=O)c2cnc(C(C)(C)O)s2)c(C(C)C)c1] | +++ |
| 273 | 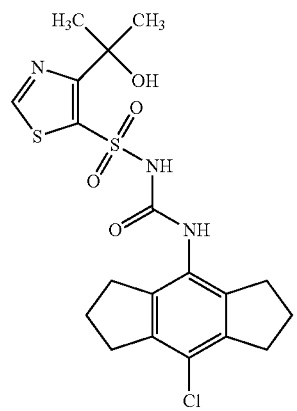 | ++ |
| 274 | | ++ | and pharmaceutically acceptable salts thereof.

Pharmaceutical Compositions and Administration

General

In some embodiments, a chemical entity (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-400% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methoxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry,* 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP1 or NLRP3 or both NLRP1 and NLRP3 activity (e.g., an increase, e.g., NLRP1/3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune diseases such as rheumatoid arthritis, systemic Lupus erythematosus, auto-immune thyroiditis; Addison's disease, and pernicious anemia, cancer, and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR_014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20

In some embodiments, the methods described herein further include the step of identifying a subject (e.g., a patient) in need of treatment for an indication related to NLRP1 activity, such as an indication related NLRP1 polymorphism.

In some embodiments, the methods described herein further include the step of identifying a subject (e.g., a patient) in need of treatment for an indication related to NLRP1 activity, such as an indication related to NLRP1 where polymorphism is a gain of function In some embodiments, the methods described herein further include the step of identifying a subject (e.g., a patient) in need of treatment for an indication related to NLRP1 activity, such as an indication related NLRP1 polymorphism found in vitiligo Vitiligo-Associated Autoimmune Disease.

In some embodiments, the methods described herein further include the step of identifying a subject (e.g., a patient) in need of treatment for an indication related to NLRP1 activity, such as an indication related where NLRP1 polymorphism is VAR_033239 (L155H)

In some embodiments, the methods described herein further include the step of identifying a subject (e.g., a patient) in need of treatment for an indication related to NLRP1 activity, such as an indication related where NLRP1 polymorphism is a natural variant reported in http://www.uniprot.org/uniprot/Q9C000

In some embodiments, the methods described herein further include the step of identifying a subject (e.g., a patient) in need of treatment for an indication related to NLRP1/3 activity, such as an indication related to point mutation of NLRP1/3 signaling.

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L.

Paquette, ed., Encyclopedia of Reagents for Organic Synthesis, John Wiley and Sons (1995), and subsequent editions thereof.

Scheme 1 shows an example of a method of preparation of compounds disclosed herein:

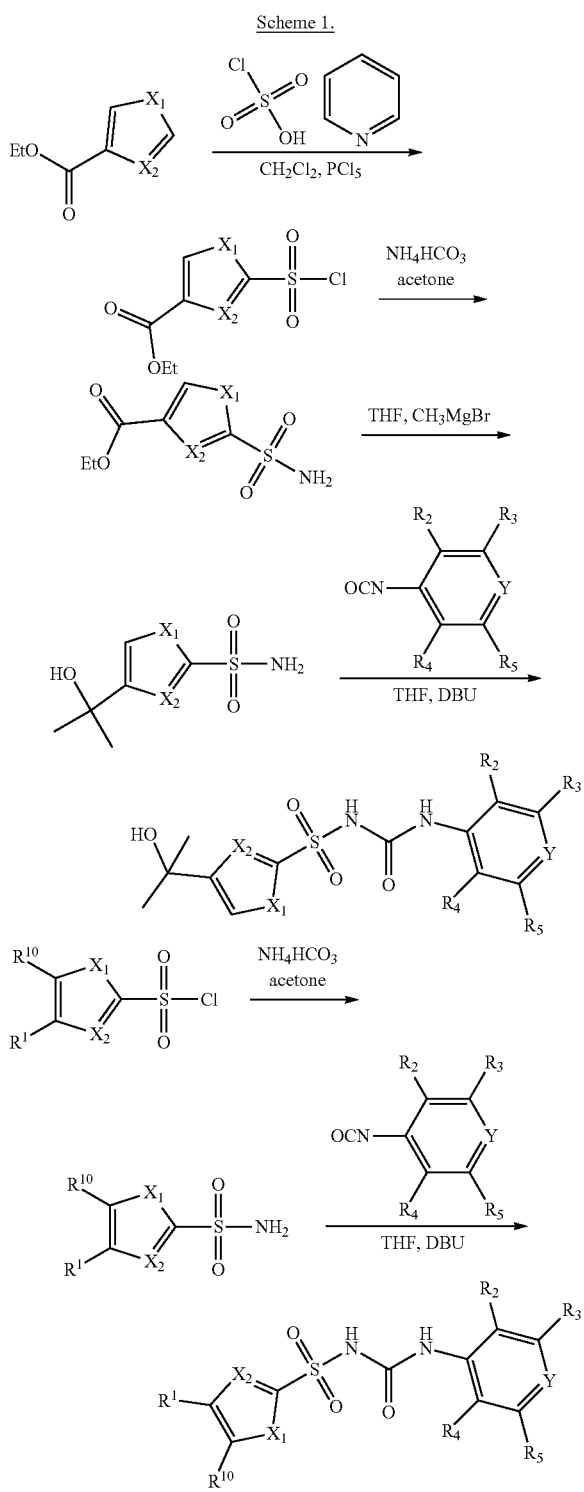

ACN=acetonitrile
AcOH=acetic acid
BTC=trichloromethyl chloroformate
DBU=1,8-diazabicycloundec-7-ene
DCM=dichloromethane
Dess-Martin=(1,1,1-triacetoxy)-1,1-dihydro-1,2-benziodoxol-3(1H)-one
DMEDA=N,N-dimethylethylenediamine
DMF=N,N-dimethylformamide
DMSO=dimethyl sulfoxide
Et=ethyl
EtOH=ethanol
LC-MS=liquid chromatography-mass spectrometry
LDA=lithium diisopropylamide
Me=methyl
MeOH=methanol
n-Bu=n-butyl
NBS=N-bromosuccinimide
NCS=N-chlorosuccinimide
NIS=N-iodosuccinimide
NMR=nuclear magnetic resonance
Pd(dppf)Cl$_2$=dichloro[1,1'-bis(diphenylphosphino)ferrocene]palladium
Pd(PPh$_3$)$_4$=tetrakis(triphenylphosphine)Palladium(0)
Ph=phenyl
HPLC=high performance liquid chromatography
PTSA=p-toluenesulfonic acid
Py=pyridine
RT=room temperature
TBAF=tetrabutylammonium fluoride
TBDPSCl=tert-butyldiphenylsilyl chloride
t-Bu=tert-butyl
TEA=triethylamine
TFA=trifluoroacetic acid
THF=tetrahydrofuran
Ti(i-PrO)$_4$=tetraisopropyl titanate
TLC=thin layer chromatography Materials and Methods The progress of reactions was often monitored by TLC or LC-MS. The identity of the products was often confirmed by LC-MS. The LC-MS was recorded using one of the following methods.

Method A: Shim-pack XR-ODS, C18, 3×50 mm, 2.5 um column, 1.0 uL injection 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, 1.5 mL/min flow rate, 90-900 amu scan range, 190-400 nm UV range, 10-95% (1.1 min), 95% (0.6 min) gradient with ACN and water (0.5% NH$_4$HCO$_3$), 2 minute total run time.

Method C: Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 um column, 1.0 uL injection, 1.5 mL/min flow rate, 90-900 amu scan range, 190-400 nm UV range, 10-95% (2.1 min), 95% (0.6 min) gradient with ACN and water (0.5% NH$_4$HCO$_3$), 3 minute total run time.

The final targets were purified by Prep-HPLC. The Prep-HPLC was carried out using the following method.

Method E: Pre-HPLC: Column, XBridge Shield RP18 OBD (19×250 mm, 10 um); mobile phase, Water (10 mmol/L NH$_4$HCO$_3$) and ACN, UV detection 254/210 nm.

NMR was recorded on BRUKER NMR 300.03 Mz, DUL-C-H, ULTRASHIELD™ 300, AVANCE II 300

PREPARATIVE EXAMPLES

Preparative Example 1

Compound 247

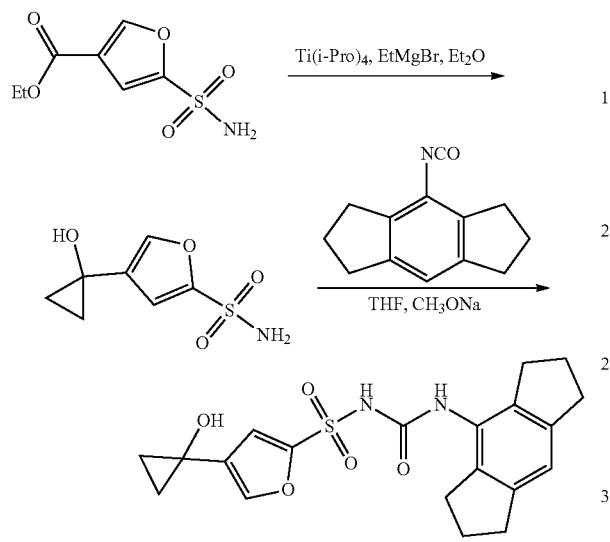

1. Synthesis of 4-(1-hydroxycyclopropyl)furan-2-sulfonamide

Into a 100-mL 3-necked round-bottom flask, was placed a solution of ethyl 5-sulfamoylfuran-3-carboxylate (1.314 g, 5.99 mmol, 1.00 equiv) and Ti(i-Pro)$_4$ (0.18 mL, 0.10 equiv) in ether (30 mL). To the solution was added EtMgBr (3 M in THF, 4.26 mL) dropwise at 0° C. in ice/water bath. The resulting solution was stirred overnight at room temperature. The reaction was then quenched by the addition of H$_2$SO$_4$ aqueous (2 M, 10 mL). The resulting solution was extracted with ethyl acetate (3×20 mL) and the combined organic layers were concentrated under vacuum. The residue was applied onto a silica gel column with ethyl acetate/petroleum ether (1:1). This resulted in 70 mg (6%) of 4-(1-hydroxycyclopropyl)furan-2-sulfonamide as a light yellow solid.

LC-MS: (ES, m/z): [M-H]$^+$=204.0

2. Synthesis of 1-(1,2,3,5,6,7-hexahydro-s-indacen-4-yl)-3-[4-(1-hydroxycyclopropyl)furan-2-sulfonyl] urea (Compound 130)

Into a 50-mL round-bottom flask, was placed a solution of 4-(1-hydroxycyclopropyl)furan-2-sulfonamide (70 mg, 0.34 mmol, 1.00 equiv) in tetrahydrofuran (20 mL). To the solution were added DBU (79 mg, 0.52 mmol, 1.51 equiv) and 4-isocyanato-1,2,3,5,6,7-hexahydro-s-indacene (76 mg, 0.38 mmol, 1.11 equiv). The resulting solution was stirred overnight at room temperature. The resulting mixture was concentrated under vacuum. The crude product was purified by Prep-HPLC with the following conditions (HPLC-10): Column, X Bridge Prep C18 OBD Column, 30*100 mm, 5 um; mobile phase, Water (10 mmol/L NH$_4$HCO$_3$) and ACN (30.0% ACN up to 40.0% in 10 min); Detector, UV 254/210 nm. This resulted in 21.3 mg (15%) of 1-(1,2,3,5,6,7-hexahydro-s-indacen-4-yl)-3-[4-(1-hydroxycyclopropyl)furan-2-sulfonyl]urea as a white solid.

LC-MS: (ES, m/z): [M-H]$^+$=401.1

H-NMR: (CD$_3$OD, 400 MHz, ppm): δ 7.55 (s, 1H), 6.92 (s, 1H), 6.78 (s, 1H), 2.91-2.83 (m, 4H), 2.75 (t, J=7.2 Hz, 4H), 2.10-1.96 (m, 4H), 1.11-1.08 (m, 2H), 0.92-0.85 (m, 2H).

Schemes of Final Targets: Schemes 2-5 Illustrate Several Conditions used for Coupling of Amine 1 and Sulfonamide 2 to Afford sulfonyl urea 3

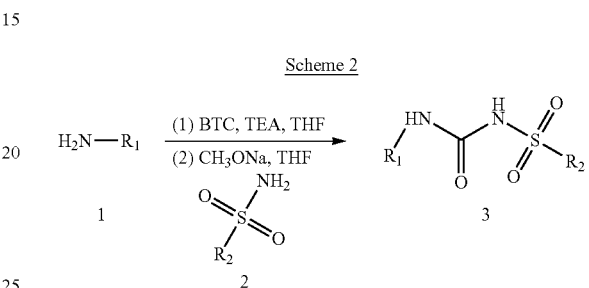

Scheme 2

Scheme 3

Scheme 4

Scheme 5

Schemes of Sulfonamides Intermediates: Schemes 6-13 Illustrate the Preparation of Sulfonamide Intermediates.

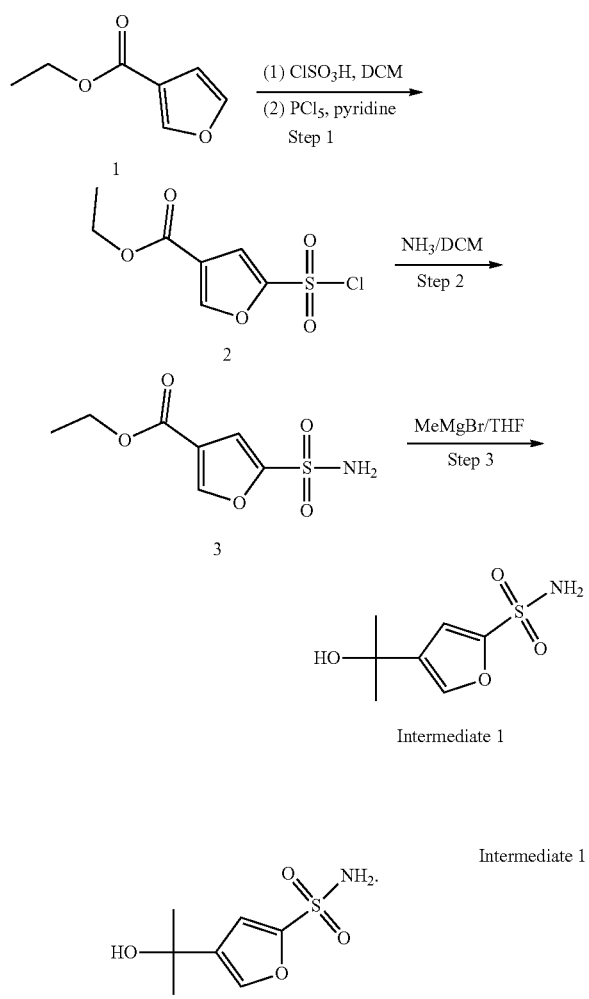

4-(2-Hydroxypropan-2-yl)furan-2-sulfonamide

Step 1: Ethyl 5-(chlorosulfonyl)furan-3-carboxylate

Into a 500-mL 3-necked round-bottom flask, was placed ethyl furan-3-carboxylate (7 g, 50 mmol) and DCM (200 mL). This was followed by the addition of chloranesulfonic acid (5.8 g, 49.8 mmol) dropwise with stirring at −10° C. Then the reaction was stirred for 48 h at RT and the system was cooled to −10° C. Then to the above was added pyridine (3.96 g, 50.1 mmol) and phosphorus pentachloride (11.46 g, 55.0 mmol). The resulting solution was stirred for 12 h at RT and then was quenched by the addition of 200 mL of water. The resulting solution was extracted with 3×200 mL of DCM and the organic layers combined and dried over anhydrous $Na_2SO_4$, then concentrated under vacuum. This resulted in 7.13 g (60%) of the title compound as light brown oil. The crude product was used in the next step.

Step 2: Ethyl 5-sulfamoylfuran-3-carboxylate

Into a 250-mL round-bottom flask, was placed a solution of ethyl 5-(chlorosulfonyl)furan-3-carboxylate (6.111 g, 25.61 mmol) in DCM (60 mL). To the above was added a saturated solution of ammonia in DCM (40 mL). The resulting solution was stirred for 3 h at RT and then was concentrated under vacuum. The residue was applied onto a silica gel column and eluted with ethyl acetate/petroleum ether (1:4 to 1:2). This resulted in 3.698 g (66%) of the title compound as a light yellow solid. MS-ESI: 218.0 (M−1).

Step 3: 4-(2-Hydroxypropan-2-yl)furan-2-sulfonamide

Into a 250-mL 3-necked round-bottom flask purged with and maintained under nitrogen, was placed a solution of ethyl 5-sulfamoylfuran-3-carboxylate (3.698 g, 16.87 mmol) in THF (100 mL). This was followed by the addition of MeMgBr/THF (3 M, 25 mL) dropwise with stirring at −10° C. The resulting solution was stirred for 10 h at RT and then was quenched by the addition of 50 mL of $NH_4Cl$ (sat.). The resulting solution was extracted with 3×50 mL of ethyl acetate and the organic layers combined and dried over anhydrous $Na_2SO_4$, then concentrated under vacuum. The residue was applied onto a silica gel column and eluted with ethyl acetate/petroleum ether (1:3 to 1:1). This resulted in 2.6 g (75%) of the title compound as a light yellow solid. MS-ESI: 204.0 (M−1).

TABLE 3

The Intermediates in the following Table were prepared using the similar procedures for converting compound 1 to Intermediate 1 shown in Scheme 6.

| Intermediate # | Structure | IUPAC Name | Mass Spec[M − H]⁻ |
|---|---|---|---|
| Intermediate 2 | (structure shown) | 4-(2-hydroxypropan-2-yl)thiophene-2-sulfonamide | 220.0 |

TABLE 3-continued

The Intermediates in the following Table were prepared using the similar procedures for converting compound 1 to Intermediate 1 shown in Scheme 6.

| Intermediate # | Structure | IUPAC Name | Mass Spec[M − H]⁻ |
|---|---|---|---|
| Intermediate 3 | 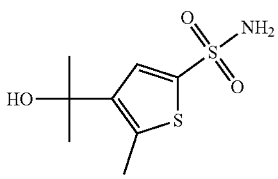 | 4-(2-hydroxypropan-2-yl)-5-methylthiophene-2-sulfonamide | 234.0 |

TABLE 4

The Intermediate in the following Table was prepared using the similar procedures for converting compound 2 to Intermediate 1 shown in Scheme 6.

| Intermediate # | Structure | IUPAC Name | Mass Spec[M − H]⁻ |
|---|---|---|---|
| Intermediate 4 | 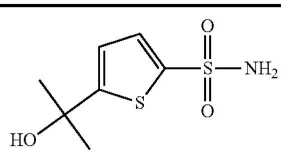 | 5-(2-hydroxypropan-2-yl)thiophene-2-sulfonamide | 220.0 |

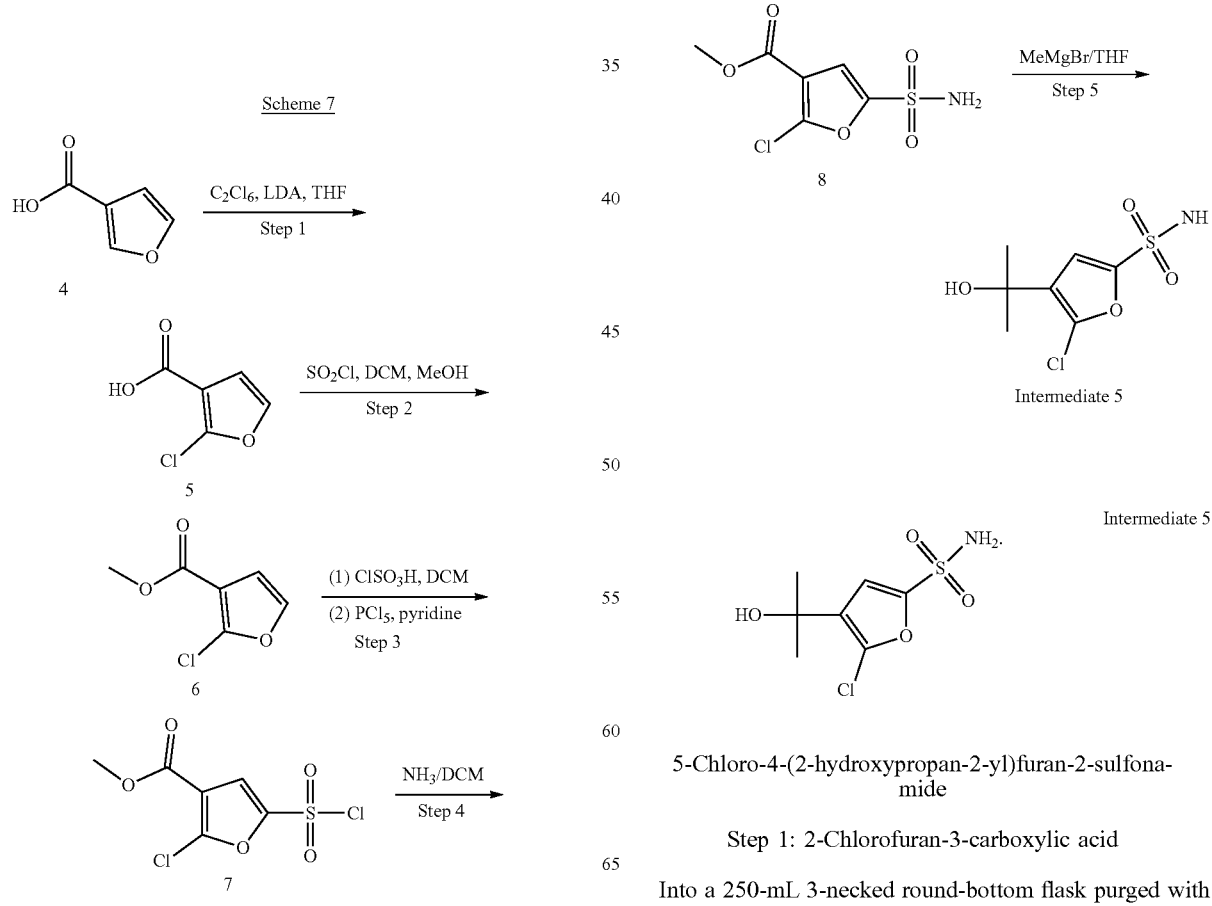

5-Chloro-4-(2-hydroxypropan-2-yl)furan-2-sulfonamide

Step 1: 2-Chlorofuran-3-carboxylic acid

Into a 250-mL 3-necked round-bottom flask purged with and maintained under nitrogen, was placed furan-3-carboxylic acid (2.24 g, 19.99 mmol) and THF (100 mL). This was followed by the addition of LDA/THF (2 M, 20 mL) dropwise with stirring at −78° C. and the resulting solution was stirred for 4 h at −78° C. Then to the resulting mixture was added hexachloroethane (5.208 g, 22.00 mmol) dropwise with stirring at −78° C. The resulting solution was stirred overnight at RT and then the pH value of the solution was adjusted to 2 with HCl (2 N). The resulting solution was extracted with 3×100 mL of ethyl acetate and the organic layers combined and concentrated under vacuum. The residue was applied onto a silica gel column and eluted with ethyl acetate/petroleum ether (1:3 to 1:1). This resulted in 2.099 g (72%) of the title compound as a light yellow solid. MS-ESI: 145.0, 147.0 (M−1).

Step 2: Methyl 2-chlorofuran-3-carboxylate

Into a 100-mL round-bottom flask, was placed 2-chlorofuran-3-carboxylic acid (1.052 g, 7.18 mmol) and DCM (20 mL). This was followed by the addition of SOCl$_2$ (5 mL) dropwise with stirring at 0° C. The resulting solution was stirred for 2 h at 42° C. The system was cooled to RT and MeOH (20 mL) was added and the resulting solution was stirred for 2 h at RT. The product was unstable and stored in MeOH solution.

Steps 3-5 used similar procedure for converting compound 1 to Intermediate 1 shown in Scheme 6 to afford Intermediate 5. MS-ESI: 238.0, 240.0 (M−1).

Scheme 8

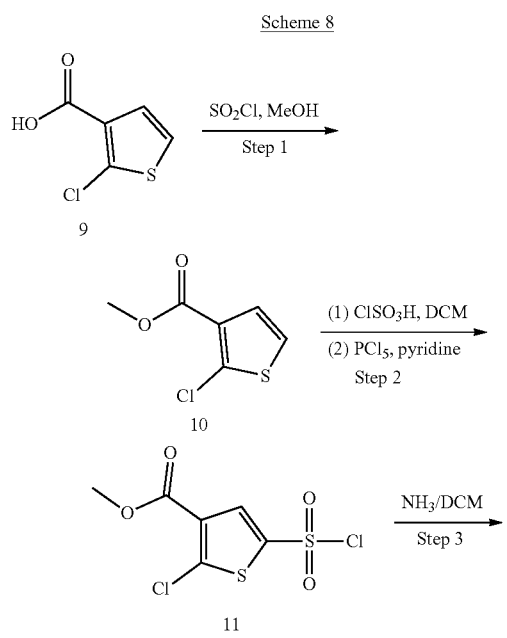

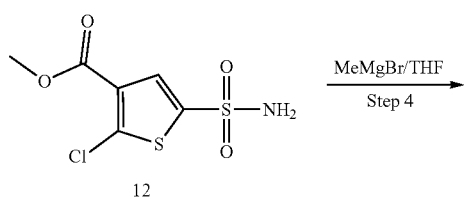

-continued

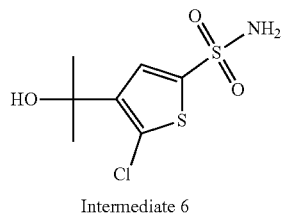

Intermediate 6

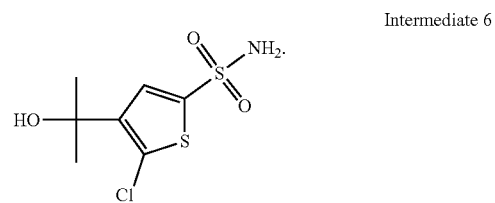

Intermediate 6

5-Chloro-4-(2-hydroxypropan-2-yl)thiophene-2-sulfonamide

Step 1: Methyl 2-chlorothiophene-3-carboxylate

Into a 100-mL round-bottom flask, was placed 2-chlorothiophene-3-carboxylic acid (3 g, 18.45 mmol) and MeOH (50 mL). This was followed by the addition of SO$_2$Cl (4.4 g, 37.29 mmol) dropwise with stirring at 0° C. The resulting solution was stirred for 3 h at RT and then was concentrated under vacuum. The residue was applied onto a silica gel column and with eluted ethyl acetate/petroleum ether (1:10 to 1:8). This resulted in 3.2 g (98%) of the title compound as a yellow oil.

Steps 2-4 used similar procedures for converting compound 1 to Intermediate 1 shown in Scheme 6 to afford Intermediate 6. MS-ESI: 254.0, 256.0 (M−1).

Scheme 9

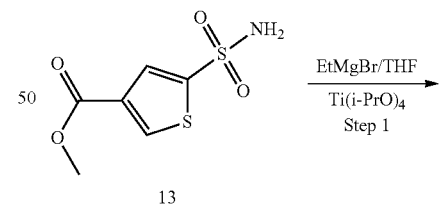

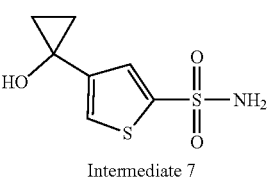

Intermediate 7

193

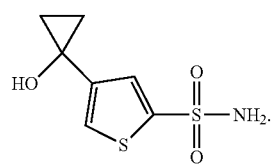

Intermediate 7

4-(1-Hydroxycyclopropyl)thiophene-2-sulfonamide

Step 1:
4-(1-Hydroxycyclopropyl)thiophene-2-sulfonamide

Into a 500-mL 3-necked round-bottom flask purged with and maintained under nitrogen, was placed methyl 5-sulfamoylthiophene-3-carboxylate (5.525 g, 24.97 mmol), THF (80 mL), and Ti(i-PrO)$_4$ (1.5 mL). This was followed by the addition of EtMgBr/THF (3 M, 21 mL) dropwise with stirring at 0° C. The resulting solution was stirred for 2 h at RT and then was quenched by the addition of 30 mL of NH$_4$Cl (sat.). The resulting solution was extracted with 3×40 mL of ethyl acetate and the organic layers combined and concentrated under vacuum. The residue was applied onto a silica gel column and eluted with ethyl acetate/petroleum ether (1:3 to 1:1). This resulted in 662 mg (12%) of the title compound as a light yellow solid. MS-ESI: 218.0 (M−1).

TABLE 5

The Intermediates in the following Table were prepared using the similar procedure for converting compound 13 to Intermediate 7 shown in Scheme 9.

| Intermediate # | Structure | IUPAC Name | Mass Spec[M − H]$^-$ |
|---|---|---|---|
| Intermediate 8 | 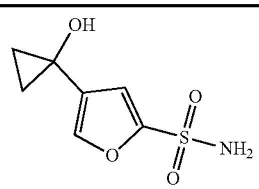 | 4-(1-hydroxycyclopropyl)furan-2-sulfonamide | 202.0 |
| Intermediate 9 | 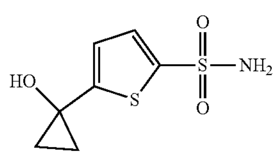 [SMILES: NS(=O)(=O)c1ccc(C2(O)CC2)s1] | 5-(1-hydroxycyclopropyl)thiophene-2-sulfonamide | 218.0 |

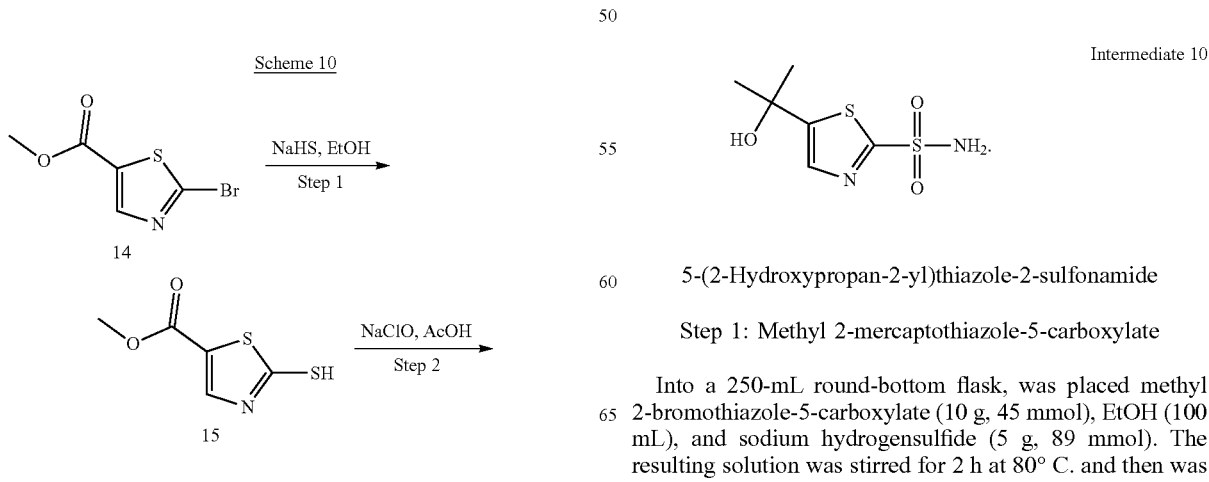

5-(2-Hydroxypropan-2-yl)thiazole-2-sulfonamide

Step 1: Methyl 2-mercaptothiazole-5-carboxylate

Into a 250-mL round-bottom flask, was placed methyl 2-bromothiazole-5-carboxylate (10 g, 45 mmol), EtOH (100 mL), and sodium hydrogensulfide (5 g, 89 mmol). The resulting solution was stirred for 2 h at 80° C. and then was cooled to 0° C. with a water/ice bath. The pH value of the solution was adjusted to 3 with an aqueous solution of hydrogen chloride (1 N). The solids were collected by filtration. This resulted in 6 g (76%) of the title compound as a light yellow solid.

MS-ESI: 176.0 (M+1).

Step 2: Methyl 2-(chlorosulfonyl)thiazole-5-carboxylate

Into a 250-mL round-bottom flask, was placed methyl 2-mercaptothiazole-5-carboxylate (6 g, 34 mmol) and acetic acid (60 mL). This was followed by the addition of sodium hypochloride (60 mL, 8%-10% wt) in portions at 0° C. The resulting solution was stirred for 1 h at RT and then was diluted with 100 mL of water. The solution was extracted with 3×50 mL of DCM and the organic layers combined and dried over anhydrous $Na_2SO_4$, then concentrated under vacuum. This resulted in 5 g (crude, 60%) of the title compound as yellow oil. The crude product was used in the next step.

Step 3: Methyl 2-sulfamoylthiazole-5-carboxylate

Into a 250-mL round-bottom flask, was placed methyl 2-(chlorosulfonyl)thiazole-5-carboxylate (5 g, 21 mmol) and DCM (50 mL). This was followed by the addition of a saturated solution of ammonia in DCM (10 mL) in portions at RT. The resulting solution was stirred for 2 h at RT and then was concentrated under vacuum. The residue was applied onto a silica gel column and eluted with ethyl acetate/petroleum ether (1:5 to 1:3). This resulted in 3 g (65%) of the title compound as a white solid. MS-ESI: 223.0 (M+1).

Step 4: 5-(2-Hydroxypropan-2-yl)thiazole-2-sulfonamide

Into a 250-mL round-bottom flask purged with and maintained under nitrogen, was placed a solution of methyl 2-sulfamoylthiazole-5-carboxylate (3 g, 13.5 mmol) in THF (25 mL). This was followed by the addition of MeMgBr/THF (3 M, 18 mL) dropwise with stirring at 0° C. The resulting solution was stirred for 14 h at RT and then was quenched by the addition of 20 mL of $NH_4Cl$ (sat.). The resulting solution was extracted with 3×30 mL of DCM and the organic layers combined and dried over anhydrous $Na_2SO_4$, then concentrated under vacuum. The residue was applied onto a silica gel column and eluted with ethyl acetate/petroleum ether (1:5 to 1:3). This resulted in 2.3 g (78%) of the title compound as a white solid. MS-ESI: 223.0 (M+1), 221.0 (M−1).

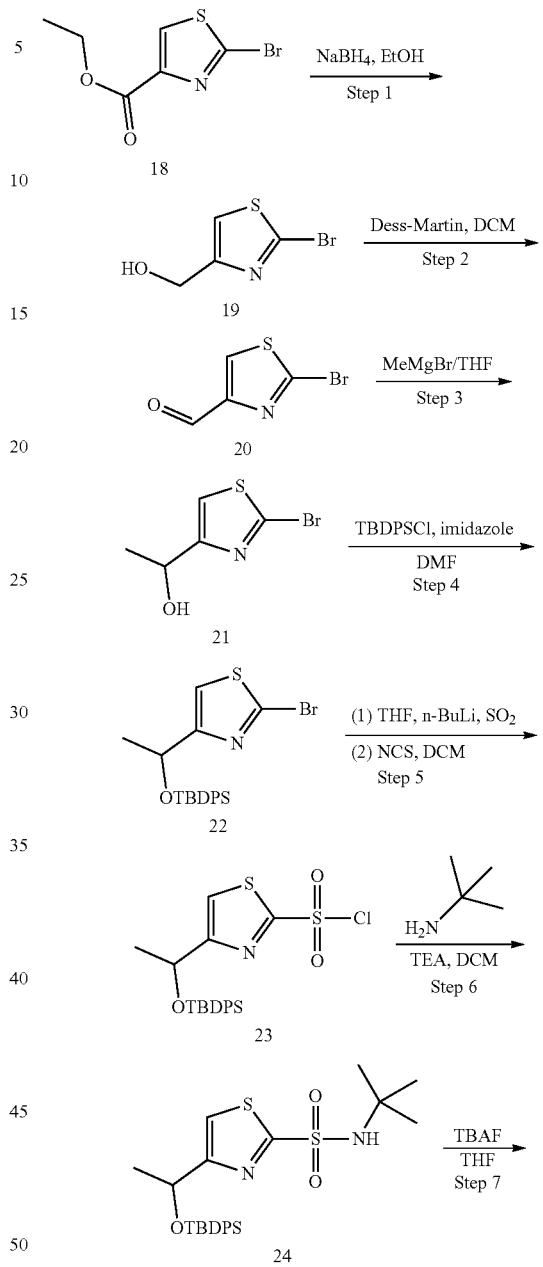

Scheme 11

TABLE 6

The Intermediate in the following Table was prepared using the similar procedures for converting compound 14 to Intermediate 10 shown in Scheme 10.

| Intermediate # | Structure | IUPAC Name | Mass Spec[M − H]⁻ |
|---|---|---|---|
| Intermediate 11 | 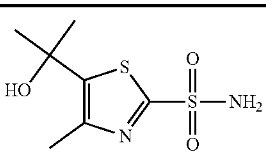 | 5-(2-hydroxypropan-2-yl)-4-methylthiazole-2-sulfonamide | 235.0 |

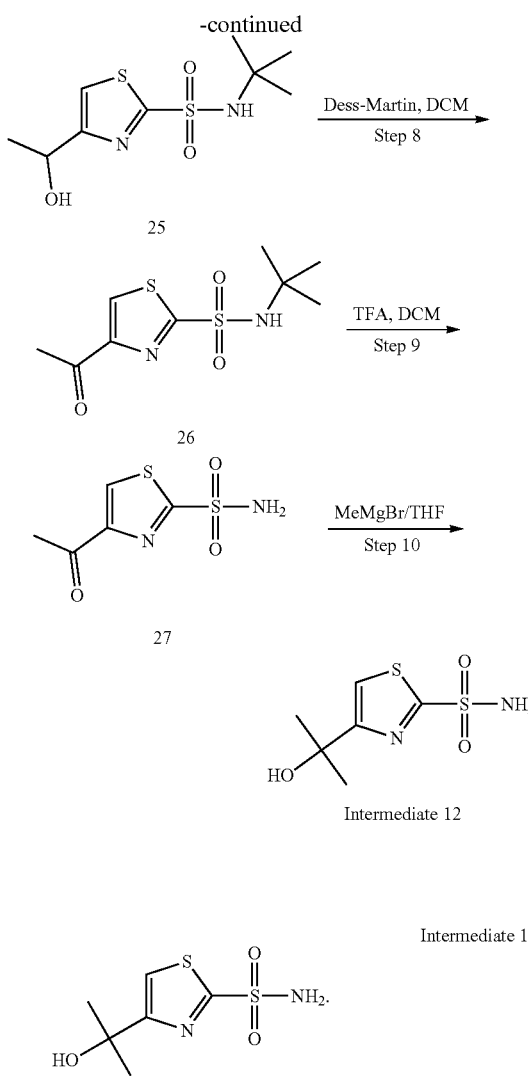

4-(2-Hydroxypropan-2-yl)thiazole-2-sulfonamide

Step 1: (2-Bromothiazol-4-yl)methanol

Into a 500-mL round-bottom flask, was placed ethyl 2-bromothiazole-4-carboxylate (14 g, 59.30 mmol) and EtOH (200 mL). This was followed by the addition of NaBH$_4$ (2.3 g, 60.53 mmol) in portions at 0° C. The resulting solution was stirred for 3 h at RT and then was quenched by the addition of 100 mL of water. The resulting solution was extracted with 2×200 mL of DCM and the organic layers combined and dried over anhydrous Na$_2$SO$_4$, then concentrated under vacuum. This resulted in 10 g (87%) of the title compound as colorless oil. MS-ESI: 195.9, 193.9 (M+1).

Step 2: 2-Bromothiazole-4-carbaldehyde

Into a 250-mL round-bottom flask, was placed (2-bromothiazol-4-yl)methanol (10 g, 51.53 mmol), DCM (100 mL) and Dess-Martin reagent (24 g, 56.60 mmol). The resulting solution was stirred for 2 h at RT and then was concentrated under vacuum. The residue was applied onto a silica gel column and eluted with ethyl acetate/petroleum ether (1:50 to 1:20). This resulted in 8 g (81%) of the title compound as yellow oil. MS-ESI: 193.9, 191.9 (M+1).

Step 3: 1-(2-Bromothiazol-4-yl)ethanol

Into a 250-mL 3-necked round-bottom flask purged with and maintained under nitrogen, was placed 2-bromothiazole-4-carbaldehyde (8 g, 41.66 mmol) and THF (100 mL). This was followed by the addition of MeMgBr/THF (3 M, 15 mL) dropwise with stirring at 0° C. The resulting solution was stirred for 2 h at RT and then was quenched by the addition of 100 mL of NH$_4$Cl (sat.). The resulting solution was extracted with 3×100 mL of DCM and the organic layers combined and concentrated under vacuum. The residue was applied onto a silica gel column and eluted with ethyl acetate/petroleum ether (1:10 to 1:5). This resulted in 6 g (69%) of the title compound as brown oil. MS-ESI: 209.9, 207.9 (M+1).

Step 4: 2-Bromo-4-(1-(tert-butyldiphenylsilyloxy)ethyl)thiazole

Into a 250-mL round-bottom flask, was placed 1-(2-bromothiazol-4-yl)ethanol (6 g, 28.84 mmol), DMF (50 mL), imidazole (4 g, 58.82 mmol) and TBDPSCl (8.7 g, 31.64 mmol). The resulting solution was stirred for 12 h at RT and then was diluted with 100 mL of water. The resulting solution was extracted with 3×100 mL of DCM and the organic layers combined and concentrated under vacuum. The residue was applied onto a silica gel column and eluted with ethyl acetate/petroleum ether (1:100 to 1:50). This resulted in 10 g (78%) of the title compound as a light yellow oil. MS-ESI: 448.1, 446.1 (M+1).

Step 5: 4-(1-(Tert-butyldiphenylsilyloxy)ethyl)thiazole-2-sulfonyl chloride

Into a 250-mL 3-necked round-bottom flask purged with and maintained under nitrogen, was placed 2-bromo-4-(1-(tert-butyldiphenylsilyloxy)ethyl)thiazole (10 g, 22.40 mmol) and THF (100 mL). This was followed by the addition of n-BuLi (2.5 M, 11 mL) dropwise with stirring at −78° C. The resulting solution was stirred for 30 min at −78° C., followed by the introduction of SO$_2$. The reaction was warmed to RT and stirred for 30 min and then was concentrated under vacuum. The residue was diluted with DCM (100 mL) and then NCS (3.6 g, 26.96 mmol) was added. The resulting solution was stirred for 30 min at RT and then was concentrated under vacuum. This resulted in 8 g (crude, 77%) of the title compound as a white solid. The crude product was used in the next step.

Step 6: N-tert-butyl-4-(1-(tert-butyldiphenylsilyloxy)ethyl)thiazole-2-sulfonamide Into a 100-mL round-bottom flask purged with and maintained under nitrogen, was placed 4-(1-(tert-butyldiphenylsilyloxy)ethyl)thiazole-2-sulfonyl chloride (8 g, 17.16 mmol), DCM (50 mL), TEA (3.5 g, 34.59 mmol) and 2-methylpropan-2-amine (1.9 g, 25.98 mmol). The resulting solution was stirred for 2 h at RT and then was concentrated under vacuum. The residue was applied onto a silica gel column and eluted with ethyl acetate/petroleum ether (1:15 to 1:5). This resulted in 8 g (93%) of the title compound as brown oil. MS-ESI: 503.2 (M+1).

Step 7: N-tert-butyl-4-(1-hydroxyethyl)thiazole-2-sulfonamide

Into a 250-mL round-bottom flask, was placed N-tert-butyl-4-(1-(tert-butyldiphenylsilyloxy)ethyl)thiazole-2-sulfonamide (8 g, 15.91 mmol), THF (100 mL) and TBAF (9.6 g, 292.46 mmol). The resulting solution was stirred for 2 h at RT and then was diluted with 100 mL of water. The resulting solution was extracted with 3×100 mL of DCM and the organic layers combined and concentrated under vacuum. The residue was applied onto a silica gel column and eluted with ethyl acetate/petroleum ether (1:10 to 1:3). This resulted in 4 g (95%) of the title compound as light yellow oil. MS-ESI: 265.1 (M+1).

Step 8: 4-Acetyl-N-tert-butylthiazole-2-sulfonamide

Into a 100-mL round-bottom flask, was placed N-tert-butyl-4-(1-hydroxyethyl)thiazole-2-sulfonamide (4 g, 15.13 mmol), DCM (50 mL) and Dess-Martin reagent (7.1 g, 16.64 mmol). The resulting solution was stirred for 2 h at RT and then was concentrated under vacuum. The residue was applied onto a silica gel column and eluted with ethyl acetate/petroleum ether (1:10 to 1:3). This resulted in 3.5 g (88%) of the title compound as light yellow oil. MS-ESI: 263.0 (M+1).

Step 9: 4-Acetylthiazole-2-sulfonamide

Into a 100-mL round-bottom flask, was placed 4-acetyl-N-tert-butylthiazole-2-sulfonamide (3.5 g, 13.34 mmol), DCM (5 mL) and TFA (20 mL). The resulting solution was stirred for 14 h at 40° C. and then was concentrated under vacuum. The residue was applied onto a silica gel column and eluted with ethyl acetate/petroleum ether (1:10 to 1:3). This resulted in 2.5 g (91%) of the title compound as a gray solid. MS-ESI: 207.0 (M+1).

Step 10: 4-(2-Hydroxypropan-2-yl)thiazole-2-sulfonamide

Into a 100-mL 3-necked round-bottom flask purged with and maintained under nitrogen, was placed 4-acetylthiazole-2-sulfonamide (412 mg, 2.00 mmol) and THF (10 mL). This was followed by the addition of MeMgBr/THF (3 M, 2.67 mL) dropwise with stirring at 0° C. The resulting solution was stirred for 3 h at RT and then was quenched by the addition of 10 mL of NH4Cl (sat.). The resulting solution was extracted with 4×10 mL of ethyl acetate and the organic layers combined and concentrated under vacuum. The residue was applied onto a silica gel column and eluted with ethyl acetate/petroleum ether (1:1 to 2:3). This resulted in 200 mg (45%) of the title compound as a light yellow solid. MS-ESI: 223.0 (M+1).

Scheme 12

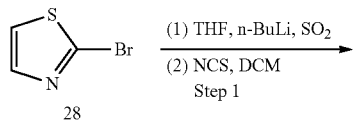

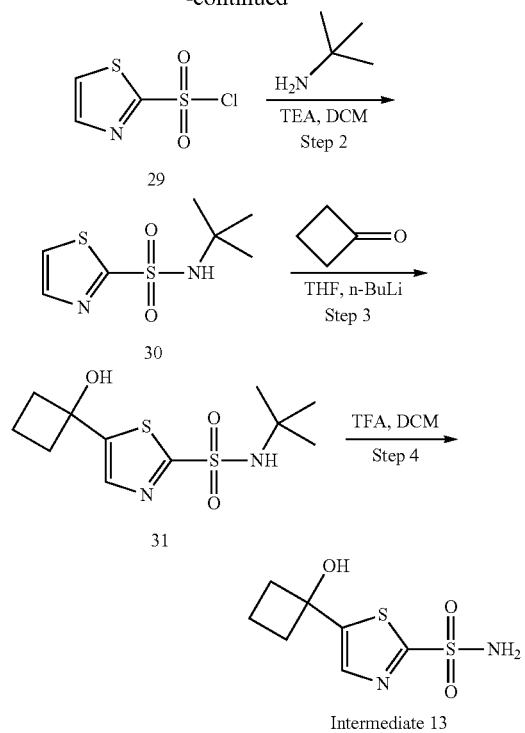

5-(1-Hydroxycyclobutyl)thiazole-2-sulfonamide

Steps 1-2 used the similar procedures for converting compound 22 to compound 24 shown in Scheme 12 to afford compound 30. MS-ESI: 219.0 (M−1).

Step 3: N-tert-butyl-5-(1-hydroxycyclobutyl)thiazole-2-sulfonamide

Into a 100-mL 3-necked round-bottom flask purged with and maintained under nitrogen, was placed N-tert-butylthiazole-2-sulfonamide (500 mg, 2.27 mmol), THF (20 mL). This was followed by the addition of n-BuLi (2.5 M, 2 mL) dropwise with stirring at −78° C. The resulting solution was stirred for 20 min at −78° C. and then to the above was added cyclobutanone (317 mg, 4.52 mmol) dropwise with stirring at −78° C. The resulting solution was stirred for 20 min at −78° C. and then was quenched by the addition of 20 mL of NH4Cl (sat.). The resulting solution was extracted with 3×20 mL of DCM and the organic layers combined and concentrated under vacuum. The residue was applied onto a silica gel column and eluted with ethyl acetate/petroleum ether (1:5 to 1:3). This resulted in 300 mg (46%) of the title compound as a light yellow solid. MS-ESI: 289.1 (M−1).

Step 4:
5-(1-Hydroxycyclobutyl)thiazole-2-sulfonamide

Into a 50-mL round-bottom flask, was placed N-tert-butyl-5-(1-hydroxycyclobutyl)thiazole-2-sulfonamide (300 mg, 1.03 mmol), DCM (10 mL), and TFA (10 mL). The resulting solution was stirred for 12 h at 40° C. and then was concentrated under vacuum. The residue was applied onto a silica gel column and eluted with ethyl acetate/petroleum ether (1:3 to 1:1). This resulted in 100 mg (41%) of the title compound as a yellow solid.

MS-ESI: 233.0 (M−1).

Scheme 13

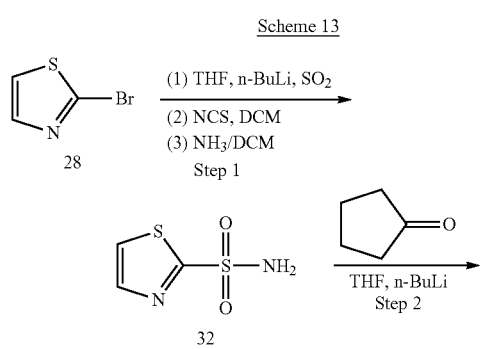

5-(1-Hydroxycyclopentyl)thiazole-2-sulfonamide

Step 1: Thiazole-2-sulfonamide

Into a 100-mL 3-necked round-bottom flask purged with and maintained under nitrogen, was placed 2-bromothiazole (2 g, 12.19 mmol) and THF (20 mL). This was followed by the addition of n-BuLi (2.5 M, 5.4 mL) dropwise with stirring at −78° C. The resulting solution was stirred for 30 min at −78° C. To the above solution was introduced $SO_2$. The reaction was warmed to RT and stirred for 30 min and then was concentrated under vacuum. The residue was diluted with DCM (20 mL) and then NCS (1.95 g, 14.60 mmol) was added. The resulting solution was stirred for 30 min at RT. To the above was added a saturated solution of ammonia in DCM (30 mL). The resulting solution was stirred for 2 h at RT and then was concentrated under vacuum. The residue was applied onto a silica gel column and eluted with ethyl acetate/petroleum ether (1:5 to 1:3). This resulted in 1.3 g (65%) of the title compound as a light yellow solid. MS-ESI: 163.0 (M−1). Step 2 used similar procedure for converting compound 30 to compound 31 shown in Scheme 12 to afford Intermediate 14. MS-ESI: 247.0 (M−1).

TABLE 7

The Intermediate in the following Table was prepared using the similar procedures for converting compound 28 to Intermediate 14 shown in Scheme 13.

| Intermediate # | Structure | IUPAC Name | Mass Spec[M − H]⁻ |
|---|---|---|---|
| Intermediate 15 | 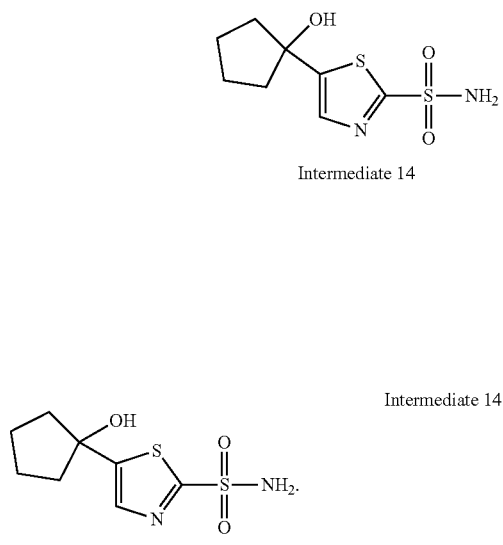 | 5-(1-hydroxycyclohexyl)thiazole-2-sulfonamide | 261.0 |

Schemes for amine Intermediates: Schemes 14-23 illustrate the amine intermediates preparation.

Scheme 14

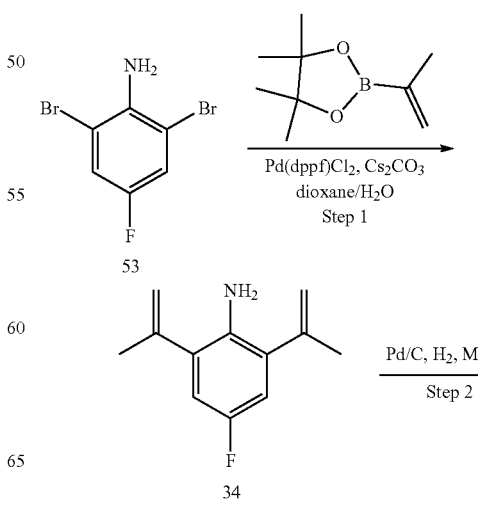

-continued

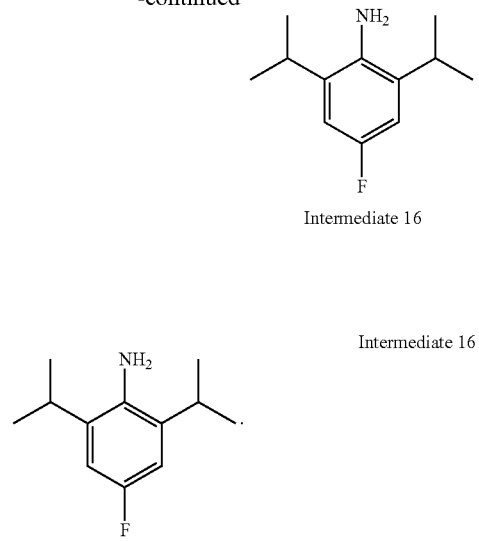

Intermediate 16

4-Fluoro-2,6-diisopropylbenzenamine

Step 1: 4-Fluoro-2,6-di(prop-1-en-2-yl)benzenamine

Into a 500-mL round-bottom flask purged with and maintained under nitrogen, was placed 2,6-dibromo-4-fluorobenzenamine (15 g, 55.8 mmol), dioxane (150 mL), water (15 mL), Cs$_2$CO$_3$ (55 g, 169 mmol), 4,4,5,5-tetramethyl-2-(prop-1-en-2-yl)-1,3,2-dioxaborolane (25 g, 149 mmol), and Pd(dppf)Cl$_2$ (4 g, 5.47 mmol). The resulting solution was stirred for 15 h at 100° C. and then was concentrated under vacuum. The residue was applied onto a silica gel column and eluted with ethyl acetate/petroleum ether (1:10 to 1:8). This resulted in 9.2 g (86%) of the title compound as a brown oil. MS-ESI: 192.1 (M+1).

Step 2: 4-Fluoro-2,6-diisopropylbenzenamine

Into a 500-mL round-bottom flask, was placed 4-fluoro-2,6-di(prop-1-en-2-yl)benzenamine (9.2 g, 48.1 mmol) and MeOH (200 mL). Then Pd/C (10% wt, 900 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:10 to 1:8). This resulted in 7.2 g (77%) of the title compound as brown oil. MS-ESI: 196.1 (M+1).

Scheme 15

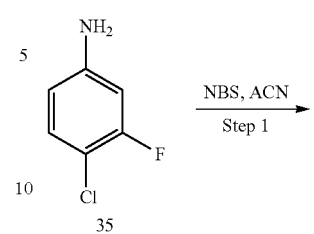

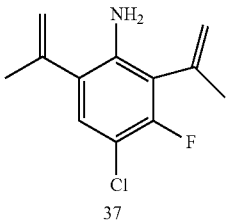

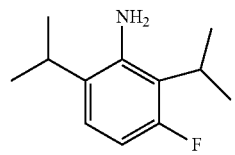

Intermediate 18

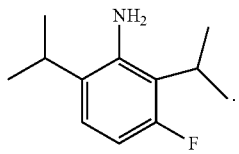

Intermediate 18

TABLE 8

The Intermediate in the following Table was prepared using the similar procedures for converting compound 33 to Intermediate 16 shown in Scheme 14.

| Intermediate # | Structure | IUPAC Name | Mass Spec[M + H]$^+$ |
|---|---|---|---|
| Intermediate 17 | H$_2$N–⬡ (2,6-diethyl-4-fluorophenyl) | 2,6-diethyl-4-fluorobenzenamine | 168.1 |

3-Fluoro-2,6-diisopropylbenzenamine

Step 1: 2,6-Dibromo-4-chloro-3-fluorobenzenamine

Into a 500-mL round-bottom flask, was placed 4-chloro-3-fluorobenzenamine (5.08 g, 34.9 mmol), ACN (200 mL) and NBS (18.69 g, 105.0 mmol). The resulting solution was stirred for 12 h at RT and then was concentrated under vacuum. The residue was applied onto a silica gel column and eluted with ethyl acetate/petroleum ether (1:200 to 1:100). This resulted in 9.7 g (92%) of the title compound as a light yellow solid. MS-ESI: 303.8, 305.8, 301.8 (M+1).

Step 2: 4-Chloro-3-fluoro-2,6-di(prop-1-en-2-yl)benzenamine

Into a 500-mL round-bottom flask purged with and maintained under nitrogen, was placed 2,6-dibromo-4-chloro-3-fluorobenzenamine (9.03 g, 29.8 mmol), dioxane (200 mL), water (20 mL), 4,4,5,5-tetramethyl-2-(prop-1-en-2-yl)-1,3,2-dioxaborolane (15.12 g, 89.98 mmol), $Cs_2CO_3$ (29.34 g, 90.05 mmol), and $Pd(dppf)Cl_2$ (2.20 g, 3.01 mmol). The resulting solution was stirred for 12 h at 100° C. and then was concentrated under vacuum. The residue was applied onto a silica gel column and eluted with ethyl acetate/petroleum ether (1:30 to 1:20). This resulted in 4.3 g (64%) of the title compound as yellow oil. MS-ESI: 226.1, 228.1 (M+1).

Step 3: 3-Fluoro-2,6-diisopropylbenzenamine

Into a 250-mL pressure tank reactor (10 atm) purged with and maintained under nitrogen, was placed 4-chloro-3-fluoro-2,6-di(prop-1-en-2-yl)benzenamine (4.3 g, 19.1 mmol), MeOH (100 mL), and TEA (2.0 g, 19.8 mmol). Then Pd/C (10% wt, 0.5 g) was added. The flask was evacuated and flushed three times with hydrogen. The resulting solution was stirred for 7 days at 100° C. under an atmosphere of hydrogen. The solids were filtered out. The resulting mixture was concentrated under vacuum. The residue was applied onto a silica gel column and eluted with ethyl acetate/petroleum ether (1:5 to 1:3). This resulted in 3.6 g (97%) of the title compound as light yellow oil. MS-ESI: 196.1 (M+1).

Scheme 16

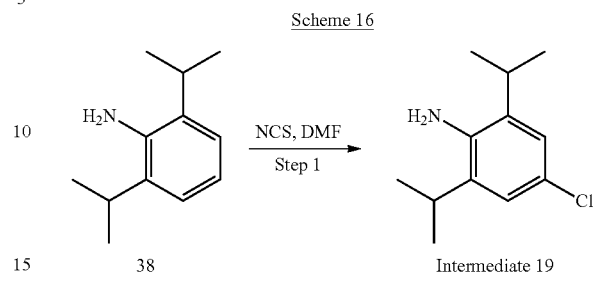

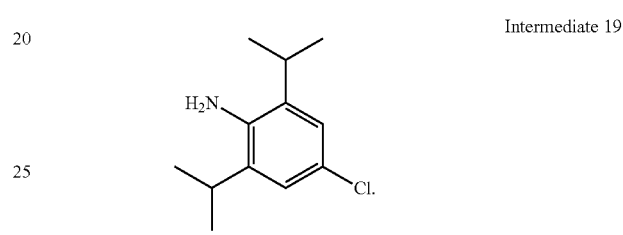

4-Chloro-2,6-diisopropylbenzenamine

Step 1: 4-Chloro-2,6-diisopropylbenzenamine

Into a 100-mL round-bottom flask, was placed 2,6-diisopropylbenzenamine (5 g, 28.2 mmol), DMF (20 mL), and NCS (4.9 g, 36.7 mmol). The resulting solution was stirred for 15 h at RT and then was diluted with 20 mL of water. The resulting solution was extracted with 3×20 mL of DCM and the organic layers combined and concentrated under vacuum. The residue was applied onto a silica gel column and eluted with ethyl acetate/petroleum ether (1:10 to 1:5). This resulted in 3.7 g (62%) of the title compound as brown oil. MS-ESI: 212.1, 214.1 (M+1).

TABLE 9

The Intermediates in the following Table were prepared using the similar procedures for converting compound 38 to Intermediate 19 shown in Scheme 16.

| Intermediate # | Structure | IUPAC Name | Mass Spec[M + H]+ |
|---|---|---|---|
| Intermediate 20 | ![structure] | 4-chloro-2,6-diethylbenzenamine | 184.1 |
| Intermediate 21 | ![structure] | 8-chloro-1,2,3,5,6,7-hexahydros-indacen-4-amine | 208.1 |

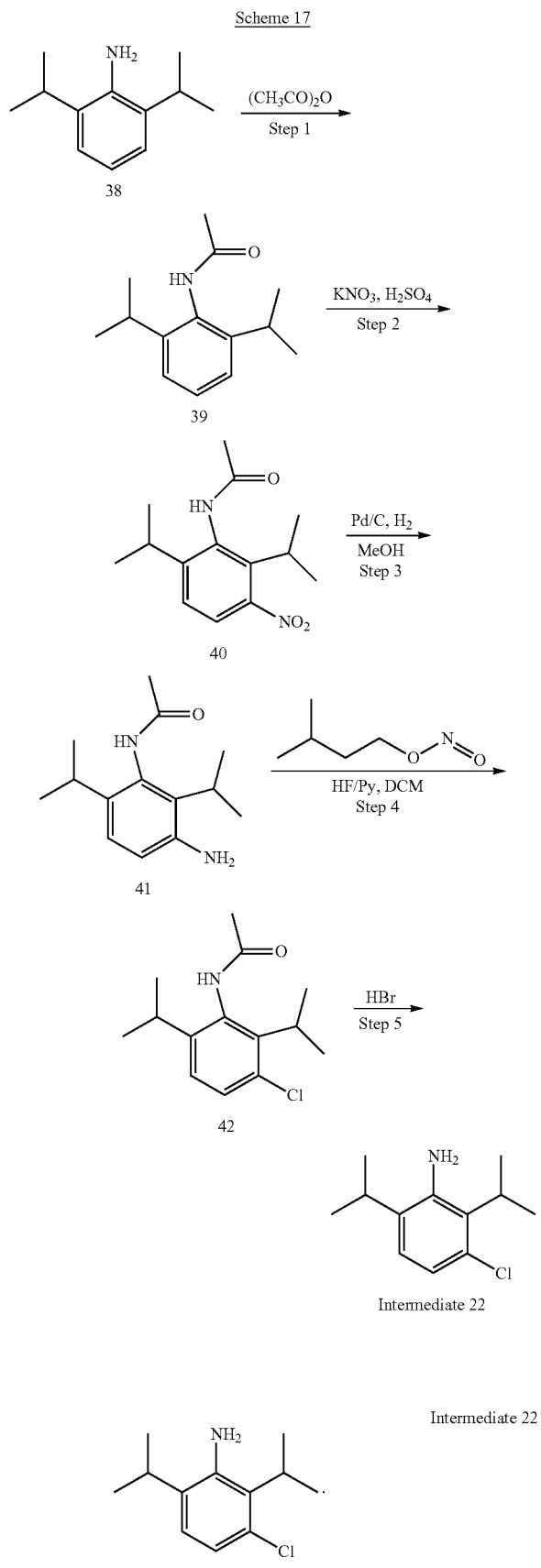

3-Chloro-2,6-diisopropylbenzenamine

Step 1: N-(2,6-diisopropylphenyl)acetamide

Into a 250-mL round-bottom flask, was placed 2,6-diisopropylbenzenamine (12.4 g, 69.94 mmol) and acetyl acetate (50 mL). The resulting solution was stirred for 1 h at 60° C. and then was concentrated under vacuum. This resulted in 14 g (91%) of the title compound as an off-white solid. MS-ESI: 220.2 (M+1).

Step 2: N-(2,6-diisopropyl-3-nitrophenyl)acetamide

Into a 250-mL round-bottom flask, was placed N-(2,6-diisopropylphenyl)acetamide (10.7 g, 48.79 mmol) and $H_2SO_4$ (98% wt, 50 mL). This was followed by the addition of $KNO_3$ (4.7 g, 46.49 mmol) in portions at 0° C. The resulting solution was stirred for 2 h at RT and then was quenched by the addition of 200 mL of water/ice. The resulting solution was extracted with 3×200 mL of DCM and the organic layers combined and concentrated under vacuum. The residue was applied onto a silica gel column and eluted with ethyl acetate/petroleum ether (1:50 to 1:30). This resulted in 12 g (93%) of the title compound as a light yellow solid. MS-ESI: 265.1 (M+1).

Step 3: N-(3-amino-2,6-diisopropylphenyl)acetamide

Into a 250-mL round-bottom flask, was placed N-(2,6-diisopropyl-3-nitrophenyl)acetamide (12 g, 45.40 mmol) and MeOH (120 mL). Then Pd/C (10% wt, 500 mg) was added. The flask was evacuated and flushed three times with hydrogen. The resulting solution was stirred for 12 h at RT under an atmosphere of hydrogen. The solids were filtered out. The mixture was concentrated under vacuum. This resulted in 9.7 g (91%) of the title compound as a off-white solid. MS-ESI: 235.2 (M+1).

Step 4: N-(3-chloro-2,6-diisopropylphenyl)acetamide

Into a 250-mL round-bottom flask, was placed N-(3-amino-2,6-diisopropylphenyl)acetamide (6.2 g, 26.46 mmol), DCM (30 mL), isopentyl nitrite (4.1 g, 35.00 mmol), and HF/Py (70% wt, 10 g). The resulting solution was stirred for 2 h at RT and then was diluted with 50 mL of water. The resulting solution was extracted with 3×50 mL of DCM and the organic layers combined and dried over anhydrous $Na_2SO_4$, then concentrated under vacuum. This resulted in 2 g (crude) of the title compound as a off-white solid. MS-ESI: 254.2, 256.2 (M+1).

Step 5: 3-Chloro-2,6-diisopropylbenzenamine

Into a 100-mL round-bottom flask, was placed N-(3-chloro-2,6-diisopropylphenyl)acetamide (2 g, 7.88 mmol) and HBr (40% wt, 30 mL). The resulting solution was stirred for 72 h at 130° C. in an oil bath. The pH value of the solution was adjusted to 8 with NaOH (1 M). The resulting solution was extracted with 3×30 mL of DCM and the organic layers combined and concentrated under vacuum. The residue was applied onto a silica gel column and eluted with ethyl acetate/petroleum ether (1:10). This resulted in 550 mg (33%) of the title compound as a white solid. MS-ESI: 212.1, 214.1 (M+1).

Scheme 18

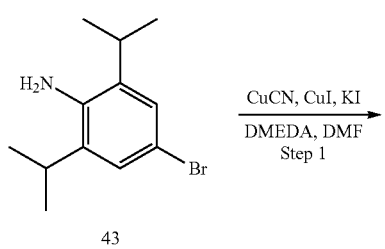

43

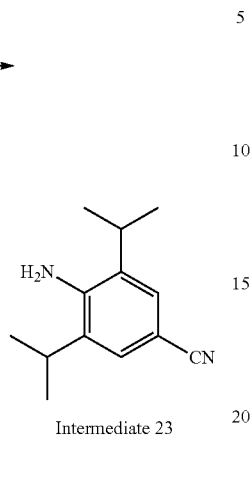

Intermediate 23

Intermediate 23

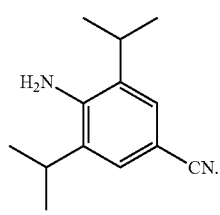

4-Amino-3,5-diisopropylbenzonitrile

Step 1: 4-Amino-3,5-diisopropylbenzonitrile

Into a 100-mL round-bottom flask purged with and maintained under nitrogen, was placed 4-bromo-2,6-diisopropylbenzenamine (commercial available, 5.1 g, 19.9 mmol), DME (30 mL), CuCN (2.16 g, 23.9 mmol), CuI (380 mg, 2.00 mmol), KI (664 mg, 3.98 mmol), and DMEDA (2.0 mL). The resulting solution was stirred for 24 h at 100° C. and then was diluted with 30 mL of water. The solution was extracted with 3×30 mL of ethyl acetate and the organic layers combined and concentrated under vacuum. The residue was applied onto a silica gel column and eluted with ethyl acetate/petroleum ether (1:30 to 1:20). This resulted in 1.2 g (30%) of the title compound as a yellow solid. MS-ESI: 203.1 (M+1).

Scheme 19

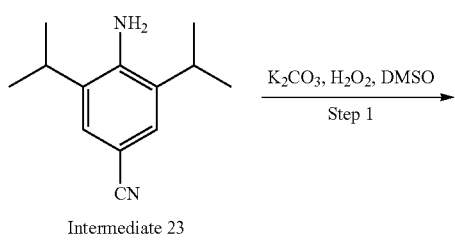

Intermediate 23

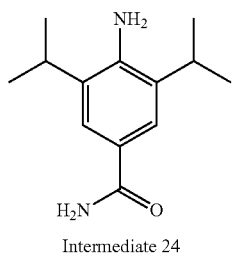

Intermediate 24

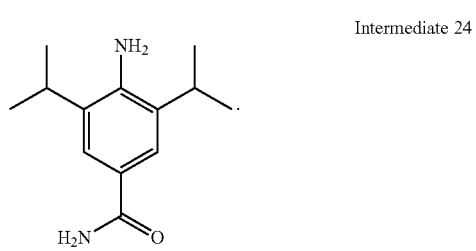 [SMILES: CC(C)c1cc(C(N)=O)cc(C(C)C)c1N ; "."]

Intermediate 24

4-Amino-3,5-diisopropylbenzamide

Step 1: 4-Amino-3,5-diisopropylbenzamide

Into a 25-mL round-bottom flask, was placed 4-amino-3, 5-diisopropylbenzonitrile (141 mg, 0.70 mmol), DMSO (3 mL), $K_2CO_3$ (70 mg, 0.51 mmol), and $H_2O_2$ (0.2 mL). The resulting solution was stirred for 3 h at RT and then was diluted with 5 mL of water. The resulting solution was extracted with 3×5 mL of ethyl acetate and the organic layers combined and dried over anhydrous $Na_2SO_4$, then concentrated under vacuum. This resulted in 145 mg (94%) of the title compound as a yellow solid. MS-ESI: 221.2 (M+1).

Scheme 20

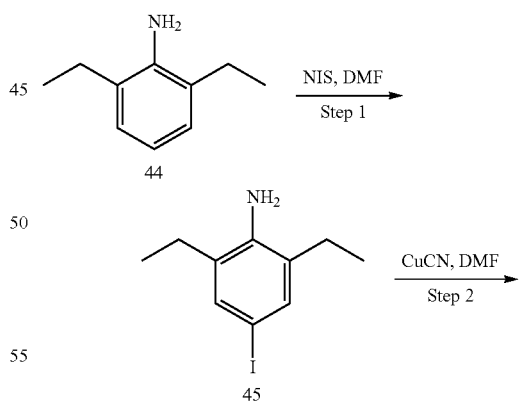

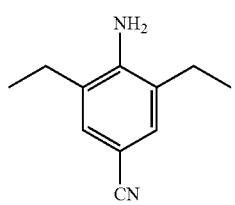

Intermediate 25

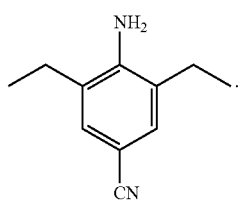

Intermediate 25

4-Amino-3,5-diethylbenzonitrile

Step 1: 2,6-Diethyl-4-iodobenzenamine

Into a 50-mL round-bottom flask, was placed 2,6-diethylbenzenamine (1.341 g, 8.99 mmol), DMF (10 mL), and NIS (2.229 g, 9.91 mmol). The resulting solution was stirred overnight at RT and then was diluted with 50 mL of ethyl acetate. The resulting mixture was washed with 3×5 mL of water and then was concentrated under vacuum. The residue was applied onto a silica gel column and eluted with ethyl acetate/petroleum ether (1:40 to 1:20). This resulted in 1.433 g (58%) of the title compound as a purple oil. MS-ESI: 276.0 (M+1).

Step 2: 4-Amino-3,5-diethylbenzonitrile

Into a 40-mL sealed tube, was placed 2,6-diethyl-4-iodobenzenamine (825 mg, 3.00 mmol), DMF (5 mL), CuCN (540 mg, 6.03 mmol). The resulting solution was stirred overnight at 130° C. and then was concentrated under vacuum. The residue was applied onto a silica gel column and eluted with ethyl acetate/petroleum ether (1:30 to 1:10). This resulted in 231 mg (44%) of the title compound as a brown solid. MS-ESI: 175.1 (M+1).

Scheme 21

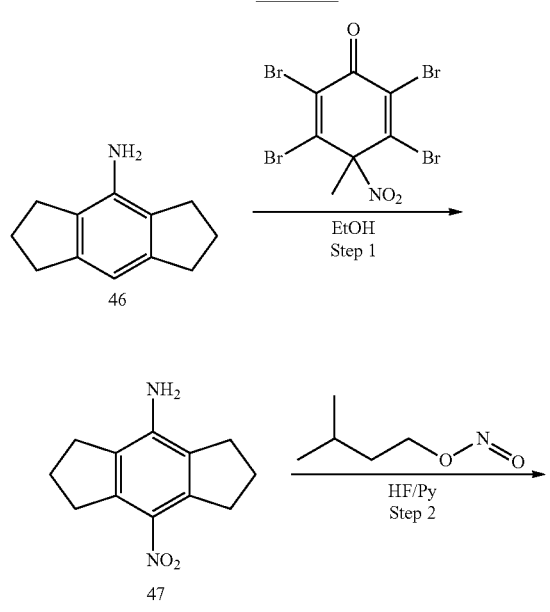

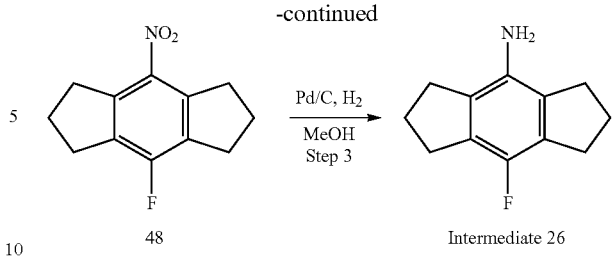

Intermediate 26

8-Fluoro-1,2,3,5,6,7-hexahydros-indacen-4-amine

Step 1: 8-Nitro-1,2,3,5,6,7-hexahydros-indacen-4-amine

Into a 500-mL round-bottom flask, was placed 1,2,3,5,6,7-hexahydros-indacen-4-amine (8 g, 46.17 mmol), EtOH (200 mL), and 2,3,5,6-tetrabromo-4-methyl-4-nitrocyclohexa-2,5-dienone (21.6 g, 46.08 mmol). The resulting solution was stirred for 12 h at RT and then was concentrated under vacuum. The residue was applied onto a silica gel column and eluted with ethyl acetate/petroleum ether (1:50 to 1:30). This resulted in 5 g (50%) of the title compound as a yellow solid. MS-ESI: 219.1 (M+1).

Step 2: 4-Fluoro-8-nitro-1,2,3,5,6,7-hexahydros-indacene

Into a 100-mL round-bottom flask, was placed 8-nitro-1,2,3,5,6,7-hexahydros-indacen-4-amine (5 g, 22.91 mmol) and HF/Py (70% wt, 20 mL). This was followed by the addition of 3-methylbutyl nitrite (3 g, 25.61 mmol) dropwise with stirring at 0° C. The resulting solution was stirred for 2 h at RT and then was diluted with 50 mL of water. The resulting solution was extracted with 3×50 mL of DCM and the organic layers combined and dried over anhydrous $Na_2SO_4$, then concentrated under vacuum. This resulted in 4 g (crude, 79%) of the title compound as brown oil.

Step 3: 8-Fluoro-1,2,3,5,6,7-hexahydros-indacen-4-amine

Into a 100-mL round-bottom flask, was placed 4-fluoro-8-nitro-1,2,3,5,6,7-hexahydros-indacene (4 g, 18.08 mmol) and MeOH (50 mL). Then Pd/C (10% wt, 0.5 g) was added. The flask was evacuated and flushed three times with hydrogen. The resulting solution was stirred for 12 h at RT under an atmosphere of hydrogen. The solids were filtered out and the mixture was concentrated under vacuum. The residue was applied onto a silica gel column and eluted with ethyl acetate/petroleum ether (1:10 to 1:5). This resulted in 2 g (58%) of the title compound as a white solid. MS-ESI: 192.1 (M+1).

Scheme 22

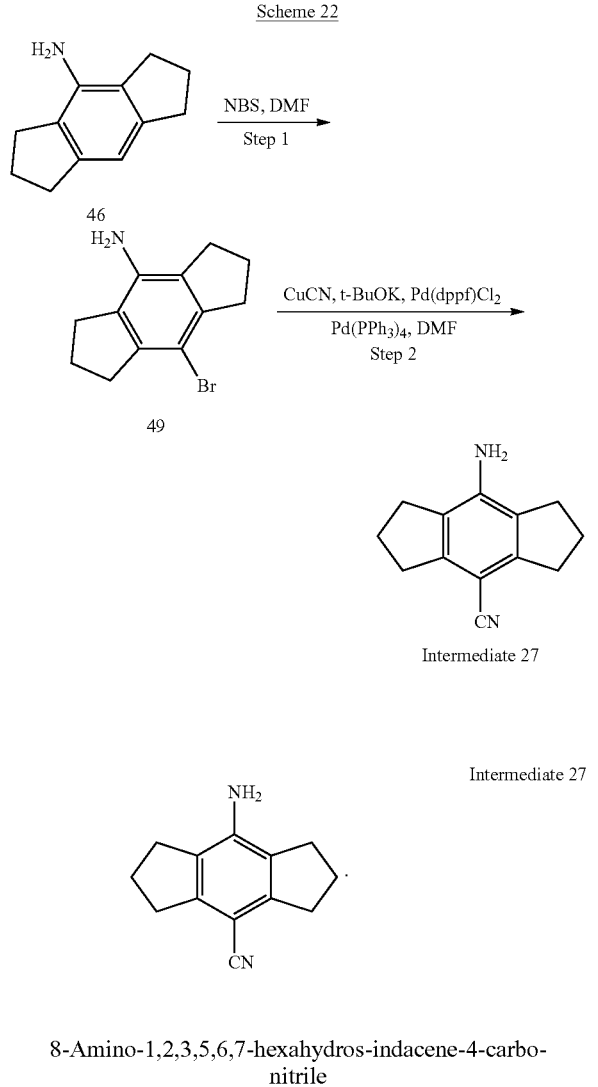

8-Amino-1,2,3,5,6,7-hexahydros-indacene-4-carbonitrile

Step 1:
8-Bromo-1,2,3,5,6,7-hexahydros-indacen-4-amine

Into a 100-mL round-bottom flask, was placed 1,2,3,5,6,7-hexahydro-s-indacen-4-amine (2.6 g, 15.0 mmol), DMF (30 mL), and NBS (2.9 g, 16.3 mmol). The resulting solution was stirred for 12 h at RT and then was diluted with 80 mL of ethyl acetate. The resulting mixture was washed with 3×20 mL of water. The resulting mixture was concentrated under vacuum. The residue was applied onto a silica gel column and eluted with ethyl acetate/petroleum ether (1:30 to 1:20). This resulted in 3.0 g (79%) of the title compound as a brown solid. MS-ESI: 252.0, 254.0 (M+1).

Step 2: 8-Amino-1,2,3,5,6,7-hexahydros-indacene-4-carbonitrile

Into a 50-mL round-bottom flask purged with and maintained under nitrogen, was placed 8-bromo-1,2,3,5,6,7-hexahydros-indacen-4-amine (725 mg, 2.88 mmol), DMF (10 mL), t-BuOK (330 mg, 2.90 mmol), CuCN (386 mg, 4.32 mmol), Pd(dppf)Cl$_2$ (424 mg, 0.58 mmol), and Pd(PPh$_3$)$_4$ (334 mg, 0.29 mmol). The resulting solution was stirred for 12 h at 120° C. and diluted with 20 mL of water. The resulting solution was extracted with 3×20 mL ethyl acetate and the organic layers combined and dried over anhydrous Na$_2$SO$_4$, then concentrated under vacuum. The residue was applied onto a silica gel column and eluted with ethyl acetate/petroleum ether (1:60 to 1:40). This resulted in 192 mg (34%) of the title compound as a yellow solid. MS-ESI: 199.1 (M+1).

Scheme 23

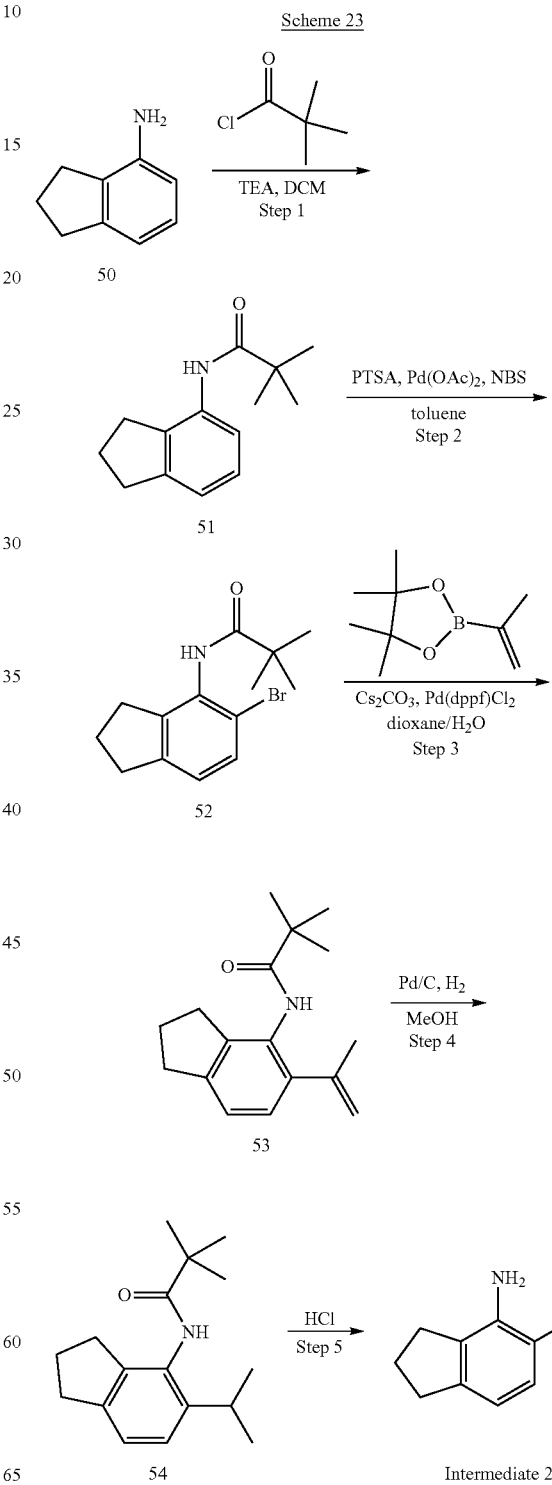

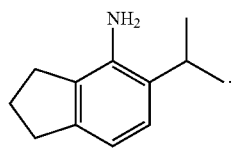

Intermediate 28

5-Isopropyl-2,3-dihydro-1H-inden-4-amine

Step 1: N-(2,3-dihydro-1H-inden-4-yl)pivalamide

Into a 250-mL round-bottom flask, was placed 2,3-dihydro-1H-inden-4-amine (10 g, 75.08 mmol), DCM (100 mL), and TEA (11.4 g, 112.66 mmol). This was followed by the addition of pivaloyl chloride (9.1 g, 75.47 mmol) dropwise with stirring at 0° C. The resulting solution was stirred for 1 h at RT and then was quenched by the addition of 100 mL of water. The resulting solution was extracted with 3×100 mL of DCM and the organic layers combined and dried over anhydrous $Na_2SO_4$, then concentrated under vacuum. This resulted in 16 g (crude, 98%) of the title compound as a off-white solid. MS-ESI: 218.1 (M+1).

Step 2: N-(5-bromo-2,3-dihydro-1H-inden-4-yl)pivalamide

Into a 250-mL round-bottom flask, was placed N-(2,3-dihydro-1H-inden-4-yl)pivalamide (16 g, 73.63 mmol), toluene (100 mL), Pd(OAc)$_2$ (845 mg, 3.76 mmol), NBS (16 g, 89.90 mmol), and PTSA (6.34 g, 36.82 mmol). The resulting solution was stirred overnight at RT and then was concentrated under vacuum. The resulting solution was quenched with 50 mL of NaHCO$_3$ (sat.). The resulting solution was extracted with 3×50 mL of DCM and the organic layers combined and dried over anhydrous $Na_2SO_4$, then concentrated under vacuum. The residue was applied onto a silica gel column and eluted with ethyl acetate/petroleum ether (1:40 to 1:20). This resulted in 18 g (83%) of the title compound as an off-white solid. MS-ESI: 296.1, 298.1 (M+1).

Step 3: N-(5-(prop-1-en-2-yl)-2,3-dihydro-1H-inden-4-yl)pivalamide

Into a 250-mL round-bottom flask purged with and maintained under nitrogen, was placed N-(5-bromo-2,3-dihydro-1H-inden-4-yl)pivalamide (8 g, 27.01 mmol), dioxane (100 mL), water (20 mL), 4,4,5,5-tetramethyl-2-(prop-1-en-2-yl)-1,3,2-dioxaborolane (5.45 g, 32.43 mmol), Cs$_2$CO$_3$ (26.44 g, 81.15 mmol), and Pd(dppf)Cl$_2$ (1.98 g, 2.71 mmol). The resulting solution was stirred overnight at 100° C. and then was concentrated under vacuum. The residue was applied onto a silica gel column and eluted with ethyl acetate/petroleum ether (1:40 to 1:20). This resulted in 5.3 g (76%) of the title compound as a white solid. MS-ESI: 258.2 (M+1).

Step 4: N-(5-isopropyl-2,3-dihydro-1H-inden-4-yl)pivalamide

Into a 250-mL round-bottom flask, was placed N-(5-(prop-1-en-2-yl)-2,3-dihydro-1H-inden-4-yl)pivalamide (5.3 g, 20.59 mmol) and MeOH (70 mL). Then Pd/C (10% wt, 500 mg) was added. The flask was evacuated and flushed three times with hydrogen. The resulting solution was stirred for 12 h at RT under an atmosphere of hydrogen. The solids were filtered out. The resulting mixture was concentrated under vacuum. This resulted in 5.2 g (crude) of the title compound as a white solid. MS-ESI: 260.2 (M+1).

Step 5: 5-Isopropyl-2,3-dihydro-1H-inden-4-amine

Into a 40-mL sealed tube, was placed N-(5-isopropyl-2,3-dihydro-1H-inden-4-yl)pivalamide (1 g, 3.86 mmol) and HCl (12 mol/L, 25 mL). The resulting solution was stirred for 2 days at 100° C. and then was diluted with 30 mL of water. The pH value of the solution was adjusted to 9 with Na$_2$CO$_3$. The resulting solution was extracted with 3×20 mL of DCM and the organic layers combined and dried over anhydrous Na$_2$SO$_4$, then concentrated under vacuum. The residue was applied onto a silica gel column and eluted with ethyl acetate/petroleum ether (1:20 to 1:10). This resulted in 370 mg (55%) of the title compound as light brown oil. MS-ESI: 176.1 (M+1).

TABLE 10

The Intermediate in the following Table was prepared using the similar procedures for converting compound 50 to Intermediate 28 shown in Scheme 23.

| Intermediate # | Structure | IUPAC Name | Mass Spec[M + H]$^+$ |
|---|---|---|---|
| Intermediate 29 | ![structure] | 5-ethyl-2,3-dihydro-1H-inden-4-amine | 162.1 |

Schemes for other Intermediates: Schemes 24-26 illustrate other intermediates preparation.

Scheme 24

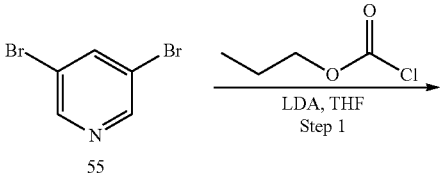

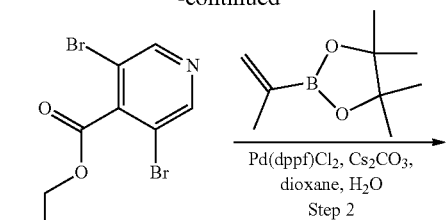

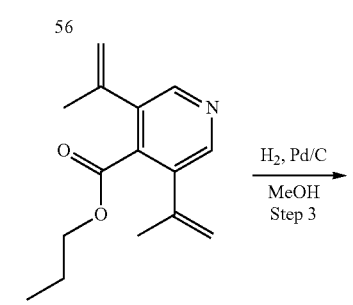

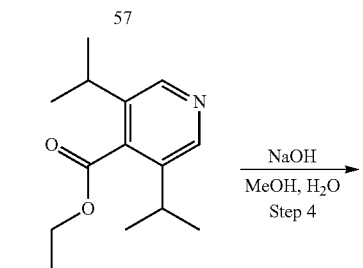

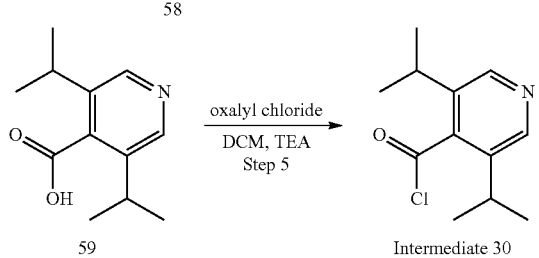

3,5-Diisopropylisonicotinoyl Chloride

Step 1: Propyl 3,5-dibromoisonicotinate

Into a 500-mL 3-necked round-bottom flask purged with and maintained under nitrogen, was placed 3,5-dibromopyridine (10 g, 42.21 mmol) and THF (200 mL). This was followed by the addition of LDA (1 M, 42.63 mL) dropwise with stirring at −78° C. The resulting solution was stirred for 30 min at −78° C. and then added propyl carbonochloridate (26 g, 212.16 mmol) dropwise with stirring at −78° C. The resulting solution was stirred for 5 h at −78° C. and then was quenched by the addition of 100 mL of NH$_4$Cl (sat.). The resulting solution was extracted with 3×100 mL of ethyl acetate and the organic layers combined and dried over anhydrous Na$_2$SO$_4$, then concentrated under vacuum. The residue was applied onto a silica gel column and eluted with ethyl acetate/petroleum ether (1:20 to 1:10). This resulted in 11.6 g (85%) of the title compound as brown oil. MS-ESI: 323.9, 321.9, 325.9 (M+1).

Step 2: Propyl 3,5-di(prop-1-en-2-yl)isonicotinate

Into a 250-mL round-bottom flask, was placed propyl 3,5-dibromoisonicotinate (5 g, 15.48 mmol), dioxane (50 mL), water (5 mL), 4,4,5,5-tetramethyl-2-(prop-1-en-2-yl)-1,3,2-dioxaborolane (7.53 g, 44.81 mmol), Cs$_2$CO$_3$ (9.7 g, 29.77 mmol), and Pd(dppf)Cl$_2$ (2.18 g, 2.98 mmol). The resulting solution was stirred for 16 h at 110° C. and then was quenched by the addition of 100 mL of water. The resulting solution was extracted with 3×100 mL of DCM and the organic layers combined and dried over anhydrous Na$_2$SO$_4$, then concentrated under vacuum. The residue was applied onto a silica gel column and eluted with ethyl acetate/petroleum ether (1:6 to 1:4). This resulted in 2.11 g (56%) of the title compound as yellow crude oil. MS-ESI: 246.1 (M+1).

Step 3: Propyl 3,5-diisopropylisonicotinate

Into a 100-mL round-bottom flask, was placed propyl 3,5-di(prop-1-en-2-yl)isonicotinate (2.11 g, 8.60 mmol) and MeOH (30 mL). Then Pd/C (10% wt, 300 mg) was added. The flask was evacuated and flushed three times with hydrogen. The resulting solution was stirred for 12 h at RT under an atmosphere of hydrogen. The solids were filtered out. The resulting mixture was concentrated under vacuum. This resulted in 1.88 g (88%) of the title compound as a light yellow oil. MS-ESI: 250.2 (M+1).

Step 4: 3,5-Diisopropylisonicotinic Acid

Into a 40-mL sealed tube, was placed 3,5-diisopropylisonicotinate (800 mg, 3.21 mmol), NaOH (6 M, 8 mL), and MeOH (5 mL). The resulting solution was stirred for 24 h at 100° C. and then the pH value of the solution was adjusted to 2 with HCl (1 N). The resulting mixture was concentrated under vacuum. The crude product was purified by Prep-HPLC with the following conditions: Column,)(Bridge C18 OBD Prep Column, 100 Å, 10 um, 19 mm×250 mm; mobile phase, Water (0.05% TFA) and ACN (20.0% ACN up to 40.0% in 10 min); Detector, UV 254/220 nm. This resulted in 350 mg (53%) of the title compound as light yellow oil. MS-ESI: 208.1 (M+1).

Step 5: 3,5-Diisopropylisonicotinoyl Chloride

Into a 50-mL round-bottom flask, was placed 3,5-diisopropylisonicotinic acid (110 mg, 0.53 mmol), DCM (5 mL), TEA (170 mg, 1.68 mmol), and oxalyl chloride (100 mg, 0.79 mmol). The resulting solution was stirred for 1.5 h at RT and was quenched by the addition of 5 mL of water/ice. The resulting solution was extracted with 3×5 mL of DCM and the organic layers combined and dried over anhydrous Na$_2$SO$_4$, then concentrated under vacuum. The crude product was used directly without further purification.

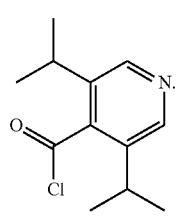

Scheme 25

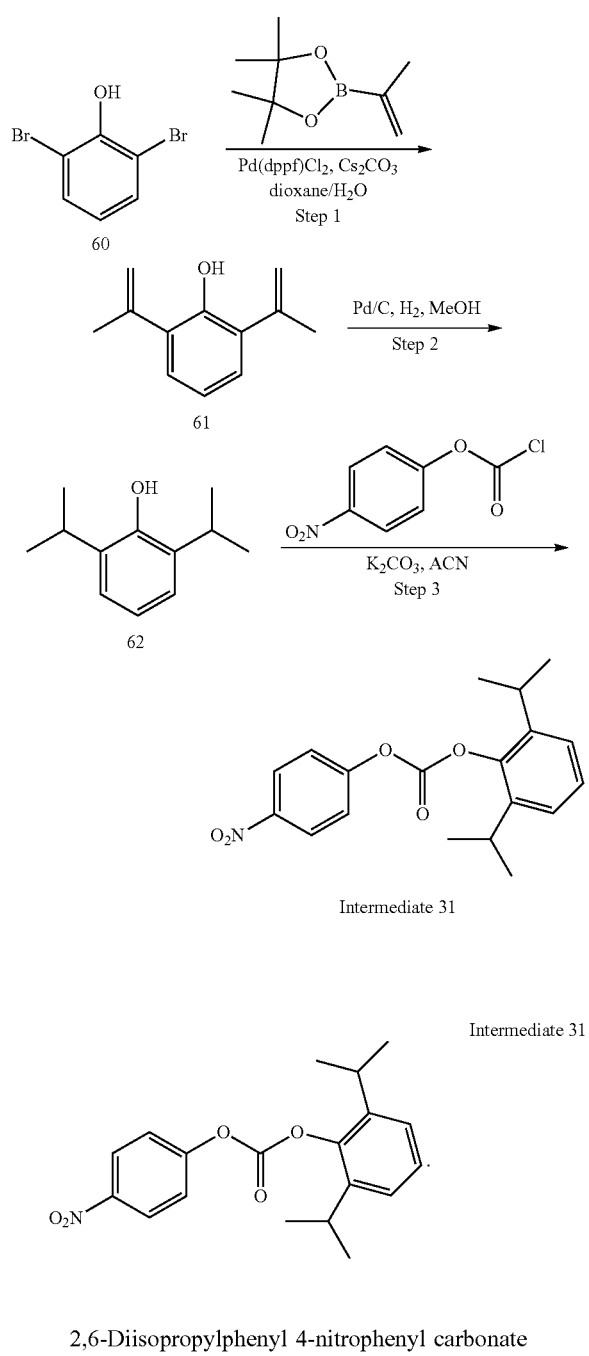

Intermediate 31

2,6-Diisopropylphenyl 4-nitrophenyl carbonate

Step 1: 2,6-Di(prop-1-en-2-yl)phenol

Into a 250-mL 3-necked round-bottom flask purged with and maintained under nitrogen, was placed 2,6-dibromophenol (2 g, 7.94 mmol), dioxane (100 mL), water (5 mL), Cs$_2$CO$_3$ (7.78 g, 23.88 mmol), 4,4,5,5-tetramethyl-2-(prop-1-en-2-yl)-1,3,2-dioxaborolane (3.34 g, 19.88 mmol), and Pd(dppf)Cl$_2$ (580 mg, 0.79 mmol). The resulting solution was stirred overnight at 90° C. and then was concentrated under vacuum. The residue was applied onto a silica gel column and eluted with ethyl acetate/petroleum ether (1:10 to 1:5). This resulted in 280 mg (20%) of the title compound as colorless oil.

Step 2: 2,6-Diisopropylphenol

Into a 250-mL round-bottom flask, was placed 2,6-di(prop-1-en-2-yl)phenol (280 mg, 1.61 mmol) and MeOH (10 mL). Then Pd/C (10% wt, 50 mg) was added. The flask was evacuated and flushed three times with hydrogen. The resulting solution was stirred for 2 h at RT under an atmosphere of hydrogen. The solids were filtered out. The resulting mixture was concentrated under vacuum. This resulted in 160 mg (56%) of the title compound as yellow oil.

Step 3: 2,6-Diisopropylphenyl 4-nitrophenyl carbonate

Into a 50-mL round-bottom flask, was placed 2,6-diisopropylphenol (160 mg, 0.90 mmol), ACN (10 mL), K$_2$CO$_3$ (372 mg, 2.69 mmol), and 4-nitrophenyl carbonochloridate (361 mg, 1.79 mmol). The resulting solution was stirred overnight at RT and then was concentrated under vacuum. The residue was applied onto a silica gel column and eluted with ethyl acetate/petroleum ether (1:20 to 1:10). This resulted in 200 mg (65%) of the title compound as yellow oil. $^1$H NMR (300 MHz, DMSO-d$_6$) δ 8.40 (d, J=9.0 Hz, 2H), 7.64 (d, J=9.0 Hz, 2H), 7.35-7.15 (m, 3H), 3.08 (hept, J=6.8 Hz, 2H), 1.18 (d, J=6.9 Hz, 12H).

Scheme 26

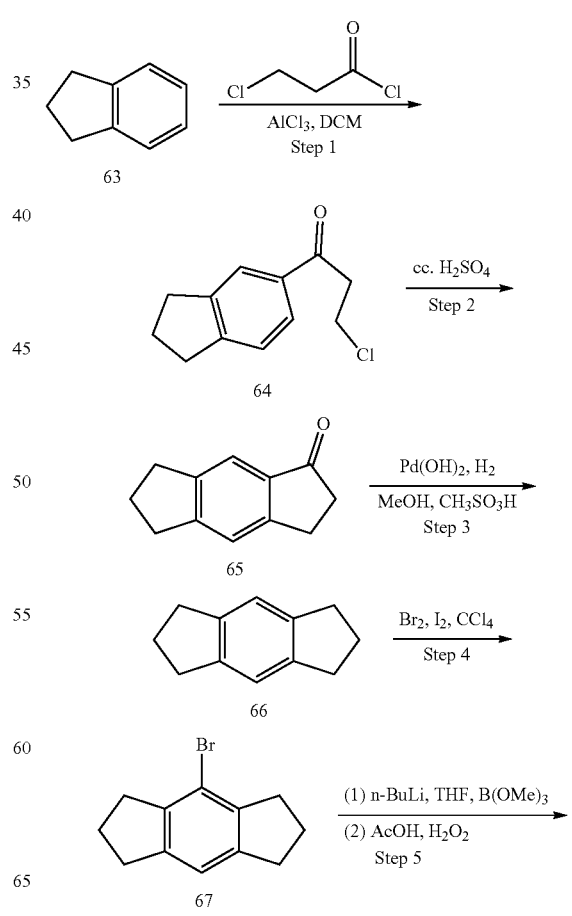

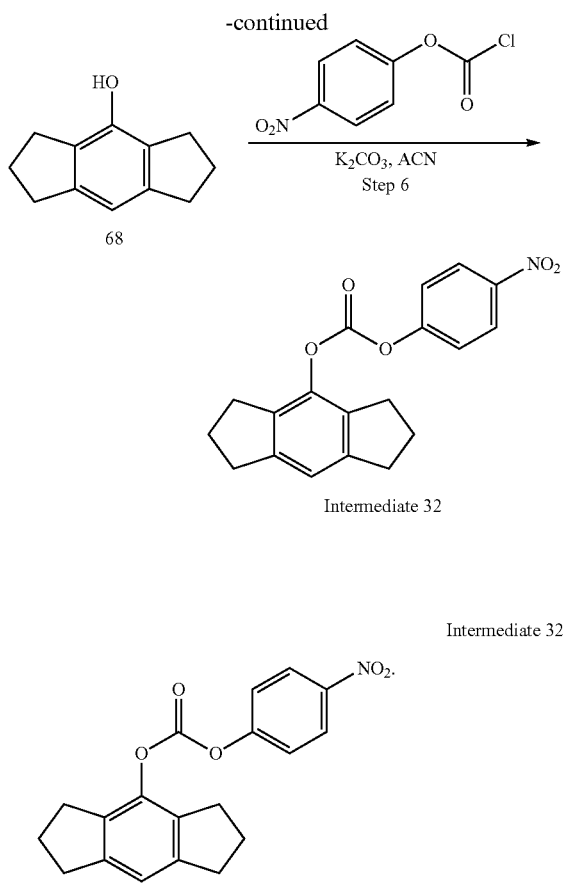

1,2,3,5,6,7-Hexahydros-indacen-4-yl 4-nitrophenyl carbonate

Step 1: 3-Chloro-1-(2,3-dihydro-1H-inden-5-yl)propan-1-one

Into a 1000-mL round-bottom flask, was placed a solution of $AlCl_3$ (37 g, 278 mmol) in DCM (400 mL). This was followed by the addition of a solution of 2,3-dihydro-1H-indene (30 g, 254 mmol) and 3-chloropropanoyl chloride (32.1 g, 253 mmol) in DCM (100 mL) dropwise with stirring at −10° C. in 30 min. The resulting solution was stirred for 16 h at RT. Then the reaction mixture was added dropwise to cold aqueous HCl (3 N, 400 mL) over 45 min at −10° C. The resulting solution was extracted with 3×200 mL of DCM and the organic layers combined and dried over anhydrous $Na_2SO_4$, then concentrated under vacuum. This resulted in 53.5 g (crude) of the title compound as a yellow solid.

Step 2: 1,2,3,5,6,7-Hexahydros-indacen-1-one

Into a 1000-mL round-bottom flask, was placed a solution of 3-chloro-1-(2,3-dihydro-1H-inden-5-yl)propan-1-one (53.5 g, 253 mmol) in cc. $H_2SO_4$ (300 mL). The resulting solution was stirred for 16 h at 55° C. and then was quenched by the addition of 1500 mL of water/ice. The solids were collected by filtration and then was dried over infrared lamp for 24 h. This resulted in 37.4 g (85%) of the title compound as a yellow solid.

Step 3: 1,2,3,5,6,7-Hexahydros-indacene

Into a 1000-mL round-bottom flask, was placed a solution of 1,2,3,5,6,7-hexahydro-indacen-1-one (37.2 g, 216.00 mmol), MeOH (300 mL), and $CH_3SO_3H$ (42 g). Then $Pd(OH)_2$/C (20% wt, 8 g) was added. The flask was evacuated and flushed three times with hydrogen. The resulting solution was stirred for 16 h at RT under an atmosphere of hydrogen. The solids were filtered out. The resulting mixture was concentrated under vacuum. The residue was applied onto a silica gel column and eluted with ethyl acetate/petroleum ether (1:150 to 1:100). This resulted in 27.1 g (79%) of the title compound as a white solid.

Step 4: 4-Bromo-1,2,3,5,6,7-hexahydros-indacene

Into a 500-mL 3-necked round-bottom flask purged with and maintained under nitrogen, was placed a solution of 1,2,3,5,6,7-hexahydros-indacene (15 g, 94.8 mmol) in $CCl_4$ (200 mL). Then $I_2$ (1.2 g, 4.72 mmol) was added. This was followed by the addition of a solution of $Br_2$ (16 g, 100 mmol) in $CCl_4$ (50 mL) dropwise with stirring at 0° C. in 10 min. The resulting solution was stirred for 2 h at 0° C. The reaction was then quenched by the addition of 150 mL of $NH_4Cl$ (sat.). The resulting solution was extracted with 3×150 mL of DCM and the organic layers combined and dried over anhydrous $Na_2SO_4$, then concentrated under vacuum. This resulted in 23.3 g (crude) of the title compound as yellow oil. $^1H$ NMR (300 MHz, DMSO-$d_6$) δ 7.02 (s, 1H), 2.95-2.75 (m, 8H), 2.03-2.01 (m, 4H)

Step 5: 1,2,3,5,6,7-Hexahydros-indacen-4-ol

Into a 100-mL 3-necked round-bottom flask purged with and maintained under nitrogen, was placed 4-bromo-1,2,3,5,6,7-hexahydros-indacene (500 mg, 2.11 mmol) and THF (5 mL). This was followed by the addition of n-BuLi (2.5 M, 1.2 mL) dropwise with stirring at −78° C. The resulting solution was stirred for 30 min at −78° C. and then to the above was added $B(OMe)_3$ (264 mg, 2.54 mmol) at −78° C. The solution was stirred for 30 min at RT. Then AcOH (208 mg, 3.46 mmol) and $H_2O_2$ (30% wt, 0.13 mL) were added. The resulting solution was stirred for 30 min at RT and then was quenched by the addition of 5 mL of $NH_4Cl$ (sat.). The resulting solution was extracted with 3×5 mL of DCM and the organic layers combined and dried over anhydrous $Na_2SO_4$, then concentrated under vacuum. This resulted in 300 mg (crude, 82%) of the title compound as a white solid.

Step 6 used the similar procedure for converting compound 62 to Intermediate 31 shown in Scheme 26 to afford Intermediate 32.

Scheme 27

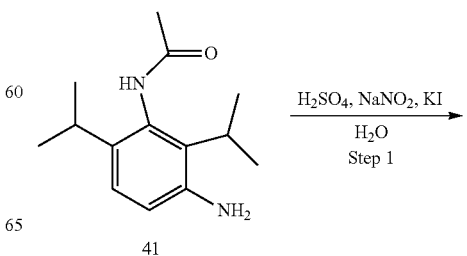

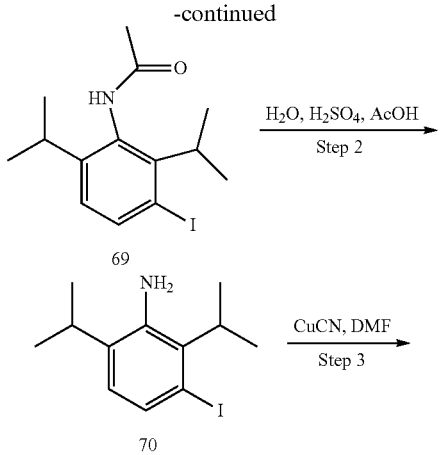

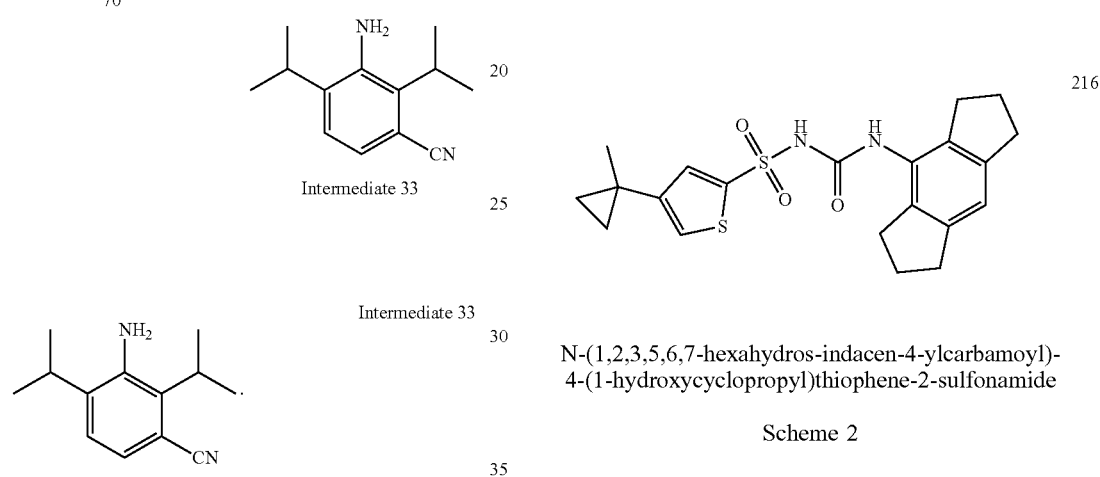

3-Amino-2,4-diisopropylbenzonitrile

Step 1: N-(3-iodo-2,6-diisopropylphenyl)acetamide

Into a 250-mL round-bottom flask purged with and maintained under nitrogen, was placed a solution of N-(3-amino-2,6-diisopropylphenyl)acetamide (6 g, 25.60 mmol) in H₂SO₄ (4 M, 30 mL). Then the system was cooled to −10° C. This was followed by the addition of a solution of NaNO₂ (1.8 g, 26.09 mmol) in water (5 mL) dropwise with stirring over 5 min. The resulting solution was stirred for 1 h at −10° C. The diazonium salt was added to a cooled solution of KI (30 g, 180.72 mmol) in water (20 mL) dropwise with stirring. The resulting solution was stirred for 2 h at 0° C. The solids were collected by filtration. This resulted in 3.3 g (37%) of the title compound as a brown solid. MS-ESI: 346.1 (M+1).

Step 2: 3-Iodo-2,6-diisopropylbenzenamine

Into a 250-mL round-bottom flask purged with and maintained under nitrogen, was placed N-(3-iodo-2,6-diisopropylphenyl)acetamide (3 g, 8.69 mmol), water (10 mL), H₂SO₄ (98% wt, 10 mL), acetic acid (20 mL). The resulting solution was stirred for 48 h at 130° C. The pH value of the solution was adjusted to 10 with NH₄OH (5 M). The resulting solution was extracted with 2×100 mL of ethyl acetate and the organic layers combined and concentrated under vacuum. The residue was applied onto a silica gel column and eluted with ethyl acetate/petroleum ether (1:20 to 1:10). This resulted in 600 mg (23%) of the title compound as brown oil. MS-ESI: 304.0 (M+1).

Step 3: 3-Amino-2,4-diisopropylbenzonitrile

Into a 100-mL round-bottom flask, was placed 3-iodo-2,6-diisopropylbenzenamine (100 mg, 0.33 mmol), DMF (3 mL), CuCN (50 mg, 0.56 mmol). The resulting solution was stirred for 3 h at 125° C. and then was diluted with 10 mL of water. The resulting solution was extracted with 2×10 mL of ethyl acetate and the organic layers combined and concentrated under vacuum. The residue was applied onto a silica gel column and eluted with ethyl acetate/petroleum ether (1:10 to 1:6). This resulted in 50 mg (75%) of the title compound as a brown solid. MS-ESI: 203.1 (M+1).

Example 2

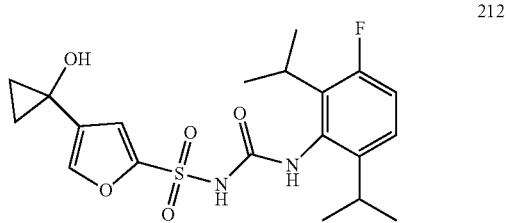 [SMILES: CC(C)c1ccc(F)c(C(C)C)c1NC(=O)NS(=O)(=O)c1cc(C2(O)CC2)co1]

N-(1,2,3,5,6,7-hexahydros-indacen-4-ylcarbamoyl)-4-(1-hydroxycyclopropyl)thiophene-2-sulfonamide Scheme 2

Into a 50-mL round-bottom flask purged with and maintained under nitrogen, was placed 1,2,3,5,6,7-hexahydros-indacen-4-amine (52 mg, 0.30 mmol), THF (5 mL), TEA (31 mg, 0.31 mmol), and BTC (30 mg, 0.10 mmol). The resulting solution was stirred for 2 h at 65° C. and then was concentrated under vacuum. The above mixture diluted in THF (1 mL) was added to a solution of 4-(1-hydroxycyclopropyl)thiophene-2-sulfonamide (66 mg, 0.30 mmol) and CH₃ONa (25 mg, 0.46 mmol) in THF (3 mL). The resulting solution was stirred overnight at RT and then was concentrated under vacuum. The crude product was purified by Prep-HPLC using method E eluted with a gradient of 2050% ACN. This resulted in 36.6 mg (29%) of the title compound as a white solid. MS-ESI: 417.1 (M−1). ¹H NMR (400 MHz, CD₃OD-d₄) δ 7.49 (s, 2H), 6.93 (s, 1H), 2.83 (t, J=7.2 Hz, 4H), 2.67 (t, J=7.2 Hz, 4H), 2.09-1.93 (m, 4H), 1.16-1.13 (m, 2H), 0.98-0.91 (m, 2H).

Example 3

N-(3-fluoro-2,6-diisopropylphenylcarbamoyl)-4-(1-hydroxycyclopropyl)furan-2-sulfonamide Scheme 3

Into a 50-mL round-bottom flask purged with and maintained under nitrogen, was placed 3-fluoro-2,6-diisopropylbenzenamine (29 mg, 0.15 mmol), THF (3 mL), TEA (15 mg, 0.15 mmol), and BTC (15 mg, 0.05 mmol). The resulting solution was stirred for 2 h at 65° C. and then was concentrated under vacuum. The above mixture diluted in THF (1 mL) was added to a solution of 4-(1-hydroxycyclopropyl)furan-2-sulfonamide (30 mg, 0.15 mmol) and DBU (27 mg, 0.18 mmol) in THF (3 mL). The resulting solution was stirred for 2 h at RT and then was concentrated under vacuum. The crude product was purified by Prep-HPLC using method E eluted with a gradient of 20~50% ACN. This resulted in 18.1 mg (29%) of title compound as a white solid. MS-ESI: 425.1 (M+1). $^1$H NMR (400 MHz, CD$_3$OD-d$_4$) δ 7.64 (s, 1H), 7.17-7.13 (m, 1H), 6.99-6.92 (m, 2H), 3.19-3.11 (m, 1H), 3.05-3.01 (m, 1H), 1.27 (d, J=6.8 Hz, 6H), 1.16-1.10 (m, 8H), 0.91-0.90 (m, 2H).

Example 4

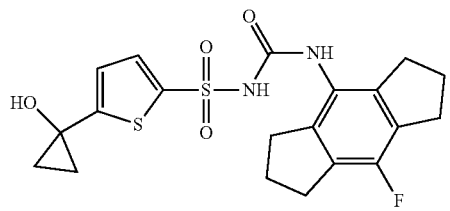

200

N-(8-fluoro-1,2,3,5,6,7-hexahydros-indacen-4-ylcarbamoyl)-5-(1-hydroxycyclopropyl)thiophene-2-sulfonamide (Scheme 4)

Into a 50-mL round-bottom flask purged with and maintained under nitrogen, was placed 8-fluoro-1,2,3,5,6,7-hexahydros-indacen-4-amine (48 mg, 0.25 mmol), THF (3 mL), TEA (25 mg, 0.25 mmol), and BTC (25 mg, 0.08 mmol). The resulting solution was stirred for 2 h at 65° C. and then was concentrated under vacuum. The above mixture diluted in DCM (1 mL) was added to a solution of 5-(1-hydroxycyclopropyl)thiophene-2-sulfonamide (55 mg, 0.25 mmol) and TEA (25 mg, 0.25 mmol) in DCM (3 mL). The resulting solution was stirred for 3 h at RT and then was concentrated under vacuum. The crude product was purified by Prep-HPLC using method E eluted with a gradient of 25~60% ACN. This resulted in 22.7 mg (21%) of the title compound as a white solid. MS-ESI: 435.1 (M−1). $^1$H NMR (400 MHz, CD$_3$OD-d$_4$) δ 7.41 (d, J=3.6 Hz, 1H), 6.69 (d, J=3.2 Hz, 1H), 2.86 (t, J=7.2 Hz, 4H), 2.78 (t, J=7.2 Hz, 4H), 2.11-2.03 (m, 4H), 1.27-1.20 (m, 2H), 1.08-1.04 (m, 2H).

Example 5

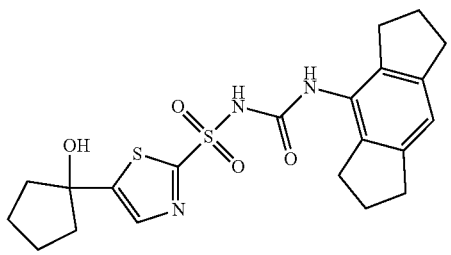

183

N-(1,2,3,5,6,7-hexahydros-indacen-4-yl carbamoyl)-5-(1-hydroxycyclopentyl)thiazole-2-sulfonamide (Scheme 5)

Into a 50-mL round-bottom flask purged with and maintained under nitrogen, was place 1,2,3,5,6,7-hexahydros-indacen-4-amine (42 mg, 0.24 mmol), THF (3 mL), TEA (25 mg, 0.25 mmol), and BTC (24 mg, 0.08 mmol). The resulting solution was stirred for 2 h at 65° C. and then was concentrated under vacuum. The above mixture diluted in THF (1 mL) was added to a solution of 5-(1-hydroxycyclopentyl)thiazole-2-sulfonamide (60 mg, 0.24 mmol) and TEA (25 mg, 0.25 mmol) in THF (3 mL). The resulting solution was stirred overnight at RT and then was concentrated under vacuum. The crude product was purified by Prep-HPLC using method E eluted with a gradient of 30-60% ACN. This resulted in 57.3 mg (53%) of the title compound as a white solid. MS-ESI: 446.1 (M−1). $^1$H NMR (400 MHz, CD$_3$OD-d$_4$) δ 7.68 (br s, 1H), 6.90 (s, 1H), 2.82 (t, J=7.2 Hz, 4H), 2.80 (t, J=7.2 Hz, 4H), 2.07-1.73 (m, 12H).

TABLE 11

Examples in the following table were prepared using similar conditions as described in Example 1 and Scheme 2 from appropriate starting materials.

| Example # | Compound | Structure | IUPAC Name | Mass Spec [M − H]⁻ |
|---|---|---|---|---|
| 6 | 104 | (structure) | N-(4-cyano-2,6-diisopropylphenyl-carbamoyl)-4-(2-hydroxypropan-2-yl)furan-2-sulfonamide | 432.2 |

TABLE 11-continued

Examples in the following table were prepared using similar conditions as described in Example 1 and Scheme 2 from appropriate starting materials.

| Example # | Compound | Structure | IUPAC Name | Mass Spec [M − H]⁻ |
|---|---|---|---|---|
| 7 | 116 | 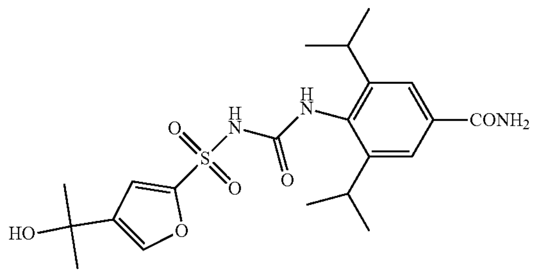 [SMILES: CC(C)c1cc(C(N)=O)cc(C(C)C)c1NC(=O)NS(=O)(=O)c1cc(C(C)(C)O)co1] | 4-(3-(4-(2-hydroxypropan-2-yl)furan-2-ylsulfonyl)ureido)-3,5-diisopropylbenzamide | 434.2 (M − OH)⁺ |
| 8 | 255 | 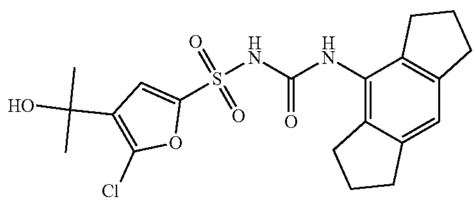 [SMILES: CC(C)(O)c1cc(S(=O)(=O)NC(=O)Nc2c3c(cc4c2CCC4)CCC3)oc1Cl] | 5-chloro-N-(1,2,3,5,6,7-hexahydros-indacen-4-ylcarbamoyl)-4-(2-hydroxypropan-2-yl)furan-2-sulfonamide | 437.1 |

TABLE 12

Examples in the following table were prepared using similar conditions as described in Example 2 and Scheme 3 from appropriate starting materials.

| Example # | Compound | Structure | IUPAC Name | Mass Spec [M − H]⁻ |
|---|---|---|---|---|
| 9 | 115 | 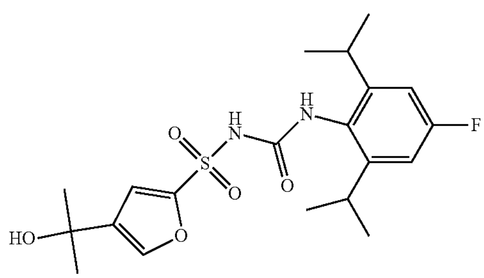 [SMILES: CC(C)c1cc(F)cc(C(C)C)c1NC(=O)NS(=O)(=O)c1cc(C(C)(C)O)co1] | N-(4-fluoro-2,6-diisopropylphenyl-carbamoyl)-4-(2-hydroxypropan-2-yl)furan-2-sulfonamide | 425.1 |
| 10 | 105 | 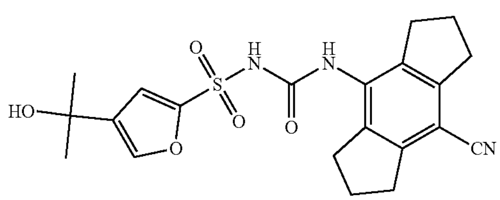 [SMILES: CC(C)(O)c1coc(S(=O)(=O)NC(=O)Nc2c3c(c(C#N)c4c2CCC4)CCC3)c1] | N-(8-cyano-1,2,3,5,6,7-hexahydros-indacen-4-ylcarbamoyl)-4-(2-hydroxypropan-2-yl)furan-2-sulfonamide | 412.2 (M − OH)⁺ |
| 11 | 207 | 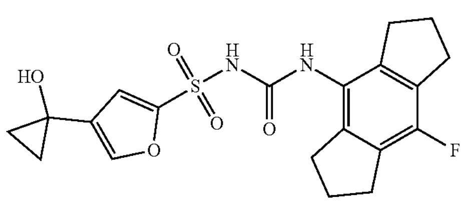 [SMILES: O=C(Nc1c2c(c(F)c3c1CCC3)CCC2)NS(=O)(=O)c1cc(C2(O)CC2)co1] | N-(8-fluoro-1,2,3,5,6,7-hexahydros-indacen-4-ylcarbamoyl)-4-(1-hydroxycyclo-propyl)furan-2-sulfonamide | 419.1 |

TABLE 12-continued

Examples in the following table were prepared using similar conditions as described in
Example 2 and Scheme 3 from appropriate starting materials.

| Example # | Compound | Structure | IUPAC Name | Mass Spec [M − H]⁻ |
|---|---|---|---|---|
| 12 | 247 | 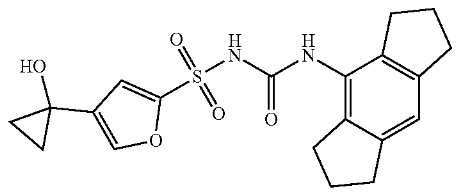 [SMILES: O=C(Nc1c2c(cc3c1CCC3)CCC2)NS(=O)(=O)c1cc(C2(O)CC2)co1] | N-(1,2,3,5,6,7-hexahydros-indacen-4-ylcarbamoyl)-4-(1-hydroxycyclo-propyl)furan-2-sulfonamide | 401.1 |
| 13 | 235 | 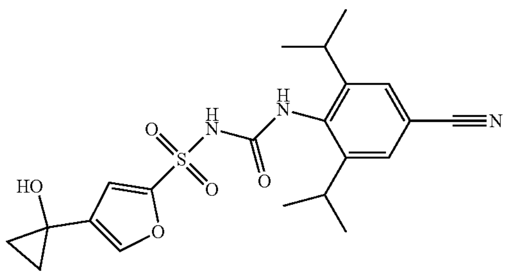 [SMILES: CC(C)c1cc(C#N)cc(C(C)C)c1NC(=O)NS(=O)(=O)c1cc(C2(O)CC2)co1] | N-(4-cyano-2,6-diisopropylphenyl-carbamoyl)-4-(1-hydroxycyclo-propyl)furan-2-sulfonamide | 430.1 |
| 14 | 205 | 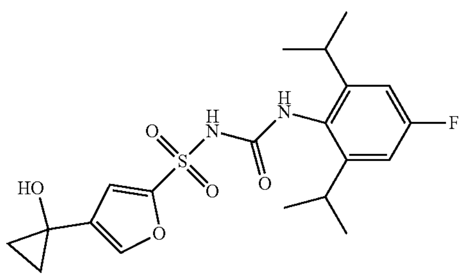 | N-(4-fluoro-2,6-diisopropylphenyl-carbamoyl)-4-(1-hydroxycyclo-propyl)furan-2-sulfonamide | 423.1 |
| 15 | 236 | 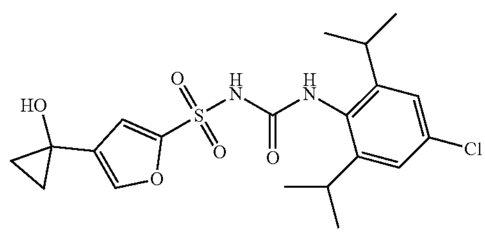 [SMILES: CC(C)c1cc(Cl)cc(C(C)C)c1NC(=O)NS(=O)(=O)c1cc(C2(O)CC2)co1] | N-(4-chloro-2,6-diisopropylphenyl-carbamoyl)-4-(1-hydroxycyclo-propyl)furan-2-sulfonamide | 439.1 |
| 16 | 130 | 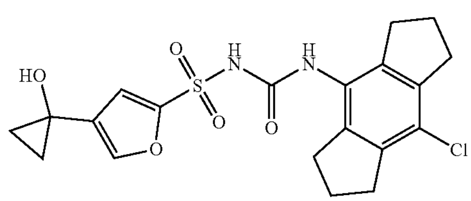 | N-(8-chloro-1,2,3,5,6,7-hexahydros-indacen-4-ylcarbamoyl)-4-(1-hydroxycyclo-propyl)furan-2-sulfonamide | 435.1 |
| 17 | 210 | 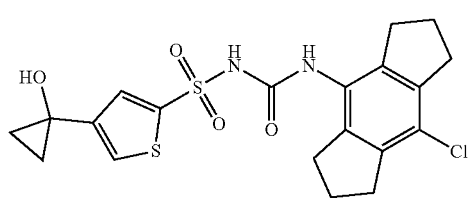 [SMILES: O=C(Nc1c2c(c(Cl)c3c1CCC3)CCC2)NS(=O)(=O)c1cc(C2(O)CC2)co1] | N-(8-chloro-1,2,3,5,6,7-hexahydros-indacen-4-ylcarbamoyl)-4-(1-hydroxycyclo-propyl)thiophene-2-sulfonamide | 451.0 |

TABLE 12-continued

Examples in the following table were prepared using similar conditions as described in Example 2 and Scheme 3 from appropriate starting materials.

| Example # | Compound | Structure | IUPAC Name | Mass Spec [M − H]⁻ |
|---|---|---|---|---|
| 18 | 204 | 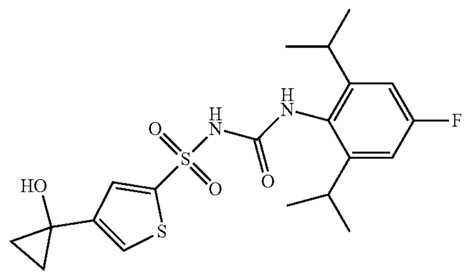 [SMILES: CC(C)c1cc(F)cc(C(C)C)c1NC(=O)NS(=O)(=O)c1cc(C2(O)CC2)cs1] | N-(4-fluoro-2,6-diisopropylphenylcarbamoyl)-4-(1-hydroxycyclopropyl)thiophene-2-sulfonamide | 439.1 |
| 19 | 214 | 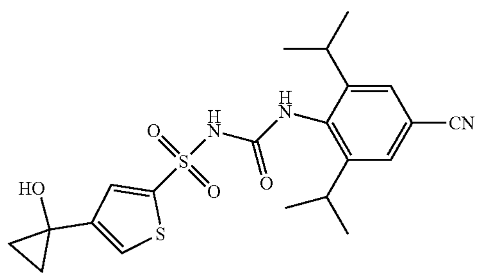 [SMILES: CC(C)c1cc(C#N)cc(C(C)C)c1NC(=O)NS(=O)(=O)c1cc(C2(O)CC2)cs1] | N-(4-cyano-2,6-diisopropylphenylcarbamoyl)-4-(1-hydroxycyclopropyl)thiophene-2-sulfonamide | 446.1 |
| 20 | 218 | 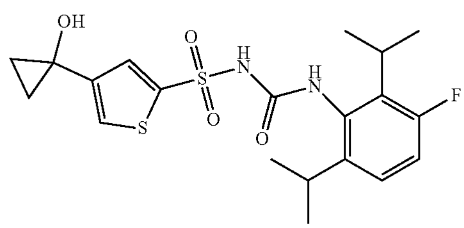 [SMILES: CC(C)c1ccc(F)c(C(C)C)c1NC(=O)NS(=O)(=O)c1cc(C2(O)CC2)cs1] | N-(3-fluoro-2,6-diisopropylphenylcarbamoyl)-4-(1-hydroxycyclopropyl)thiophene-2-sulfonamide | 439.1 |
| 21 | 223 | 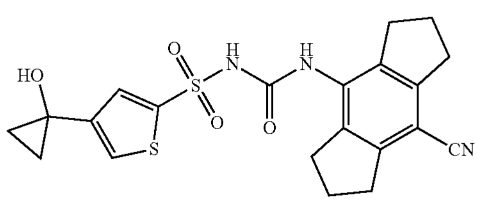 [SMILES: N#Cc1c2c(c(NC(=O)NS(=O)(=O)c3cc(C4(O)CC4)cs3)c3c1CCC3)CCC2] | N-(8-cyano-1,2,3,5,6,7-hexahydros-indacen-4-ylcarbamoyl)-4-(1-hydroxycyclopropyl)thiophene-2-sulfonamide | 442.1 |
| 22 | 230 | 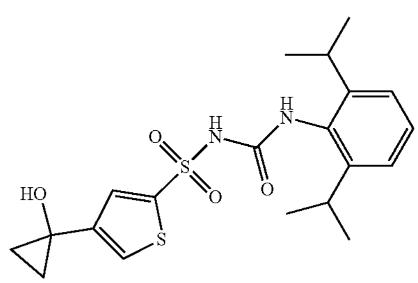 [SMILES: CC(C)c1cccc(C(C)C)c1NC(=O)NS(=O)(=O)c1cc(C2(O)CC2)cs1] | N-(2,6-diisopropylphenylcarbamoyl)-4-(1-hydroxycyclopropyl)thiophene-2-sulfonamide | 421.1 |

TABLE 12-continued

Examples in the following table were prepared using similar conditions as described in Example 2 and Scheme 3 from appropriate starting materials.

| Example # | Compound | Structure | IUPAC Name | Mass Spec [M − H]⁻ |
|---|---|---|---|---|
| 23 | 229 | 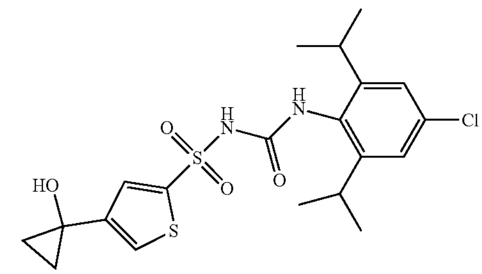 [SMILES: CC(C)c1cc(Cl)cc(C(C)C)c1NC(=O)NS(=O)(=O)c1cc(C2(O)CC2)cs1] | N-(4-chloro-2,6-diisopropylphenyl-carbamoyl)-4-(1-hydroxycyclopropyl)thiophene-2-sulfonamide | 455.1 |
| 24 | 217 | 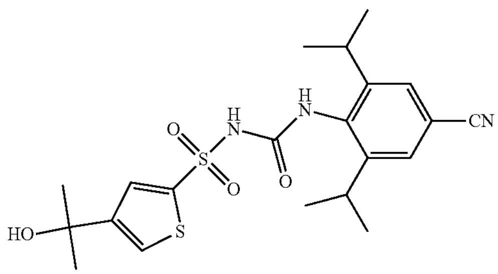 [SMILES: CC(C)c1cc(C#N)cc(C(C)C)c1NC(=O)NS(=O)(=O)c1cc(C(C)(C)O)cs1] | N-(4-cyano-2,6-diisopropylphenyl-carbamoyl)-4-(2-hydroxypropan-2-yl)thiophene-2-sulfonamide | 448.2 |
| 25 | 211 | 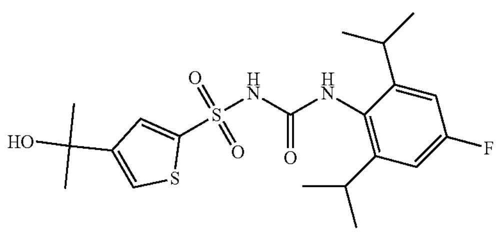 [SMILES: CC(C)c1cc(F)cc(C(C)C)c1NC(=O)NS(=O)(=O)c1cc(C(C)(C)O)cs1] | N-(4-fluoro-2,6-diisopropylphenyl-carbamoyl)-4-(2-hydroxypropan-2-yl)thiophene-2-sulfonamide | 441.1 |
| 26 | 232 | 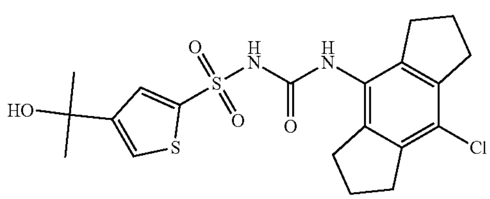 [SMILES: CC(C)(O)c1csc(S(=O)(=O)NC(=O)Nc2c3c(c(Cl)c4c2CCC4)CCC3)c1] | N-(8-chloro-1,2,3,5,6,7-hexahydros-indacen-4-ylcarbamoyl)-4-(2-hydroxypropan-2-yl)thiophene-2-sulfonamide | 453.1 |
| 27 | 224 | 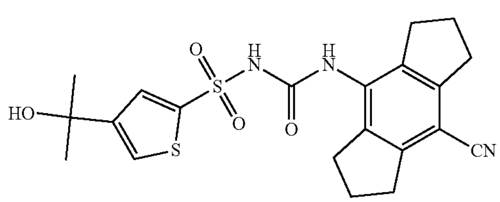 | N-(8-cyano-1,2,3,5,6,7-hexahydros-indacen-4-ylcarbamoyl)-4-(2-hydroxypropan-2-yl)thiophene-2-sulfonamide | 444.1 |
| 28 | 228 | 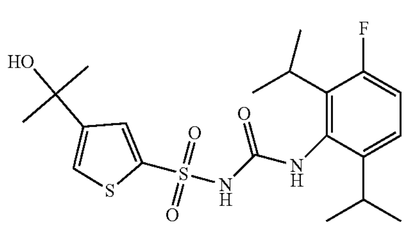 [SMILES: CC(C)c1ccc(F)c(C(C)C)c1NC(=O)NS(=O)(=O)c1cc(C(C)(C)O)cs1] | N-(3-fluoro-2,6-diisopropylphenyl-carbamoyl)-4-(2-hydroxypropan-2-yl)thiophene-2-sulfonamide | 441.1 |

TABLE 12-continued

Examples in the following table were prepared using similar conditions as described in Example 2 and Scheme 3 from appropriate starting materials.

| Example # | Compound | Structure | IUPAC Name | Mass Spec [M − H]⁻ |
|---|---|---|---|---|
| 29 | 157 | 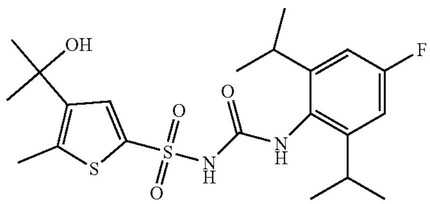 [SMILES: Cc1sc(S(=O)(=O)NC(=O)Nc2c(C(C)C)cc(F)cc2C(C)C)cc1C(C)(C)O] | N-(4-fluoro-2,6-diisopropylphenylcarbamoyl)-4-(2-hydroxypropan-2-yl)-5-methylthiophene-2-sulfonamide | 455.1 |
| 30 | 156 | 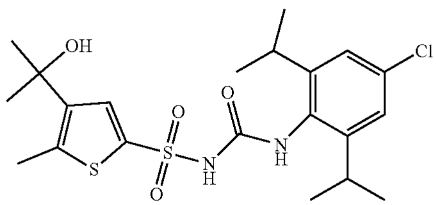 [SMILES: Cc1sc(S(=O)(=O)NC(=O)Nc2c(C(C)C)cc(Cl)cc2C(C)C)cc1C(C)(C)O] | N-(4-chloro-2,6-diisopropylphenylcarbamoyl)-4-(2-hydroxypropan-2-yl)-5-methylthiophene-2-sulfonamide | 471.1 |
| 31 | 162 | 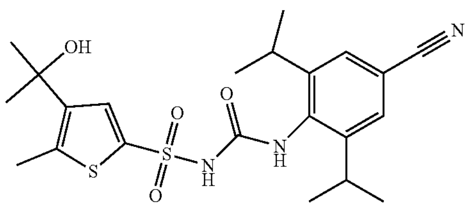 [SMILES: Cc1sc(S(=O)(=O)NC(=O)Nc2c(C(C)C)cc(C#N)cc2C(C)C)cc1C(C)(C)O] | N-(4-cyano-2,6-diisopropylphenylcarbamoyl)-4-(2-hydroxypropan-2-yl)-5-methylthiophene-2-sulfonamide | 462.1 |
| 32 | 153 | 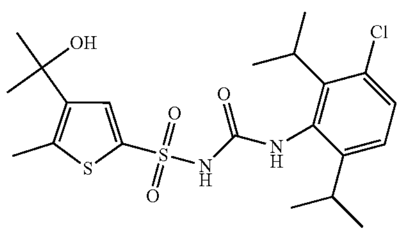 [SMILES: Cc1sc(S(=O)(=O)NC(=O)Nc2c(C(C)C)ccc(Cl)c2C(C)C)cc1C(C)(C)O] | N-(3-chloro-2,6-diisopropylphenylcarbamoyl)-4-(2-hydroxypropan-2-yl)-5-methylthiophene-2-sulfonamide | 475.2 (M + 1) |
| 33 | 254 | 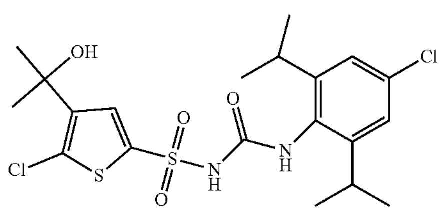 [SMILES: CC(C)c1cc(Cl)cc(C(C)C)c1NC(=O)NS(=O)(=O)c1cc(C(C)(C)O)c(Cl)s1] | 5-chloro-N-(4-chloro-2,6-diisopropylphenylcarbamoyl)-4-(2-hydroxypropan-2-yl)thiophene-2-sulfonamide | 491.1 |
| 34 | 253 | 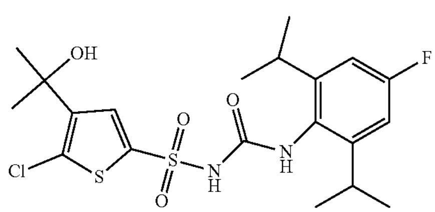 [SMILES: CC(C)c1cc(F)cc(C(C)C)c1NC(=O)NS(=O)(=O)c1cc(C(C)(C)O)c(Cl)s1] | 5-chloro-N-(4-fluoro-2,6-diisopropylphenylcarbamoyl)-4-(2-hydroxypropan-2-yl)thiophene-2-sulfonamide | 475.2 |
| 35 | 251 | 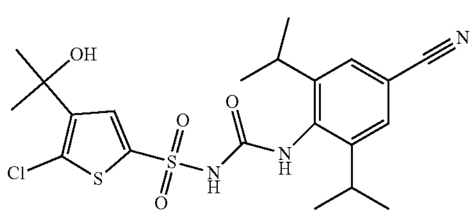 [SMILES: CC(C)c1cc(C#N)cc(C(C)C)c1NC(=O)NS(=O)(=O)c1cc(C(C)(C)O)c(Cl)s1] | 5-chloro-N-(4-cyano-2,6-diisopropylphenylcarbamoyl)-4-(2-hydroxypropan-2-yl)thiophene-2-sulfonamide | 482.1 |

TABLE 12-continued

Examples in the following table were prepared using similar conditions as described in Example 2 and Scheme 3 from appropriate starting materials.

| Example # | Compound | Structure | IUPAC Name | Mass Spec [M − H]⁻ |
|---|---|---|---|---|
| 36 | 139 | 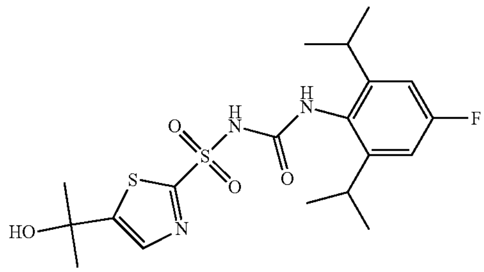 [SMILES: CC(C)c1cc(F)cc(C(C)C)c1NC(=O)NS(=O)(=O)c1ncc(C(C)(C)O)s1] | N-(4-fluoro-2,6-diisopropylphenyl-carbamoyl)-5-(2-hydroxypropan-2-yl)thiazole-2-sulfonamide | 442.1 |
| 37 | 209 | 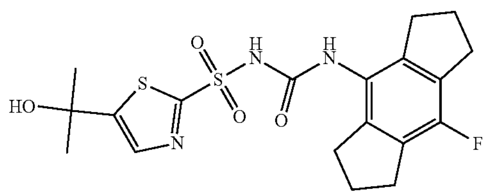 [SMILES: CC(C)(O)c1cnc(S(=O)(=O)NC(=O)Nc2c3c(c(F)c4c2CCC4)CCC3)s1] | N-(8-fluoro-1,2,3,5,6,7-hexahydros-indacen-4-ylcarbamoyl)-5-(2-hydroxypropan-2-yl)thiazole-2-sulfonamide | 438.1 |
| 38 | 233 | 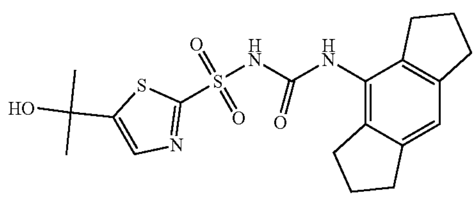 [SMILES: CC(C)(O)c1cnc(S(=O)(=O)NC(=O)Nc2c3c(cc4c2CCC4)CCC3)s1] | N-(1,2,3,5,6,7-hexahydros-indacen-4-ylcarbamoyl)-5-(2-hydroxypropan-2-yl)thiazole-2-sulfonamide | 420.0 |
| 39 | 219 | 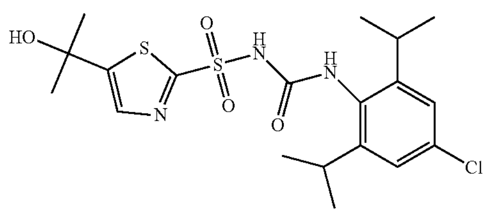 [SMILES: CC(C)c1cc(Cl)cc(C(C)C)c1NC(=O)NS(=O)(=O)c1ncc(C(C)(C)O)s1] | N-(4-chloro-2,6-diisopropylphenyl-carbamoyl)-5-(2-hydroxypropan-2-yl)thiazole-2-sulfonamide | 460.2 (M + 1) |
| 40 | 221 | 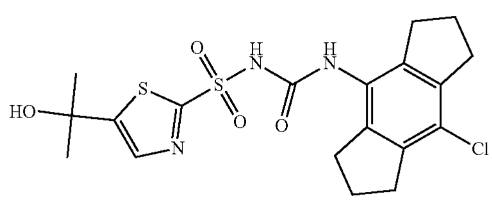 [SMILES: CC(C)(O)c1cnc(S(=O)(=O)NC(=O)Nc2c3c(c(Cl)c4c2CCC4)CCC3)s1] | N-(8-chloro-1,2,3,5,6,7-hexahydros-indacen-4-ylcarbamoyl)-5-(2-hydroxypropan-2-yl)thiazole-2-sulfonamide | 454.1 |
| 41 | 226 | 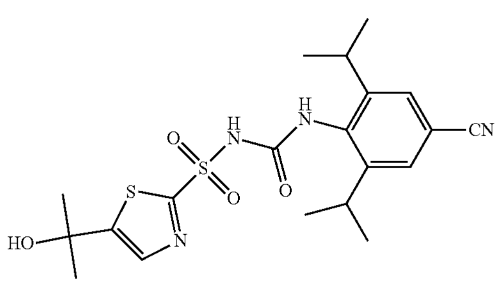 [SMILES: CC(C)c1cc(C#N)cc(C(C)C)c1NC(=O)NS(=O)(=O)c1ncc(C(C)(C)O)s1] | N-(4-cyano-2,6-diisopropylphenyl-carbamoyl)-5-(2-hydroxypropan-2-yl)thiazole-2-sulfonamide | 449.1 |

TABLE 12-continued

Examples in the following table were prepared using similar conditions as described in Example 2 and Scheme 3 from appropriate starting materials.

| Example # | Compound | Structure | IUPAC Name | Mass Spec [M − H]⁻ |
|---|---|---|---|---|
| 42 | 227 | 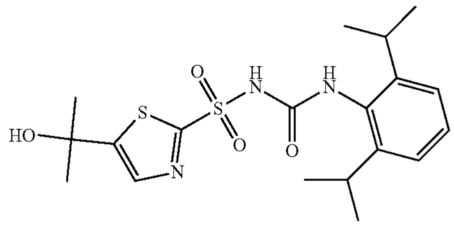 [SMILES: CC(C)c1cccc(C(C)C)c1NC(=O)NS(=O)(=O)c1ncc(C(C)(C)O)s1] | N-(2,6-diisopropylphenylcarbamoyl)-5-(2-hydroxypropan-2-yl)thiazole-2-sulfonamide | 424.2 |
| 43 | 213 | 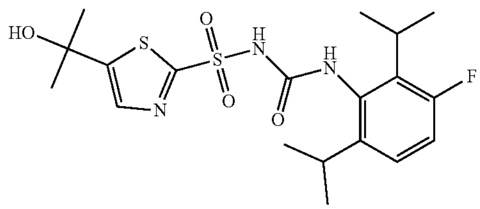 [SMILES: CC(C)c1ccc(F)c(C(C)C)c1NC(=O)NS(=O)(=O)c1ncc(C(C)(C)O)s1] | N-(3-fluoro-2,6-diisopropylphenylcarbamoyl)-5-(2-hydroxypropan-2-yl)thiazole-2-sulfonamide | 444.1 (M + 1) |
| 44 | 220 | 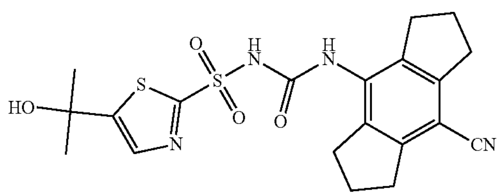 [SMILES: CC(C)(O)c1cnc(S(=O)(=O)NC(=O)Nc2c3c(c(C#N)c4c2CCC4)CCC3)s1] | N-(8-cyano-1,2,3,5,6,7-hexahydros-indacen-4-ylcarbamoyl)-5-(2-hydroxypropan-2-yl)thiazole-2-sulfonamide | 445.1 |
| 45 | 197 | 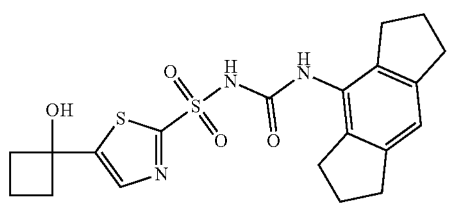 [SMILES: O=C(Nc1c2c(cc3c1CCC3)CCC2)NS(=O)(=O)c1ncc(C2(O)CCC2)s1] | N-(1,2,3,5,6,7-hexahydros-indacen-4-ylcarbamoyl)-5-(1-hydroxycyclobutyl)thiazole-2-sulfonamide | 434.1 (M + 1) |

TABLE 13

Examples in the following table were prepared using similar conditions as described in Example 4 and Scheme 4 from appropriate starting materials.

| Example # | Compound | Structure | IUPAC Name | Mass Spec [M − H]⁻ |
|---|---|---|---|---|
| 46 | 222 | 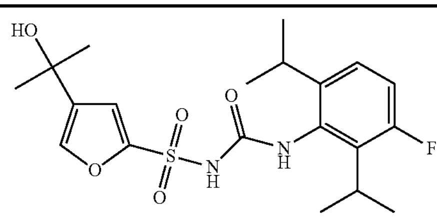 | N-(3-fluoro-2,6-diisopropylphenylcarbamoyl)-4-(2-hydroxypropan-2-yl)furan-2-sulfonamide | 425.2 |
| 47 | 206 | 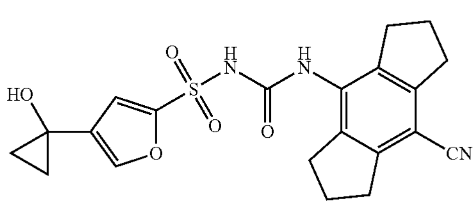 [SMILES: N#Cc1c2c(c(NC(=O)NS(=O)(=O)c3cc(C4(O)CC4)co3)c3c1CCC3)CCC2] | N-(8-cyano-1,2,3,5,6,7-hexahydros-indacen-4-ylcarbamoyl)-4-(1-hydroxycyclopropyl)furan-2-sulfonamide | 426.1 |

TABLE 13-continued

Examples in the following table were prepared using similar conditions as described in Example 4 and Scheme 4 from appropriate starting materials.

| Example # | Compound | Structure | IUPAC Name | Mass Spec [M − H]⁻ |
|---|---|---|---|---|
| 48 | 181 | 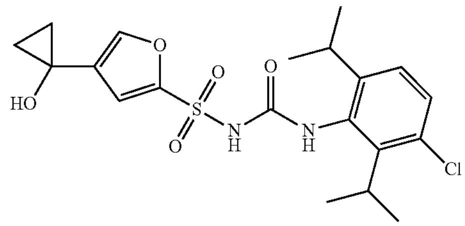 [SMILES: CC(C)c1ccc(Cl)c(C(C)C)c1NC(=O)NS(=O)(=O)c1cc(C2(O)CC2)co1] | N-(3-chloro-2,6-diisopropylphenylcarbamoyl)-4-(1-hydroxycyclopropyl)furan-2-sulfonamide | 439.1 |
| 49 | 192 | 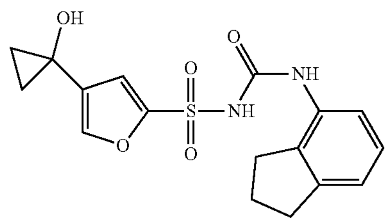 [SMILES: O=C(Nc1cccc2c1CCC2)NS(=O)(=O)c1cc(C2(O)CC2)co1] | N-(2,3-dihydro-1H-inden-4-ylcarbamoyl)-4-(1-hydroxycyclopropyl)furan-2-sulfonamide | 363.1 (M + 1) |
| 50 | 189 | 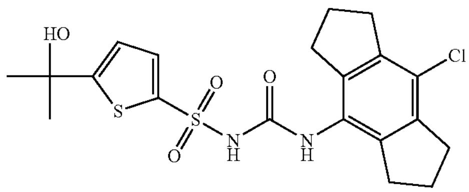 [SMILES: CC(C)(O)c1ccc(S(=O)(=O)NC(=O)Nc2c3c(c(Cl)c4c2CCC4)CCC3)s1] | N-(8-chloro-1,2,3,5,6,7-hexahydros-indacen-4-ylcarbamoyl)-5-(2-hydroxypropan-2-yl)thiophene-2-sulfonamide | 455.1 (M + 1) |
| 51 | 176 | 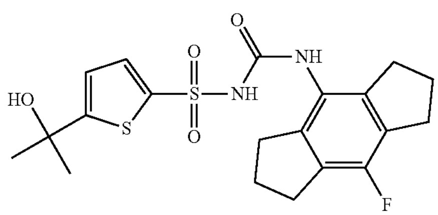 [SMILES: CC(C)(O)c1ccc(S(=O)(=O)NC(=O)Nc2c3c(c(F)c4c2CCC4)CCC3)s1] | N-(8-fluoro-1,2,3,5,6,7-hexahydros-indacen-4-ylcarbamoyl)-5-(2-hydroxypropan-2-yl)thiophene-2-sulfonamide | 439.2 (M + 1) |
| 52 | 184 | 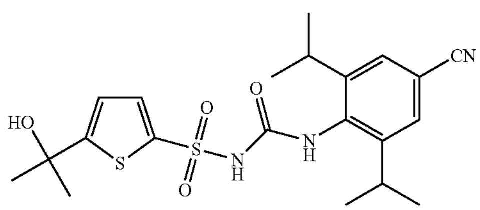 [SMILES: CC(C)c1cc(C#N)cc(C(C)C)c1NC(=O)NS(=O)(=O)c1ccc(C(C)(C)O)s1] | N-(4-cyano-2,6-diisopropylphenylcarbamoyl)-5-(2-hydroxypropan-2-yl)thiophene-2-sulfonamide | 450.2 (M + 1) |
| 53 | 187 | 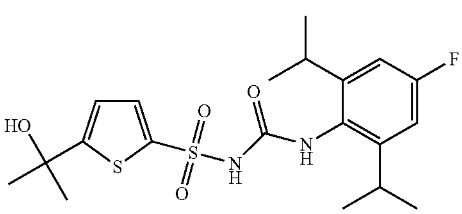 [SMILES: CC(C)c1cc(F)cc(C(C)C)c1NC(=O)NS(=O)(=O)c1ccc(C(C)(C)O)s1] | N-(4-fluoro-2,6-diisopropylphenylcarbamoyl)-5-(2-hydroxypropan-2-yl)thiophene-2-sulfonamide | 443.1 (M + 1) |
| 54 | 185 | 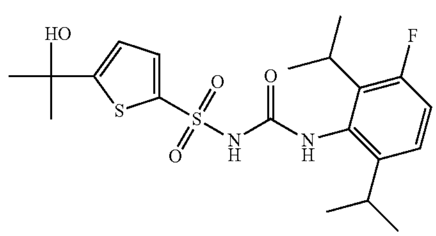 [SMILES: CC(C)c1ccc(F)c(C(C)C)c1NC(=O)NS(=O)(=O)c1ccc(C(C)(C)O)s1] | N-(3-fluoro-2,6-diisopropylphenylcarbamoyl)-5-(2-hydroxypropan-2-yl)thiophene-2-sulfonamide | 443.1 (M + 1) |

TABLE 13-continued

Examples in the following table were prepared using similar conditions as described in
Example 4 and Scheme 4 from appropriate starting materials.

| Example # | Compound | Structure | IUPAC Name | Mass Spec [M − H]⁻ |
|---|---|---|---|---|
| 55 | 188 | 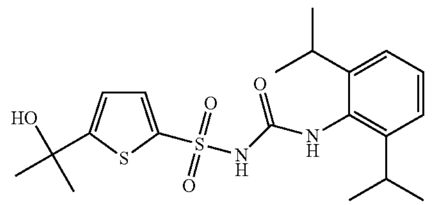 [SMILES: CC(C)c1cccc(C(C)C)c1NC(=O)NS(=O)(=O)c1ccc(C(C)(C)O)s1] | N-(2,6-diisopropylphenylcarbamoyl)-5-(2-hydroxypropan-2-yl)thiophene-2-sulfonamide | 425.1 (M + 1) |
| 56 | 180 | 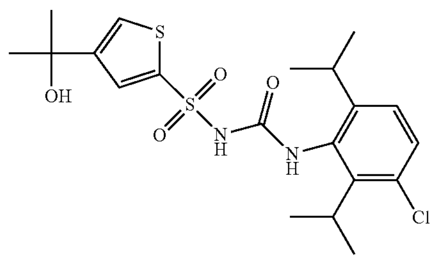 [SMILES: CC(C)c1ccc(Cl)c(C(C)C)c1NC(=O)NS(=O)(=O)c1cc(C(C)(C)O)cs1] | N-(3-chloro-2,6-diisopropylphenylcarbamoyl)-4-(2-hydroxypropan-2-yl)thiophene-2-sulfonamide | 457.1 |
| 57 | 161 | 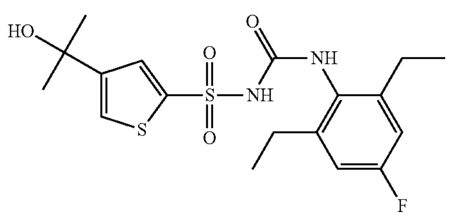 [SMILES: CCc1cc(F)cc(CC)c1NC(=O)NS(=O)(=O)c1cc(C(C)(C)O)cs1] | N-(2,6-diethyl-4-fluorophenylcarbamoyl)-4-(2-hydroxypropan-2-yl)thiophene-2-sulfonamide | 397.1 (M − OH)⁺ |
| 58 | 171 | 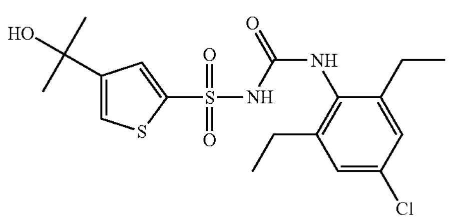 [SMILES: CCc1cc(Cl)cc(CC)c1NC(=O)NS(=O)(=O)c1cc(C(C)(C)O)cs1] | N-(4-chloro-2,6-diethylphenylcarbamoyl)-4-(2-hydroxypropan-2-yl)thiophene-2-sulfonamide | 431.2 (M + 1) |
| 59 | 159 | 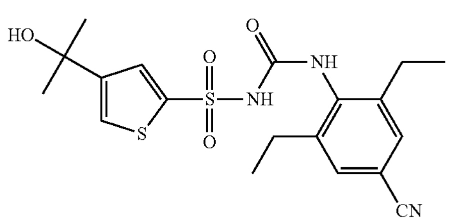 | N-(4-cyano-2,6-diethylphenylcarbamoyl)-4-(2-hydroxypropan-2-yl)thiophene-2-sulfonamide | 420.2 |
| 60 | 191 | 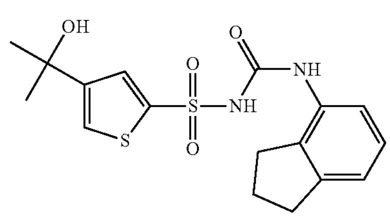 [SMILES: CC(C)(O)c1csc(S(=O)(=O)NC(=O)Nc2cccc3c2CCC3)c1] | N-(2,3-dihydro-1H-inden-4-ylcarbamoyl)-4-(2-hydroxypropan-2-yl)thiophene-2-sulfonamide | 381.0 (M + 1) |

TABLE 13-continued

Examples in the following table were prepared using similar conditions as described in Example 4 and Scheme 4 from appropriate starting materials.

| Example # | Compound | Structure | IUPAC Name | Mass Spec [M − H]⁻ |
|---|---|---|---|---|
| 61 | 166 | 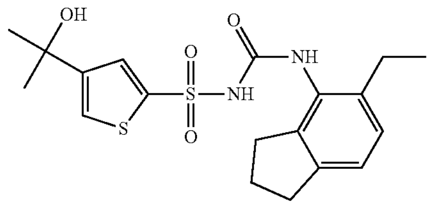 [SMILES: CCc1ccc2c(c1NC(=O)NS(=O)(=O)c1cc(C(C)(C)O)cs1)CCC2] | N-(5-ethyl-2,3-dihydro-1H-inden-4-ylcarbamoyl)-4-(2-hydroxypropan-2-yl)thiophene-2-sulfonamide | 409.2 (M + 1) |
| 62 | 173 | 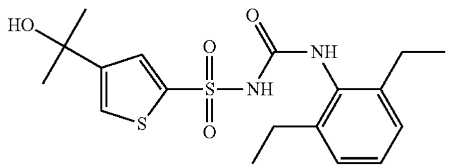 [SMILES: CCc1cccc(CC)c1NC(=O)NS(=O)(=O)c1cc(C(C)(C)O)cs1] | N-(2,6-diethylphenylcarbamoyl)-4-(2-hydroxypropan-2-yl)thiophene-2-sulfonamide | 379.2 (M − OH)⁺ |
| 63 | 175 | 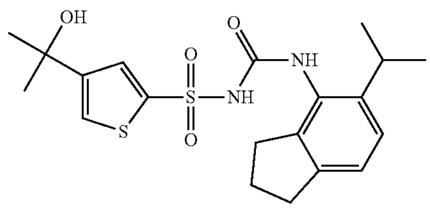 [SMILES: CC(C)c1ccc2c(c1NC(=O)NS(=O)(=O)c1cc(C(C)(C)O)cs1)CCC2] | 4-(2-hydroxypropan-2-yl)-N-(5-isopropyl-2,3-dihydro-1H-inden-4-ylcarbamoyl)thiophene-2-sulfonamide | 423.1 (M + 1) |
| 64 | 154 | 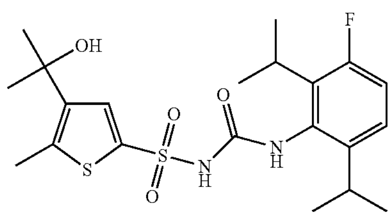 [SMILES: Cc1sc(S(=O)(=O)NC(=O)Nc2c(C(C)C)ccc(F)c2C(C)C)cc1C(C)(C)O] | N-(3-fluoro-2,6-diisopropylphenylcarbamoyl)-4-(2-hydroxypropan-2-yl)-5-methylthiophene-2-sulfonamide | 455.1 |
| 65 | 250 | 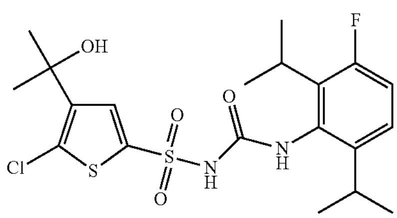 [SMILES: CC(C)c1ccc(F)c(C(C)C)c1NC(=O)NS(=O)(=O)c1cc(C(C)(C)O)c(Cl)s1] | 5-chloro-N-(3-fluoro-2,6-diisopropylphenylcarbamoyl)-4-(2-hydroxypropan-2-yl)thiophene-2-sulfonamide | 459.0 (M − OH)⁺ |
| 66 | 252 | 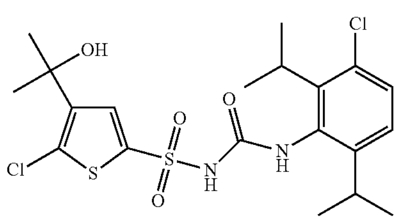 [SMILES: CC(C)c1ccc(Cl)c(C(C)C)c1NC(=O)NS(=O)(=O)c1cc(C(C)(C)O)c(Cl)s1] | 5-chloro-N-(3-chloro-2,6-diisopropylphenylcarbamoyl)-4-(2-hydroxypropan-2-yl)thiophene-2-sulfonamide | 491.0 |
| 67 | 196 | 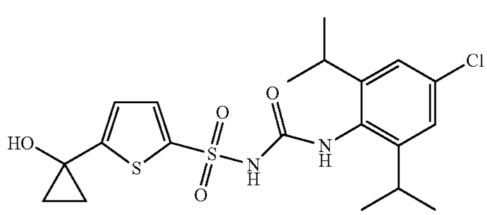 [SMILES: CC(C)c1cc(Cl)cc(C(C)C)c1NC(=O)NS(=O)(=O)c1ccc(C2(O)CC2)s1] | N-(4-chloro-2,6-diisopropylphenylcarbamoyl)-5-(1-hydroxycyclopropyl)thiophene-2-sulfonamide | 455.1 |

TABLE 13-continued

Examples in the following table were prepared using similar conditions as described in Example 4 and Scheme 4 from appropriate starting materials.

| Example # | Compound | Structure | IUPAC Name | Mass Spec [M − H]⁻ |
|---|---|---|---|---|
| 68 | 202 | 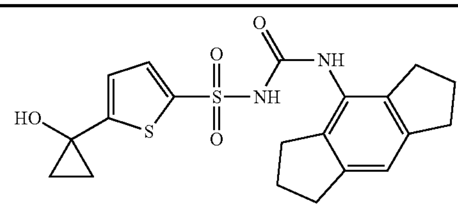 | N-(1,2,3,5,6,7-hexahydros-indacen-4-ylcarbamoyl)-5-(1-hydroxycyclopropyl)thiophene-2-sulfonamide | 417.1 |
| 69 | 198 | 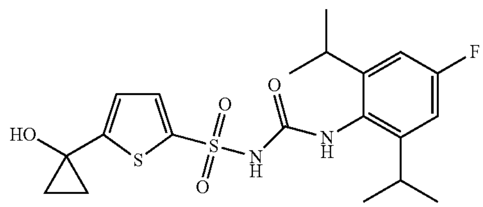 [SMILES: CC(C)c1cc(F)cc(C(C)C)c1NC(=O)NS(=O)(=O)c1ccc(C2(O)CC2)s1] | N-(4-fluoro-2,6-diisopropylphenylcarbamoyl)-5-(1-hydroxycyclopropyl)thiophene-2-sulfonamide | 441.1 (M + 1) |
| 70 | 195 | 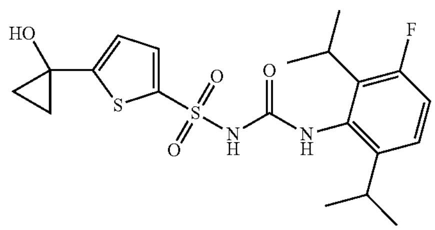 [SMILES: CC(C)c1ccc(F)c(C(C)C)c1NC(=O)NS(=O)(=O)c1ccc(C2(O)CC2)s1] | N-(3-fluoro-2,6-diisopropylphenylcarbamoyl)-5-(1-hydroxycyclopropyl)thiophene-2-sulfonamide | 439.1 |
| 71 | 199 | 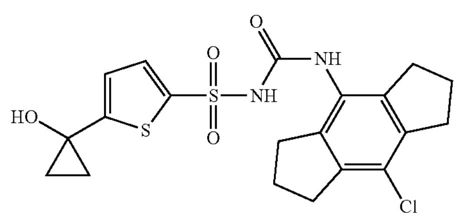 [SMILES: O=C(Nc1c2c(c(Cl)c3c1CCC3)CCC2)NS(=O)(=O)c1ccc(C2(O)CC2)s1] | N-(8-chloro-1,2,3,5,6,7-hexahydros-indacen-4-ylcarbamoyl)-5-(1-hydroxycyclopropyl)thiophene-2-sulfonamide | 451.1 |
| 72 | 201 | 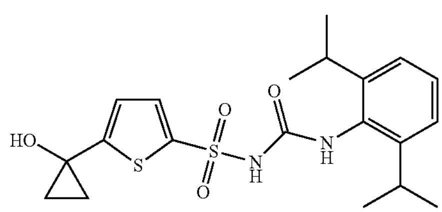 [SMILES: CC(C)c1cccc(C(C)C)c1NC(=O)NS(=O)(=O)c1ccc(C2(O)CC2)s1] | N-(2,6-diisopropylphenylcarbamoyl)-5-(1-hydroxycyclopropyl)thiophene-2-sulfonamide | 421.1 |
| 73 | 194 | 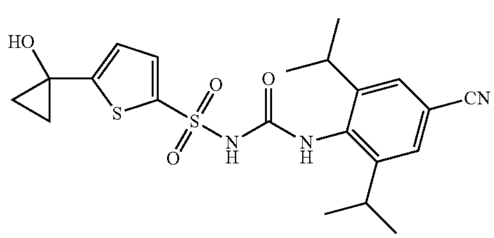 [SMILES: CC(C)c1cc(C#N)cc(C(C)C)c1NC(=O)NS(=O)(=O)c1ccc(C2(O)CC2)s1] | N-(4-cyano-2,6-diisopropylphenylcarbamoyl)-5-(1-hydroxycyclopropyl)thiophene-2-sulfonamide | 446.3 |
| 74 | 178 | 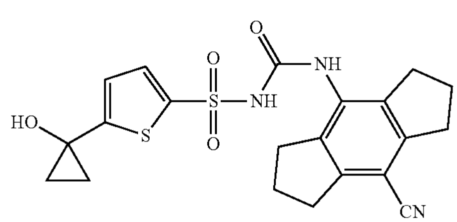 [SMILES: N#Cc1c2c(c(NC(=O)NS(=O)(=O)c3ccc(C4(O)CC4)s3)c3c1CCC3)CCC2] | N-(8-cyano-1,2,3,5,6,7-hexahydros-indacen-4-ylcarbamoyl)-5-(1-hydroxycyclopropyl)thiophene-2-sulfonamide | 444.1 (M + 1) |

TABLE 13-continued

Examples in the following table were prepared using similar conditions as described in
Example 4 and Scheme 4 from appropriate starting materials.

| Example # | Compound | Structure | IUPAC Name | Mass Spec [M − H]⁻ |
|---|---|---|---|---|
| 75 | 145 | 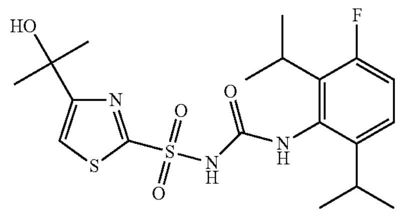 [SMILES: CC(C)c1ccc(F)c(C(C)C)c1NC(=O)NS(=O)(=O)c1nc(C(C)(C)O)cs1] | N-(3-fluoro-2,6-diisopropylphenylcarbamoyl)-4-(2-hydroxypropan-2-yl)thiazole-2-sulfonamide | 442.1 |
| 76 | 147 | 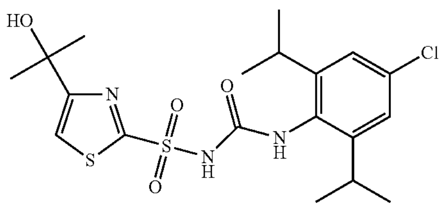 [SMILES: CC(C)c1cc(Cl)cc(C(C)C)c1NC(=O)NS(=O)(=O)c1nc(C(C)(C)O)cs1] | N-(4-chloro-2,6-diisopropylphenylcarbamoyl)-4-(2-hydroxypropan-2-yl)thiazole-2-sulfonamide | 442.2 (M − OH)⁺ |
| 77 | 148 | 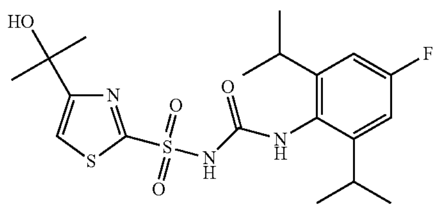 [SMILES: CC(C)c1cc(F)cc(C(C)C)c1NC(=O)NS(=O)(=O)c1nc(C(C)(C)O)cs1] | N-(4-fluoro-2,6-diisopropylphenylcarbamoyl)-4-(2-hydroxypropan-2-yl) thiazole-2-sulfonamide | 444.2 (M + 1) |
| 78 | 144 | 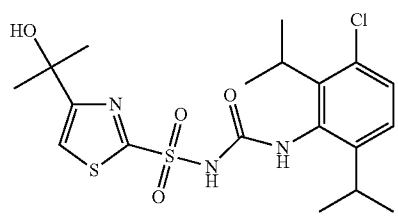 | N-(3-chloro-2,6-diisopropylphenylcarbamoyl)-4-(2-hydroxypropan-2-yl) thiazole-2-sulfonamide | 458.0 |
| 79 | 146 | 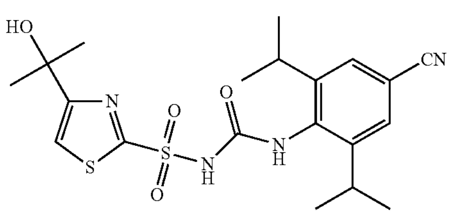 [SMILES: CC(C)c1cc(C#N)cc(C(C)C)c1NC(=O)NS(=O)(=O)c1nc(C(C)(C)O)cs1] | N-(4-cyano-2,6-diisopropylphenylcarbamoyl)-4-(2-hydroxypropan-2-yl)thiazole-2-sulfonamide | 449.1 |
| 80 | 190 | 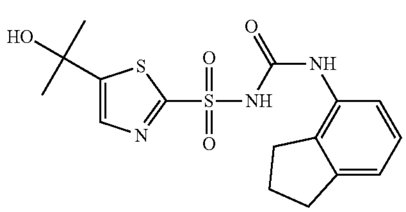 [SMILES: CC(C)(O)c1cnc(S(=O)(=O)NC(=O)Nc2cccc3c2CCC3)s1] | N-(2,3-dihydro-1H-inden-4-ylcarbamoyl)-5-(2-hydroxypropan-2-yl)thiazole-2-sulfonamide | 382.1 (M + 1) |
| 81 | 158 | 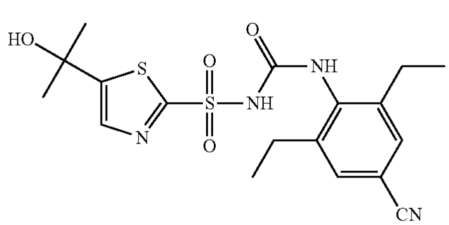 | N-(4-cyano-2,6-diethylphenylcarbamoyl)-5-(2-hydroxypropan-2-yl)thiazole-2-sulfonamide | 421.1 |

TABLE 13-continued

Examples in the following table were prepared using similar conditions as described in Example 4 and Scheme 4 from appropriate starting materials.

| Example # | Compound | Structure | IUPAC Name | Mass Spec [M − H]⁻ |
|---|---|---|---|---|
| 82 | 182 | 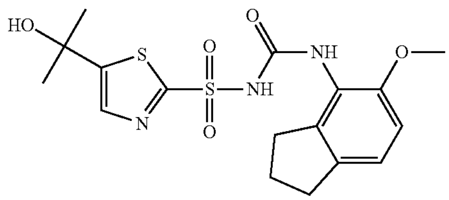 [SMILES: COc1ccc2c(c1NC(=O)NS(=O)(=O)c1ncc(C(C)(C)O)s1)CCC2] | 5-(2-hydroxypropan-2-yl)-N-(5-methoxy-2,3-dihydro-1H-inden-4-ylcarbamoyl)thiazole-2-sulfonamide | 412.1 (M + 1) |
| 83 | 179 | 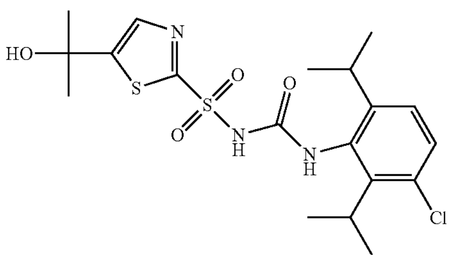 [SMILES: CC(C)c1ccc(Cl)c(C(C)C)c1NC(=O)NS(=O)(=O)c1ncc(C(C)(C)O)s1] | N-(3-chloro-2,6-diisopropylphenylcarbamoyl)-5-(2-hydroxypropan-2-yl)thiazole-2-sulfonamide | 458.1 |
| 84 | 165 | 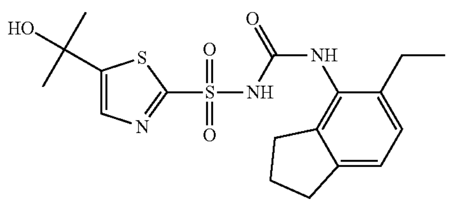 [SMILES: CCc1ccc2c(c1NC(=O)NS(=O)(=O)c1ncc(C(C)(C)O)s1)CCC2] | N-(5-ethyl-2,3-dihydro-1H-inden-4-ylcarbamoyl)-5-(2-hydroxypropan-2-yl)thiazole-2-sulfonamide | 410.1 (M + 1) |
| 85 | 172 | 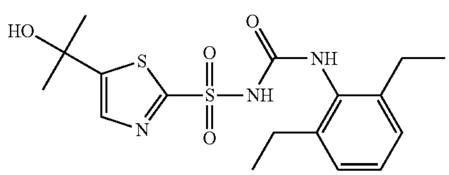 [SMILES: CCc1cccc(CC)c1NC(=O)NS(=O)(=O)c1ncc(C(C)(C)O)s1] | N-(2,6-diethylphenylcarbamoyl)-5-(2-hydroxypropan-2-yl)thiazole-2-sulfonamide | 398.2 (M + 1) |
| 86 | 170 | 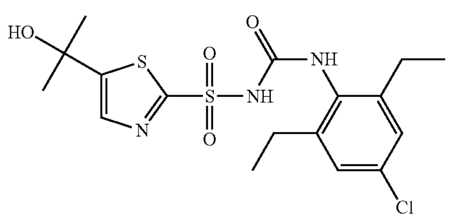 | N-(4-chloro-2,6-diethylphenylcarbamoyl)-5-(2-hydroxypropan-2-yl)thiazole-2-sulfonamide | 432.2 (M + 1) |
| 87 | 151 | 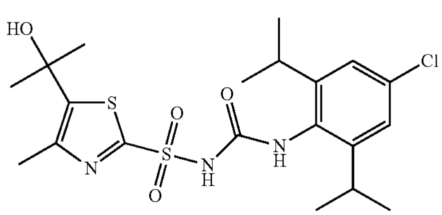 [SMILES: Cc1nc(S(=O)(=O)NC(=O)Nc2c(C(C)C)cc(Cl)cc2C(C)C)sc1C(C)(C)O] | N-(4-chloro-2,6-diisopropylphenylcarbamoyl)-5-(2-hydroxypropan-2-yl)-4-methylthiazole-2-sulfonamide | 472.1 |
| 88 | 152 | 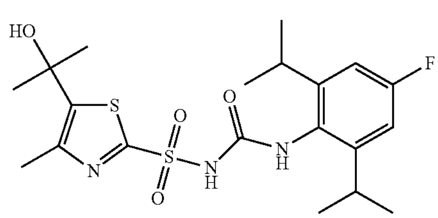 [SMILES: Cc1nc(S(=O)(=O)NC(=O)Nc2c(C(C)C)cc(F)cc2C(C)C)sc1C(C)(C)O] | N-(4-fluoro-2,6-diisopropylphenylcarbamoyl)-5-(2-hydroxypropan-2-yl)-4-methylthiazole-2-sulfonamide | 458.6 (M + 1) |

TABLE 13-continued

Examples in the following table were prepared using similar conditions as described in
Example 4 and Scheme 4 from appropriate starting materials.

| Example # | Compound | Structure | IUPAC Name | Mass Spec [M − H]⁻ |
|---|---|---|---|---|
| 90 | 150 | 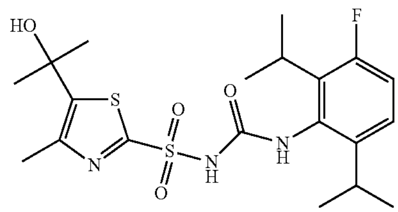 [SMILES: Cc1nc(S(=O)(=O)NC(=O)Nc2c(C(C)C)ccc(F)c2C(C)C)sc1C(C)(C)O] | N-(3-fluoro-2,6-diisopropylphenylcarbamoyl)-5-(2-hydroxypropan-2-yl)-4-methylthiazole-2-sulfonamide | 458.3 (M + 1) |
| 91 | 149 | 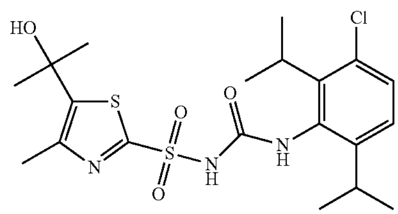 [SMILES: Cc1nc(S(=O)(=O)NC(=O)Nc2c(C(C)C)ccc(Cl)c2C(C)C)sc1C(C)(C)O] | N-(3-chloro-2,6-diisopropylphenylcarbamoyl)-5-(2-hydroxypropan-2-yl)-4-methylthiazole-2-sulfonamide | 474.2 (M + 1) |
| 92 | 169 | 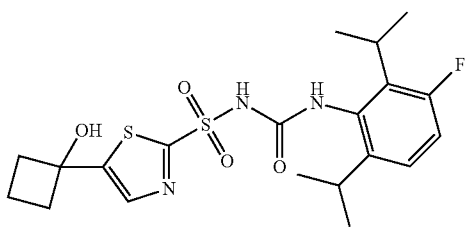 [SMILES: CC(C)c1ccc(F)c(C(C)C)c1NC(=O)NS(=O)(=O)c1ncc(C2(O)CCC2)s1] | N-(3-fluoro-2,6-diisopropylphenylcarbamoyl)-5-(1-hydroxycyclobutyl)thiazole-2-sulfonamide | 454.1 |
| 93 | 167 | 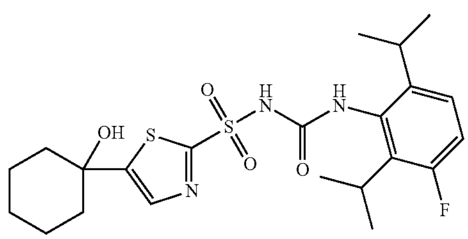 [SMILES: CC(C)c1ccc(F)c(C(C)C)c1NC(=O)NS(=O)(=O)c1ncc(C2(O)CCCCC2)s1] | N-(3-fluoro-2,6-diisopropylphenylcarbamoyl)-5-(1-hydroxycyclohexyl)thiazole-2-sulfonamide | 482.0 |
| 94 | 262 | 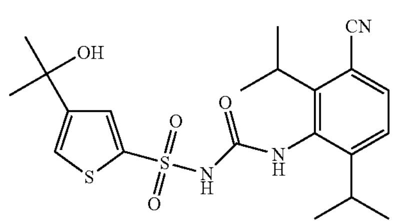 [SMILES: CC(C)c1ccc(C#N)c(C(C)C)c1NC(=O)NS(=O)(=O)c1cc(C(C)(C)O)cs1] | N-(3-cyano-2,6-diisopropylphenylcarbamoyl)-4-(2-hydroxypropan-2-yl)thiophene-2-sulfonamide | 448.2 |
| 95 | 263 | 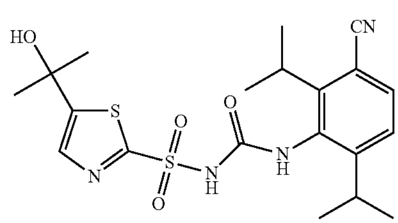 [SMILES: CC(C)c1ccc(C#N)c(C(C)C)c1NC(=O)NS(=O)(=O)c1ncc(C(C)(C)O)s1] | N-(3-cyano-2,6-diisopropylphenylcarbamoyl)-5-(2-hydroxypropan-2-yl)thiazole-2-sulfonamide | 449.2 |

TABLE 13-continued

Examples in the following table were prepared using similar conditions as described in Example 4 and Scheme 4 from appropriate starting materials.

| Example # | Compound | Structure | IUPAC Name | Mass Spec [M − H]⁻ |
|---|---|---|---|---|
| 96 | 264 | 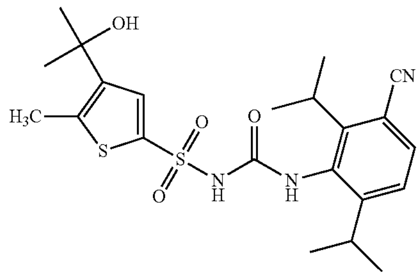 [SMILES: Cc1sc(S(=O)(=O)NC(=O)Nc2c(C(C)C)ccc(C#N)c2C(C)C)cc1C(C)(C)O] | N-(3-cyano-2,6-diisopropylphenylcarbamoyl)-4-(2-hydroxypropan-2-yl)-5-methylthiophene-2-sulfonamide | 462.1 |
| 97 | 265 | 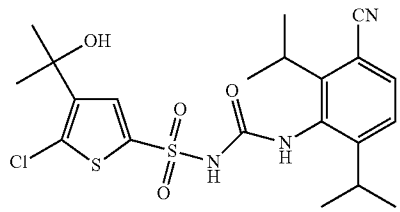 [SMILES: CC(C)c1ccc(C#N)c(C(C)C)c1NC(=O)NS(=O)(=O)c1cc(C(C)(C)O)c(Cl)s1] | 5-chloro-N-(3-cyano-2,6-diisopropylphenylcarbamoyl)-4-(2-hydroxypropan-2-yl)thiophene-2-sulfonamide | 482.2 |

TABLE 14

Examples in the following table were prepared using similar conditions as described in Example 5 and Scheme 5 from appropriate starting materials.

| Example # | Compound | Structure | IUPAC Name | Mass Spec [M − H]⁻ |
|---|---|---|---|---|
| 98 | 193 | 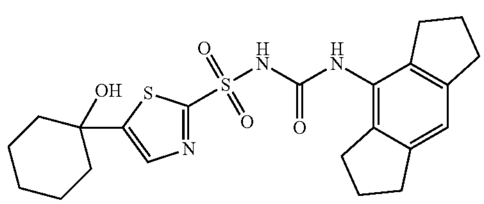 [SMILES: O=C(Nc1c2c(cc3c1CCC3)CCC2)NS(=O)(=O)c1ncc(C2(O)CCCCC2)s1] | N-(1,2,3,5,6,7-hexahydros-indacen-4-ylcarbamoyl)-5-(1-hydroxycyclohexyl)thiazole-2-sulfonamide | 462.1 (M + 1) |
| 99 | 168 | 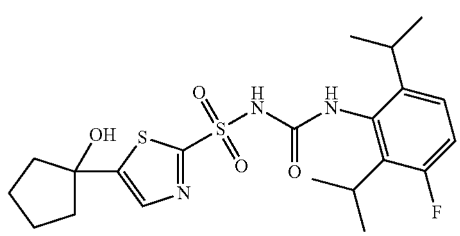 [SMILES: CC(C)c1ccc(F)c(C(C)C)c1NC(=O)NS(=O)(=O)c1ncc(C2(O)CCCC2)s1] | N-(3-fluoro-2,6-diisopropylphenylcarbamoyl)-5-(1-hydroxycyclopentyl)thiazole-2-sulfonamide | 468.1 |

Example 100

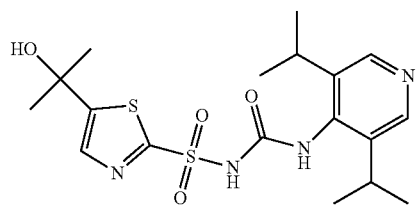

138

N-(3,5-diisopropylpyridin-4-ylcarbamoyl)-5-(2-hydroxypropan-2-yl)thiazole-2-sulfonamide

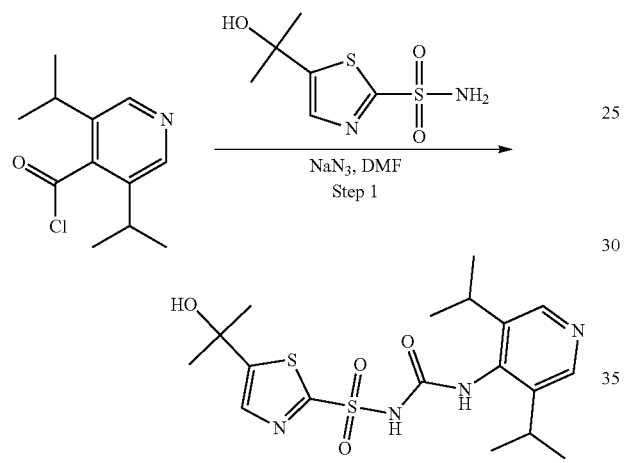

Into a 50-mL round-bottom flask, was placed 5-(2-hydroxypropan-2-yl)thiazole-2-sulfonamide (98 mg, 0.44 mmol), DMF (5 mL), NaN$_3$ (70 mg, 1.08 mmol), 3,5-diisopropylisonicotinoyl chloride (100 mg, 0.44 mmol). The resulting solution was stirred overnight at RT and then was diluted with 5 mL of water. The resulting solution was washed with 5 mL of DCM and the aqueous layer was purified by Prep-HPLC using method E eluted with a gradient of 8-30% ACN. This resulted in 41.4 mg (22%) of the title compound as a white solid. MS-ESI: 427.0 (M+1).

$^1$HTEM NMR (300 MHz, DMSO-d$_6$, 353 K) δ 7.89 (s, 2H), 7.74 (s, 1H), 3.00-2.95 (m, 2H), 1.56 (s, 6H), 1.19 (d, J=6.6 Hz, 12H).

Example 101

261

2,6-Diisopropylphenyl 5-(2-hydroxypropan-2-yl)thiazol-2-ylsulfonylcarbamate

Into a 50-mL round-bottom flask, was placed 2,6-diisopropylphenyl 4-nitrophenyl carbonate (120 mg, 0.35 mmol), ACN (10 mL), K$_2$CO$_3$ (150 mg, 1.09 mmol), 5-(2-hydroxypropan-2-yl)thiazole-2-sulfonamide (116 mg, 0.52 mmol). The resulting solution was stirred overnight at 80° C. and then was concentrated under vacuum. The crude product was purified by Prep-HPLC using method E eluted with a gradient of 14-50% ACN. This resulted in 94 mg (63%) of the title compound as a yellow solid. MS-ESI: 427.1 (M+1). $^1$H NMR (300 MHz, MeOD-d$_4$) δ 7.68 (s, 1H), 7.11-7.04 (m, 3H), 3.08-2.98 (m, 2H), 1.61 (s, 6H), 1.12 (d, J=6.9 Hz, 12H).

TABLE 15

Example in the following table was prepared using similar conditions as described in Example 101 from appropriate starting materials.

| Example # | Compound | Structure | IUPAC Name | Mass Spec [M − H]$^-$ |
|---|---|---|---|---|
| 102 | 260 | 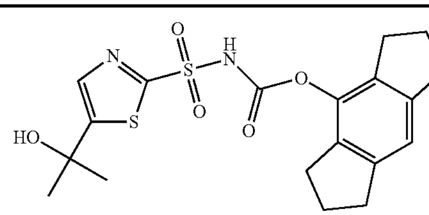 | 1,2,3,5,6,7-hexahydros-indacen-4-yl 5-(2-hydroxypropan-2-yl)thiazol-2-ylsulfonylcarbamate | 421.1 |

Bioassay:
IL-1β Production in PMA-Differentiated THP-1 Cells Stimulated with Gramicidin.
Procedure 1:

Cell culture—THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 μg/ml), and maintained in log phase prior to experimental setup. Prior to the experiment THP-1 were treated with PMA (Phorbol 12-myristate 13-acetate) (10 μg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×106 cells/ml, and 100 ul was plated in a 96 well plate. Cells were incubated with compounds for 1 hours and then stimulated with Gramicidin (5 μM) (Enzo) for 2 hours. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 μM). A vehicle only control was run concurrently with each experiment. Final DMSO concentration was 1%. Compounds exhibit a dose-related inhibition of IL-1β production in PMA-differentiated THP-1 cells.

Procedure 2:

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were dissolved in dimethyl sulfoxide (DMSO) and added to the culture medium to achieve desired concentration (e.g. 100, 33, 11, 3.7, 1.2, 0.41, 0.14, 0.046, 0.015, 0.0051, 0.0017 μM). Cells were incubated with compounds for 1 hour and then stimulated with gramicidin (5 μM) (Enzo) for 2 hours. Cell free supernatant was collected and the production of IL-1β was evaluated by HTRF (cisbio). A vehicle only control was run concurrently with each experiment. Final DMSO concentration was 0.38%. Compounds exhibited a concentration-dependent inhibition of IL-1β production in PMA-differentiated THP-1 cells.

$IC_{50}$ values (μM) of for the compounds of Tables 1 and 2 herein tested in accordance with the protocol above have $IC_{50}$ values of less than about 30 μM.

A number of embodiments of the invention have been described. Nevertheless, it will be understood that various modifications may be made without departing from the spirit and scope of the invention. Accordingly, other embodiments are within the scope of the following claims.

We claim:
1. A compound of Formula II,

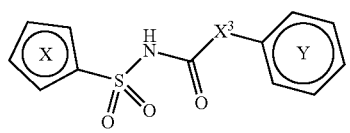

Formula II or a pharmaceutically acceptable salt thereof, wherein Formula II is selected from the group consisting of

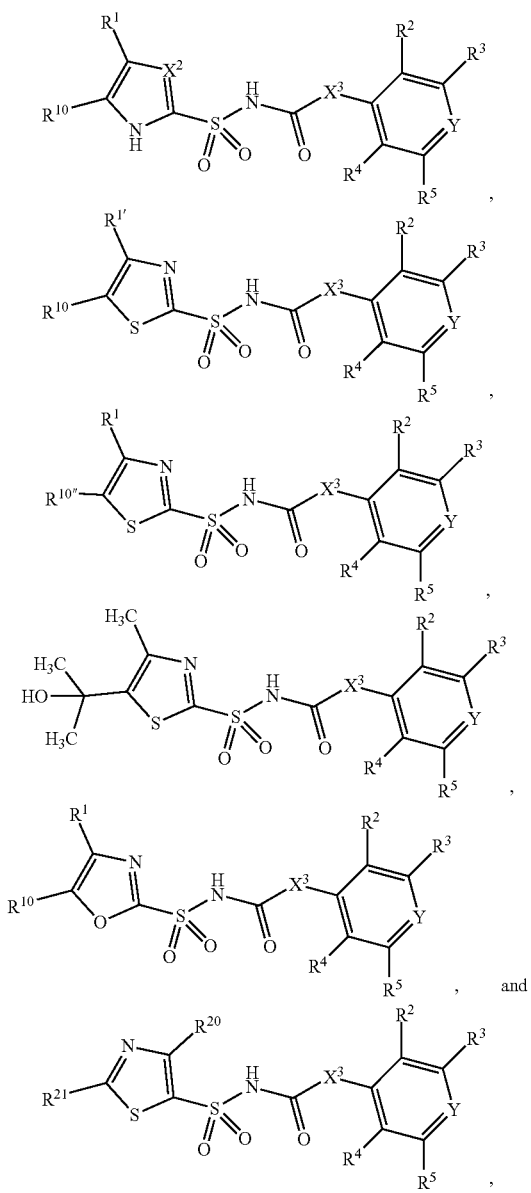

$X^2$ is N;
$X^3$ is NH or O;
or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^{8'}$ is selected from CN, $CO_2C_1$-$C_6$ alkyl, $CO_2C_3$-$C_8$ cycloalkyl, $CONR^{11}R^{12}$, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^{2'}$ is hydrogen, halo, or $C_1$-$C_6$ alkyl optionally substituted with hydroxy;

$R^{2''}$ is hydrogen or $C_1$-$C_6$ alkyl;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^{3'}$ is hydrogen, halo, or $C_1$-$C_6$ alkyl optionally substituted with hydroxy;

$R^{3''}$ is hydrogen, CN, or $C_1$-$C_6$ alkyl;

$R^4$ is hydrogen, $C_1$-$C_6$ alkoxy, halo, $C_1$-$C_6$ haloalkyl, or $C_1$-$C_6$ alkyl optionally substituted with hydroxy;

$R^{4'}$ is hydrogen, halo, or $C_1$-$C_6$ alkyl optionally substituted with hydroxy;

$R^{4''}$ is hydrogen or $C_1$-$C_6$ alkyl;

$R^5$ is hydrogen, $C_1$-$C_6$ alkoxy, halo, $C_1$-$C_6$ haloalkyl, or $C_1$-$C_6$ alkyl optionally substituted with hydroxy;

$R^{5'}$ is hydrogen, halo, or $C_1$-$C_6$ alkyl optionally substituted with hydroxy;

$R^{5''}$ is hydrogen, CN, or $C_1$-$C_6$ alkyl;

or $R^2$ and $R^3$ taken together with the carbons connecting them form a four-membered to seven-membered ring A, or $R^{2'}$ and $R^{3'}$ taken together with the carbons connecting them form a four-membered to seven-membered ring A, or $R^4$ and $R^5$ taken together with the carbons connecting them form a four-membered to seven-membered ring B, or $R^{4'}$ and $R^{5'}$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, or $R^{2'}$ and $R^{3'}$ taken together with the carbons connecting them form a four-membered to seven-membered ring A and $R^{4'}$ and $R^{5'}$ taken together with the carbons connecting them form a four-membered to seven-membered ring B, wherein ring A is

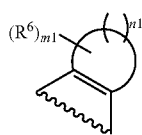

Ring A and ring B is

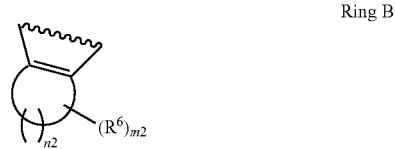

Ring B wherein ring A is a saturated carbocyclic ring;

n1 is from 2 to 5;

m1 is from 1 to 10;

wherein ring B is a saturated carbocyclic ring;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;

wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl;

wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10}$ is selected from H, Cl, $C_1$-$C_6$ alkyl, $C_3$-$C_6$ cycloalkyl and $C_3$-$C_6$ heterocycloalkyl;

wherein $C_1$-$C_6$ alkyl, $C_3$-$C_6$ cycloalkyl and $C_3$-$C_6$ heterocycloalkyl substituents are optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10''}$ is selected from Cl, $C_1$-$C_6$ alkyl, $C_3$-$C_6$ cycloalkyl, and $C_3$-$C_6$ heterocycloalkyl;

wherein $C_1$-$C_6$ alkyl, $C_3$-$C_6$ cycloalkyl, and $C_3$-$C_6$ heterocycloalkyl are optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10'''}$ is selected from Cl, $C_1$-$C_6$ alkyl substituted with hydroxy, $C_3$-$C_6$ cycloalkyl, and $C_3$-$C_6$ heterocycloalkyl;

wherein the $C_3$-$C_6$ cycloalkyl, and $C_3$-$C_6$ heterocycloalkyl above are each optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is $C_1$-$C_6$ alkyl;

$R^{20}$ is selected from H, halo, or $C_1$-$C_6$ alkyl optionally substituted with hydroxy;

$R^{21}$ is selected from H, halo, or $C_1$-$C_6$ alkyl substituted with hydroxy.

2. A compound of Formula II,

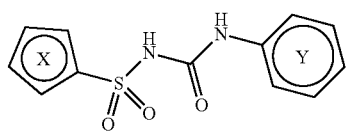

Formula II or a pharmaceutically acceptable salt thereof, wherein Formula II is selected from the group consisting of

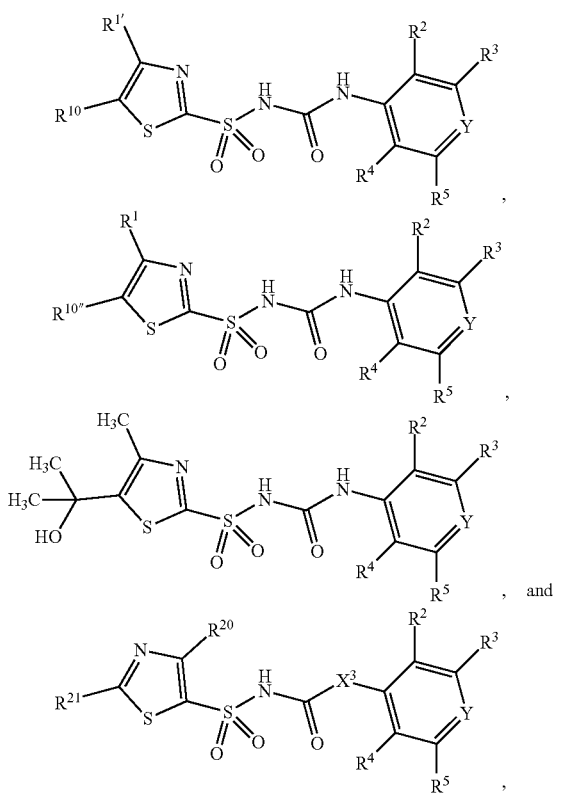

Y is N or $CR^8$;

$R^8$ is selected from H, CN, Cl, and F;

$R^{8'}$ is selected from CN and $CONR^{11}R^{12}$;

$R^2$ is hydrogen or $C_1$-$C_6$ alkyl;

$R^{2'}$ is $C_1$-$C_6$ alkyl;

$R^3$ is hydrogen, CN, $C_1$-$C_6$ alkoxy, or halo;

$R^{3'}$ is hydrogen or halo;

$R^4$ is hydrogen or $C_1$-$C_6$ alkyl;

$R^{4'}$ is $C_1$-$C_6$ alkyl;

$R^5$ is hydrogen;

$R^{5'}$ is hydrogen;

or $R^2$ and $R^3$ taken together with the carbons connecting them form a four-membered to seven-membered ring A, or $R^{2'}$ and $R^{3'}$ taken together with the carbons connecting them form a four-membered to seven-membered ring A, or $R^4$ and $R^5$ taken together with the carbons connecting them form a four-membered to seven-membered ring B, or $R^{4'}$ and $R^{5'}$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, or $R^{2'}$ and $R^{3'}$ taken together with the carbons connecting them form a four-membered to seven-membered ring A and $R^{4'}$ and $R^{5'}$ taken together with the carbons connecting them form a four-membered to seven-membered ring B, wherein ring A is

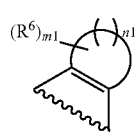

Ring A and ring B is

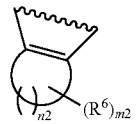

Ring B wherein ring A is a saturated carbocyclic ring;

n1 is 3;

m1 is 0;

wherein ring B is a saturated carbocyclic ring;

n2 is 3;

m2 is 0;

$R^1$ is H;

$R^{1'}$ is selected from $C(R^{19})_2OH$ and $C_3$-$C_6$ cycloalkyl;

wherein the $C_3$-$C_6$ cycloalkyl above is optionally substituted with one or more hydroxy;

$R^{10}$ is selected from H, Cl, $C_1$-$C_6$ alkyl, and $C_3$-$C_6$ cycloalkyl;

wherein $R^{10}$ is optionally substituted with one or more substituents each independently selected from hydroxy;

$R^{10''}$ is selected from $C_1$-$C_6$ alkyl, and $C_3$-$C_6$ cycloalkyl;

wherein $R^{10''}$ is optionally substituted with one or more hydroxy;

$R^{10'''}$ is selected from $C_1$-$C_6$ alkyl and $C_3$-$C_6$ cycloalkyl;

wherein $R^{10'''}$ is optionally substituted with one or more hydroxy;

each of $R^{11}$ and $R^{12}$ is hydrogen;

each $R^{19}$ is the same and is selected from $C_1$-$C_6$ alkyl.

3. The compound of claim 1, wherein the compound of Formula II is

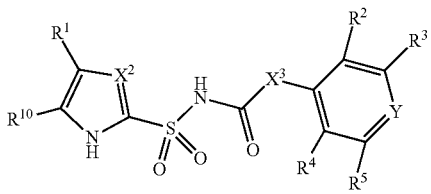

or a pharmaceutically acceptable salt thereof, and wherein:

$X^2$ is N;

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;

$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

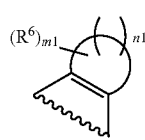

Ring A and ring B is

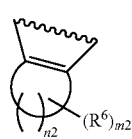

Ring B wherein ring A is a saturated carbocyclic ring;

n1 is from 2 to 5;

m1 is from 1 to 10;

wherein ring B is a saturated carbocyclic ring;

n2 is from 2 to 5;

m2 is from 1 to 10;

wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;

wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10}$ is selected from H, Cl, $C_1$-$C_6$ alkyl, $C_3$-$C_6$ cycloalkyl and $C_3$-$C_6$ heterocycloalkyl;

wherein the $C_1$-$C_6$ alkyl, $C_3$-$C_6$ cycloalkyl and $C_3$-$C_6$ heterocycloalkyl substituents are optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is selected from $C_1$-$C_6$ alkyl.

4. The compound of claim 1, wherein the compound of Formula II is

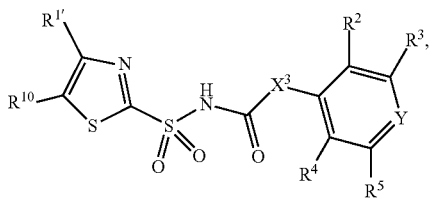

or a pharmaceutically acceptable salt thereof, wherein:

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

$R^3$ is hydrogen, CN, $C_1$-$C_6$ alkoxy, halo, $C_1$-$C_6$ haloalkyl, or $C_1$-$C_6$ alkyl optionally substituted with hydroxy;

$R^4$ is hydrogen, $C_1$-$C_6$ alkoxy, halo, $C_1$-$C_6$ haloalkyl, or $C_1$-$C_6$ alkyl optionally substituted with hydroxy;

$R^5$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A, or $R^4$ and $R^5$ taken together with the carbons connecting them form a four-membered to seven-membered ring B, or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

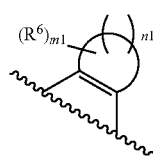

Ring A and ring B is

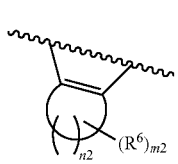

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;

or two $R^6$ taken together with the atom or atoms connecting them form a 3-to-8-membered carbocyclic or saturated heterocyclic ring containing 1 or 2 heteroatoms independently selected from O, N, and S;

$R^{1'}$ is selected from unsubstituted $C_1$-$C_6$ alkyl, $C(R^{19})_2OH$, $C(O)C_2$-$C_6$ alkyl, and $C_3$-$C_6$ cycloalkyl;

wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{10}$ is selected from H, Cl, $C_1$-$C_6$ alkyl, $C_3$-$C_6$ cycloalkyl and $C_3$-$C_6$ heterocycloalkyl;

wherein the $C_1$-$C_6$ alkyl, $C_3$-$C_6$ cycloalkyl and $C_3$-$C_6$ heterocycloalkyl are optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;

$R^{13}$ is $C_1$-$C_6$ alkyl;

each of $R^{11}$ and $R^{12}$ at each occurrence is independently selected from hydrogen, $C_1$-$C_6$ alkyl, $CO_2R^{15}$ and $CONR^{17}R^{18}$;

$R^{15}$ is $C_1$-$C_6$ alkyl;

each of $R^{17}$ and $R^{18}$ at each occurrence is independently selected from hydrogen and $C_1$-$C_6$ alkyl;

each $R^{16}$ is the same or different and is selected from H, $C_1$-$C_6$ alkyl, $C_1$-$C_6$ alkoxy, $NR^{11}R^{12}$, oxo, and $=NR^{13}$;

each $R^{19}$ is the same and is selected from $C_1$-$C_6$ alkyl.

5. The compound of claim 1, wherein the compound of Formula II is

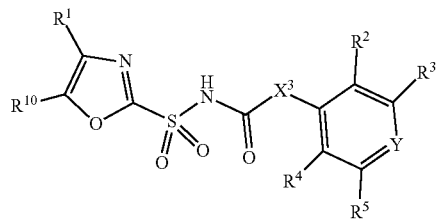

or a pharmaceutically acceptable salt thereof, and wherein:

$X^3$ is NH or O;

or when $X^3$ is NH, $X^3$ and $R^2$ taken together with the atoms connecting them form a four-to-seven-membered heterocyclic ring optionally substituted with one or more $R^{16}$;

or when $X^3$ is NH, $X^3$ and $R^4$ taken together with the atoms connecting them form a four-to-seven-membered heterocyclic ring optionally substituted with one or more $R^{16}$;

Y is N or $CR^8$;

$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;

$R^2$ is hydrogen, $C_1$-$C_6$ alkoxy, halo, $C_1$-$C_6$ haloalkyl, or $C_1$-$C_6$ alkyl optionally substituted with hydroxy;

or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

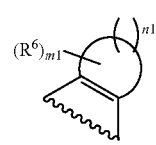

Ring A and ring B is

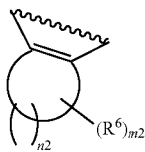

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B,
wherein ring A is

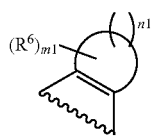

Ring A and ring B is

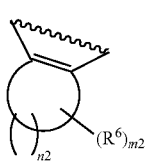

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10}$ is selected from H, Cl, $C_1$-$C_6$ alkyl, $C_3$-$C_6$ cycloalkyl and $C_3$-$C_6$ heterocycloalkyl;
wherein the $C_1$-$C_6$ alkyl, $C_3$-$C_6$ cycloalkyl and $C_3$-$C_6$ heterocycloalkyl are optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
or $R^1$ and $R^{10}$ taken together with the atoms connecting them form a 3-to-8-membered carbocyclic or heterocyclic ring containing 1 or 2 heteroatoms independently selected from O, N, and S, wherein the ring is optionally substituted with one or more substituents each independently selected from hydroxy, oxo, $C_1$-$C_6$ alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl.

6. The compound of claim 1, wherein the compound of Formula II is

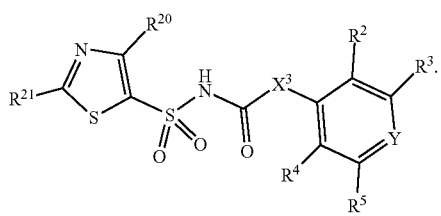

7. The compound of claim 2, wherein the compound of Formula II is

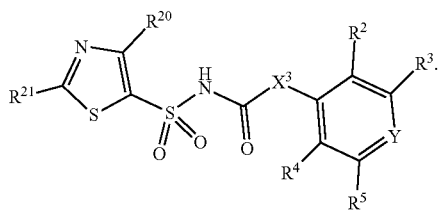

8. A compound selected from the group consisting of compounds in the Table below:

| Compound | Structure |
|---|---|
| 101 | 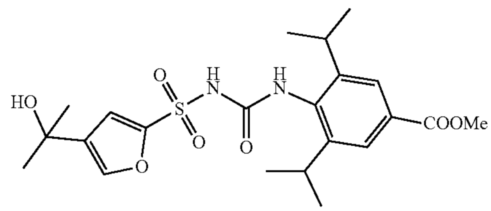 [SMILES: COC(=O)c1cc(C(C)C)c(NC(=O)NS(=O)(=O)c2cc(C(C)(C)O)co2)c(C(C)C)c1] |
| 102 | 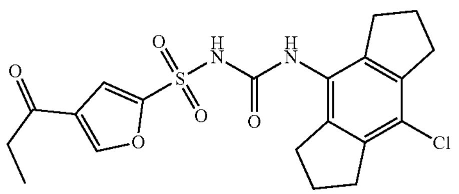 [SMILES: CCC(=O)c1coc(S(=O)(=O)NC(=O)Nc2c3c(c(Cl)c4c2CCC4)CCC3)c1] |
| 103 | 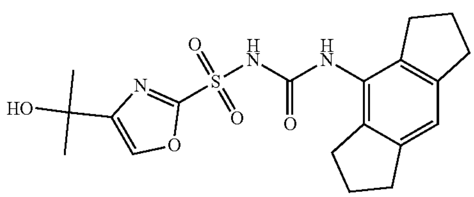 [SMILES: CC(C)(O)c1coc(S(=O)(=O)NC(=O)Nc2c3c(cc4c2CCC4)CCC3)n1] |
| 104 | 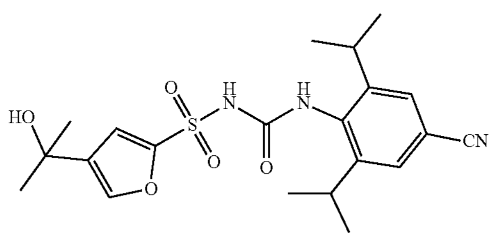 [SMILES: CC(C)c1cc(C#N)cc(C(C)C)c1NC(=O)NS(=O)(=O)c1cc(C(C)(C)O)co1] |
| 105 | 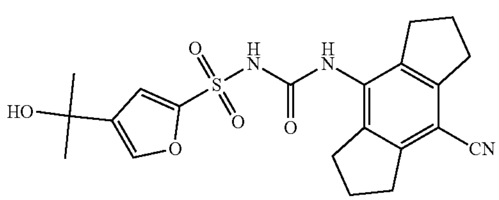 [SMILES: CC(C)(O)c1coc(S(=O)(=O)NC(=O)Nc2c3c(c(C#N)c4c2CCC4)CCC3)c1] |
| 106 | 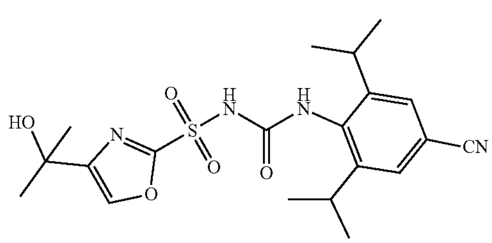 [SMILES: CC(C)c1cc(C#N)cc(C(C)C)c1NC(=O)NS(=O)(=O)c1nc(C(C)(C)O)co1] |
| 108 | 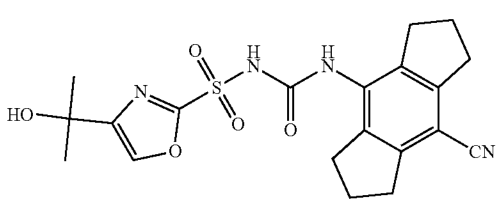 |
| 109 | |
| 110 | |
| 111 | |
| 112 | |
| 113 | |
| 114 | |
| 116 | |

273
-continued

| Compound | Structure |
|---|---|
| 117 | 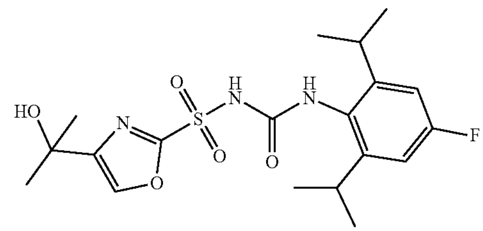 [SMILES: CC(C)c1cc(F)cc(C(C)C)c1NC(=O)NS(=O)(=O)c1nc(C(C)(C)O)co1] |
| 118 | 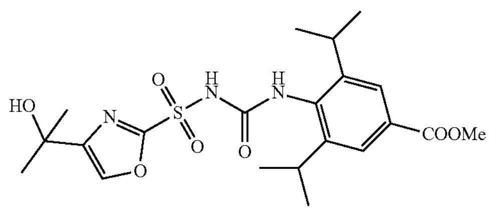 [SMILES: COC(=O)c1cc(C(C)C)c(NC(=O)NS(=O)(=O)c2nc(C(C)(C)O)co2)c(C(C)C)c1] |
| 119 | 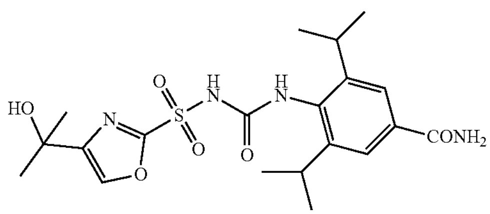 [SMILES: CC(C)c1cc(C(N)=O)cc(C(C)C)c1NC(=O)NS(=O)(=O)c1nc(C(C)(C)O)co1] |
| 120 | 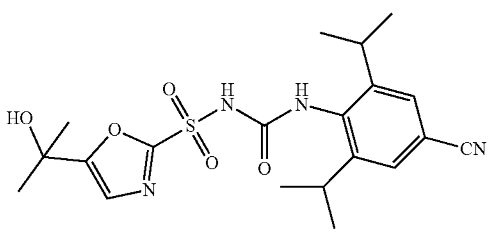 [SMILES: CC(C)c1cc(C#N)cc(C(C)C)c1NC(=O)NS(=O)(=O)c1ncc(C(C)(C)O)o1] |
| 121 | 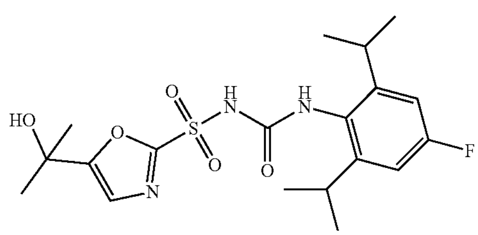 [SMILES: CC(C)c1cc(F)cc(C(C)C)c1NC(=O)NS(=O)(=O)c1ncc(C(C)(C)O)o1] |
| 122 | 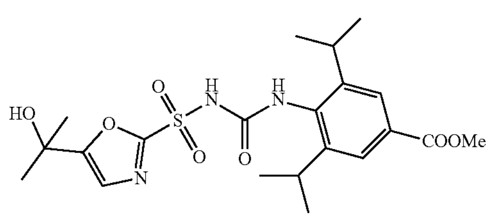 [SMILES: COC(=O)c1cc(C(C)C)c(NC(=O)NS(=O)(=O)c2ncc(C(C)(C)O)o2)c(C(C)C)c1] |
| 123 | 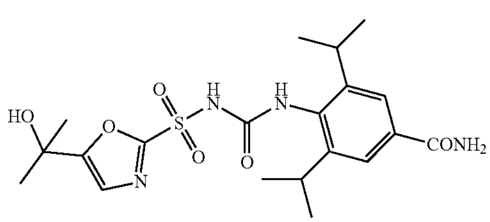 [SMILES: CC(C)c1cc(C(N)=O)cc(C(C)C)c1NC(=O)NS(=O)(=O)c1ncc(C(C)(C)O)o1] |

274
-continued

| Compound | Structure |
|---|---|
| 124 | 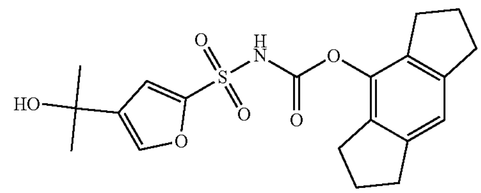 [SMILES: CC(C)(O)c1coc(S(=O)(=O)NC(=O)Oc2c3c(cc4c2CCC4)CCC3)c1] |
| 126 | 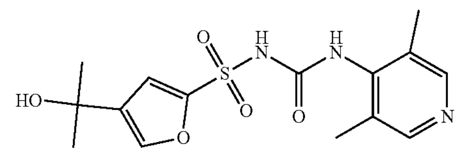 [SMILES: Cc1cncc(C)c1NC(=O)NS(=O)(=O)c1cc(C(C)(C)O)co1] |
| 127 | 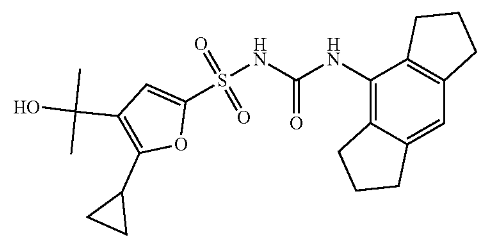 [SMILES: CC(C)(O)c1cc(S(=O)(=O)NC(=O)Nc2c3c(cc4c2CCC4)CCC3)oc1C1CC1] |
| 128 | 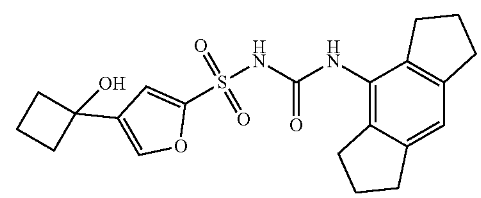 [SMILES: O=C(Nc1c2c(cc3c1CCC3)CCC2)NS(=O)(=O)c1cc(C2(O)CCC2)co1] |
| 129 | 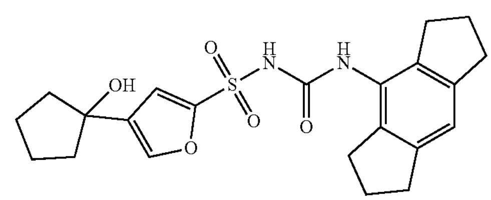 [SMILES: O=C(Nc1c2c(cc3c1CCC3)CCC2)NS(=O)(=O)c1cc(C2(O)CCCC2)co1] |
| 130 | 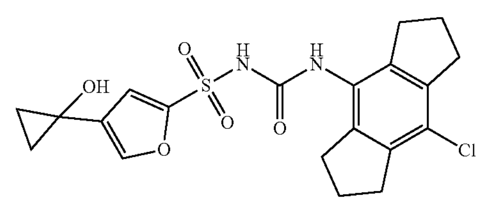 [SMILES: O=C(Nc1c2c(c(Cl)c3c1CCC3)CCC2)NS(=O)(=O)c1cc(C2(O)CC2)co1] |
| 132 | 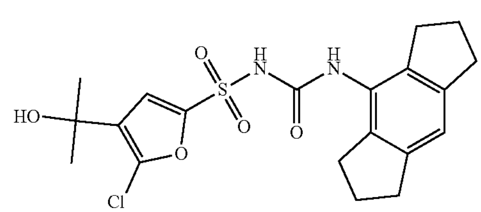 [SMILES: CC(C)(O)c1cc(S(=O)(=O)NC(=O)Nc2c3c(cc4c2CCC4)CCC3)oc1Cl] |

-continued
| Compound | Structure |
|---|---|
| 138 | 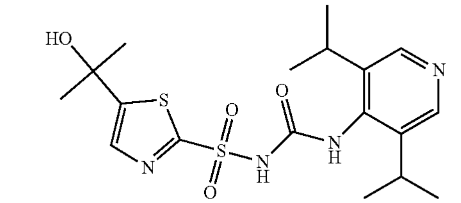 [SMILES: CC(C)c1cncc(C(C)C)c1NC(=O)NS(=O)(=O)c1ncc(C(C)(C)O)s1] |
| 139 | 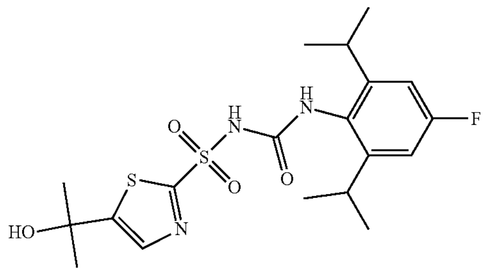 [SMILES: CC(C)c1cc(F)cc(C(C)C)c1NC(=O)NS(=O)(=O)c1ncc(C(C)(C)O)s1] |
| 142 | 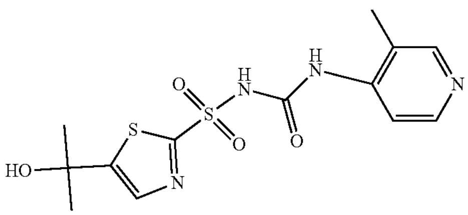 [SMILES: Cc1cnccc1NC(=O)NS(=O)(=O)c1ncc(C(C)(C)O)s1] |
| 144 | 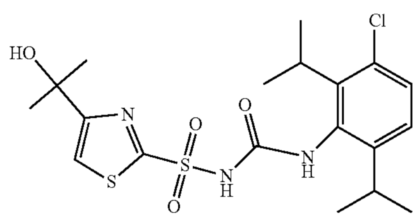 [SMILES: CC(C)c1ccc(Cl)c(C(C)C)c1NC(=O)NS(=O)(=O)c1nc(C(C)(C)O)cs1] |
| 145 | 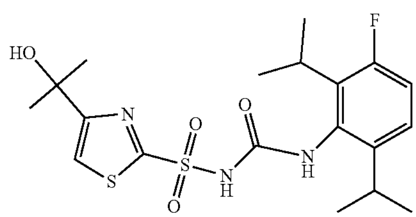 [SMILES: CC(C)c1ccc(F)c(C(C)C)c1NC(=O)NS(=O)(=O)c1nc(C(C)(C)O)cs1] |
| 146 | 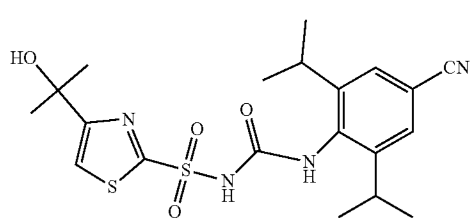 [SMILES: CC(C)c1cc(C#N)cc(C(C)C)c1NC(=O)NS(=O)(=O)c1nc(C(C)(C)O)cs1] |
| 147 | 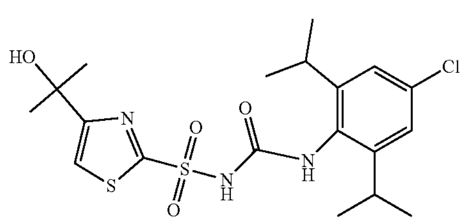 [SMILES: CC(C)c1cc(Cl)cc(C(C)C)c1NC(=O)NS(=O)(=O)c1nc(C(C)(C)O)cs1] |
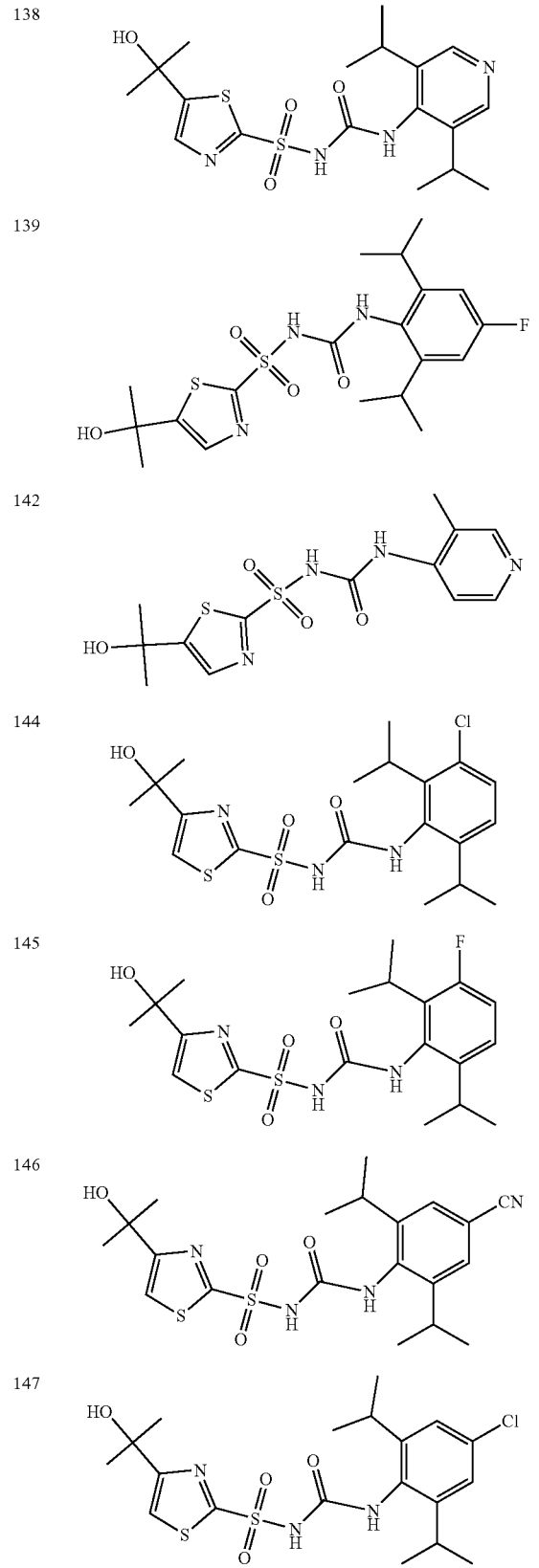
-continued
| Compound | Structure |
|---|---|
| 148 | 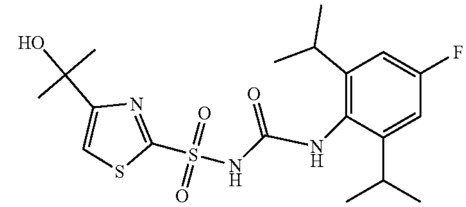 [SMILES: CC(C)c1cc(F)cc(C(C)C)c1NC(=O)NS(=O)(=O)c1nc(C(C)(C)O)cs1] |
| 149 | 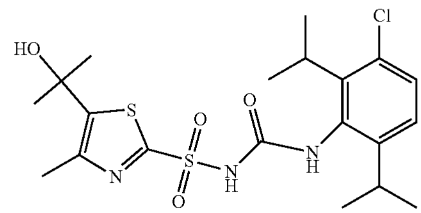 [SMILES: Cc1nc(S(=O)(=O)NC(=O)Nc2c(C(C)C)ccc(Cl)c2C(C)C)sc1C(C)(C)O] |
| 150 | 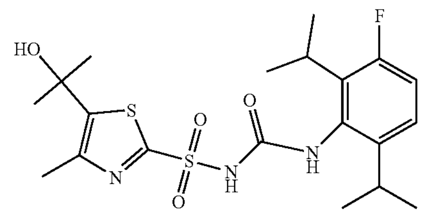 [SMILES: Cc1nc(S(=O)(=O)NC(=O)Nc2c(C(C)C)ccc(F)c2C(C)C)sc1C(C)(C)O] |
| 151 | 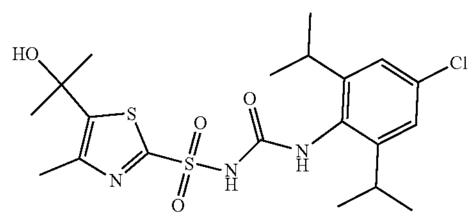 [SMILES: Cc1nc(S(=O)(=O)NC(=O)Nc2c(C(C)C)cc(Cl)cc2C(C)C)sc1C(C)(C)O] |
| 152 | 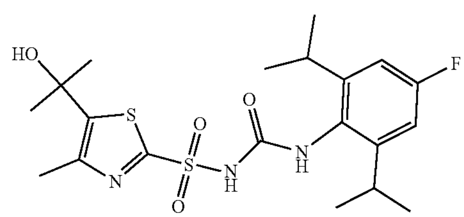 [SMILES: Cc1nc(S(=O)(=O)NC(=O)Nc2c(C(C)C)cc(F)cc2C(C)C)sc1C(C)(C)O] |
| 155 | 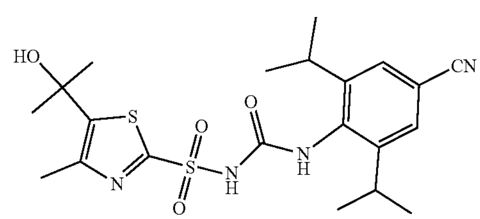 [SMILES: Cc1nc(S(=O)(=O)NC(=O)Nc2c(C(C)C)cc(C#N)cc2C(C)C)sc1C(C)(C)O] |
| 158 | 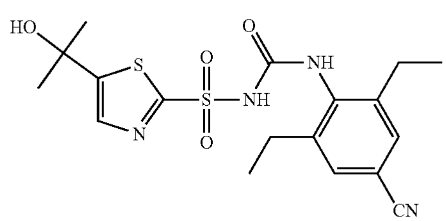 [SMILES: CCc1cc(C#N)cc(CC)c1NC(=O)NS(=O)(=O)c1ncc(C(C)(C)O)s1] |
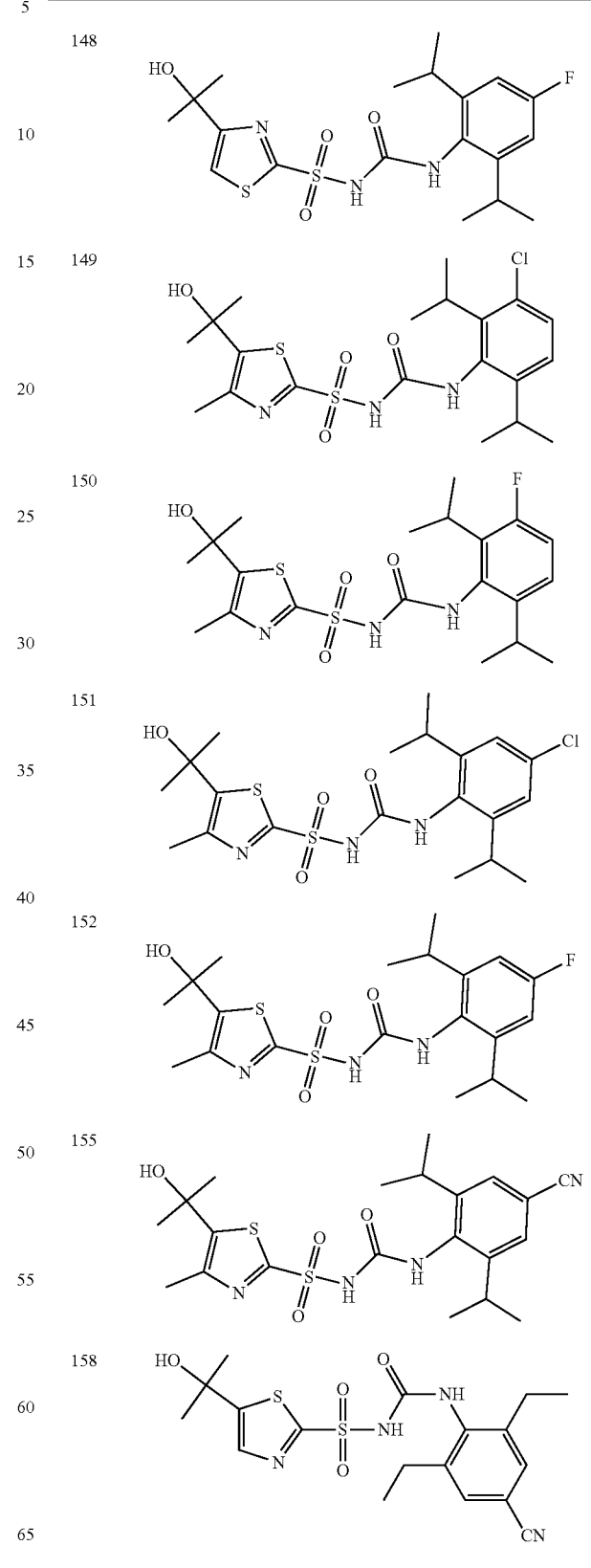

-continued

| Compound | Structure |
|---|---|
| 160 | 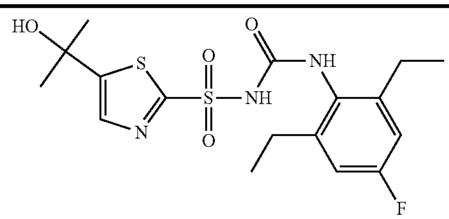 |
| 163 | 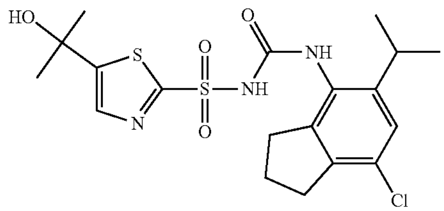 [SMILES: CC(C)c1cc(Cl)c2c(c1NC(=O)NS(=O)(=O)c1ncc(C(C)(C)O)s1)CCC2] |
| 165 | 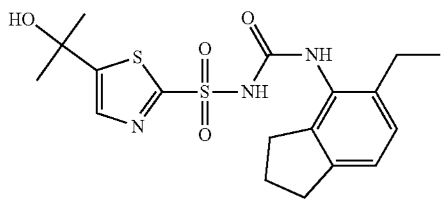 [SMILES: CCc1ccc2c(c1NC(=O)NS(=O)(=O)c1ncc(C(C)(C)O)s1)CCC2] |
| 167 | 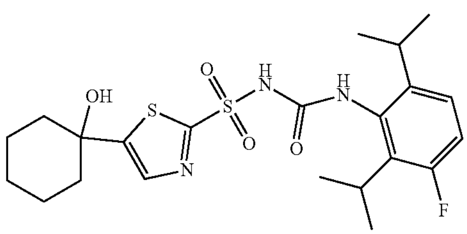 [SMILES: CC(C)c1ccc(F)c(C(C)C)c1NC(=O)NS(=O)(=O)c1ncc(C2(O)CCCCC2)s1] |
| 168 | 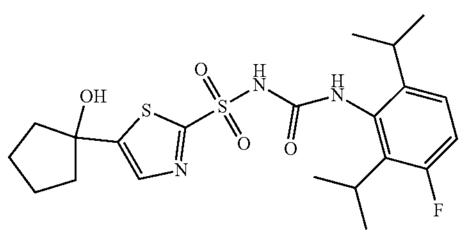 [SMILES: CC(C)c1ccc(F)c(C(C)C)c1NC(=O)NS(=O)(=O)c1ncc(C2(O)CCCC2)s1] |
| 169 | 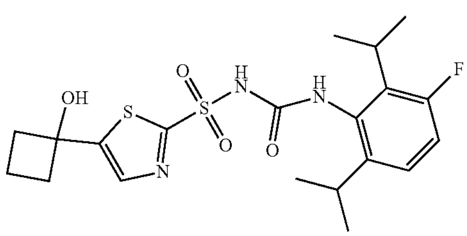 [SMILES: CC(C)c1ccc(F)c(C(C)C)c1NC(=O)NS(=O)(=O)c1ncc(C2(O)CCC2)s1] |
| 170 | 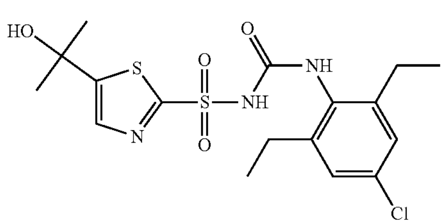 [SMILES: CCc1cc(Cl)cc(CC)c1NC(=O)NS(=O)(=O)c1ncc(C(C)(C)O)s1] |

-continued

| Compound | Structure |
|---|---|
| 172 | 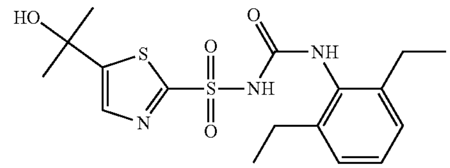 [SMILES: CCc1cccc(CC)c1NC(=O)NS(=O)(=O)c1ncc(C(C)(C)O)s1] |
| 179 | 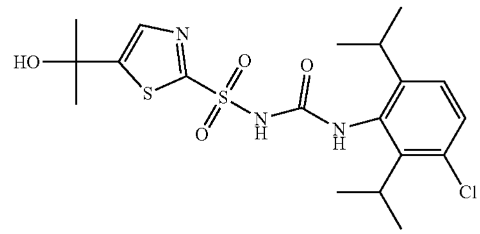 [SMILES: CC(C)c1ccc(Cl)c(C(C)C)c1NC(=O)NS(=O)(=O)c1ncc(C(C)(C)O)s1] |
| 181 | 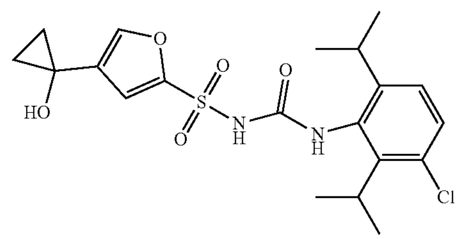 [SMILES: CC(C)c1ccc(Cl)c(C(C)C)c1NC(=O)NS(=O)(=O)c1cc(C2(O)CC2)co1] |
| 182 | 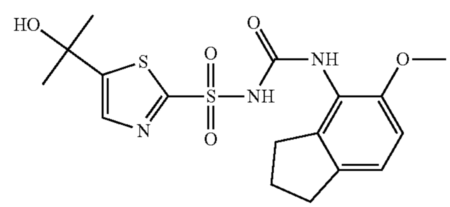 [SMILES: COc1ccc2c(c1NC(=O)NS(=O)(=O)c1ncc(C(C)(C)O)s1)CCC2] |
| 183 | 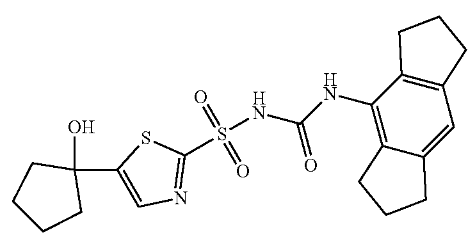 [SMILES: O=C(Nc1c2c(cc3c1CCC3)CCC2)NS(=O)(=O)c1ncc(C2(O)CCCC2)s1] |
| 190 | 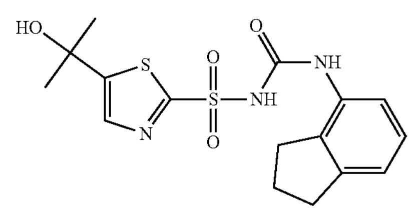 [SMILES: CC(C)(O)c1cnc(S(=O)(=O)NC(=O)Nc2cccc3c2CCC3)s1] |
| 192 | 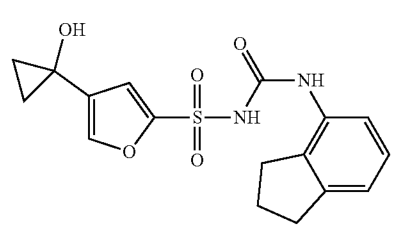 [SMILES: O=C(Nc1cccc2c1CCC2)NS(=O)(=O)c1cc(C2(O)CC2)co1] |

| Compound | Structure |
|---|---|
| 193 | 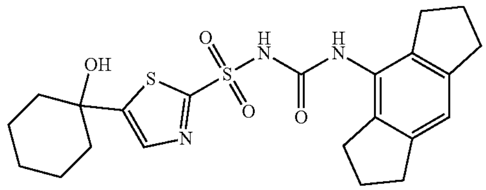 [SMILES: O=C(Nc1c2c(cc3c1CCC3)CCC2)NS(=O)(=O)c1ncc(C2(O)CCCCC2)s1] |
| 196 | 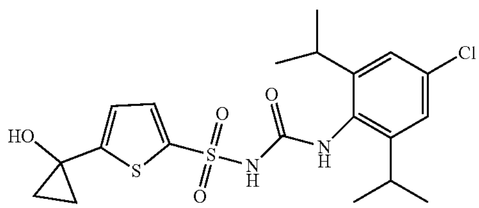 [SMILES: CC(C)c1cc(Cl)cc(C(C)C)c1NC(=O)NS(=O)(=O)c1ccc(C2(O)CC2)s1] |
| 197 | 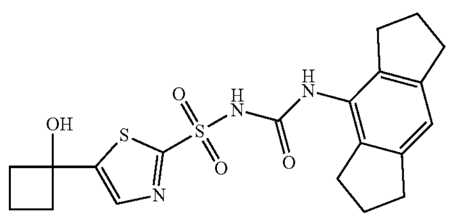 [SMILES: O=C(Nc1c2c(cc3c1CCC3)CCC2)NS(=O)(=O)c1ncc(C2(O)CCC2)s1] |
| 206 | 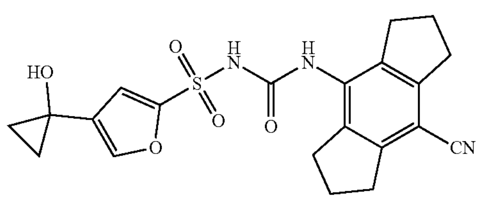 [SMILES: N#Cc1c2c(c(NC(=O)NS(=O)(=O)c3cc(C4(O)CC4)co3)c3c1CCC3)CCC2] |
| 207 | 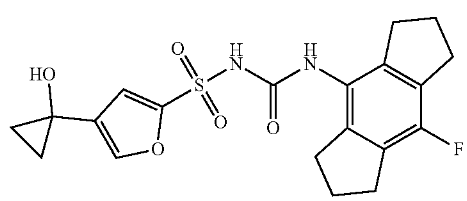 [SMILES: O=C(Nc1c2c(c(F)c3c1CCC3)CCC2)NS(=O)(=O)c1cc(C2(O)CC2)co1] |
| 209 | 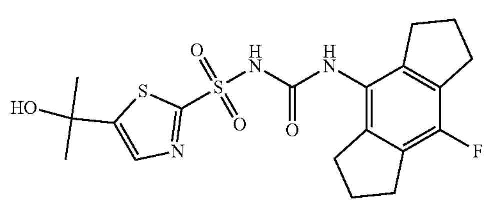 [SMILES: CC(C)(O)c1cnc(S(=O)(=O)NC(=O)Nc2c3c(c(F)c4c2CCC4)CCC3)s1] |
| 213 | 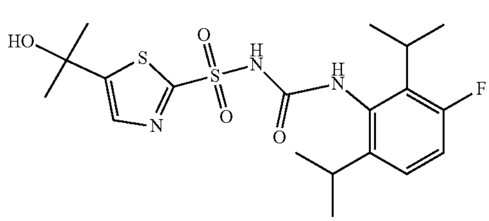 [SMILES: CC(C)c1ccc(F)c(C(C)C)c1NC(=O)NS(=O)(=O)c1ncc(C(C)(C)O)s1] |
| 219 | |
| 220 | |
| 221 | |
| 226 | |
| 227 | |
| 233 | |
| 235 | |

| Compound | Structure |
|---|---|
| 247 | 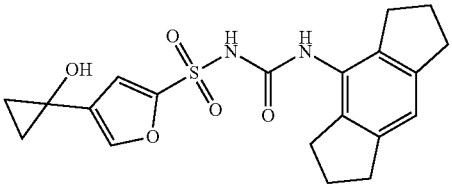 [SMILES: O=C(Nc1c2c(cc3c1CCC3)CCC2)NS(=O)(=O)c1cc(C2(O)CC2)co1] |
| 255 | 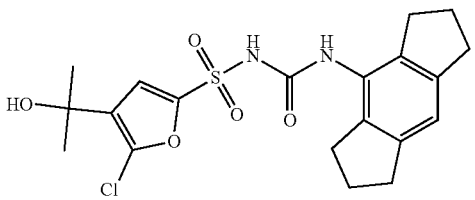 |
| 259 | 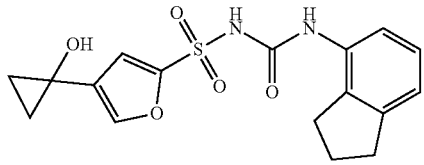 [SMILES: O=C(Nc1cccc2c1CCC2)NS(=O)(=O)c1cc(C2(O)CC2)co1] |
| 260 | 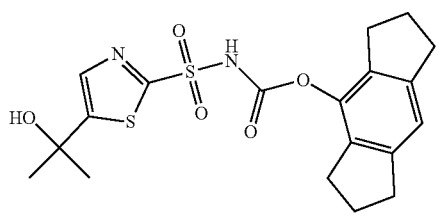 [SMILES: CC(C)(O)c1cnc(S(=O)(=O)NC(=O)Oc2c3c(cc4c2CCC4)CCC3)s1] |
| 261 | 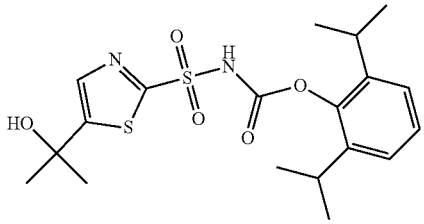 [SMILES: CC(C)c1cccc(C(C)C)c1OC(=O)NS(=O)(=O)c1ncc(C(C)(C)O)s1] |
| 263 | 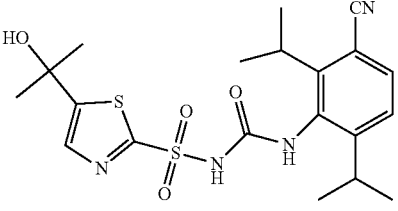 [SMILES: CC(C)c1ccc(C#N)c(C(C)C)c1NC(=O)NS(=O)(=O)c1ncc(C(C)(C)O)s1] |
| 266 | 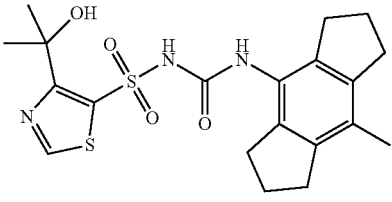 [SMILES: Cc1c2c(c(NC(=O)NS(=O)(=O)c3scnc3C(C)(C)O)c3c1CCC3)CCC2] |
| 267 | 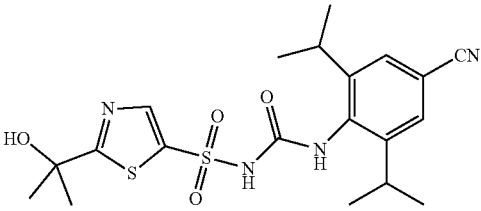 [SMILES: CC(C)c1cc(C#N)cc(C(C)C)c1NC(=O)NS(=O)(=O)c1cnc(C(C)(C)O)s1] |
| 268 | 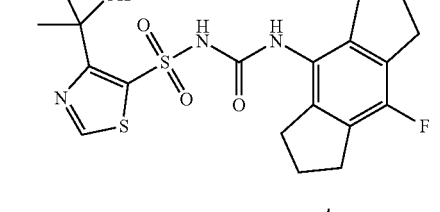 |
| 269 | 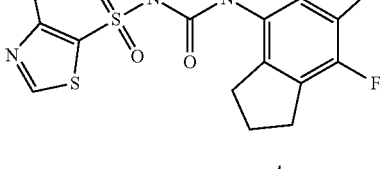 |
| 270 | 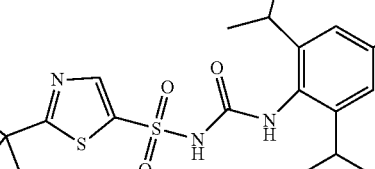 |
| 271 | 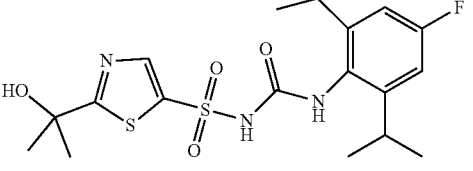 |
| 272 | 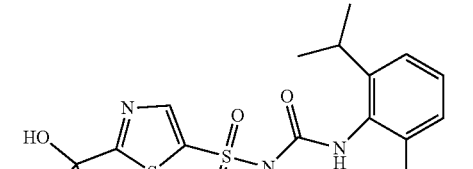 |
| 273 | 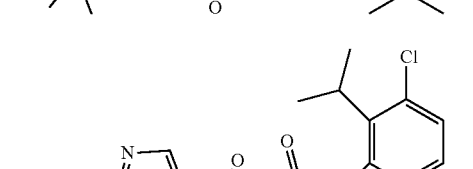 |

| Compound | Structure |
|---|---|
| 274 | ![structure with thiazole, HO-C(CH3)2 group, sulfonylurea linker, and 2,6-diisopropyl-3-fluorophenyl] | and pharmaceutically acceptable salts thereof.

9. A pharmaceutical composition comprising a compound or salt as claimed in claim 1 and one or more pharmaceutically acceptable excipients.

10. A pharmaceutical composition comprising a compound or salt as claimed in claim 2 and one or more pharmaceutically acceptable excipients.

11. The compound of claim 1, wherein the compound of Formula II is

[structure showing thiazole with $R^1$, $R^{10''}$, sulfonamide, $X^3$, phenyl/pyridyl ring with $R^2$, $R^3$, $R^4$, $R^5$, and Y]

or a pharmaceutically acceptable salt thereof, wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$;
Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

[Ring A structure with $(R^6)_{m1}$ and n1]

and ring B is

[Ring B structure with $(R^6)_{m2}$ and n2]

wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^1$ is selected from H, unsubstituted $C_1$-$C_6$ alkyl, $C(R^{19})_2OH$, $C(O)C_2$-$C_6$ alkyl, and $C_3$-$C_6$ cycloalkyl;
wherein each $C(O)C_2$-$C_6$ alkyl and $C_3$-$C_6$ cycloalkyl above is optionally substituted with one or more substituents each independently selected from hydroxy, $C_1$-$C_6$ alkoxy, $NR^{11}R^{12}$, $=NR^{13}$, $COOC_1$-$C_6$ alkyl, and $CONR^{11}R^{12}$;
$R^{10''}$ is selected from Cl, $C_1$-$C_6$ alkyl, $C_3$-$C_6$ cycloalkyl, and C3-C6 heterocycloalkyl; wherein the Ci-C6 alkyl, C3-C6 cycloalkyl, and C3-C6 heterocycloalkyl are optionally substituted with one or more substituents each independently selected from hydroxy, Ci-C6 alkoxy, $NR^{11}R^{12}$, $=NR^{13}$, $COOC_1$-$C_6$ alkyl, and $CONR^{11}R^{12}$;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is C1-C6 alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$;
each $R^{19}$ is the same and is selected from $C_1$-$C_6$ alkyl.

12. The compound of claim 1, wherein the compound of Formula II is

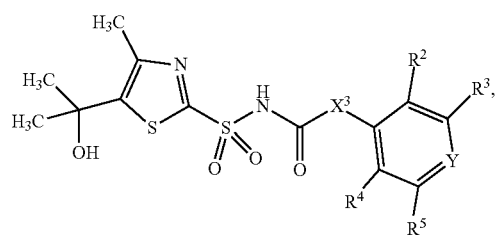

or a pharmaceutically acceptable salt thereof, wherein:
$X^3$ is NH or O;
or when $X^3$ is NH, $X^3$ and $R^2$ taken together with the atoms connecting them form a four-to-seven-membered heterocyclic ring optionally substituted with one or more $R^{16}$;
or when $X^3$ is NH, $X^3$ and $R^4$ taken together with the atoms connecting them form a four-to-seven-membered heterocyclic ring optionally substituted with one or more $R^{16}$; Y is N or $CR^8$;
$R^8$ is selected from H, CN, Cl, F, $CO_2C_1$-$C_6$ alkyl, $CO_2C_3$-$C_8$ cycloalkyl, $CONR^{11}R^{12}$, $C_1$-$C_6$ alkyl, $C_1$-$C_6$ haloalkoxy, and $C_1$-$C_6$ haloalkyl;
$R^2$ is hydrogen, $C_1$-$C_6$ alkoxy, halo, $C_1$-$C_6$ haloalkyl, or $C_1$-$C_6$ alkyl optionally substituted with hydroxy;
$R^3$ is hydrogen, CN, $C_1$-$C_6$ alkoxy, halo, $C_1$-$C_6$ haloalkyl, or $C_1$-$C_6$ alkyl optionally substituted with hydroxy;
$R^4$ is hydrogen, $C_1$-$C_6$ alkoxy, halo, $C_1$-$C_6$ haloalkyl, or $C_1$-$C_6$ alkyl optionally substituted with hydroxy;
$R^5$ is hydrogen, $C_1$-$C_6$ alkoxy, halo, $C_1$-$C_6$ haloalkyl, or $C_1$-$C_6$ alkyl optionally substituted with hydroxy;
or $R^2$ and $R^3$ taken together with the carbons connecting them form a four-membered to seven-membered ring A,
or $R^4$ and $R^5$ taken together with the carbons connecting them form a four-membered to seven-membered ring B,
or $R^2$ and $R^3$ taken together with the carbons connecting them form a four-membered to seven-membered ring A and $R^4$ and $R^5$ taken together with the carbons connecting them form a four-membered to seven-membered ring B, wherein ring A is

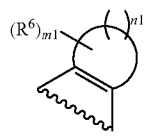

Ring A and ring B is

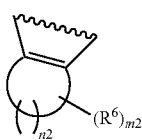

Ring B wherein
ring A is a saturated carbocyclic ring;
n1 is from 2 to 5;
m1 is from 1 to 10;
wherein ring B is a saturated carbocyclic ring;
n2 is from 2 to 5;
m2 is from 1 to 10;
wherein each $R^6$ in each ring is the same or different and is selected from H, $C_1$-$C_6$ alkyl, $C_1$-$C_6$ alkoxy, $NR^{11}R^{12}$, oxo, and $=NR^{13}$;
or two $R^6$ taken together with the atom or atoms connecting them form a 3-to-8-membered carbocyclic or saturated heterocyclic ring containing 1 or 2 heteroatoms independently selected from O, N, and S;
$R^{13}$ is $C_1$-$C_6$ alkyl;
each of $R^{11}$ and $R^{12}$ at each occurrence is independently selected from hydrogen, $C_1$-$C_6$ alkyl, $CO_2R^{15}$ and $CONR^{17}R^{18}$;
$R^{15}$ is $C_1$-$C_6$ alkyl;
each of $R^{17}$ and $R^{18}$ at each occurrence is independently selected from hydrogen and $C_1$-$C_6$ alkyl;
each $R^{16}$ is the same or different and is selected from H, $C_1$-$C_6$ alkyl, $C_1$-$C_6$ alkoxy, $NR^{11}R^{12}$, oxo, and $=NR^{13}$.

* * * * *